US007045528B2

(12) United States Patent
Collins et al.

(10) Patent No.: US 7,045,528 B2
(45) Date of Patent: May 16, 2006

(54) BENZOFUSED HETEROZRYL AMIDE DERIVATIVES OF THIENOPYRIDINES USEFUL AS THERAPEUTIC AGENTS, PHARMACEUTICAL COMPOSITIONS INCLUDING THE SAME, AND METHODS FOR THEIR USE

(75) Inventors: Michael Collins, San Diego, CA (US); Stephan Cripps, San Diego, CA (US); Judith Deal, Wildomar, CA (US); Robert Steven Kania, San Diego, CA (US); Jihong Lou, San Diego, CA (US); Mingying He, San Diego, CA (US); Cynthia Louise Palmer, La Mesa, CA (US); William Henry Romines, III, San Diego, CA (US); Ru Zhou, Carlsbad, CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 123 days.

(21) Appl. No.: 10/796,226

(22) Filed: Mar. 9, 2004

(65) Prior Publication Data
US 2004/0186126 A1 Sep. 23, 2004

Related U.S. Application Data

(62) Division of application No. 10/460,010, filed on Jun. 11, 2003.

(60) Provisional application No. 60/389,110, filed on Jun. 14, 2002.

(51) Int. Cl.
*A61K 31/4365* (2006.01)
*C07D 495/04* (2006.01)

(52) U.S. Cl. ............ 514/301; 546/114; 544/127; 544/180; 544/331; 544/336; 544/362; 514/233.8; 514/241; 514/253; 514/275

(58) Field of Classification Search ........ 514/301, 514/233.8, 241, 253, 275; 546/114; 544/127, 544/180, 331, 336, 362
See application file for complete search history.

(56) References Cited

U.S. PATENT DOCUMENTS

| 5,587,458 | A | 12/1996 | King et al. |
|---|---|---|---|
| 5,747,498 | A | 5/1998 | Schnur |
| 5,792,783 | A | 8/1998 | Tang et al. |
| 5,834,504 | A | 11/1998 | Tang et al. |
| 5,861,510 | A | 1/1999 | Piscopio et al. |
| 5,863,949 | A | 1/1999 | Robinson et al. |
| 5,877,305 | A | 3/1999 | Huston et al. |
| 5,883,113 | A | 3/1999 | Tang et al. |
| 5,886,020 | A | 3/1999 | Tang et al. |
| 6,071,935 | A | 6/2000 | Lyssikatos |
| 6,225,318 | B1 | 5/2001 | Sobolov-Jaynes et al. |
| 6,492,383 | B1 | 12/2002 | Munchhof et al. |
| 6,502,129 | B1 | 12/2002 | Stewart et al. |

FOREIGN PATENT DOCUMENTS

| EP | 0606046 | 12/1993 |
|---|---|---|
| EP | 0 780 386 | 10/2002 |
| EP | 0 931 788 | 11/2002 |
| WO | WO 90/05719 | 5/1990 |
| WO | WO 95/19970 | 7/1995 |
| WO | WO 95/21613 | 8/1995 |
| WO | WO 95/23141 | 8/1995 |
| WO | WO 96/14843 | 5/1996 |
| WO | WO 96/27583 | 9/1996 |
| WO | WO 96/30347 | 10/1996 |
| WO | WO 96/33172 | 10/1996 |
| WO | WO 96/40142 | 12/1996 |
| WO | WO 97/13760 | 4/1997 |
| WO | WO 97/13771 | 4/1997 |
| WO | WO 97/22596 | 6/1997 |
| WO | WO 97/32856 | 9/1997 |
| WO | WO 97/34876 | 9/1997 |

(Continued)

OTHER PUBLICATIONS

Bagshawe, et. al., "Antibody-Directed Enzyme Therapy: A Review," *Drug Development and Research*, 1995, 220-230, 34.

(Continued)

*Primary Examiner*—Charanjit S. Aulakh
(74) *Attorney, Agent, or Firm*—Edward D. Robinson; Bryan C. Zielinski

(57) ABSTRACT

The invention relates to compounds represented by the formula I

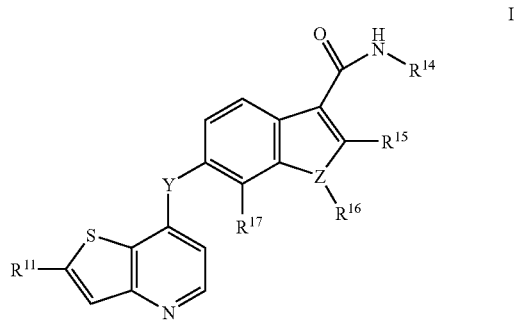

and to prodrugs or metabolites thereof, or pharmaceutically acceptable salts or solvates of said compounds, said prodrugs, and said metabolites, wherein Z, Y, $R^{11}$ and $R^{14}$, $R^{15}$, $R^{16}$, and $R^{17}$ are as defined herein. The invention also relates to pharmaceutical compositions containing the compounds of formula I and to methods of treating hyperproliferative disorders in a mammal by administering the compounds of formula I.

30 Claims, No Drawings

FOREIGN PATENT DOCUMENTS

| WO | WO 97/49688 | 12/1997 |
|---|---|---|
| WO | WO 98/01113 | 1/1998 |
| WO | WO 98/02434 | 1/1998 |
| WO | WO 98/02437 | 1/1998 |
| WO | WO98/02438 | 1/1998 |
| WO | WO 98/03516 | 1/1998 |
| WO | WO 98/07697 | 2/1998 |
| WO | WO 98/14451 | 4/1998 |
| WO | WO 98/23613 | 6/1998 |
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 98/50356 | 11/1998 |
| WO | WO 98/54093 | 12/1998 |
| WO | WO 99/00797 | 1/1999 |
| WO | WO 99/10349 | 3/1999 |
| WO | WO 99/16755 | 4/1999 |
| WO | WO 99/21845 | 5/1999 |
| WO | WO 99/24440 | 5/1999 |
| WO | WO 99/29667 | 6/1999 |
| WO | WO 99/35132 | 7/1999 |
| WO | WO 99/35146 | 7/1999 |
| WO | WO 99/52889 | 10/1999 |
| WO | WO 99/52910 | 10/1999 |
| WO | WO 99/61422 | 12/1999 |
| WO | WO 00/38665 | 7/2000 |
| WO | WO 01/94353 | 12/2001 |
| WO | WO 03/000194 | 1/2003 |
| WO | WO 03/074529 | 9/2003 |

OTHER PUBLICATIONS

Bertolini, et. al., "A New Rational Hypothesis for the Pharmacophore of the Active Metabolite of Leflunomide, a Potent Immunosuppressive Drug," *Journal of Medicinal Chemistry*, 1997, 2011-2016, 40.

Bodor, et. al., "Novel Approaches to the Design of Safer Drugs: Soft Drugs and Site-Specific Chemical Delivery Systems," *Advances in Drug Res.*, 1984, 224-331, 13.

Bundgaard, et. al., *Design and Application of Prodrugs, Drug Design and Development*, Harwood Academic Press, 1991.

Bundgaard, et. al., *Design of Prodrugs*, Elsevier Press, 1985, New York.

Buttery, et. al., "Preparation of 2,3-Disubstituted Indoles from Indole-3-carboxylic Acids and Amides by Deprotonation," *Journal of Chem. Soc. Perkin Trans*, 1993, 1425-1431.

Pagano, Michele ed., Cell Cycle: Materials and Methods, 1995, Berlin, Germany.

Fleisher, et. al., , "Improved Oral Drug Delivery: Solubility Limitations Overcome by the Use of Prodrugs," *Advanced Drug Delivery Reviews* 1996, 115-130, vol. 19.

Green, T., et. al., *Protecting Groups in Chemical Synthesis (3rd Edition)*, 1999, John Wiley & Sons, New York.

Mohammadi., et. al., "Identification of Six N0vel Autophosphorylation Sites on Fibroblast Growth Factor Receptor 1 and Elucidation of Their Importance in Receptor Activation and Signal Transduction," *Molecular Cell and Biology*, 1996, 977-989, vol. 16, No. 3.

Parast, et. al., "Characterization and Kinetic Mechanism of Catalytic Domain of Human Vascular Endothelial Growth Factor Receptor-2 Tyrosine Kinase (VEGFR 2 TK), a Key Enzyme in Angiogenesis," *Biochemistry*, 1998, 16788-16801, 37.

Robinson, et. al., "Discovery of the Hemifumarate and (a-L-Alanylogy) methyl Ether as Prodrugs of an Antirheumatic Oxiindole: Prodrugs for the Enolic OH Group," *Journal of Medicinal Chemistry*, 1996, 39, 1, 10-18.

Shan, et. al., , "Prodrug Strategies Based on Intramolecular Cyclization Reactions," *Journal of Pharmaceutical Science*, 1997, 765-767, vol. 86, No. 7.

Still, et. al., "Rapid Chromatographic Technique for Preparative Separations with Moderate Resolution," *Journal of Organic Chemistry*, 1978, 2923-2925, vol. 43, No. 14.

Swain, et. al., "Novel 5-$HT_3$ Antagonists: Indol-3-ylspiro(azabicycloalkane-3,5' (4'H)-oxazoles)," *Journal of Med. Chemistry*, 1992, 1019-1031, 35.

BENZOFUSED HETEROZRYL AMIDE DERIVATIVES OF THIENOPYRIDINES USEFUL AS THERAPEUTIC AGENTS, PHARMACEUTICAL COMPOSITIONS INCLUDING THE SAME, AND METHODS FOR THEIR USE

The present patent application is a division of U.S. patent application Ser. No. 10/460,010, filed Jun. 11, 2003, which also claims priority to U.S. Ser. No. 60/389,110, filed Jun. 14, 2002, which is hereby incorporated by reference in its entirety for all purposes.

FIELD OF THE INVENTION

This invention relates to novel thienopyridine and thienopyridine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

BACKGROUND OF THE INVENTION

It is known that a cell may become cancerous by virtue of the transformation of a portion of its DNA into an oncogene (i.e., a gene that upon activation leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate a specific tyrosine residue in proteins and hence to influence cell proliferation. The foregoing tyrosine kinases may be classified as growth factor receptor (e.g. EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995), hereby incorporated by reference in its entirety.

It is known that polypeptide growth factors such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995), hereby incorporated by reference in its entirety. Agents, such as the compounds of the present invention, that are capable of binding to or modulating the KDR/FLK-1 receptor may be used to treat disorders related to vasculogenesis or angiogenesis such as diabetes, diabetic retinopathy, age related macular degeneration, hemangioma, glioma, melanoma, Kaposi's sarcoma and ovarian, breast, lung, pancreatic, prostate, colon and epidermoid cancer.

Compounds that are useful in the treatment of hyperproliferative diseases are also disclosed in the following patents and applications: PCT international patent application publication number WO 00/38665 (published Jul. 6, 2001), PCT international patent application publication number WO 97/49688 (published Dec. 31, 1997), PCT international patent application publication number WO 98/23613 (published Jun. 4, 1998), U.S. patent application No. 60/360,952 (filed Mar. 1, 2002), U.S. patent application No. 60/299,879 (filed Jun. 21, 2001), U.S. patent application Ser. No. 09/502,129 (filed Feb. 10, 2000), U.S. patent application No. 60/209,686 (filed Jun. 6, 2000), U.S. patent application No. 60/214,373 (filed Jun. 28, 2000), U.S. patent application Ser. No. 08/953,078 (filed Oct. 17, 1997), U.S. Pat. No. 6,071,935 issued Jun. 6, 2000, PCT international patent application publication number WO 96/30347 (published Oct. 3, 1996), PCT international patent application publication number WO 96/40142 (published Dec. 19, 1996), PCT international patent application publication number WO 97/13771 (published Apr. 17, 1997), and PCT international patent application publication number WO 95/23141 (published Aug. 31, 1995). The foregoing patent and applications are each incorporated herein by reference in their entirety.

SUMMARY OF THE INVENTION

In one of the aspects, the present invention relates to a compound represented by the formula I:

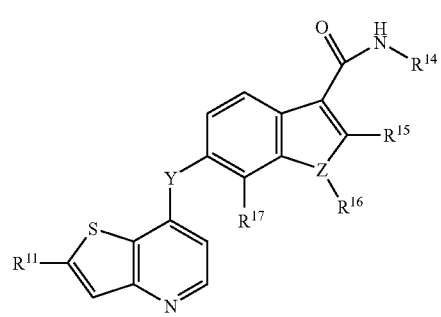

wherein:
Y is —NH—, —O—S—, or —CH$_2$—;
Z is —O—, —S—, or —N—;
$R^{14}$ is a $C_1$–$C_6$ alkyl, $C_1$–$C_6$ alkylamino, $C_1$–$C_6$ alkylhydroxy, $C_3$–$C_{10}$ cycloalkylamino, or methylureido group;
$R^{15}$ and $R^{17}$ are independently H, halo, or a $C_1$–$C_6$ alkyl group unsubstituted or substituted by one or more $R^5$ groups;

$R^{16}$ is H or a $C_1$–$C_6$ alkyl group, preferably methyl, when Z is N, and $R^{16}$ is absent when Z is —O— or —S—;

$R^{11}$ is H, $C_1$–$C_6$ alkyl, $C_3$–$C_{10}$ cycloalkyl, —C(O)NR$^{12}$R$^{13}$, —C(O)(C$_6$–C$_{10}$ aryl), CH$_2)_t$(C$_6$–C$_{10}$ aryl), —(CH$_2)_t$(5 to 10 membered heterocyclic), —(CH$_2)_t$NR$^{12}$R$^{13}$, —SO$_2$NR$^{12}$R$^{13}$ or —CO$_2$R$^{12}$, wherein said $C_1$–$C_6$ alkyl, —C(O)(C$_6$–C$_{10}$ aryl), —(CH$_2)_t$(C$_6$–C$_{10}$ aryl), and —(CH$_2)_t$(5 to 10 membered heterocyclic) moieties of the said $R^{11}$ groups are unsubstituted or substituted by one or more $R^5$ groups;

each $R^5$ is independently selected from halo, cyano, nitro, trifluoromethoxy, trifluoromethyl, azido, —C(O)R$^8$, —C(O)OR$^8$, —OC(O)R$^8$, —OC(O)OR$^8$, —NR$^6$C(O)R$^7$, —C(O)NR$^6$R$^7$, —NR$^6$R$^7$, —OR$^9$, —SO$_2$NR$^6$R$^7$, $C_1$–$C_6$ alkyl, $C_3$–$C_{10}$ cycloalkyl, $C_1$–$C_6$ alkylamino, —(CH$_2)_t$O(CH$_2)_q$NR$^6$R$^7$, —(CH$_2)_t$O(CH$_2)_q$OR$^9$, —(CH$_2)_t$OR$^9$, —S(O)$_j$(C$_1$–C$_6$ alkyl), —(CH$_2)_t$(C$_6$–C$_{10}$ aryl), —(CH$_2)_t$(5 to 10 membered heterocyclic), —C(O)(CH$_2)_t$(C$_6$–C$_{10}$ aryl), —(CH$_2)_t$O(CH$_2)_q$(C$_6$–C$_{10}$ aryl), —(CH$_2)_t$O(CH$_2)_q$(5 to 10 membered heterocyclic), —C(O)(CH$_2)_t$(5 to 10 membered heterocyclic), —(CH$_2)_j$NR$^7$(CH$_2)_q$NR$^6$R$^7$, —(CH$_2)_t$NR$^7$CH$_2$C(O)NR$^6$R$^7$, —(CH$_2)_t$NR$^7$(CH$_2)_q$NR$^9$C(O)R$^8$, (CH$_2)_t$NR$^7$(CH$_2)_t$O(CH$_2)_q$OR$^9$, —(CH$_2)_t$NR$^7$(CH$_2)_q$S(O)$_j$(C$_1$–C$_6$ alkyl), —(CH$_2)_j$NR$^7$(CH$_2)_t$R$^6$, —SO$_2$(CH$_2)_t$(C$_6$–C$_{10}$ aryl), and —SO$_2$(CH$_2)_t$(5 to 10 membered heterocyclic), the —(CH$_2)_q$— and —(CH$_2)_t$— moieties of the said $R^5$ groups optionally include a carbon-carbon double or triple bond where t is an integer between 2 and 6, and the alkyl, aryl and heterocyclic moieties of the said $R^5$ groups are unsubstituted or substituted with one or more substituents independently selected from halo, cyano, nitro, trifluoromethyl, azido, —OH, —C(O)R$^8$, —C(O)OR$^8$, —OC(O)R$^8$, —OC(O)OR$^8$, —NR$^6$C(O)R$^7$, —C(O)NR$^6$R$^7$, —(CH$_2)_t$NR$^6$R$^7$, $C_1$–$C_6$ alkyl, $C_3$–$C_{10}$ cycloalkyl, —(CH$_2)_t$(C$_6$–C$_{10}$ aryl), —(CH$_2)_t$(5 to 10 membered heterocyclic), —(CH$_2)_t$O(CH$_2)_q$OR$^9$, and —(CH$_2)_t$OR$^9$;

each $R^6$ and $R^7$ is independently selected from H, OH, $C_1$–$C_6$ alkyl, $C_3$–$C_{10}$ cycloalkyl, —(CH$_2)_t$(C$_6$–C$_{10}$ aryl), —(CH$_2)_t$(5 to 10 membered heterocyclic), —(CH$_2)_t$O(CH$_2)_q$OR$^9$, —(CH$_2)_t$CN(CH$_2)_t$OR$^9$, —(CH$^3)_t$CN(CH$_2)_t$R$^9$ and —(CH$_2)_t$OR$^9$, and the alkyl, aryl and heterocyclic moieties of the said $R^6$ and $R^7$ groups are unsubstituted or substituted with one or more substituents independently selected from hydroxy, halo, cyano, nitro, trifluoromethyl, azido, —C(O)R$^8$, —C(O)OR$^8$, —CO(O)R$^8$, —OC(O)R$^8$, —NR$^9$C(O)R$^{10}$, —C(O)NR$^9$R$^{10}$, —NR$^9$R$^{10}$, $C_1$–$C_6$ alkyl, —(CH$_2)_t$(C$_6$–C$_{10}$ aryl), —(CH$_2$)1(5 to 10 membered heterocyclic), —(CH$_2)_t$O(CH$_2)_q$OR$^9$, and —(CH$_2)_t$OR$^9$, where when $R^6$ and $R^7$ are both attached to the same nitrogen, then $R^6$ and $R^7$ are not both bonded to the nitrogen directly through an oxygen;

each $R^8$ is independently selected from H, $C_1$–$C_{10}$ alkyl, $C_3$–$C_{10}$ cycloalkyl, —(CH$_2)_t$(C$_6$–C$_{10}$ aryl), and —(CH$_2)_t$(5 to 10 membered heterocyclic);

each $R^9$ and $R^{10}$ is independently selected from H, —OR$^6$, $C_1$–$C_6$ alkyl, and $C_3$–$C_{10}$ cycloalkyl;

wherein j is an integer from 0 to 2, t is an integer from 0 to 6, q is an integer from 2 to 6; and each $R^{12}$ and $R^{13}$ is independently selected from H, $C_1$–$C_6$ alkyl, $C_3$–$C_{10}$ cycloalkyl, —(CH$_2)_t$(C$_3$–C$_{10}$ cycloalkyl), —(CH$_2)_t$(C$_6$–C$_{10}$ aryl), —(CH$_2)_t$(5 to 10 membered heterocyclic), —(CH$_2)_t$O(CH$_2)_q$OR$^9$, and —(CH$_2)_t$OR$^9$, and the alkyl, aryl and heterocyclic moieties of the said $R^{12}$ and $R^{13}$ groups are unsubstituted or substituted with one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl rings are unsubstituted or substituted with one or more $R^5$ substituents, where $R^{12}$ and $R^{13}$ are not both bonded to the nitrogen directly through an oxygen;

or prodrugs thereof, or pharmaceutically acceptable salts or solvates of said compounds and said prodrugs.

In one embodiment of the compound of formula I, $R^{11}$ is —(CH$_2)_t$(5 to 10 membered heterocyclic), —C(O)NR$^{12}$R$^{13}$, —SO$_2$NR$^{12}$R$^{13}$ and —CO$_2$R$^{12}$, wherein said $R^{11}$ group —(CH$_2)_t$(5 to 10 membered heterocyclic) is unsubstituted or substituted by one or more $R^5$ groups and wherein each $R^{12}$ and $R^{13}$ is independently selected from H, $C_1$–$C_6$ alkyl, $C_3$–$C_{10}$ cycloalkyl, —(CH$_2)_t$(C$_3$–C$_{10}$ cycloalkyl), —(CH$_2)_t$(C$_6$–C$_{10}$ aryl), —(CH$_2)_t$(5 to 10 membered heterocyclic), —(CH$_2)_t$O(CH$_2)_q$OR$^9$, —(CH$_2)_t$OR$^9$, and the alkyl, aryl and heterocyclic moieties of said $R^{12}$ and $R^{13}$ groups are unsubstituted or substituted by one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted by one or more $R^5$ substituents, where said $R^{12}$ and $R^{13}$ are not both bonded to the nitrogen directly through an oxygen.

In another embodiment of the compound of formula I, $R^{11}$ is —(CH$_2)_t$(5 to 10 membered heterocyclic), and —C(O)NR$^{12}$R$^{13}$.

In still another embodiment of the compound of formula I, $R^{11}$ is —C(O)NR$^{12}$R$^{13}$, wherein $R^{12}$ and $R^{13}$ are independently selected from H, $C_1$–$C_6$ alkyl, $C_3$–$C_{10}$ cycloalkyl, —(CH$_2)_t$(C$_3$–C$_{10}$ cycloalkyl), —(CH$_2)_t$(C$_6$–C$_{10}$ aryl), —(CH$_2)_t$(5 to 10 membered heterocyclic), —(CH$_2)_t$O(CH$_2)_q$OR$^9$, —(CH$_2)_t$OR$^9$, wherein t is an integer from 0 to 6, q is an integer from 2 to 6, and the alkyl, aryl and heterocyclic moieties of said $R^{12}$ and $R^{13}$ groups are unsubstituted or substituted with one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 $R^5$ substituents, where $R^{12}$ and $R^{13}$ are not both bonded to the nitrogen directly through an oxygen.

In another embodiment of the compound of formula I, $R^{11}$ is —C(O)NR$^{12}$R$^{13}$, wherein $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 $R^5$ substituents.

In still another embodiment of the compound of formula I, $R^{11}$ is —C(O)NR$^{12}$R$^{13}$, wherein $R^{12}$ and $R^{13}$ are taken together with the nitrogen to which they are attached to form a pyrrolidinyl, piperidinyl, piperazinyl, morpholinyl, thiomorpholinyl, isoquinolinyl, or dihydroisoquinolinyl ring, wherein said pyrrolidinyl, piperidinyl, piperazinyl, morpholinyl, thiomorpholinyl, isoquinolinyl, or dihydroisoquinolinyl ring are unsubstituted or substituted with 1 to 5 $R^5$ substituents.

In still another embodiment of the compound of formula I, $R^{11}$ is —C(O)NR$^{12}$R$^{13}$, wherein $R^{12}$ and $R^{13}$ are taken together with the nitrogen to which they are attached to form a pyrrolidinyl, piperidinyl, piperazinyl, morpholinyl, or thiomorpholinyl ring, wherein said pyrrolidinyl, piperidinyl, piperazinyl, morpholinyl, or thiomorpholinyl rings are unsubstituted or substituted with 1 to 5 $R^5$ substituents.

In still another embodiment of the compound of formula I, $R^{11}$ is —C(O)NR$^{12}$R$^{13}$, wherein $R^{12}$ and $R^{13}$ are taken together with the nitrogen to which they are attached to form a pyrrolidinyl or piperidinyl ring, wherein said pyrrolidinyl or piperidinyl ring are unsubstituted or substituted with 1 to 5 $R^5$ substituents.

In still another embodiment of the compound of formula I, $R^{11}$ is —C(O)NR$^{12}$R$^{13}$, wherein $R^{12}$ and $R^{13}$ are taken together with the nitrogen to which they are attached to form a pyrrolidinyl ring, wherein said pyrrolidinyl is unsubstituted or substituted with 1 to 5 $R^5$ substituents.

In still another embodiment of the compound of formula I, $R^{11}$ is —C(O)NR$^{12}$R$^{13}$, wherein $R^{12}$ and $R^{13}$ are taken together with the nitrogen to which they are attached to form a pyrrolidin-1-yl ring, wherein said pyrrolidin-1-yl is unsubstituted or substituted by 1 to 5 $R^5$ substituents.

In still another embodiment of the compound of formula I, $R^{11}$ is —(CH$_2$)$_t$(5 to 10 membered heterocyclic) group, wherein said —(CH$_2$)$_t$(5 to 10 membered heterocyclic) group is unsubstituted or substituted by 1 to 5 $R^5$ groups.

In still another embodiment of the compound of formula I, $R^{11}$ is —(CH$_2$)$_t$(5–8 membered heterocyclic) group, said —(CH$_2$)$_t$(5–8 membered heterocyclic) group is unsubstituted or substituted by 1 to 5 $R^5$ groups.

In still another embodiment of the compound of formula I, $R^{11}$ is —(CH$_2$)$_t$(5 or 6 membered heterocyclic) group, said —(CH$_2$)$_t$(5 or 6 membered heterocyclic) group is unsubstituted or substituted by 1 to 5 $R^5$ groups.

In still another embodiment of the compound of formula I, $R^{11}$ is —(CH$_2$)$_t$(5 membered heterocyclic) group, said —(CH$_2$)$_t$(5 membered heterocyclic) group is unsubstituted or substituted by 1 to 5 $R^5$ groups.

In still another embodiment the compound of formula I, $R^{11}$ is —(CH$_2$)$_t$thiazolyl, wherein t is an integer from 0 to 6, said —(CH$_2$)$_t$thiazolyl is unsubstituted or substituted by 1 to 5 $R^5$ groups.

In still another embodiment, the compound of formula I, $R^{11}$ is a thiazolyl, said thiazolyl is unsubstituted or substituted by 1 to 5 $R^5$ groups.

In still another embodiment of the compound of formula I, $R^{11}$ is an imidazolyl, said imidazolyl is unsubstituted or substituted by 1 to 5 $R^5$ groups.

The present invention also relates to compounds represented by formula II:

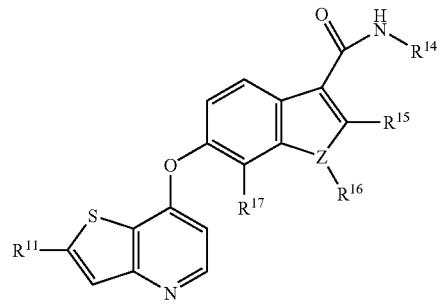

wherein:
Z is —O—, —S—, or —N—;
$R^{14}$ is a $C_1$–$C_6$ alkyl, $C_1$–$C_6$ alkylamino, $C_1$–$C_6$ alkylhydroxy, $C_3$–$C_{10}$ cycloalkylamino, or methylureido group;
$R^{15}$ and $R^{17}$ are independently H, halo, or a $C_1$–$C_6$ alkyl group;
$R^{16}$ is H or a $C_1$–$C_6$ alkyl group when Z is N; and $R^{16}$ is absent when Z is —O— or —S—; and
wherein $R^{11}$ are as defined for said compounds, prodrug, metabolite, salt or solvate of formula I or prodrugs or metabolites thereof, pharmaceutically acceptable salts or solvates of said compounds, said prodrugs, and said metabolites.

In one embodiment, $R^{16}$ is methyl.

In another embodiment, $R^{14}$ is methyl.

The present invention further relates to compounds represented by the formula III:

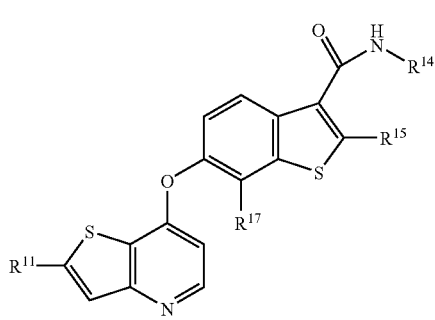

wherein:
$R^{14}$ is a $C_1$–$C_6$ alkyl, $C_1$–$C_6$ alkylamino, $C_1$–$C_6$ alkylhydroxy, $C_3$–$C_{10}$ cycloalkylamino, or methylureido group;
$R^{15}$ and $R^{17}$ are independently H or a $C_1$–$C_6$ alkyl group; and
$R^{11}$ is a heterocyclic or a heteroaryl group unsubstituted or substituted by one or more groups selected from —C(O)OR$^8$, $C_1$–$C_6$ alkyl, and —(CH$_2$)$_t$OR$^9$, wherein t is an integer from 0 to 6;
each $R^8$ is independently selected from H, $C_1$–$C_{10}$ alkyl, $C_3$–$C_{10}$ cycloalkyl, —(CH$_2$)$_t$(C$_6$–C$_{10}$ aryl), and —(CH$_2$)$_t$(5 to 10 membered heterocyclic), wherein t is an integer from 0 to 6;

each $R^9$ is independently selected from H, $C_1$–$C_6$ alkyl, and $C_3$–$C_{10}$ cycloalkyl; or prodrugs thereof, pharmaceutically acceptable salts or solvates of said compounds and said prodrugs.

In another embodiment, the present invention is a compound represented by the formula IV:

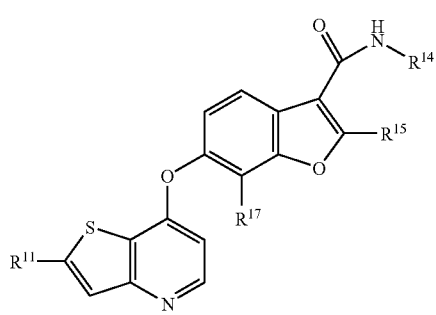

wherein:
- $R^{14}$ is a $C_1$–$C_6$ alkyl, $C_1$–$C_6$ alkylamino, $C_1$–$C_6$ alkylhydroxy, $C_3$–$C_{10}$ cycloalkylamino, or methylureido group;
- $R^{15}$ and $R^{17}$ are independently H or a $C_1$–$C_6$ alkyl group; and
- $R^{11}$ is a heterocyclic or a heteroaryl group unsubstituted or substituted by one or more groups selected from —C(O)OR$^8$, $C_1$–$C_6$ alkyl, and —(CH$_2$)$_t$OR$^9$, wherein t is an integer from 0 to 6;
- each $R^8$ is independently selected from H, $C_1$–$C_{10}$ alkyl, $C_3$–$C_{10}$ cycloalkyl, —(CH$_2$)$_t$($C_6$–$C_{10}$ aryl), and —(CH$_2$)$_t$(5 to 10 membered heterocyclic), wherein t is an integer from 0 to 6;
- each $R^9$ is independently selected from H, $C_1$–$C_6$ alkyl, and $C_3$–$C_{10}$ cycloalkyl;

or prodrugs or metabolites thereof, pharmaceutically acceptable salts or solvates of said compounds, said prodrugs, and said metabolites.

The above compounds of formulas II, III, and IV may be used to prepare the above compounds represented by formula I.

In another embodiment, the present invention comprises compounds selected from the group consisting of:

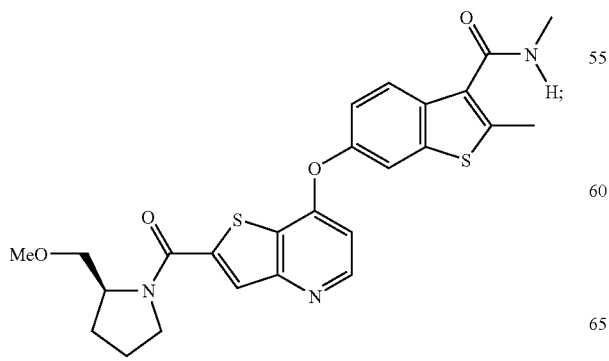

-continued

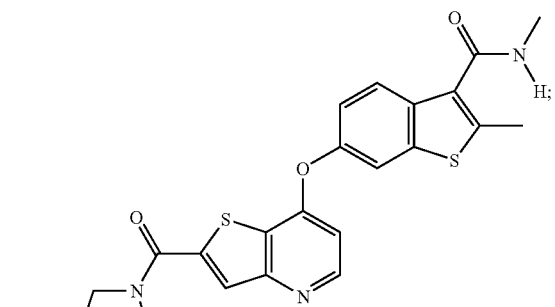

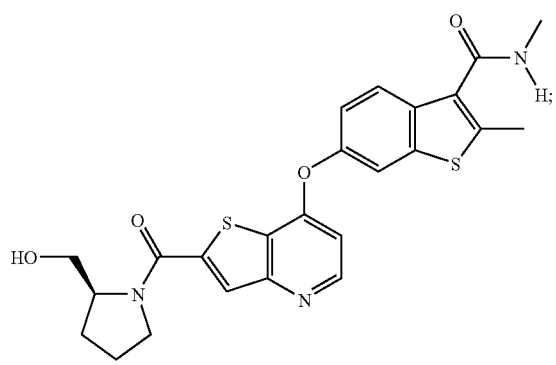

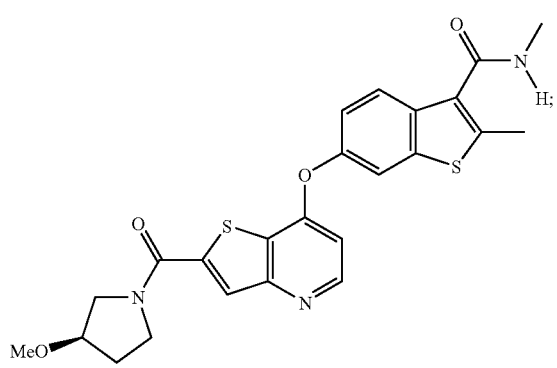

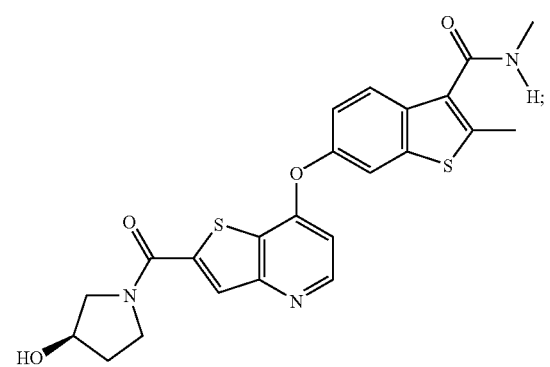
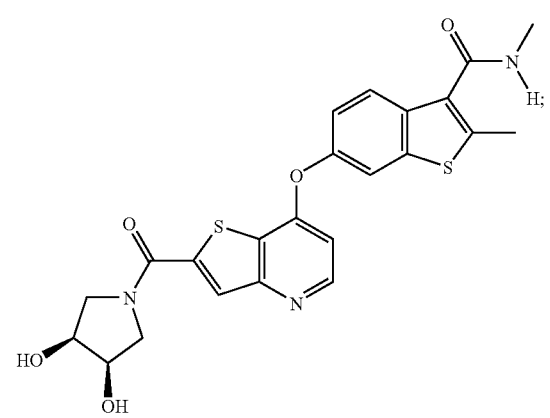
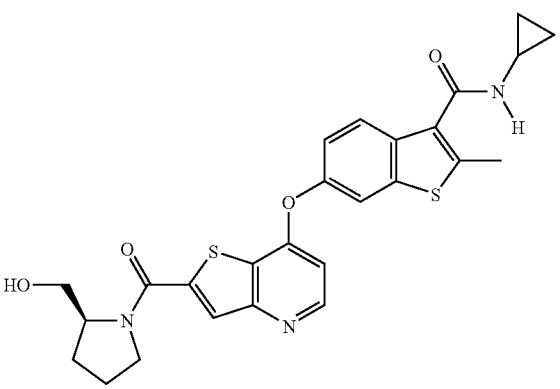
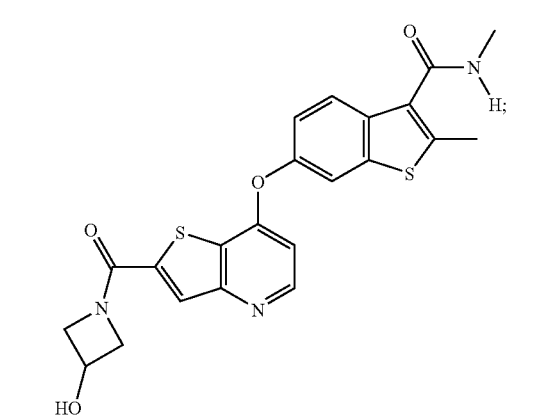
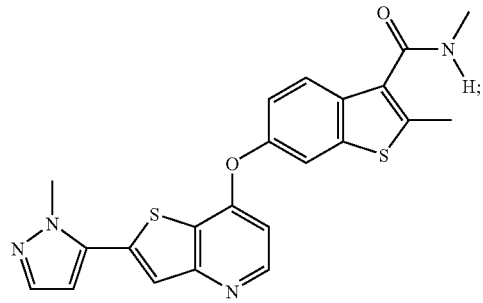
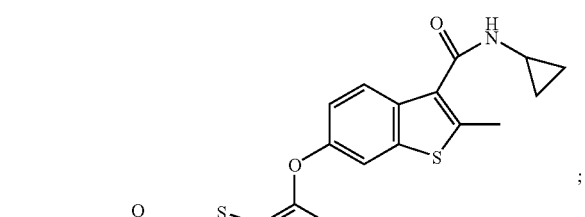
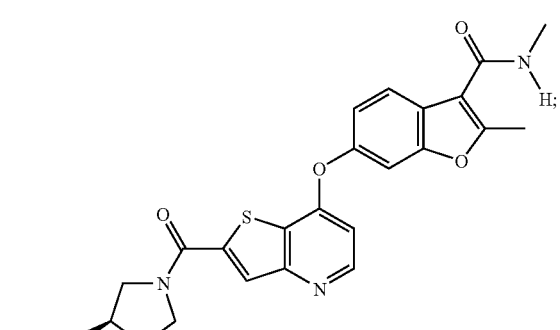
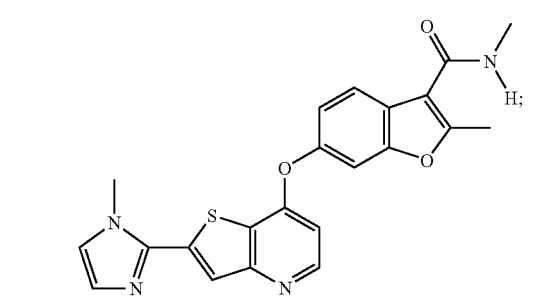
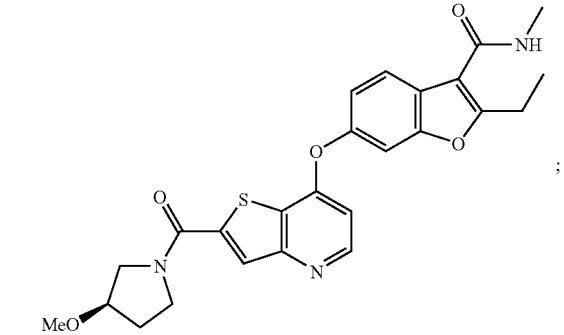

-continued
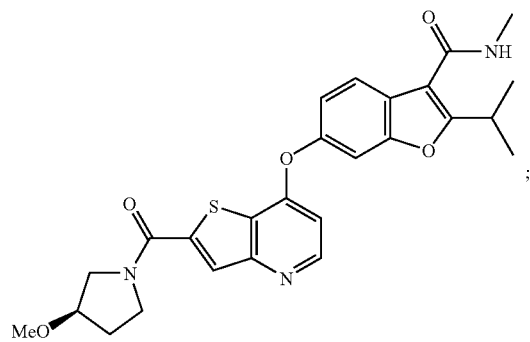
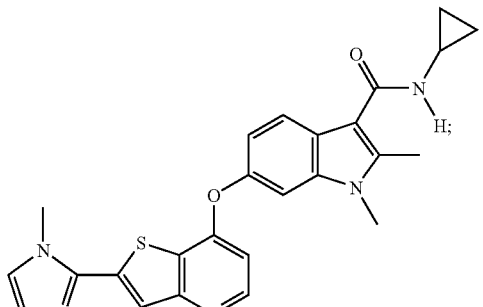
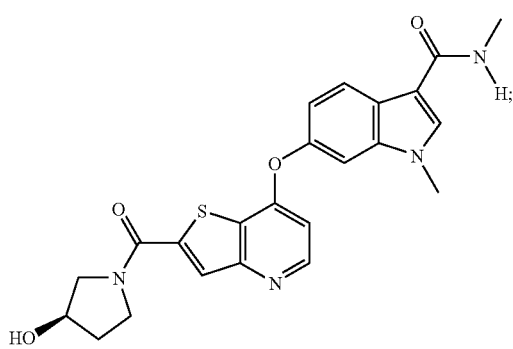
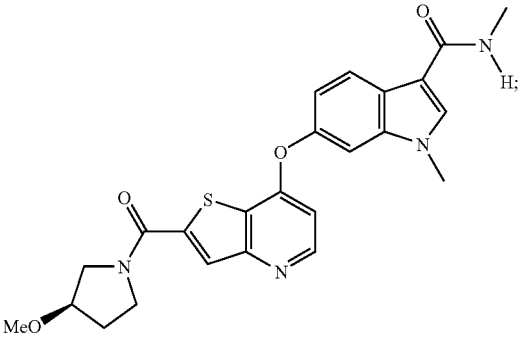
; and
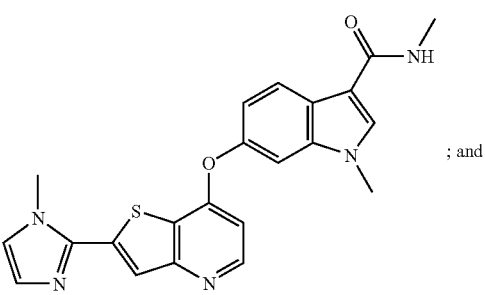
; or
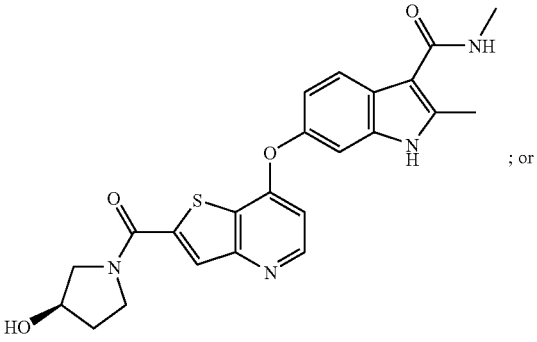

prodrugs or metabolites thereof, or pharmaceutically acceptable salts or solvates of said compounds, said prodrugs, and said metabolites.

Patients that can be treated with the compounds of formula I, and prodrugs thereof, pharmaceutically acceptable salts or solvates of said compounds and said prodrugs, according to the methods of this invention include, for example, patients that have been diagnosed as having psoriasis, BPH, lung cancer, eye cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to pharmaceutical compositions containing and methods for treating abnormal cell growth through administering prodrugs of compounds of the formula I. Compounds of formula I having free amino, amido, hydroxy or carboxylic groups that can be converted into prodrugs.

The invention also relates to a pharmaceutical composition for the treatment of a hyperproliferative disorder in a mammal which comprises a therapeutically effective amount of a compound of formula I, or prodrugs thereof, pharmaceutically acceptable salts or solvates of said compounds and said prodrugs, and a pharmaceutically acceptable carrier. In one embodiment, said pharmaceutical composition is for the treatment of cancer such as brain, lung, ophthalmic, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula I, or prodrugs thereof, pharmaceutically acceptable salts or solvates of said compounds and said prodrugs, and a pharmaceutically acceptable carrier.

The invention also relates to a pharmaceutical composition for the prevention of blastocyte implantation in a mammal which comprises a therapeutically effective amount of a compound of formula I, or prodrugs thereof, pharmaceutically acceptable salts or solvates of said compounds and said prodrugs, and a pharmaceutically acceptable carrier.

The invention also relates to a pharmaceutical composition for treating a disease related to vasculogenesis or angiogenesis in a mammal which comprises a therapeutically effective amount of a compound of formula I, or prodrugs thereof, pharmaceutically acceptable salts or solvates of said compounds and said prodrugs, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula I, or prodrugs thereof, pharmaceutically acceptable salts or solvates of said compounds and said prodrugs. In one embodiment, said method relates to the treatment of cancer such as brain, ophthalmic, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula I, or prodrugs thereof, pharmaceutically acceptable salts or solvates of said compounds and said prodrugs, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The treatment of a hyperproliferative disorder in a mammal which comprises administering to said mammal a therapeutically effective amount of a VEGF receptor tyrosine kinase inhibitor may lead to a sustained increase in blood pressure. The compounds of the present invention may be used in conjunction with an anti-hypertensive, such as NORVASC or PROCARDIA XL, commercially available from Pfizer, for use in the treatment of a hyperproliferative disorder in a mammal.

This invention also relates to a pharmaceutical composition for treating a disease related to vasculogenesis or angiogenesis in a mammal comprising a therapeutically effective amount of a compound, prodrug, metabolite, salt or solvate of claim 1, a therapeutically effective amount of a compound, prodrug, metabolite, salt or solvate of an anti-hypertensive agent, and a pharmaceutically acceptable carrier.

This invention also relates to a pharmaceutical composition for inhibiting abnormal cell growth in a mammal, including a human, comprising an amount of a compound of the formula I as defined above, or prodrug thereof, pharmaceutically acceptable salt or solvate of said compound and said prodrug, that is effective in inhibiting farnesyl protein transferase, and a pharmaceutically acceptable carrier.

This invention also relates to a pharmaceutical composition for inhibiting abnormal cell growth in a mammal which comprises an amount of a compound of formula I, or prodrug thereof, pharmaceutically acceptable salt or solvate of said compound and said prodrug, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of a compound of formula I, or prodrug thereof, pharmaceutically acceptable salt or solvate of said compound and said prodrug, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula I can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula I or prodrug thereof, pharmaceutically acceptable salt or solvate of said compound and said prodrug, which amount is effective in sensitizing abnormal cells to treatment with radiation. The amount of the compound, salt, solvate or prodrug in this method can be determined according to the means for ascertaining effective amounts of such compounds described herein.

This invention also relates to a method of and to a pharmaceutical composition for inhibiting abnormal cell growth in a mammal which comprises an amount of a compound of formula I, or prodrug thereof, pharmaceutically acceptable salt or solvate of said compound and said prodrug, or an isotopically-labelled derivative thereof, and an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are Prinomastat, RO 32-3555, RS 13-0830, and the compounds recited in the following list:
3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide;
4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide;
(R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide;
3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;
and pharmaceutically acceptable salts and solvates of said compounds. Other anti-angiogenesis agents, including other COX-II inhibitors and other MMP inhibitors, can also be used in the present invention.

This invention further releates to a method for treating a disease related to vasculogenesis or angiogenesis in a mammal comprising administering to said mammal a therapeutically effective amount of a compound, prodrug, metabolite, salt or solvate of claim 1 in conjunction with a therapeutically effective amount of an anti-hypertensive agent.

A compound of formula I, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2, receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compounds of the present invention.

The compounds of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) that is incorporated by reference in its entirety, however other CTLA4 antibodies can be used in the present invention.

The subject invention also includes isotopically-labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I, l, III, or IV of this invention and prodrugs thereof can generally be prepared by carrying out the procedures disclosed in the Schemes and/or in the Examples below, by substituting a readily available isotopically labelled reagent for a non-isotopically labelled reagent. The compounds of formula I and their pharmaceutically acceptable salts and solvates can each independently also be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals having straight, cyclic or branched moieties. Said "alkyl" group may include an optional carbon-carbon double or triple bond where said alkyl group comprises at least two carbon atoms. It is understood that for cyclic moieties at least three carbon atoms are required in said alkyl group.

The term "alkoxy", as used herein, unless otherwise indicated, means O-alkyl groups wherein "alkyl" is as defined above.

The term "aryl", as used herein, unless otherwise indicated, means an organic radical derived from an aromatic hydrocarbon by removal of one hydrogen, such as phenyl or naphthyl.

The term "hetero cyclic group", as used herein, includes aromatic and non-aromatic heterocyclic groups. Unless otherwise indicated, preferred heterocyclic groups include groups having from 3 to 13 ring atoms, more preferably from 5 to 10 ring atoms, and still more preferably from 5 to 6 ring atoms. In addition, preferred heterocyclic groups include groups containing one to four heteroatoms each selected from O, S and N. The heterocyclic groups include benzo-fused ring systems and ring systems substituted with one or two oxo (=O) moieties such as pyrrolidin-2-one. An example of a 5 membered heterocyclic group is thiazolyl, an example of a 10 memembered heterocyclic group is quinolinyl, and an example of a 13 membered heterocyclic group is a carbazole group. Examples of non-aromatic heterocyclic groups include pyrrolidinyl, piperidino, morpholino, thiomorpholino and piperazinyl. Examples of aromatic heterocyclic groups include pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl, benzofuranyl, and benzo[1,3]dioxolyl.

The phrase "pharmaceutically acceptable salt(s)", as used herein, unless otherwise indicated, means salts of acidic or basic groups which may be present in the compounds or prodrugs of formula I. The compounds and prodrugs of formula I that are basic in nature are capable of forming a wide variety of salts with various inorganic and organic acids. The acids that may be used to prepare pharmaceutically acceptable acid addition salts of such basic compounds and prodrugs of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds and prodrugs of the formulas I that are acidic in nature, are capable of forming base salts with various pharmacologically acceptable cations. Examples of such salts include the alkali metal or alkaline earth metal salts and particularly, the sodium and potassium salts.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of present invention may in certain instances exist as tautomers. This invention relates to the use of all such tautomers and mixtures thereof.

The term "prodrug", as used herein, unless otherwise indicated, means compounds that are drug precursors, which following administration, release the drug in vivo via some chemical or physiological process (e.g., a prodrug on being brought to the physiological pH is converted to the desired drug form).

Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

It will be appreciated that any solvate (e.g. hydrate) form of compounds of formula I and prodrugs thereof can be used for the purpose of the present invention.

The terms "comprising" and "including" are used herein in their open, non-limiting sense.

The term "alkyl" as used herein refers to straight- and branched-chain alkyl groups having from one to twelve carbon atoms, preferably from 1 to 6 carbons, and more preferably from 1 to 3 carbons. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like.

The term "heteroalkyl" as used herein refers to straight- and branched-chain alkyl groups containing one or more heteroatoms selected from S, O, and N.

The term "alkenyl" refers to straight- and branched-chain alkenyl groups having from two to twelve carbon atoms, preferably from 2 to 6 carbons, and more preferably from 2 to 4 carbons. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from two to twelve carbon atoms, preferably from 2 to 6 carbons, and more preferably from 2 to 4 carbons. Illustrative alkynyl groups include prop-2-ynyl, but-2-ynyl, but-3-ynyl, 2-methylbut-2-ynyl, hex-2-ynyl, and the like.

The term "aryl" (Ar) refers to monocyclic and polycyclic aromatic ring structures containing only carbon and hydrogen. Preferred aryl groups have from 4 to 20 ring atoms, and more preferably from 6 to 14 ring atoms. Illustrative examples of aryl groups include the following moieties:

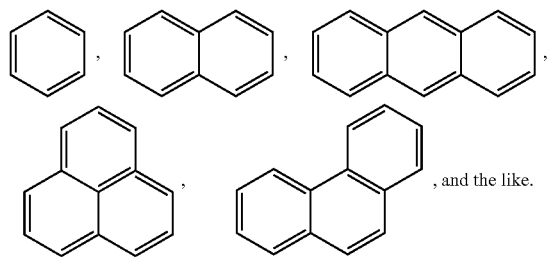

, and the like.

The term "heteroaryl" (heteroAr) refers to an aryl group that includes one or more ring heteroatoms selected from nitrogen, oxygen and sulfur. The polycyclic heteroaryl group may be fused or non-fused. Illustrative examples of aryl groups include the following moieties:

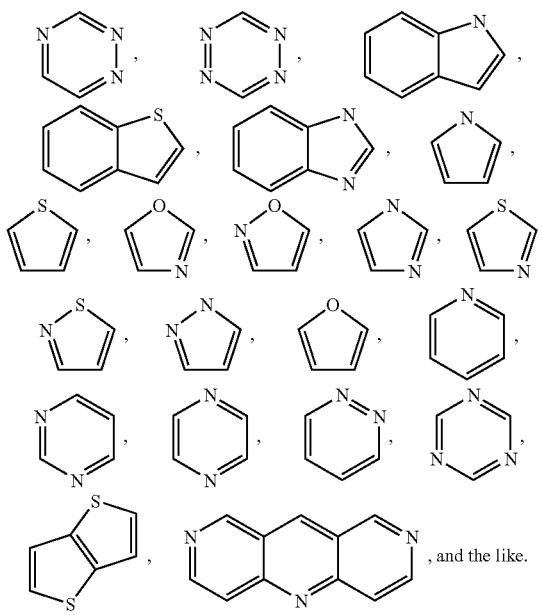

, and the like.

The term "cycloalkyl" refers to a monocyclic or polycyclic radical which contain only carbon and hydrogen, and may be saturated, partially unsaturated, or fully unsaturated. Preferred cycloalkyl groups include groups having from three to twelve ring atoms, more preferably from 5 to 10 ring atoms, and still more preferably from 5 to 6 ring atoms. Illustrative examples of cycloalkyl groups include the following moieties:

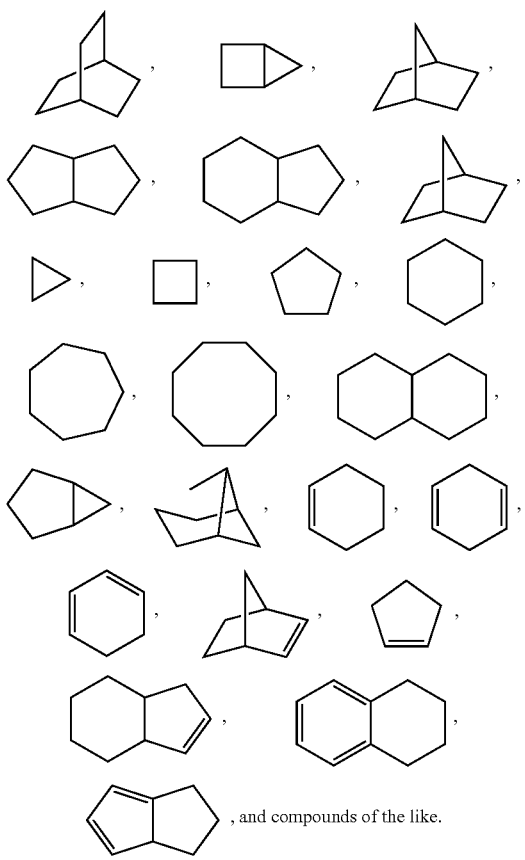

, and compounds of the like.

A "heterocycloalkyl" group refers to a cycloalkyl group that includes at least one heteroatom selected from nitrogen, oxygen and sulfur. The radicals may be fused with an aryl or heteroaryl. Illustrative examples of heterocycloalkyl groups include

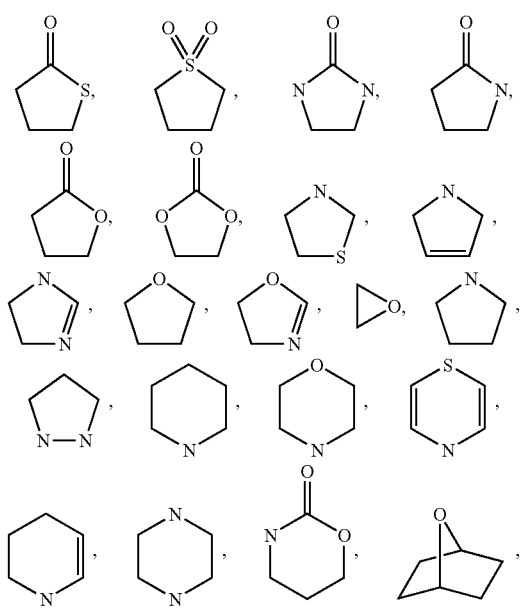

-continued

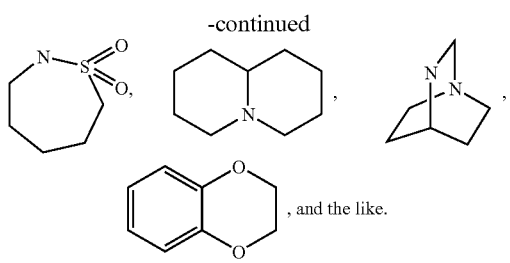

, and the like.

The term "heterocyclic" comprises both heterocycloalkyl and heteroaryl groups.

The term "alkoxy" refers to the radical —O—R where R is an alkyl as defined above. Examples of alkoxy groups include methoxy, ethoxy, propoxy, and the like.

The term "halogen" represents chlorine, fluorine, bromine or iodine. The term "halo" represents chloro, fluoro, bromo or iodo.

The term "alcohol" refers to the radical —R—OH where R is alkyl, alkenyl, alkynyl, Ar, heteroaryl, heterocycloalkyl, or cycloalkyl as defined above. Examples of alcohols include methanol, ethanol, propanol, phenol and the like.

The term "acyl" represents —C(O)R, —C(O)OR, —OC(O)R or —OC(O)OR where R is alkyl, alkenyl, alkynyl, Ar, heteroaryl, heterocycloalkyl, or cycloalkyl as defined as above.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl as defined above.

The term "substituted" as used herein means that the group in question, e.g., alkyl group, etc., may bear one or more substituents.

The alkyl, cycloalkyl, aryl, heterocycloalkyl and heteroaryl groups and the substituents containing these groups, as defined hereinabove, may be optionally substituted by at least one other substituent. The term "optionally substituted" is intended to expressly indicate that the specified group is unsubstituted or substituted by one or more substituents as defined herein. Various groups may be unsubstituted or substituted (i.e., they are optionally substituted) as indicated.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Some of the inventive compounds may exist in various stereoisomeric or tautomeric forms. The present invention encompasses all such cell proliferation-inhibiting compounds, including active compounds in the form of single pure enantiomers (i.e., essentially free of other stereoisomers), racemates, mixtures of enantiomers and/or diastereomers, and/or tautomers. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure.

Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulae are intended to cover solvated as well as unsolvated forms of the identified structures. For example, Formula I includes compounds of the indicated structure in both hydrated and non-hydrated forms. Additional examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

The term "pharmaceutically acceptable" means pharmacologically acceptable and substantially non-toxic to the subject being administered the agent.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs, Drug Design and Development* (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid, 2-acetoxybenzoic acid or cinnamic acid, a sulfonic acid, such as p-toluenesulfonic acid, methanesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of protein kinases. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of one or more kinases, for example protein kinases such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Agents that potently regulate, modulate, or inhibit cell proliferation are preferred. For certain mechanisms, inhibition of the protein kinase activity associated with CDK complexes, among others, and those which inhibit angiogenesis and/or inflammation are preferred. The present invention is further directed to methods of modulating or inhibiting protein kinase activity, for example in mammalian tissue, by administering an inventive agent. The activity of agents as anti-proliferatives is easily measured by known methods, for example by using whole cell cultures in an MTT assay. The activity of the inventive agents as modulators of protein kinase activity, such as the activity of kinases, may be measured by any of the methods available to those skilled in the art, including in vivo and/or in vitro assays. Examples of suitable assays for activity measurements include those described in International Publication No. WO 99/21845; Parast et al., *Biochemistry*, 37, 16788–16801 (1998); Connell-Crowley and Harpes, *Cell Cycle: Materials and Methods*, (Michele Pagano, ed. Springer, Berlin, Germany)(1995); International Publication No. WO 97/34876; and International Publication No. WO 96/14843. These, properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I or Formula II and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals. Administration of prodrugs is typically dosed at weight levels that are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

Proper formulation is dependent upon the route of administration chosen. For injection, the agents of the invention may be formulated into aqueous solutions, preferably in physiologically compatible buffers such as Hanks's solution, Ringers solution, or physiological saline buffer. For transmucosal administration, penetrants appropriate to the barrier to be permeated are used in the formulation. Such penetrants are generally known in the art.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of agents.

Pharmaceutical preparations that can be used orally include push-fit capsules made of gelatin, as well as soft, sealed capsules made of gelatin and a plasticizer, such as glycerol or sorbitol. The push-fit capsules can contain the agents in admixture with fillers such as lactose, binders such as starches, and/or lubricants such as talc or magnesium stearate, and, optionally, stabilizers. In soft capsules, the agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions take the form of tablets or lozenges formulated in conventional manners.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the agents in water-soluble form. Additionally, suspensions of the agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For administration to the eye, the agent is delivered in a pharmaceutically acceptable ophthalmic vehicle such that the compound is maintained in contact with the ocular surface for a sufficient time period to allow the compound to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

Alternatively, the agents may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the agents may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The agents of the invention may be useful in combination with known anti-cancer treatments such as: DNA interactive agents such as cisplatin or doxorubicin; topoisomerase II inhibitors such as etoposide; topoisomerase I inhibitors such as CPT-11 or topotecan; tubulin interacting agents such as paclitaxel, docetaxel or the epothilones; hormonal agents such as tamoxifen; thymidilate synthase inhibitors such as 5-fluorouracil; and anti-metabolites such as methotrexate. They may be administered together or sequentially, and when administered sequentially, the agents may be administered either prior to or after administration of the known anticancer or cytotoxic agent.

The agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other anti-proliferatives or protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

DETAILED DESCRIPTION OF THE INVENTION

EXAMPLES

In the examples described below, unless otherwise indicated, all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF), N,N-dimethylformamide (DMF), dichloromethane, toluene, and dioxane were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel: crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

In one general synthetic process, compounds of Formula I are prepared according to the following reaction scheme:

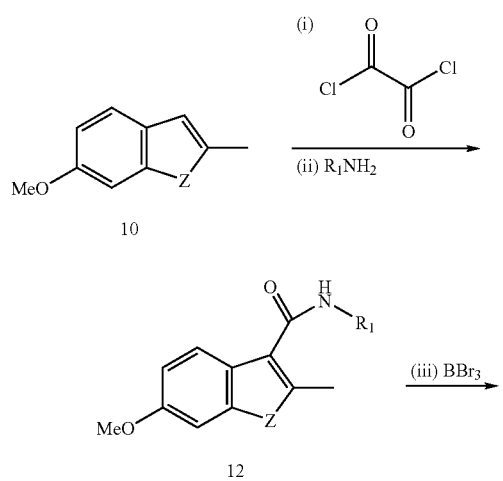

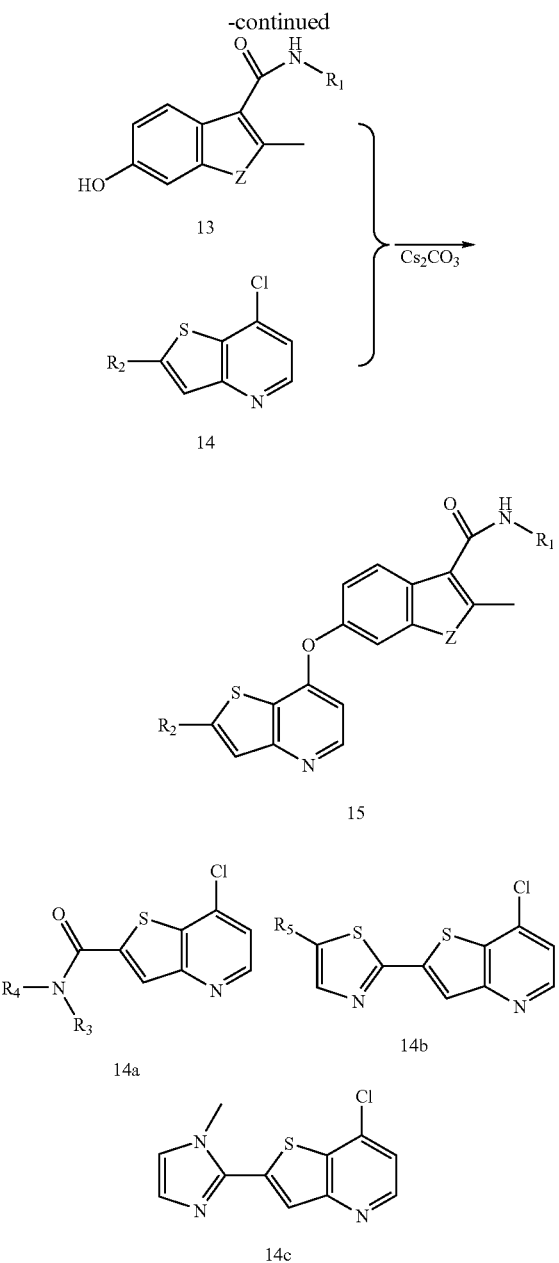

6-Methoxy-2-methylbenzo[b]thiophene or the corresponding benzofuran (compound 10), which are known in the literature, are acylated with oxalyl chloride in the presence of aluminum trichloride. Treatment of the resulting acid chloride with an excess of the appropriate amine, e.g. methylamine, provides the requisite amide derivative of formula 12. Demethylation with a suitable reagent, such as boron tribromide, gives compounds of formula 13. Compounds of formula 13 and 14 are combined by heating them with base, preferably $Cs_2CO_3$, in a solvent such as DMSO, DMF or acetonitrile to form compounds of formula 15. Alternatively to using compounds of formula 14a, 14b and 14c, compounds of formula 14 where $R_2$ is a carboxylic acid may be used in the coupling reaction that generates compounds of formula 15. Amide formation may then be the final step.

Indole analogs may be made in a similar fashion as described above for benzofurans and benzothiophenes.

Example (1a)

6-methoxybenzo[b]thiophene

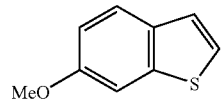

A mixture of 3-methoxybenzenethiol (10 ml, 11.30 g, 80 mmole), $K_2CO_3$ (11.15 g, 80 mmole) and bromoacetaldehyde diethyl acetal (12 ml, 15.72 g, 80 mmole) in acetone (100 ml) was stirred at ambient temperature for 16 hours, then filtered. The filtrate was subsequently concentrated, in vacuo. The residue obtained was partitioned between $H_2O$ (150 ml) and $Et_2O$ (150 ml). The layers were separated and the aqueous phase was extracted with $Et_2O$ (150 ml). The combined organic extracts were washed with 0.5 M KOH (aq), $H_2O$ and brine, then dried over $Na_2SO_4$ and concentrated, in vacuo, to give 20.4 g of an amber oil which was used directly in the subsequent cyclization without any further purification.

Method A: A solution of this crude 1-(2,2-diethoxyethylsulfanyl)-3-methoxybenzene (6.41 g, 25 mmole) in $CH_2Cl_2$ (50 ml) was added, dropwise, to a solution of boron trifluoride etherate (3.4 ml, 3.81 g, 27 mmole) in $CH_2Cl_2$ (500 ml). The resultant solution was stirred at ambient temperature for an additional 30 minutes. Aqueous saturated $NaHCO_3$ (200 ml) was added and the two-phase mixture was stirred for another hour. The layers were separated and the aqueous phase was extracted with $CH_2Cl_2$ (150 ml). The combined organic extracts were dried over $Na_2SO_4$ and concentrated, in vacuo, to give 4.3 g of a red oil which was purified by silica gel chromatography. Elution with hexane: $Et_2O$ (98:2) and evaporation of the appropriate fractions gave 1.62 g (39%) of a colourless oil.

Method B: A solution of the crude 1-(2,2-diethoxyethylsulfanyl)-3-methoxybenzene (8.27 g, 32.3 mmole) in hexane (100 ml) was added, dropwise, to a solution of methanesulfonic acid (1.05 ml, 1.55 g, 16.1 mmole) in hexane (1000 ml) containing 16.5 g of celite (2 wt. eq.). The resultant solution was heated at reflux for one hour. After cooling to room temperature, the reaction was quenched by addition of $Et_3N$ (4.5 ml, 3.26 g, 32.3 mmole). The crude reaction mixture was filtered and the filtrate was concentrated, in vacuo, to give a red oil which was purified by silica gel chromatography. Elution with hexane: $Et_2O$ (98:2) and evaporation of the appropriate fractions gave 3.35 g (63%) of a colorless oil. $^1H$ NMR (DMSO-$d_6$) δ 7.74 (1H, d, J=8.7 Hz), 7.56 (1H, d, J=2.3 Hz), 7.52 (1H, d, J=5.3 Hz), 7.33 (1H, d, J=5.3 Hz), 6.99 (1H, dd, J=2.3, 8.7 Hz), 3.81 (3H, s). Anal. Calcd. for $C_9H_8OS$: C, 65.82; H, 4.91; S, 19.53. Found: C, 66.01; H, 5.00; S, 19.40.

Example 1(b)

6-methoxy-2-methylbenzo[b]thiophene

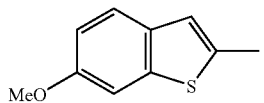

A 2.5 M solution of n-butyllithium in hexanes (20 ml, 50 mmole) was added under argon to a solution of 6-methoxybenzo[b]thiophene 1a (3.68 g, 22.4 mmole) in THF (150 ml) at −75°. After stirring at −75° for a further 30 minutes, the cooling bath was exchanged and the reaction warmed to −10° C. prior to addition of $CH_3I$ (4.2 ml, 9.58 g, 67 mmole). The resultant mixture was stirred at 0° C. for an additional 30 minutes, then allowed to gradually warm to room temperature before diluting with saturated $NaHCO_3$ (150 ml). The layers were separated and the aqueous phase was extracted with EtOAc (2×100 ml). The combined organic extracts were dried over $Na_2SO_4$ and concentrated, in vacuo, to give 4.2 g of an amber oil which was purified by silica gel chromatography. Elution with hexane: $Et_2O$ (98:2) and evaporation of the appropriate fractions gave 3.639 (91%) of a colourless oil. $^1H$ NMR (DMSO-$d_6$) δ 7.57 (1H, d, J=8.7 Hz), 7.43 (1H, d, J=2.4 Hz), 6.99 (1H, s), 6.92 (1H, dd, J=2.4, 8.7 Hz), 3.78 (3H, s), 2.50 (3H, s). Anal. Calcd. for $C_{10}H_{10}OS$: C, 67.38; H, 5.66; S, 17.99. Found: C, 67.42; H, 5.74; S, 17.87.

Example 1(c)

6-methoxy-2-methylbenzo[b]thiophene-3-carboxylic acid methylamide

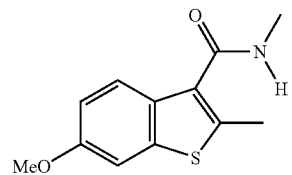

A 2.0 M solution of oxalyl chloride in $CH_2Cl_2$ (10 ml, 20 mmole) was added to a slurry of $AlCl_3$ (2.69 g, 20 mmole) in $CH_2Cl_2$ (20 ml) at 0°. After stirring at 0° for a further 30 minutes, a solution of 6-methoxy-2-methylbenzo[b]thiophene 1b (725 mg, 4.1 mmole) in $CH_2Cl_2$ (40 ml) was added over a 10 minute interval. The cooling bath was removed and the reaction was stirred at ambient temperature for 3 hours prior to addition of crushed ice (50 ml). The layers were separated and the aqueous phase was extracted with $CH_2Cl_2$ (3×50 ml). The combined organic extracts were dried over $Na_2SO_4$ and concentrated, in vacuo, to give 950 mg of an amber resin which was employed without further purification.

A solution of this crude 6-methoxy-2-methylbenzo[b]thiophene-3-carbonyl chloride in THF (50 ml) was combined with a 2.0 M solution of $CH_3NH_2$ in THF (20 ml, 40 mmole). The resultant reaction mixture was stirred at ambient temperature for 3 hours. The solvent was removed by concentration, in vacuo, and the residue obtained was partitioned between $H_2O$ (50 ml) and $CH_2Cl_2$ (50 ml). The layers were separated and the aqueous phase was extracted with $CH_2Cl_2$ (2×30 ml). The combined organic extracts were dried over $Na_2SO_4$ and concentrated, in vacuo, to give 0.8 g of an amber solid which was purified by silica gel chromatography. Elution with $CH_2Cl_2$: EtOAc (80:20) and evaporation of the appropriate fractions gave 693 mg (72%) of an off-white solid. $^1H$ NMR (DMSO-$d_6$) δ 8.15 (1H, q, J=4.6 Hz), 7.62 (1H, d, J=8.9 Hz), 7.47 (1H, d, J=2.4 Hz), 6.97 (1H, dd, J=2.4, 8.9 Hz), 3.79 (3H, s), 2.80 (3H, d, J=4.6 Hz), 2.53 (3H, s). Anal. Calcd. for $C_{12}H_{13}NO_2S$: C, 61.25; H, 5.57; N, 5.95; S, 13.63. Found: C, 60.97; H, 5.56; N, 5.85; S, 13.44.

Example 1(d)

6-hydroxy-2-methylbenzo[b]thiophene-3-carboxylic acid methylamide

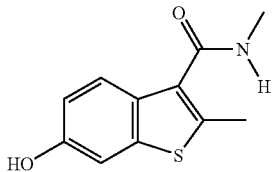

A 1.0 M solution of BBr₃ in CH₂Cl₂ (6 ml, 6 mmole) was added to a solution of 6-methoxy-2-methylbenzo[b]thiophene-3-carboxylic acid methylamide 1c (683 mg, 2.9 mmole) in CH₂Cl₂ (60 ml) at 0°. The reaction was left stirring for 14 hours, gradually warming to ambient temperature, then poured onto crushed ice (~70 g). The layers were separated and the aqueous phase was extracted with EtOAc (2×50 ml). The combined organic extracts were dried over Na₂SO₄ and concentrated, in vacuo, to give 623 mg (97%) of a beige solid which was employed without further purification. ¹H NMR (DMSO-d6) δ 9.56 (1H, s), 8.11 (1H, q, J=4.4 Hz), 7.53 (1H, d, J=8.7 Hz), 7.18 (1H, d, J=2.3 Hz), 6.83 (1H, dd, J=2.3, 8.7 Hz), 2.79 (3H, d, J=4.4 Hz), 2.50 (3H, s).

Example 1(e)

7-chloro-2-(1-methyl-1H-imidazol-2-yl)thieno[3,2-b]pyridine

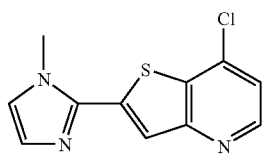

The title compound was prepared by the method described in PCT application WO-99/24440, Example 149; incorporated herein by reference.

Example 1

2-methyl-6-(2-[1-methyl-1H-imidazol-2-yl]thieno[3,2-b]pyridin-7-yloxy)benzo[b]thiophene-3-carboxylic acid methylamide

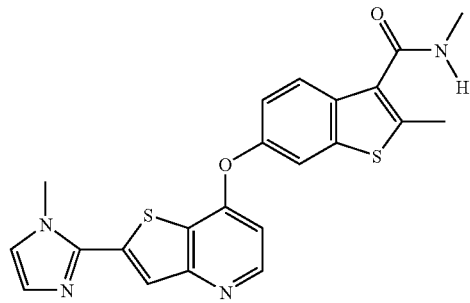

A solution of 7-chloro-2-(1-methyl-1H-imidazol-2-yl)thieno[3,2-b]pyridine 1e (100 mg, 0.4 mmole) and 6-hydroxy-2-methylbenzo[b]thiophene-3-carboxylic acid methylamide 1d (133 mg, 0.6 mmole) in DMSO (10 ml) was purged with argon for minutes at ambient temperature prior to addition of freshly crushed Cs₂CO₃ (651 mg, 2 mmole). The resultant reaction mixture was heated at 110° for 2 hours. After cooling to room temperature, the crude reaction mixture was poured into cold water (60 ml). The precipitate that formed was collected by filtration and purified by silica gel chromatography. Elution with CH₂Cl₂:CH₃OH (95:5) and evaporation of the appropriate fractions gave 69 mg (40%) of an off-white solid. ¹H NMR (DMSO-d6): δ 8.52 (1H, d, J=5.4 Hz), 8.29 (1H, q, J=4.6 Hz), 7.95 (1H, d, J=2.3 Hz), 7.88 (1H, s), 7.85 (1H, d, J=8.8 Hz), 7.40 (1H, d, J=0.8 Hz), 7.32 (1H, dd, J=2.3, 8.8 Hz), 7.02 (1H, d, J=0.8 Hz), 6.70 (1H, d, J=5.4 Hz), 3.98 (3H, s), 2.83 (3H, d, J=4.6 Hz), 2.60 (3H, s). Anal. Calcd. for C₂₂H₁₈N₄O₂S₂.0.3 CH₂Cl₂.0.2 CH₃OH: C, 57.94; H, 4.19; N, 12.01. Found: C, 57.67; H, 4.13; N, 12.04.

Example 2(a)

7-chloro-2-[(S)-2-(methoxymethyl)pyrrolidine-1-carbonyl]thieno[3,2-b]pyridine

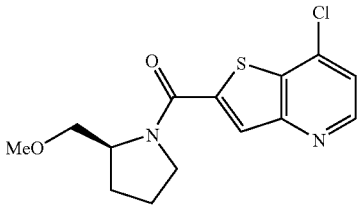

To a mixture of lithium 7-chlorothieno[3,2-b]pyridine-2-carboxylate (6.59 g, 30 mmole) in DMF (100 ml) were added diisopropylethylamine, (6 ml, 4.45 g, 34.4 mmole), benzotriazol-1-yloxytris(pyrrolidino)phosphonium hexafluorophosphate (16.16 g, 31 mmole) and S-(+)-2-(methoxymethyl)pyrrolidine (3.73 g, 32.4 mmole). The resultant reaction mixture was stirred at ambient temperaure for 16 hours. The crude reaction mixture was poured into water (600 ml) and extracted with EtOAc (3×200 ml). The combined organic extracts were washed with water (4×200 ml), dried over Na₂SO₄ and concentrated, in vacuo, to give 8.8 g of an amber oil, which was purified by silica gel chromatography. Elution with Et₂O:EtOAc (67:33) and evaporation of the appropriate fractions gave 6.89 g (74%) of an orange syrup. ¹H NMR (DMSO-d₆): δ 8.62 (1H, d, J=5.0 Hz), 7.88 (1H, s), 7.35 (1H, d, J=5.0 Hz), 4.54–4.47 (1H, m), 3.93–3.75 (2H, m), 3.71–3.55 (2H, m), 3.37 (3H, s), 2.15–1.92 (4H, m). Anal. Calcd. for C₁₄H₁₅N₂O₂SCl: C, 54.10; H, 4.87; N, 9.01; S, 10.32; Cl, 11.41. Found: C, 53.96;

Example 2

6-(2-[(S)-2-(methoxymethyl)pyrrolidine-1-carbonyl] thieno[3,2-b]pyridin-7-yloxy)-2-methylbenzo[b] thiophene-3-carboxylic acid methylamide

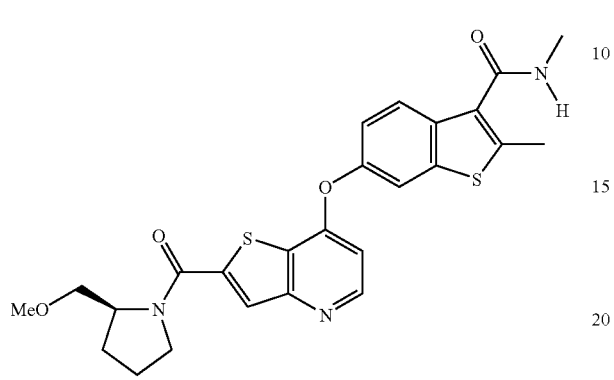

This material was prepared by the reaction of 7-chloro-2-[(S)-2-(methoxymethyl)pyrrolidine-1-carbonyl]thieno[3,2-b]pyridine 2a (153 mg, 0.5 mmole) with 6-hydroxy-2-methylbenzo[b]thiophene-3-carboxylic acid methylamide 1d (164 mg, 0.7 mmole) and Cs$_2$CO$_3$ (868 mg, 2.7 mmole) in a manner as previously described for example 1 to give 178 mg (73%) of a yellow solid. $^1$H NMR (DMSO-d$_6$): δ 8.57 (1H, d, J=5.4 Hz), 8.29 (1H, q, J=4.5 Hz), 8.02 (1H, s), 7.95 (1H, d, J=2.2 Hz), 7.85 (1H, d, J=8.8 Hz), 7.32 (1H, dd, J=2.2, 8.8 Hz), 6.75 (1H, d, J=5.4 Hz), 4.37–4.23 (1H, m), 3.95–3.74 (2H, m), 3.60–3.48 (2H, m), 3.27 (3H, s), 2.83 (3H, d, J=4.5 Hz), 2.60 (3H, s), 2.08–1.81 (4H, m). Anal. Calcd. for C$_{25}$H$_{25}$N$_3$O$_4$S$_2$: C, 60.58; H, 5.08; N, 8.48; S, 12.94. Found: C, 60.55; H, 5.33; N, 8.27; S, 12.68.

Example 3(a)

7-chloro-2-[(S)-2-(hydroxymethyl)pyrrolidine-1-carbonyl]thieno [3,2-b]pyridine

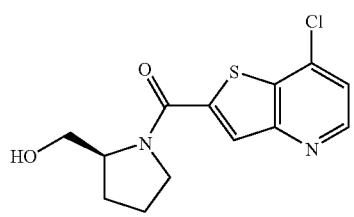

This material was prepared by the coupling of lithium 7-chlorothieno[3,2-b]pyridine-2-carboxylate and S-(+)-2-(hydroxymethyl)pyrrolidine in a manner as previously described for example 2a to give 4.95 g (55%) of an off-white solid. $^1$H NMR (DMSO-d$_6$): δ 8.72 (1H, d, J=5.1 Hz), 8.08 (1H, s), 7.68 (1H, d, J=5.1 Hz), 4.27–4.13 (1H, m), 3.94–3.73 (2H, m), 3.67–3.44 (2H, m), 2.09–1.79 (4H, m).
Anal. Calcd. for C$_{13}$H$_{13}$N$_2$O$_2$SCl: C, 52.61; H, 4.42; N, 9.44; S, 10.80; Cl, 11.95. Found: C, 52.61; H, 4.52; N, 9.62; S, 10.59; Cl, 11.96.

Example 3(b)

7-chloro-2-[(S)-2-([t-butyldimethylsilyloxy]methyl) pyrrolidine-1-carbonyl]thieno[3,2-b]pyridine

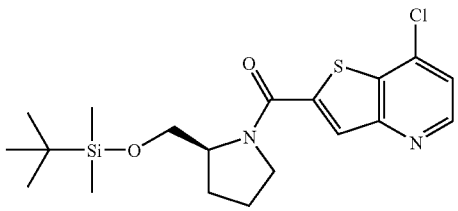

To a stirred solution of 7-chloro-2-[(S)-2-(hydroxymethyl)pyrrolidine-1-carbonyl]thieno[3,2-b]pyridine 3a (4.50 g, 15 mmole) were added t-butyldimethylchlorosilane (3.18 g, 21 mmole) and triethylamine (3.4 ml, 2.47 g, 24 mmole). The resultant reaction mixture was stirred at ambient temperaure for 16 hours. The crude reaction mixture was poured into water (150 ml) and extracted with CH$_2$Cl$_2$ (150 ml). The combined organic extracts were washed with brine (150 ml), dried over Na$_2$SO$_4$ and concentrated, in vacuo, to give 7.8 g of an orange syrup, which was purified by silica gel chromatography. Elution with Et$_2$O:hexane (67:33) and evaporation of the appropriate fractions gave 5.73 g (92%) of an off-white solid. $^1$H NMR (DMSO-d$_6$): δ 8.72 (1H, d, J=5.0 Hz), 8.07 (1H, s), 7.68 (1H, d, J=5.0 Hz), 4.30–4.15 (1H, m), 3.94–3.67 (4H, m), 2.12–1.81 (4H, m), 0.85 (9H, s), 0.03 (3H, s), 0.00 (3H, s). Anal. Calcd. for C$_{19}$H$_{27}$N$_2$O$_2$SClSi: C, 55.52; H, 6.62; N, 6.82; S, 7.80; Cl, 8.63. Found: C, 55.49; H, 6.46; N, 6.92; S, 7.80; Cl, 8.88.

Example 3

6(2-[(S-2-(hydroxymethyl)pyrrolidine-1-carbonyl] thieno[3,2-b]pyridin-7-yloxy)-2-methylbenzo[b] thiophene-3-carboxylic acid methylamide

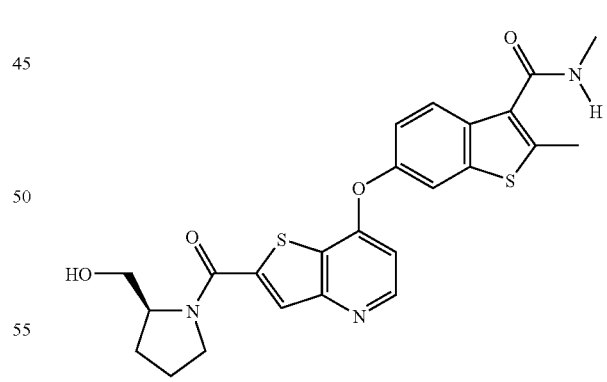

Example 3 was prepared by the reaction of 7-chloro-2-[(S)-2-([t-butyldimethylsilyloxy]methyl)-pyrrolidine-1-carbonyl]thieno[3,2-b]pyridine 3b (812 mg, 2 mmole) with 6-hydroxy-2-methylbenzo[b]thiophene-3-carboxylic acid methylamide 1d (656 mg, 3 mmole) and Cs$_2$CO$_3$ (3.47 g, 11 mmole) in a manner as previously described for example 1 to give 302 mg (32%) of a yellow solid. $^1$H NMR (DMSO-d$_6$): δ 8.57 (1H, d, J=5.3 Hz), 8.29 (1H, q, J=4.5 Hz), 8.01 (1H, s), 7.96 (1H, d, J=2.2 Hz), 7.85 (1H, d, J=8.8 Hz), 7.32

(1H, dd, J=2.2, 8.8 Hz), 6.75 (1H, d, J=5.3 Hz), 4.81 (1H, t, J=5.9 Hz), 4.24–4.12 (1H, m), 3.92–374 (2H, m), 3.63–3.44 (2H, m), 2.83 (3H, d, J=4.5 Hz), 2.60 (3H, s), 2.08–1.81 (4H, m).

Anal. Calcd. for $C_{24}H_{23}N_3O_4S_2 \cdot 0.4\ CH_2Cl_2$: C, 56.84; H, 4.65; N, 8.15; S, 12.44. Found: C, 56.81; H, 4.78; N, 7.99; S, 12.49.

Example 4(a)

7-chloro-2-[(R)-3-hydroxypyrrolidine-1-carbonyl]thieno[3,2-b]pyridine

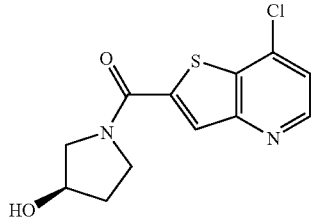

This material was prepared by the coupling of lithium 7-chlorothieno[3,2-b]pyridine-2-carboxylate and (R)-3-hydroxypyrrolidine in a manner as previously described for example 2a to give 3.06 g (36%) of an off-white solid. $^1$H NMR (DMSO-$d_6$): δ 8.73 (1H, d, J=5.1 Hz), 8.15, 8.09 (1H, s), 7.69 (1H, d, J=5.1 Hz), 5.10–5.06 (1H, m), 4.43–4.29 (1H, m), 4.05–3.89 (2H, m), 3.72–3.43 (2H, m), 2.08–1.79 (2H, m).

Example 4(b)

7-chloro-2-[(R)-3-methoxypyrrolidine-1-carbonyl]thieno[3,2-b]pyridine

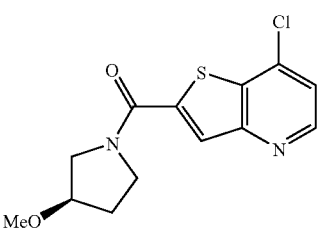

A solution of 7-chloro-2-[(R)-3-hydroxypyrrolidine-1-carbonyl]thieno[3,2-b]pyridine 4a (1.86 g, 6.6 mmole) in THF (150 ml) was cooled to −10° prior to addition of NaH (920 mg, 23 mmole as a 60% by wt. mineral oil dispersion). The resultant mixture was stirred at 0° for 40 minutes. Iodomethane (4 ml, 9.12 g, 64 mmole) was then added to the reaction which was stirred for another 3 hours, gradually warming to room temperature. The crude reaction mixture was quenched with saturated NaHCO3 (150 ml), then extracted with EtOAc (2×100 ml). The combined organic extracts were dried over $Na_2SO_4$ and concentrated, in vacuo, to give 2.4 g of an amber paste, which was purified by silica gel chromatography. Elution with $CH_2Cl_2$: $CH_3OH$ (98:2) and evaporation of the appropriate fractions gave 1.64 g (84%) of a yellow solid. $^1$H NMR (DMSO-$d_6$): δ 8.73 (1H, d, J=5.1 Hz), 8.15 (1H, s), 7.69 (1H, d, J=5.1 Hz), 4.11–3.83 (3H, m), 3.69–3.47 (2H, m), 3.27, 3.24 (3H, s), 2.18–1.93 (2H, m). Anal. Calcd. for $C_{13}H_{23}N_2O_2SCl$: C, 52.61; H, 4.42; N, 9.44; S, 10.80; Cl, 11.95. Found: C, 52.76; H, 4.47; N, 9.38; S, 10.84; Cl, 12.01.

Example 4

6-(2-[(R)-3-methoxypyrrolidine-1-carbonyl]thieno[3,2-b]pyridin-7-yloxy)-2-methylbenzo[b]thiophene-3-carboxylic acid methylamide

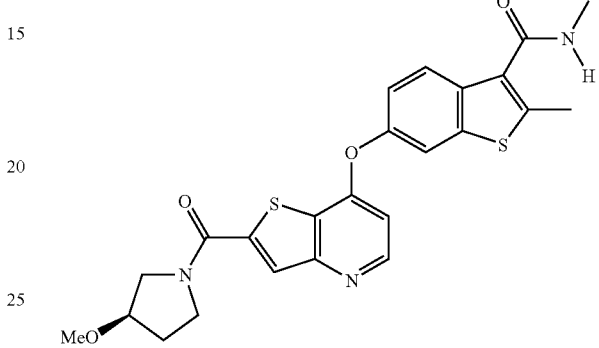

This material was prepared by the reaction of 7-chloro-2-[(R)-3-methoxypyrrolidine-1-carbonyl]thieno[3,2-b]pyridine 4b (267 mg, 0.9 mmole) with 6-hydroxy-2-methylbenzo[b]thiophene-3-carboxylic acid methylamide 1d (299 mg, 1.4 mmole) and $Cs_2CO_3$ (1.47 g, 4.5 mmole) in a manner as previously described for example 1 to give 356 mg (82%) of a yellow solid. $^1$H NMR (DMSO-$d_6$): 8.58 (1H, d, J=5.4 Hz), 8.29 (1H, q, J=4.6 Hz), 8.06 (1H, s), 7.96 (1H, d, J=2.3 Hz), 7.85 (1H, d, J=8.7 Hz), 7.32 (1H, dd, J=2.3, 8.7 Hz), 6.75 (1H, d, J=5.4 Hz), 4.11–3.82 (3H, m), 3.68–3.45 (2H, m), 3.27, 3.24 (3H, s), 2.83 (3H, d, J=4.6 Hz), 2.60 (3H, s), 2.17–1.93 (2H, m). Anal. Calcd. for $C_{24}H_{23}N_3O_4S_2 0.4\ H_2O$: C, 58.97; H, 4.91; N, 8.60; S, 13.12. Found: C, 58.98; H, 4.98; N, 8.40; S, 13.37.

Example 5(a)

3,4-cis-dihydroxy-pyrrolidine-1-carboxylic acid benzyl ester

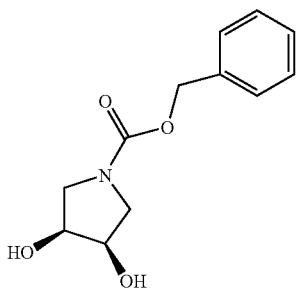

To a solution of benzyl 3-pyrroline-1-carboxylate (15 g, 90%, 66.4 mmole) in THF (100 ml) and water (25 ml) was added osmium tetroxide (10 ml, 2.5 wt. % solution in 2-methyl-2-propanol, 0.8 mmole) and 4-methylmorpholine N-oxide (8.56 g, 73 mmole) as solid. The mixture was stirred at room temperature overnight and concentrated, in vacuo. The residue was re-dissolved in EtOAc (300 ml) and washed with aqueous Na$_2$SO$_3$ (1.5 g in 100 ml water) solution, aqueous NaHCO$_3$ solution and brine. The combined aqueous layer was extracted once with EtOAc (100 ml). The combined organic extracts were dried over Na$_2$SO$_4$ and concentrated in vacuo. The crude was further purified by flash column chromatography eluting with 4–5% MeOH in CH$_2$Cl$_2$ to give 15.26 g (97%) of a white solid. $^1$H NMR (300 MHz, CDCl$_3$) δ 7.34 (5H, m), 5.11 (2H, bs), 4.26 (2H, m), 3.66 (2H, m), 3.41 (2H, m), 1.56 (2H, bs).

Example 5(b)

3,4-cis-dimethoxy-pyrrolidine-1-carboxylic acid benzyl ester

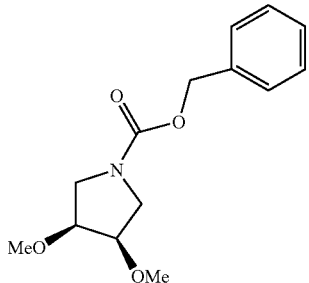

To a stirred solution of 3,4-cis-dihydroxy-pyrrolidine-1-carboxylic acid benzyl ester 5a (15.2 g, 64.3 mmole) in anhydrous THF (130 ml) was added iodomethane (36 g, 257 mmole) at 0°; sodium hydride (6.4 g, 60% in mineral oil, 160 mmole) was then added slowly as at 0°. The mixture was allowed to warm to room temperature and stirred at room temperature for 3 hours. Aqueous 1N HCl (30 ml) was then added to the mixture which was concentrated, in vacuo, to remove THF. The residue was re-dissolved in EtOAc (300 ml) and washed with water and brine. The organic layer was dried over Na$_2$SO$_4$, filtered, and concentrated, in vacuo. The crude was further purified by flash column chromatography eluting with 5–25% EtOAc in CH$_2$Cl$_2$ to give 17 g (99%) of a yellow oil. $^1$H NMR (300 MHz, CDCl$_3$) δ 7.35 (5H, m), 5.12 (2H, m), 3.87 (2H, m), 3.55 (2H, m), 3.42 (6H, bs), 1.58 (2H, s).

Example 5(c)

3,4-cis-Dimethoxy-pyrrolidine

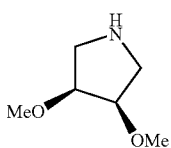

To a stirred solution of 3,4-cis-dimethoxy-pyrrolidine-1-carboxylic acid benzyl ester 5b (16.95 g, 63.9 mmole) in MeOH (150 ml) was added 10% Pd on C (1.3 g). The mixture was stirred under H$_2$ balloon at room temperature for 3 hours and filtered through celite. The filtrate was concentrated, in vacuo, re-dissolved in CH$_2$Cl$_2$ and dried over Na$_2$SO$_4$. The solution was concentrated to give 8.3 g (99%) of a yellow oil. $^1$H NMR (300 MHz, CDCl$_3$) δ 3.80 (2H, m), 3.47 (2H, bs), 3.41 (6H, s), 3.01 (2H, bs).

Example (5d)

7-chloro-2-[meso-3,4-dimethoxypyrrolidine-1-carbonyl]thieno [3,2-b]pyridine

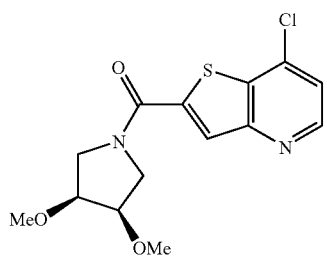

This material was prepared by the coupling of lithium 7-chlorothieno[3,2-b]pyridine-2-carboxylate and 3,4-cis-dimethoxypyrrolidine 5c in a manner as previously described for example 2a to give a pale yellow syrup. $^1$H NMR (CD$_3$OD): δ 8.70 (1H, d, J=5.1 Hz), 8.03 (1H, s), 7.61 (1H, d, J=5.1 Hz), 4.20–4.07 (2H, m), 3.97–3.75 (2H, m), 3.52 (3H, s), 3.48 (3H, s), 3.35–3.29 (2H, m).

Example (5)

6-(2-[meso-3,4-dimethoxypyrrolidine-1-carbonyl]thieno[3,2-b]pyridin-7-yloxy)-2-methylbenzo[b]thiophene-3-carboxylic acid methylamide

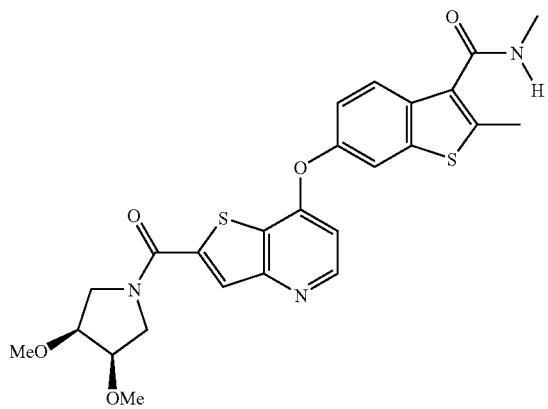

This material was prepared by the reaction of 7-chloro-2-[meso-3,4-dimethoxypyrrolidine-1-carbonyl]thieno[3,2-b]pyridine 5d (164 mg, 0.5 mmole) with 6-hydroxy-2-methylbenzo[b]thiophene-3-carboxylic acid methylamide 1d (164 mg, 0.7 mmole) and Cs$_2$CO$_3$ (868 mg, 2.7 mmole) in a manner as previously described for example 1 to give 123 mg (48%) of an off-white solid. $^1$H NMR (DMSO-d$_6$): δ8.59 (1H, d, J=5.4 Hz), 8.29 (1H, q J=4.7 Hz), 8.07 (1H, s), 7.96 (1H, d, J=2.3 Hz), 7.85 (1H, d, J=8.8 Hz), 7.32 (1H, dd, J=2.3, 8.8 Hz), 6.76 (1H, d, J=5.4 Hz), 4.12–3.98 (3H, m), 3.83 (1H, dd, J=3.6, 9.1 Hz), 3.66 (1H, dd, J=4.8, 12.9 Hz), 3.51 (1H, dd, J=4.2, 12.9 Hz), 3.36 (6H, s), 2.83 (3H, d, J=4.7 Hz), 2.60 (3H, s). Anal. Calcd. for $C_{25}H_{25}N_3O_5S_2 \cdot 0.6\ H_2O$: C, 57.47; H, 5.06; N, 8.04; S, 12.28. Found: C, 57.35; H, 5.02; N, 7.89; S, 12.37.

Example 6

6-(2-[(R)-3-hydroxypyrrolidine-1-carbonyl]thieno[3,2-b]pyridin-7-yloxy)-2-methylbenzo[b]thiophene-3-carboxylic acid methylamide

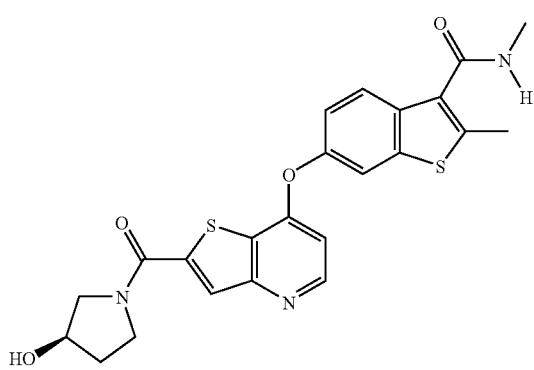

This material was prepared from 6-(2-[(R)-3-methoxypyrrolidine-1-carbonyl]thieno[3,2-b]pyridin-7-yloxy)-2-methylbenzo[b]thiophene-3-carboxylic acid methylamide 4 (172 mg, 0.4 mmole) by treatment with $BBr_3$ in a manner as previously described for example 1d to give 108 mg (65%) of an off-white solid. $^1$H NMR (DMSO-$d_6$): δ 8.58 (1H, d, J=5.3 Hz), 8.29 (1H, q, J=4.4 Hz), 8.06 (1H, s), 7.96 (1H, d, J=1.2 Hz), 7.85 (1H, d, J=8.7 Hz), 7.33 (1H, dd, J=1.2, 8.7 Hz), 6.75 (1H, d, J=5.3 Hz), 4.44–4.27 (1H,m), 4.05–3.88 (1H, m), 3.71–3.42 (3H, m), 2.83 (3H, d, J=4.4 Hz), 2.60 (3H, s), 2.10–1.77 (2H, m). Anal. Calcd. for $C_{23}H_{21}N_3O_4S_2 \cdot 1.0\ CH_3OH$: C, 57.70; H, 5.04; N, 8.41; S, 12.84. Found: C, 57.41; H, 4.98; N, 8.42; S, 12.63.

Example 7

6-(2-[meso-3,4-dihydroxypyrrolidine-1-carbonyl]thieno[3,2-b]pyridin-7-yloxy)-2-methylbenzo[b]thiophene-3-carboxylic acid methylamide

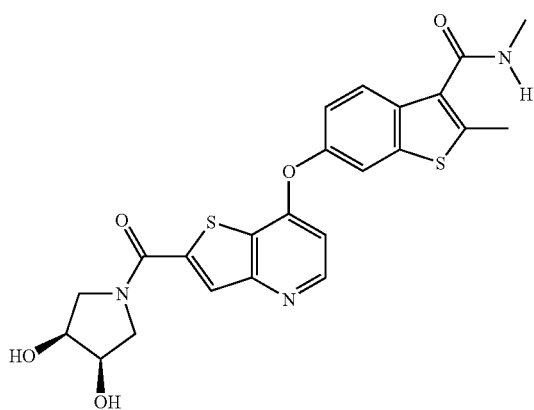

Example 7 was prepared from 6-(2-[meso-3,4-dimethoxypyrrolidine-1-carbonyl]thieno[3,2-b]pyridin-7-yloxy)-2-methylbenzo[b]thiophene-3-carboxylic acid methylamide 5 (74 mg, 0.1 mmole) by treatment with $BBr_3$ in a manner as previously described for example 1d to give 51 mg (73%) of an off-white solid. $^1$H NMR (DMSO-$d_6$): δ 8.58 (1H, d, J=5.4 Hz), 8.29 (1H, q, J=4.6 Hz), 7.99 (1H, s), 7.96 (1H, d, J=2.3 Hz), 7.85 (1H, d, J=8.8 Hz), 7.32 (1H, dd, J=2.3, 8.8 Hz), 6.75 (1H, d, J=5.4 Hz), 5.1-(2H, d, J=5.3 Hz), 4.18–4.07 (2H, m), 4.02 (1H, dd, J=5.6, 10.2 Hz), 3.66 (1H, dd, J=4.9, 10.2 Hz), 3.62 (1H, dd, J=5.1, 12.8 Hz), 3.40 (1H, dd, J=4.4, 12.8 Hz), 2.83 (3H, d, J=4.7 Hz), 2.60 (3H, s). Anal. Calcd. for $C_{25}H_{25}N_3O_5S_2 \cdot 0.5\ NaBr \cdot H_2O$: C, 49.95; H, 4.19; N, 7.60; S, 11.60. Found: C, 49.93; H, 4.15; N, 7.44; S, 11.44.

Example 8a 6-hydroxy-2-methylbenzo[b]thiophene

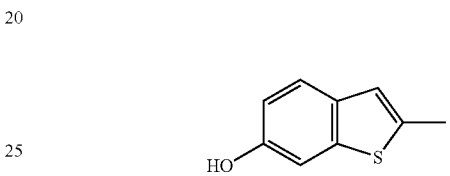

This material was prepared from 6-methoxy-2-methylbenzo[b]thiophene 1b (2.92 g, 16.4 mmole) by treatment with $BBr_3$ in a manner as previously described for example 1d to give 2.51 g (93%) of a white solid. $^1$H NMR (DMSO-$d_6$) δ 9.43 (1H, s), 7.47 (1H, d, J=8.5 Hz), 7.14 (1H, d, J=2.2 Hz), 6.92 (1H, s), 6.78 (1H, dd, J=2.2, 8.5 Hz), 2.46 (3H, s). Anal. Calcd. for $C_9H_8OS$: C, 65.82; H, 4.91; S, 19.53. Found: C, 65.96; H, 5.11; S, 19.69.

Example 8(b)

6-acetoxy-2-methylbenzo[b]thiophene

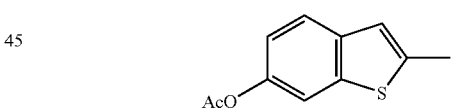

Acetyl chloride (1.5 ml, 1.66 g, 21 mmole) and $Et_3N$ (3 ml, 2.18 g, 21.5 mmole) were added, sequentially, to a solution of 6-hydroxy-2-methylbenzo[b]thiophene 8a (2.51 g, 15 mmole) in THF (120 ml) at 0°. The reaction was left stirring for 14 hours, gradually warming to ambient temperature, then diluted with EtOAc (100 ml) and washed with $H_2O$ (100 ml) and brine (100 ml). The combined aqueous layers were extracted with EtOAc (100 ml). The combined organic extracts were subsequently dried over $Na_2SO_4$ and concentrated, in vacuo, to give 3.9 g of a yellow solid which was purified by silica gel chromatography. Elution with hexane: $Et_2O$ (90:10) and evaporation of the appropriate fractions gave 2.93 g (93%) of a white solid. $^1$H NMR (DMSO-$d_6$) δ 7.70 (1H, d, J=8.6 Hz), 7.66 (1H, d, J=2.2 Hz), 7.12 (1H, s), 7.07 (1H, dd, J=2.2, 8.6 Hz), 2.54 (3H, s), 2.27 (3H, s). Anal. Calcd. for $C_{11}H_{10}O_2S$: C, 64.05; H, 4.89; S, 15.55. Found: C, 63.84; H, 4.93; S, 15.57.

Example (8c)

6-hydroxy-2-methylbenzo[b]thiophene-3-carboxylic acid cyclopropylamide

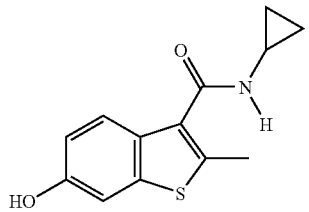

This material was prepared from 6-acetoxy-2-methylbenzo[b]thiophene 8b (413 mg, 2 mmole) by acylation with oxalyl chloride in the presence of $AlCl_3$, followed by treatment with cyclopropylamine in a manner as previously described for example 1c to give 384 mg (78%) of a pale yellow solid. $^1$H NMR (DMSO-$d_6$) δ 9.56 (1H, s), 8.29 (1H, d, J=4.3 Hz), 7.48 (1H, d, J=8.7 Hz), 7.17 (1H, d, J=2.2 Hz), 6.83 (1H, dd, J=2.2, 8.7 Hz), 2.92–2.81 (1H, m), 2.46 (3H, s), 0.74–0.66 (2H, m), 0.58–0.51 (2H, m). Anal. Calcd. for $C_{13}H_{13}NO_2S.0.2\ H_2O$: C, 62.23; H, 5.38; N, 5.60. Found: C, 62.22; H, 5.36; N, 5.60.

Example 8

6-(2-[(S)-2-(hydroxymethyl)pyrrolidine-1-carbonyl]thieno[3,2-b]pyridin-7-yloxy)-2-methylbenzo[b]thiophene-3-carboxylic acid cyclopropylamide

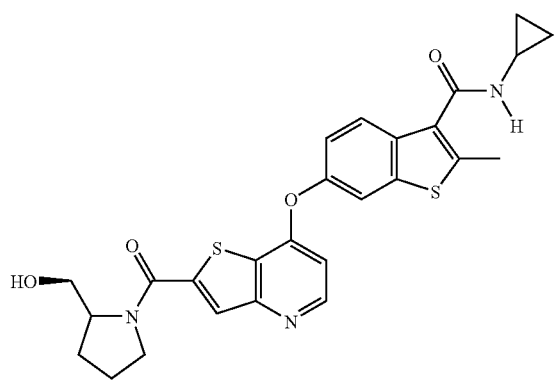

This material was prepared by the reaction of 7-chloro-2-[(S)-2-([t-butyldimethylsilyloxy]methyl)-pyrrolidine-1-carbonyl]thieno[3,2-b]pyridine 3b (206 mg, 0.5 mmole) with 6-hydroxy-2-methylbenzo[b]thiophene-3-carboxylic acid cyclopropylamide 8c (186 mg, 0.75 mmole) and $Cs_2CO_3$ (868 mg, 2.7 mmole) in a manner as previously described for example 1 to give 132 mg (52%) of a yellow solid. $^1$H NMR (DMSO-$d_6$): δ 8.58 (1H, d, J=5.4 Hz), 8.46 (1H, d, J=4.3 Hz), 8.00 (1H, s), 7.95 (1H, d, J=2.3 Hz), 7.80 (1H, d, J=8.8 Hz), 7.32 (1H, dd, J=2.3, 8.8 Hz), 6.75 (1H, d, J=5.4 Hz), 4.90–4.72 (1H, m), 4.24–4.11(1H, m), 3.92–374 (2H, m), 3.64–3.43 (2H, m), 2.95–2.84 (1H, m), 2.57 (3H, s), 2.09–1.80 (4H, m) 0.77–0.67 (2H, m), 0.60–0.52 (2H, m). Anal. Calcd. for $C_{24}H_{23}N_3O_4S_2.0.4\ CH_2Cl_2.0.4\ CH_3OH$: C, 58.06; H, 4.98; N, 7.58. Found: C, 58.03; H, 4.98; N, 7.52.

Example 9(a)

1-benzhydrylazetidin-3-ol

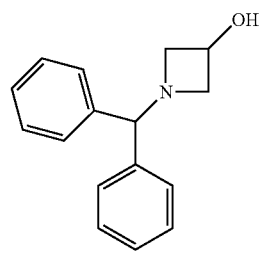

A mixture of (diphenylmethyl)amine (2.2 ml, 12.8 mmole), 2-chloromethyloxirane (2.0 ml, 25.6 mmole) in DMF (25 ml) were heated at 95° C. for 72 hours. The resultant yellow solution was cooled to 0° and treated with 0.5 M HCl (250 ml). The aqueous layer was washed with methyl tert-butyl ether (3×150 ml), and the organic layers were discarded. The aqueous layer was made basic with NaOH and the resultant milky white suspension was extracted with methyl tert-butyl ether (3×150 ml). The combined organic layers were washed with brine, dried over $MgSO_4$ and concentrated, in vacuo, to a clear oil (3.1 g). The oil was triturated with cyclohexane and methyl tert-butyl ether and provided a white solid (2.3 g, 74%): TLC (4% methanol-chloroform with 0.1% ammonium hydroxide) $R_f$ 0.3; $^1$H-NMR (DMSO-$d_6$, 400 MHz) δ 7.40–7.38 (4H, m), 7.27–7.23 (4H, m), 7.17–7.13 (2H, m), 5.28 (1H, d, J=6.3 Hz), 4.34 (1H, s), 4.22–4.18 (1H,m), 3.36–3.34 (2H,m), 2.69–2.66 (2H,m).

Example 9(b)

3-hydroxyazetidine-1-carboxylic acid tert-butyl ester

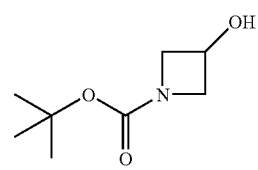

1-Benzhydryl-azetidin-3-ol 9a (4.0 g, 16.7 mmole), EtOAc (150 ml), di-tert-butyl dicarbonate (4.4 g, 20.1 mmole) and 20% Pd(OH)$_2$ on carbon (0.8 g, 20 wt. %) were sequentially added to a round bottom flask. The mixture was degassed and purged with hydrogen. The hydrogenolysis was completed after 24 hours at one atmosphere. The reaction mixture was filtered through celite and concentrated, in vacuo, to a clear oil (7.0 g). The crude product was dissolved in $CH_2Cl_2$ (10 ml) and purified over a silica gel plug (35 g), which was eluted with $CH_2Cl_2$ (150 ml) followed by EtOAc (150 ml). The EtOAc fractions were concentrated, in vacuo, to a clear oil (3.1 g, >100%): TLC (50% ethyl acetate-cyclohexane) $R_f$ 0.4 ($I_2$ stain); $^1$H-NMR (DMSO-d$_6$, 300 MHz) δ 5.62 (1H, d, J=6.4 Hz), 4.39–4.32 (1H, m), 3.97 (2H, t, J=7.8 Hz), 3.57 (2H, t, J=4.4 Hz), 1.35 (9H, s).

Example 9(c)

Azetidin-3-ol trifluoroacetic acid salt

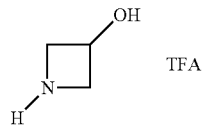

3-Hydroxy-azetidine-1-carboxylic acid tert-butyl ester 9b (0.73 g, 4.2 mmole) was dissolved in CH$_2$Cl$_2$ (2 ml) and trifluoroacetic acid (2 ml). CAUTION: The deprotection generated a rapid evolution of gas. The clear solution was stirred for 75 minutes and the solvent was removed, in vacuo, to a clear oil (1.4 g, >100%): $^1$H-NMR (DMSO-d$_6$, 400 MHz) δ 8.63 (2H, br. s), 4.55–4.48 (1H, m), 4.09–4.02 (2H, m), 3.76–3.68 (2H, m).

Example 9(d)

7-Chloro-2-[3-hydroxyazetidin-1-carbonyl]thieno[3,2-b]pyridine

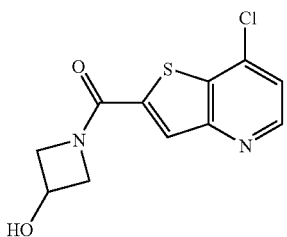

A mixture of the lithium salt of 7-chlorothieno[3,2-b]pyridine-2-carboxylic acid (0.92 g, 4.2 mmole), —(CH$_2$Cl$_2$ (40 ml) and thionyl chloride (0.92 ml, 12.6 mmole) was heated to reflux. The resultant white slurry gave rise to an amber solution upon the addition of DMF (5 ml). After 60 minutes the reaction mixture was concentrated, in vacuo, to a white slurry. The acid chloride was suspended in CH$_2$Cl$_2$ (40 ml) and treated with a solution of azetidin-3-ol trifluoroacetic acid salt 9c (0.78 g, 4.2 mmole) and Et$_3$N (0.58 ml, 4.2 mmole) in DMF (2 ml). After 60 minutes the CH$_2$Cl$_2$ layer was removed, in vacuo, and the resultant beige residue was poured into saturated NaHCO$_3$ (100 ml). The aqueous layer was extracted with EtOAc (3×100 mL). The combined organic layers were washed with brine, dried over MgSO$_4$ and concentrated, in vacuo, to a beige slurry (1.7 g). The slurry was triturated with methyl tert-butyl ether and provided a beige solid (0.23 g, 21%): TLC (5% methanol-dichloromethane) R$_f$ 0.4; $^1$H-NMR (DMSO-d$_6$, 400 MHz) δ 8.74 (1H, d, J=5.1 Hz), 7.99 (1H, s), 7.70 (1H, d, J=4.8 Hz), 5.88 (1H,d, J=6.3 Hz), 4.80–4.78 (1H, m), 4.60–4.56 (1H, m), 4.37–4.34 (2H, m), 3.86–3.84 (1H, m); ESIMS m/z 269 (M+H)$^+$.

Example 9

6-(2-[3-Hydroxyazetidine-1-carbonyl]thieno[3,2-b]pyridin-7-yloxy)-2-methylbenzo[b]thiophene-3-carboxylic acid methylamide

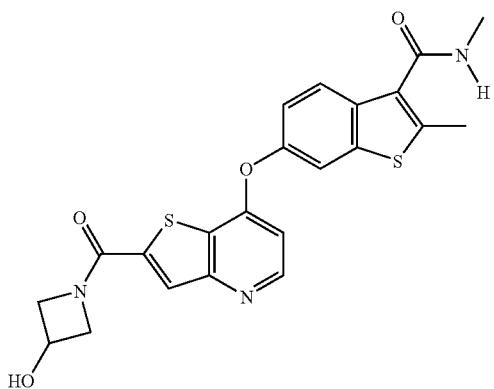

A slurry of 7-chloro-2-[3-hydroxyazetidin-1-carbonyl]thieno[3,2-b]pyridine 9d (120 mg, 0.45 mmole), 6-hydroxy-2-methylbenzo[b]thiophene-3-carboxylic acid methylamide 1d (100 mg, 0.45 mmole) and Cs$_2$CO$_3$ (0.73 g, 2.2 mmole) in acetonitrile (15 ml) was heated to 70°. After 30 hours both starting materials remained, but the reaction was stopped. The reaction mixture was poured into a solution of 50% saturated NaHCO$_3$ (150 ml). The aqueous layer was extracted with 10% isopropanol-chloroform (3×150 ml). The combined organic layers were dried with brine, magnesium sulfate, filtered and concentrated, in vacuo, to a white solid (0.18 g). The crude product was purified by silica gel radial chromatography and the gradient mobile phase was 5–10% CH$_3$OH—CH2Cl$_2$ with 0.1% NH$_4$OH. The product was triturated with ethyl acetate—cyclohexane and isolated as a white solid (40 mg, 20%): TLC (5% CH$_3$OH—CH2Cl$_2$) R$_f$ 0.2; $^1$H-NMR (DMSO-d$_6$, 400 MHz) δ 8.58 (1H, d, J=5.3 Hz), 8.30–8.27 (1H, m), 7.96–7.84 (3H, m), 7.32 (1H, d, J=8.9 Hz), 6.75 (1H, d, J=5.3 Hz), 5.88 (1H, d, J=6.6 Hz), 4.80–4.78 (1H, m), 4.58–4.55 (1H, m), 4.35–4.30 (2H, m), 3.87–3.82 (1H, m), 2.84 (3H, d, J=4.3 Hz), 2.60 (3H, s). ESIMS m/z 454 (M+H)$^+$. mp 237–239° C. Anal. Calcd for C$_{22}$H$_{19}$N$_3$O$_4$S$_2$.0.9 H$_2$O: C, 56.25; H, 4.46; N, 8.95; S, 13.65. Found: C, 56.36; H, 4.22; N, 9.00; S, 13.51.

Example 10(a)

1-Methyl-5-trimethylstannanyl-1H-pyrazole

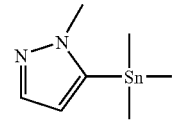

A solution of 1-methyl-1H-pyrazole (1.6 g, 20.0 mmole) in Et$_2$O was treated with n-butyllithium (12.5 ml, 1.6 M in hexanes, 20.0 mmole) over a period of 10 minutes at room temperature. The yellow slurry was stirred for a further 90 minutes. Subsequently, trimethyltin chloride (4.0 g, 20.0 mmole) was added in one portion. The brown slurry was stirred for 30 minutes, filtered and the filtrate was concentrated, in vacuo, to a black oil (5.0 g). The product was isolated by distillation at 1.5 Torr (67–72° C.) as a clear oil (2.1 g, 42%): $^1$H-NMR (DMSO-d$_6$, 400 MHz) δ 7.40 (1H, d, J=1.5 Hz), 6.27 (1H, d, J=1.7 Hz), 3.84 (3H, s), 0.34 (9H, s). ESIMS m/z 243–247 ion cluster (M+H)$^+$.

Example 10(b)

7-Chloro-2-(2-methyl-2H-pyrazol-3-yl)thieno[3,2-b]pyridine

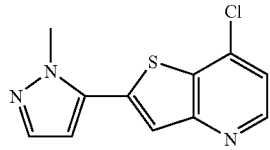

A mixture of 1-methyl-5-trimethylstannanyl-1H-pyrazole 10a (2.1 g, 8.5 mmole), 7-chloro-2-iodo-thieno[3,2-b]pyridine (2.5 g, 8.5 mmole), tetrakis(triphenylphosphine)palladium(0) (0.5 g, 0.4 mmole, 5 mol %) in o-xylene (85 ml was degassed, purged with nitrogen and heated to 120°, which gave an orange solution. After 14 hours the black reaction mixture was diluted with toluene (100 ml) and extracted with 1.2 M HCl (3×60 ml). The combined aqueous layers were washed with toluene (100 ml). The organic layers were discarded and the aqueous layer was treated with NaOH to pH 14. The resultant white solid was collected (1.1 g, 52%): TLC (6% methanol-dichloromethane) R$_f$ 0.8; $^1$H-NMR (DMSO-d$_6$, 400 MHz) δ 8.70 (1H, d, J=5.3 Hz), 8.00 (1H, s), 7.63 (1H,d, J=5.3 Hz), 7.56 (1H, d, J=2.0 Hz), 6.79 (1H, d, J=2.0 Hz), 4.09 (3H, s). ESIMS m/z 250 (M+H)$^+$.

Example 10

2-Methyl-6-(2-[2-methyl-2H-pyrazol-3-yl]thieno[3,2-b]pyridin-7-yloxy)benzo[b]thiophene-3-carboxylic acid methylamide

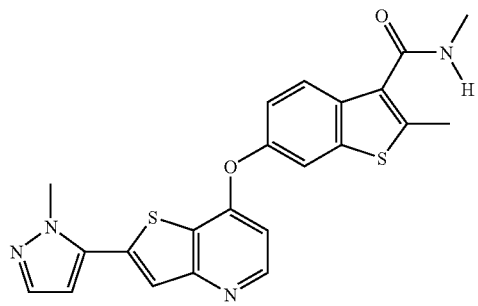

Example 10 was prepared by the reaction of 7-Chloro-2-(2-methyl-2H-pyrazol-3-yl)thieno[3,2-b]pyridine 10b with 6-hydroxy-2-methylbenzo[b]thiophene-3-carboxylic acid methylamide 1d and Cs$_2$CO$_3$ in a manner as previously described for example 1 to give 115 mg of a beige solid (60%): TLC (6% methanol-dichloromethane) R$_f$ 0.6; $^1$H-NMR (DMSO-d$_6$, 400 MHz) δ 8.54 (1H, d, J=5.5 Hz), 8.28 (1H, q, J=4.5 Hz), 7.96 (1H, d, J=2.3 Hz), 7.92 (1H, s), 7.86 (1H, d, J=8.8 Hz), 7.54 (1H, d, J=2.0 Hz), 7.33 (1H, dd, J=2.3, 8.8 Hz), 6.72 (1H, d, J=2.0 Hz), 6.68 (1H, d, J=5.5 Hz), 4.08 (3H, s), 2.84 (1H, d, J=4.5 Hz), 2.60 (3H, s). ESIMS m/z 435 (M+H)$^+$. mp 210–212° C. Anal. Calcd for C$_{22}$H$_{18}$N$_4$O$_2$S$_2$.1.3 H$_2$O: C, 57.70; H, 4.53; N, 12.23; S, 14.00. Found: C, 57.75; H, 4.55; N, 12.21; S, 14.13.

Example 11(a)

Methyl 6-hydroxy-2-methylbenzo[b]thiophene-3-carboxylate

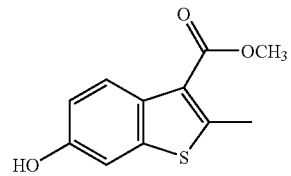

This material was prepared from 6-acetoxy-2-methylbenzo[b]thiophene 8b (500 mg, 2.42 mmole) by acylation with oxalyl chloride in the presence of AlCl$_3$ as previously described for example 1c. A solution of the crude 6-methoxy-2-methylbenzo[b]thiophene-3-carbonyl chloride in MeOH (24 ml) was cooled to 0° C. prior to the addition of K$_2$CO$_3$ (351 mg, 2.66 mmole). The reaction was warmed to ambient temperature and stirred 3 hours. The solvent was removed, in vacuo, and the resulting residue was diluted with CH$_2$Cl$_2$ (75 ml) and H$_2$O (25 ml). The organic layer was separated and the aqueous layer was extracted with CH$_2$Cl$_2$ (50 ml). The combined organics were washed with brine (25 ml), dried (Na$_2$SO$_4$), filtered, and concentrated in vacuo to afford the 468 mg (87%) of a pale brown solid. $^1$H NMR (300 MHz, DMSO-d6) δ 9.68 (1H, s), 8.06 (1H, d, J=8.9 Hz), 7.23 (1H, d, J=2.3 Hz), 6.91 (1H, dd, J=2.3, 8.9 Hz).

Example 11(b)

Methyl 6-[(2-{[(3R)-3-methoxypyrrolidin-1-yl]carbonyl}thieno[3,2-b]pyridin-7-yl)oxy]-2-methylbenzo[b]thiophene-3-carboxylate

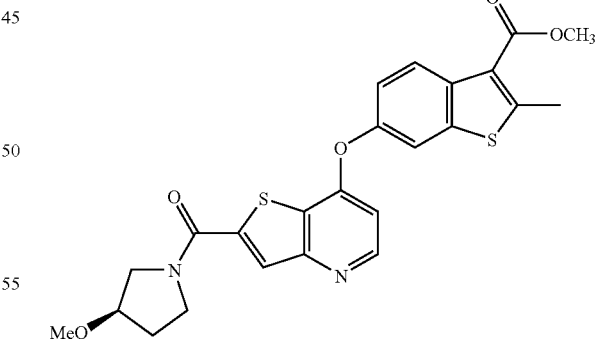

Example 11(b) was prepared by the reaction of 7-chloro-2-[(R)-3-methoxypyrrolidine-1-carbonyl]thieno[3,2-b]pyridine 4b (417 mg, 1.40 mmole) with methyl 6-hydroxy-2-methylbenzo[b]thiophene-3-carboxylate 11a (417 mg, 2.11 mmole) and Cs$_2$CO$_3$ (2.29 g, 7.02 mmole) in a manner as previously described for example 1 to give 290 mg (43%) of a yellow solid. $^1$H NMR (DMSO-d$_6$): δ8.58 (1H, d, J=5.4 Hz), 8.39 (1H, d, J=9.0 Hz), 8.07 (1H, s), 8.02 (1H, d, J=2.3 Hz), 7.42 (1H, dd, J=2.3, 9.0 Hz), 6.79 (1H, d, J=5.4 Hz), 4.08–3.99 (3H, m), 3.87–3.86 (2H, m), 3.91 (3H, s), 3.64–3.59 (2H, m), 3.27, 3.24 (3H, s), 2.82 (3H, s).

Example 11(c)

6-[(2-{[(3R)-3-methoxypyrrolidin-1-yl]carbonyl}thieno[3,2-b]pyridin-7-yl)oxy]-2-methyl-benzo[b]thiophene-3-carboxylic acid

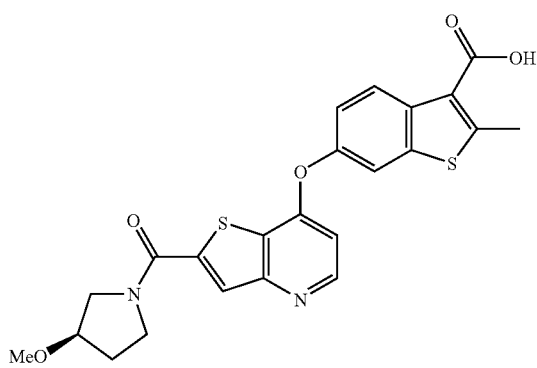

To a solution of methyl 6-[(2-{[(3R)-3-methoxypyrrolidin-1-yl]carbonyl}thieno[3,2-b]pyridin-7-yl)oxy]-2-methylbenzo[b]thiophene-3-carboxylate 11b (258 mg, 0.535 mmole) in a mixture of THF/MeOH/H$_2$O (3:2:1, 6 ml) was added LiOH.H$_2$O (224 mg, 5.35 mmole). The reaction was stirred 24 hours at ambient temperature. The mixture was diluted with H$_2$O (10 ml) and acidified to pH 1 with 1 M HCl. The precipitate was collected by vacuum filtration, rinsed with MeOH, and dried at 50° C. under vacuum to afford 116 mg (45%) of a pale brown solid. $^1$H NMR (DMSO-d$_6$) δ 8.58 (1H, d, J=5.4 Hz), 8.44 (1H, d, J=8.9 Hz), 8.07 (1H, s), 8.00 (1H, d, J=24 Hz), 7.39 (1H, dd, J=2.4, 8.9 Hz), 6.78 (1H, d, J=5.4 Hz), 4.10–3.81 (3H, m), 3.69–3.54 (4H, m), 3.27, 3.24 (3H, s), 2.81 (3H, s).

Example 11

6-[(2-{[(3R)-3-methoxypyrrolidin-1-yl]carbonyl}thieno[3,2-b]pyridin-7-yl)oxy]-2-methyl-benzo[b]thiophene-3-carboxylic acid cyclopropylamide

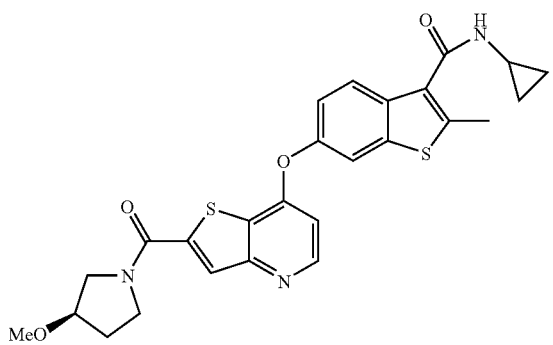

Thionyl chloride (31 μl, 0.427 mmole) was added to a suspension of 6-[(2-{[(3R)-3-methoxypyrrolidin-1-yl]carbonyl}thieno[3,2-b]pyridin-7-yl)oxy]-2-methylbenzo[b]thiophene-3-carboxylic acid 11c (40 mg, 0.085 mmole) in dichloroethane (1 ml). The reaction mixture was heated to reflux for 90 minutes, cooled to room temperature, and concentrated in vacuo. The yellow residue was dissolved in CH$_2$Cl$_2$ (1 ml) and cyclopropylamine (30 μl, 0.427 mmole) was added. The resulting mixture was stirred at ambient temperature for 16 hours, diluted with CH$_2$Cl$_2$ (10 ml), and washed with H$_2$O (5 ml). The aqueous layer was extracted with CH$_2$Cl$_2$ (2×5 ml) and the combined organics were dried (Na$_2$SO$_4$), filtered, and concentrated in vacuo. The crude mixture was purified by silica gel chromatography (5% MeOH/EtOAc) to afford 20 mg (46%) of a pale yellow solid. $^1$H NMR (DMSO-d$_6$, 300 MHz) δ 8.58 (1H, d, J=5.3 Hz), 8.46 (1H, d, J=4.5 Hz), 8.06 (1H, s) 7.96 (1H, d, J=2.3 Hz), 7.81 (1H, J=8.7 Hz), 7.32 (1H, dd, J=2.3, 8.7 Hz), 6.75 (1H, d, J=5.3 Hz), 4.10–3.82 (4H, m), 3.61 (2H, m), 3.27, 3.24 (3H, s), 2.91 (1H, m), 2.72 (1H, m), 2.57 (3H, s), 0.76–0.70 (2H, m), 0.50–0.55 (2H, m.

Anal. Calcd. for C$_{26}$H$_{25}$N$_3$O$_4$S$_2$: C, 61.52; H, 4.96; N, 8.28; S, 12.63. Found: C, 59.30; H, 4.78; N, 7.95; S, 12.23.

Example 12(a)

6-methoxy-2-methylbenzofuran

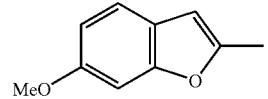

A pressure tube was charged with a stir bar 2-Iodo-5-methoxyphenol (500 mg, 2.0 mmol) (prepared according to Heterocycles 45, (6), 1997, 1137), Cl$_2$Pd(PPh$_3$)$_2$ (70 mg, 0.1 mmol), CuI (19 mg, 0.1 mmol), 1,1,3,3-Tetramethylguanidine (2.5 ml, 20.0 mmol) and DMF (10 ml), then cooled to −78° while propyne gas was condensed. The tube was sealed and allowed to warm to room temperature. After 18 hours, the contents of the tube were poured into sat NaCl solution and extracted with EtOAc (2×). The combined organic layers were washed with brine (3×), dried (MgSO$_4$) and concentrated under reduced pressure. The residue was flash chromatographed on silica gel eluting 3:1 (hexanes/ethyl acetate) to give 239 mg (74%) of an amber liquid. $^1$H NMR (DMSO-d$_6$) δ 7.31 (1H, d, J=8.3 Hz), 6.95 (1H, d, J=2.2 Hz), 6.80 (1H, dd, J=2.2, 8.3 Hz), 6.27 (1H, s), 3.85 (3H, s), 2.40 (3H, s). Anal. Calcd for C$_{10}$H$_{10}$O$_2$.0.05 hexanes: C, 74.30; H, 6.48. Found: C, 74.63; H, 6.48.

Example 12(b)

6-methoxy-2-methylbenzofuran-3-carboxylic acid methylamide

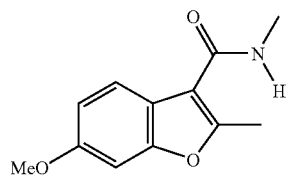

This material was prepared from 6-methoxy-2methylbenzofuran 11a (500 mg, 3.1 mmole) by acylation with oxalyl chloride in the presence of AlCl$_3$, followed by treatment with methylamine in a manner as previously described for example 1c to give 541 mg (80%) of an off-white solid. ¹H NMR (CDCl₃) δ (as a pair of rotamers) 7.48, 7.41 (1H, d, J=8.6 Hz), 6.98, 6.55 (1H, s), 6.89, 6.71 (1H, dd, J=2.3, 8.6 Hz), 6.22, 5.83 (1H, bs), 3.84, 3.82 (3H, s,), 3.03, 2.93 (3H, d, J=4.8 Hz), 2.69, 2.38 (3H, s,). Anal. Calcd for C₁₂H₁₃NO₃: C, 65.74; H, 5.98; N, 6.39. Found: C, 65.86; H, 5.96; N, 6.35.

Example (12c)

6-hydroxy-2-methylbenzofuran-3-carboxylic acid methylamide

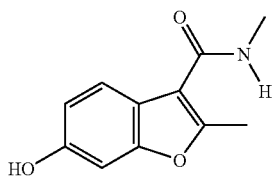

This material was prepared from 6-methoxy2methylbenzo[b]furan-3-carboxylic acid methylamide 11b (516 mg, 2.35 mmol) by treatment with BBr₃ in a manner as previously described for example 1d to give 429 mg (89%) of an off-white solid. ¹H NMR (DMSO-d₆) δ 9.54 (1H, s), 7.80 (1H, d, J=4.5 Hz), 7.50 (1H, d, J=8.3 Hz), 6.88 (1H, s), 6.72 (1H, d, J=8.3 Hz), 2.79 (3H, d, J=4.5 Hz), 2.57 (3H, s). Anal. Calcd for C₁₁H₁₁NO₃.0.1 EtOAc: C, 63.97; H, 5.56; N, 6.54. Found: C, 63.87; H, 5.68; N, 6.45.

Example 12

6-(2-[3-methoxypyrrolidine-1-carbonyl]thieno[3,2-b]pyridin-7-yloxy)-2-methylbenzofuran-3-carboxylic acid methylamide

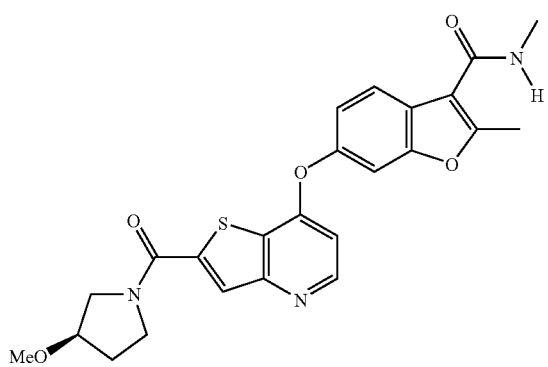

This material was prepared by the reaction of 7-chloro-2-[(R)-3-methoxypyrrolidine-1-carbonyl]thieno[3,2-b]pyridine 4b (144 mg, 0.5 mmole) with 6-hydroxy-2-methylbenzo[b]furan-3-carboxylic acid methylamide 11c (120 mg, 0.6 mmole) and Cs₂CO₃ (794 mg, 2.4 mmole) in a manner as previously described for example 1 to give 134 mg (59%) of an off-white solid. ¹H NMR (DMSO-d₆) δ 8.58 (1H, d, J=5.3 Hz), 8.07 (1H, s), 7.97 (1H, d, J=4.5 Hz), 7.83 (1H, d, J=8.6 Hz), 7.65 (1H, d, J=2.0 Hz), 7.24 (1H, dd, J=2.0, 8.6 Hz), 6.72 (1H, d, J=5.3 Hz), 4.25–3.75 (3H, m), 3.65–3.45 (2H, m), 3.27, 3.24 (3H, s), 2.82 (3H, d, J=4.3 Hz), 2.62 (3H, s), 2.15–1.95 (2H, m). Anal. Calcd for C₂₄H₂₃N₃O₅S.0.5H₂O: C, 60.74; H, 5.10; N, 8.86; S, 6.76. Found: C, 60.89; H, 5.16; N, 8.69; S, 6.58.

Example 13

2-methyl-[2-(1-methyl-1H-imidazol-2-yl)thieno[3,2-b]pyridin-7-yloxy]-benzofuran-3-carboxylic acid methylamide

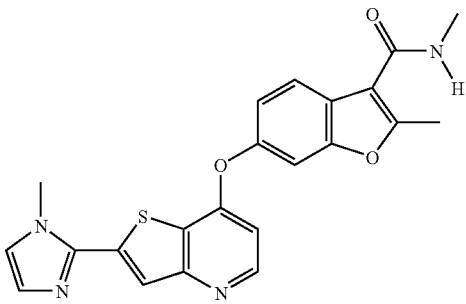

This material was prepared by the reaction of 7-chloro-2-(1-methyl-1H-imidazol-2-yl)thieno[3,2-b]pyridine 1e with 6-hydroxy-2-methylbenzo[b]furan-3-carboxylic acid methylamide 11c and Cs₂CO₃ in a manner as previously described for example 1 to give a 51% yield of a light yellow solid. ¹H NMR (DMSO-d₆) δ 8.50 (1H, d, J=5.6 Hz), 8.01 (1H, d, J=4.5 Hz), 7.88 (1H, s), 7.82 (1H, d, J=8.6 Hz), 7.64 (1H, s), 7.40 (1H, s), 7.25 (1H, d, J=8.3 Hz), 7.03 (1H, s), 6.66 (1H, d, J=5.6 Hz), 3.97 (3H, s), 2.81 (3H, d, J=4.5 Hz), 2.64 (3H,s). Anal. Calcd for C₂₂H₁₈N₄O₃S.0.25H₂O: C, 62.47; H, 4.41; N, 13.25; S, 7.29. Found: C, 62.57; H, 4.37; N, 13.05; S, 7.29.

Example 14(a)

6-methoxy-2-ethylbenzofuran

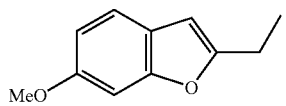

This material was prepared from 2-iodo-5-methoxyphenol (1 g, 4 mmole) and 1-butyne in a manner as previously described for example 12a to give 570 mg (81%) of a brown oil. ¹H NMR (CDCl₃) δ 7.33 (1H, d, J=8.6 Hz), 6.97 (1H, d, J=2.2 Hz), 6.80 (1H, dd, J=2.2, 8.6 Hz), 6.26 (1H, s), 3.83 (3H, s), 3.04 (2H, q, J=7.3 Hz), 1.28 (3H, t, J=7.3 Hz).

Example 14(b)

methoxy-2-ethylbenzofuran-3-carboxylic acid methylamide

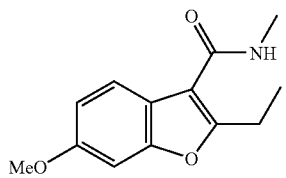

Example 14(b) was prepared from 6-methoxy-2-ethylbenzofuran 14a (522 mg, 2.96 mmole) by acylation with oxalyl chloride in the presence of AlCl₃, followed by treatment with methylamine in a manner as previously described in Example 1c to give 433 mg (63%) of an off-white solid. ¹H NMR (DMSO-d$_6$) δ 7.83 (1H, d, J=4.8 Hz), 7.56 (1H, d, J=8.8 Hz), 7.23 (1H, d, J=2.3 Hz), 6.83 (1H, dd, J=2.3, 8.8 Hz), 3.78 (3H, s), 3.05 (2H, q, J=7.2 Hz), 2.80 (3H, d, J=4.8 Hz), 1.26 (3H, t, J=7.2 Hz). Anal. Calcd for C$_{13}$H$_{15}$NO$_3$: C, 66.93; H, 6.48; N, 6.00. Found: C, 66.96; H, 6.46; N, 5.95.

Example (14c)

6-hydroxy-2-ethylbenzofuran-3-carboxylic acid methylamide

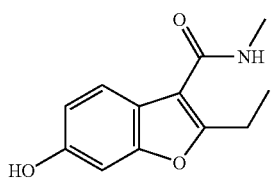

Example 14(c) was prepared from 6-methoxy-2-ethylbenzo[b]furan-3-carboxylic acid methylamide 14b (401 mg, 1.72 mmole) by treatment with BBr$_3$ in a manner as previously described for example 1d to give 318 mg (84%) of an off-white solid. $^1$H NMR (DMSO-d$_6$) δ 9.53 (1H, s), 7.79 (1H, d, J=4.6 Hz), 7.45 (1H, d, J=8.6 Hz), 6.88 (1H, d, J=2.0 Hz), 6.74 (1H, dd, J=2.0, 8.6 Hz), 3.03 (2H, q, J=7.3 Hz), 2.77 (3H, d, J=4.6 Hz), 1.24 (3H, t, J=7.3 Hz). Anal. Calcd for C$_{12}$H$_{13}$NO$_3$: C, 65.74; H, 5.98; N, 6.39. Found: C, 65.61; H, 6.06; N, 6.32.

Example 14

6-(2-[3-methoxypyrrolidine-1-carbonyl]thieno[3,2-b]pyridin-7-yloxy)-2-ethylbenzofuran-3-carboxylic acid methylamide

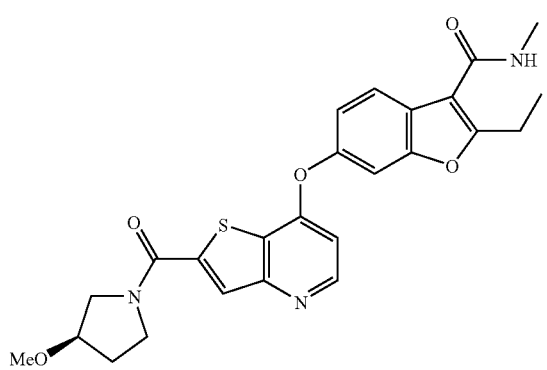

Example 14 was prepared by the reaction of 7-chloro-2-[(R)-3-methoxypyrrolidine-1-carbonyl]thieno[3,2-b]pyridine 4b (135 mg, 0.46 mmole) with 6-hydroxy-2-ethylbenzo[b]furan-3-carboxylic acid methylamide 14c (120 mg, 0.55 mmole) and Cs$_2$CO$_3$ (594 mg, 1.82 mmole) in a manner as previously described for example 1 to give 75 mg (34%) of an off-white solid. $^1$H NMR (DMSO-d$_6$) δ8.57 (1H, d, J=5.4 Hz), 8.07 (1H, s), 8.01 (1H, d, J=4.5 Hz), 7.83 (1H, d, J=8.6 Hz), 7.68 (1H, d, J=2.0 Hz), 7.26 (1H, dd, J=2.0, 8.6 Hz), 6.73 (1H, d, J=5.4 Hz), 4.11–3.82 (3H, m), 3.69–3.43 (2H, m), 3.27, 3.24 (3H, s), 3.05 (2H, q, J=7.5 Hz), 2.82 (3H, d, J=4.5 Hz), 2.18–1.94 (2H, m), 1.27 (3H, t, J=7.5 Hz). Anal. Calcd for C$_{25}$H$_{25}$N$_3$O$_5$S.0.2 CH$_2$Cl$_2$.0.25 hexane: C, 61.90; H, 5.62; N, 8.11; S, 6.19. Found: C, 61.88; H, 5.64; N, 8.03; S, 6.11.

Example 15(a)

6-methoxy-2-(1-methylethyl)benzofuran

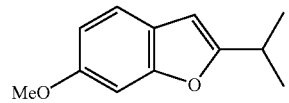

Example 15(a) was prepared from 2-iodo-5-methoxyphenol (896 mg, 3.6 mmole) and 3-methyl-1-butyne in a manner as previously described for example 12a to give 265 mg (38%) of an amber oil. $^1$H NMR (CDCl$_3$) δ 7.33 (1H, d, J=8.6 Hz), 6.97 (1H, d, J=2.2 Hz), 6.80 (1H, dd, J=2.2, 8.6 Hz), 6.26 (1H, s), 3.83 (3H, s), 3.07–3.01 (1H, m), 1.31 (6H, d, J=7.1 Hz).

Example 15(b)

6-methoxy-2-(1-methylethyl)benzofuran-3-carboxylic acid methylamide

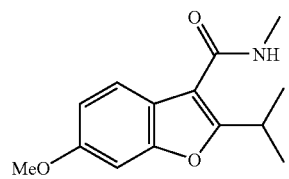

Example 15(b) was prepared from 6-methoxy-2-(1-methylethyl)benzofuran 15a (263 mg, 1.36 mmole) by acylation with oxalyl chloride in the presence of AlCl$_3$, followed by treatment with methylamine in a manner as previously described for example 1c to give 200 mg (60%) of an off-white solid. $^1$H NMR (DMSO-d$_6$) δ7.83 (1H, d, J=4.8 Hz), 7.56 (1H, d, J=8.8 Hz), 7.20 (1H, d, J=2.3 Hz), 6.89 (1H, dd, J=2.3, 8.8 Hz), 3.78 (3H, s), 3.68–3.61 (1H, m), 2.78 (3H, d, J=4.8 Hz), 1.26 (6H, d, J=6.8 Hz).

Example 15(c)

6-hydroxy-2-(1-methylethyl)benzofuran-3-carboxylic acid methylamide

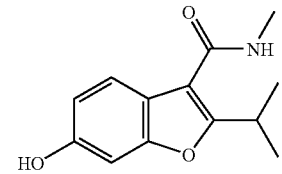

This material was prepared from 6-methoxy-2-(1-methylethyl)benzo[b]furan-3-carboxylic acid methylamide 15b (173 mg, 0.84 mmole) by treatment with BBr$_3$ in a manner as previously described for example 1d to give 157 mg (80%) of a crisp foam. $^1$H NMR (DMSO-d$_6$) δ9.54 (1H, s), 7.76 (1H, d, J=4.6 Hz), 7.45 (1H, d, J=8.6 Hz), 6.88 (1H, d, J=2.0 Hz), 6.74 (1H, dd, J=2.0, 8.6 Hz), 3.68–3.61 (1H, m), 2.75 (3H, d, J=4.6 Hz), 1.24 (6H, d, J=7.1 Hz).

Example 15

6-(2-[3-methoxypyrrolidine-1-carbonyl]thieno[3,2-b]pyridin-7-yloxy)-2-(1-methylethyl)benzofuran-3-carboxylic acid methylamide

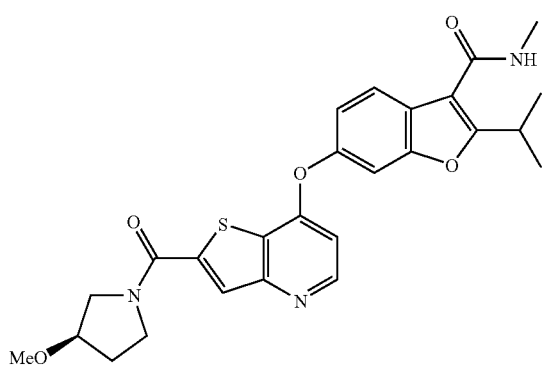

This material was prepared by the reaction of 7-chloro-2-[(R)-3-methoxypyrrolidine-1-carbonyl]thieno[3,2-b]pyridine 4b (122 mg, 0.41 mmole) with 6-hydroxy-2-(1-methylethyl)benzo[b]furan-3-carboxylic acid methylamide 15c (125 mg, 0.53 mmole) and Cs$_2$CO$_3$ (200 mg, 0.61 mmole) in a manner as previously described for example 1 to give 82 mg (40%) of a white solid. $^1$H NMR (DMSO-d$_6$) δ 8.56 (1H, d, J=5.3 Hz), 8.06 (1H, s), 8.01 (1H, d, J=4.6 Hz), 7.79 (1H, d, J=8.6 Hz), 7.68 (1H, d, J=2.2 Hz), 7.25 (1H, dd, J=2.2, 8.6 Hz), 6.73 (1H, d, J=5.3 Hz), 4.15–3.85 (3H, m), 3.70–3.45 (3H, m), 3.27, 3.24 (3H, s), 2.82 (3H, d, J=4.6 Hz), 2.15–1.95 (2H, m), 1.30 (6H, d, J=7.1 Hz). Anal. Calcd for C$_{26}$H$_{27}$N$_3$O$_5$S.0.2H$_2$O/0.2 MTBE: C, 62.99; H, 5.84; N, 8.186; S, 6.23. Found: C, 62.92; H, 5.93; N, 7.97; S, 6.07.

Example 16(a)

6-methoxy-1H-indole-3-carboxylic acid

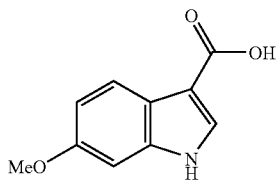

The preparation of the title compound was adapted from work previously published by Swain et al (J. Med. Chem. 1992, 35, 1019–1031). To a stirring solution of 6-methoxy-1H-indole (10 g, 68 mmole) in DMF (100 ml) at 0° C. was added triflouroacetic anhydride (21.4 ml, 150 mmole) dropwise. After the addition, the mixture was heated at 165° for 18 hours. The mixture was removed from heat and added dropwise to ice water (1 L). The resulting precipitate was collected by filtration, washed with water then suspended in 20% aq. NaOH (200 ml). The suspension was heated at 90° until homogeneous (~2 hr). The dark mixture was allowed to cool to RT and was washed with Et$_2$O (200 ml). The aqueous layer was washed with CH$_2$Cl$_2$. A precipitate formed during the extraction which was collected by filtration. The filtrate was divided into layers and the aqueous layer acidified to pH 3 using 6N HCl resulting in the formation of a precipitate. The previously collected solids were added to the suspension and the mixture was stirred for 3 hours. The mixture was acidified to pH 2 using 6N HCl and the solids collected by filtration. The solids were washed with water and dried in air to give 10.08 g (77%) of an off-white solid which was carried on without further purification. $^1$H NMR (DSMO-d$_6$) δ 11.53 (1H, broad s), 7.88 (1H, d, J=8.7 Hz), 7.75 (1H, s), 6.91 (1H, d, J=2.0 Hz), 6.74 (1H, dd, J=2.0, 8.7 Hz), 3.75 (3H, s).

Example 16(b)

6-methoxy-1-methyl-1H-indole-3-carboxylic acid

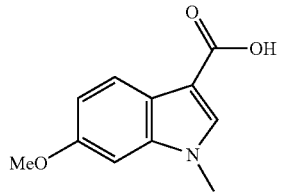

To a stirring solution of 6-methoxy-1H-indole-3-carboxylic acid 16a (8.0 g, 41.2 mmole) in anhydrous DMF (100 ml) at 0° was added NaH (60% dispersion in oil, 4.12 g, 103 mmole) in a single portion. After stirring at 0° C. for 1.3 hour, iodomethane (7.5 ml, 120 mmole) was added via syringe. The resultant mixture was stirred for 18 hours, gradually warming to room temperature, then poured into 0.2N NaOH (1L) and extracted with EtOAc (3× 250 ml). The combined extracts were washed sequentially with 1N NaOH (50 ml), water (3×50 ml), and brine (50 ml) then dried over Na$_2$SO$_4$ and concentrated, in vacuo. The resulting crude 6-methoxy-1-methyl-1H-indole-3-carboxylic acid methyl ester was triturated with hexanes and collected by filtration. This material was suspended in aqueous KOH (3.36 g, 60 mmol in 150 ml) and the resulting suspension heated at reflux for 3.5 hours. The mixture was then poured onto 200 g of ice and washed with CH$_2$Cl$_2$ (2×50 ml). The aqueous layer was acidified with 6N HCl to pH 2 resulting in a white precipitate which was collected by filtration, washed with water and air dried to yield 7.25 g (86%) of the title compound which was carried on without any further purification. $^1$H NMR (DMSO-d$_6$) δ 11.84 (1H, broad s), 7.88 (1H, s), 7.84 (1H, d, J=8.7 Hz), 7.02 (1H, d, J=2.2 Hz), 6.82 (1H, dd, J=2.2, 8.7 Hz, 3.81 (3H, s), 3.79 (3H, s). Anal. Calcd. for C$_{11}$H$_{11}$NO$_3$.0.2H$_2$O: C, 63.27; H, 5.50; N, 6.71. Found: C, 63.36; H, 5.35; N, 6.63.

Example 16(c)

1,2-dimethyl-6-methoxy-1H-indole-3-carboxylic acid

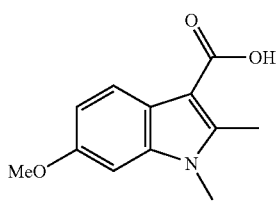

The preparation of the title compound was adapted from work previously published by Buttery et al (*J. Chem. Soc. Perkin Trans.* 1993, 1425–1431). A solution of 6-methoxy-1-methyl-1H-indole-3-carboxylic acid 16b (5.2 g, 25.4 mmole) in anhydrous THF (100 ml) was added dropwise over 30 minutes to a stirring solution of LDA [made from n-BuLi (69 mmole) and diisopropylamine (60 mmole)] in anhydrous THF (50 ml) at −78° C. The resulting mixture was allowed to warm to −10° C. over 30 minutes, then cooled to −78° C. prior to addition of iodomethane (8 ml, 128.5 mmole) via syringe. The resulting amber mixture was allowed to warm to 15° C. over 3 hours, then was washed with 1N NaOH (100 ml). A precipitate formed during the separation that was collected by filtration. The filtrate was separated into layers. The organic layer was washed again with 1N NaOH (50 ml). The solids were suspended in water and the resulting suspension acidified to pH 3 using 0.5 N HCl. The resulting thick suspension was sonicated and stirred for 15 minutes, then the solids were collected by filtration and washed with water. The combined NaOH layers from above were acidified to pH 4 using 6N HCl to yield another batch of solids which was collected by filtration and washed with water. The first batch of solids was suspended in hot $CHCl_3$:MeOH (3:1) and the insoluble material collected by filtration. This isolate was found to be desired product. The filtrate was concentrated to dryness under reduced pressure and the residue triturated twice with warm $CHCl_3$ to yield a second crop of product. The solids obtained from acidification of the basic aqueous layer were triturated three times with warm $CHCl_3$ to yield a third crop of product. The three crops were combined, triturated with MTBE and filtered to give 3.13 g (56%) of a white solid. This material was of suitable purity to be carried on without further purification. $^1$H NMR (DMSO-$d_6$) δ 11.83 (1H, broad s), 7.81 (1H, d, J=8.6 Hz), 7.03 (1H,d, J=2.3 Hz), 6.76 (1H, dd, J=2.3, 8.6 Hz), 3.79 (3H, s), 3.67 (3H, s), 2.67 (3H, s). Anal. calcd for $C_{12}H_{13}NO_3$.0.2$H_2O$: C, 64.68; H, 6.06; N, 6.29. Found: C: 64.89; H, 5.91; N, 6.29. Example 16(d)

6-methoxy-1,2-dimethyl-1H-indole-3-carboxylic acid methylamide

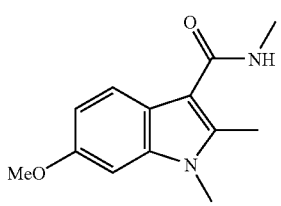

To a stirring solution of the carboxylate 16c (700 mg, 3.2 mmole) in anhydrous $CH_2Cl_2$ (15 ml) at 0° C. was added a drop of DMF, followed by oxalyl chloride (0.55 ml, 6.4 mmole) via syringe. After stirring at CPC for 15 minutes, the ice bath was removed and the mixture was stirred at ambient temperature for 55 minutes. The mixture was diluted with benzene and concentrated to dryness under reduced pressure. The residue was dissolved in $CH_2Cl_2$ (10 ml) and added via syringe to a 2 M solution of methylamine in THF (30 ml). After observing a slight exotherm upon the start of the addition, the mixture was cooled to 0° for the remainder of the addition. The reaction was stirred for a further 16 hours, gradually warming to room temperature, then partitioned between $CH_2Cl_2$ (100 ml) and 1N NaOH (100 ml). The organic layer was washed sequentially with 1N NaOH (50 ml), brine (50 ml), then dried over $Na_2SO_4$ and concentrated, in vacuo. The crude residue was triturated with MTBE and filtered to give 590 mg (79%) of a white solid. $^1$H NMR (DMSO-$d_6$) δ7.60 (1H, d, J=8.6 Hz), 7.39–7.35 (1H, m), 7.00 (1H,d, J=2.3 Hz), 6.72 (1H, dd, J=2.3, 8.6 Hz), 3.79 (3H, s), 3.63 (3H, s), 2.76 (3H, d, J=4.6 Hz), 2.53 (3H, s).

Anal. Calcd. for $C_{13}H_{16}N_2O_2$: C, 67.22; H, 6.54; N, 12.06. Found: C, 67.00; H, 6.95; N, 11.99.

Example 16(e)

6-hydroxy-1,2-dimethyl-1H-indole-3-carboxylic acid methylamide

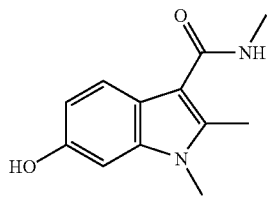

Example 16(e) was prepared from 6-methoxy-1,2-dimethyl-1H-indole-3-carboxylic acid methylamide 16d (560 mg, 2.4 mmole) by treatment with $BBr_3$ in a manner as previously described for example 1d to obtain 380 mg (73%) of white solid. $^1$H NMR (DMSO-$d_6$) δ 9.05 (1H, s), 7.50 (1H, d, J=8.59 Hz), 7.35–7.28 (1H, m), 6.73 (1H,d, J=1.77 Hz), 6.60 (1H, dd, J=8.5, 2.27 Hz), 3.54 (3H, s), 2.75 (3H, d, J=4.55 Hz), 2.53 (3H, s). Anal. Calcd. for $C_{12}H_{14}N_2O_2$.0.3$H_2O$: C, 64.44; H, 6.58; N, 12.53. Found: C, 64.55; H, 6.49; N, 12.35.

Example 16

6-[2-(2-Hydroxymethyl-pyrrolidine-1-carbonyl)-thieno[3,2-b]pyridin-7-yloxy]-1,2-dimethyl-1H-indole-3-carboxylic acid methylamide

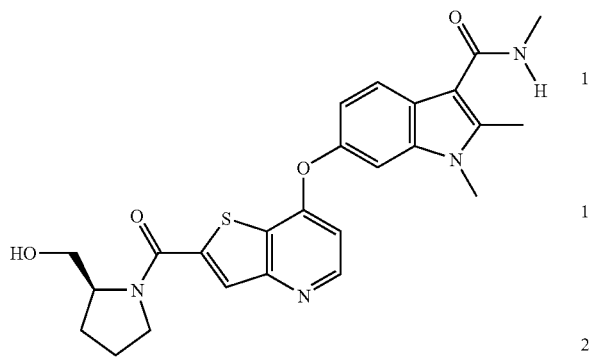

This material was prepared by the reaction of 7-chloro-2-[(S)-2-([t-butyldimethylsilyloxy]methyl)-pyrrolidine-1-carbonyl]thieno[3,2-b]pyridine 3b (76 mg, 0.3 mmole) with 6-hydroxy-1,2-dimethyl-1H-indole-3-carboxylic acid methylamide 16e (100 mg, 0.46 mmole) and $Cs_2CO_3$ (488 mg, 1.5 mmole) in a manner as previously described for example 1 to give 53 mg (43%) of an off-white solid. $^1$H NMR (DMSO-$d_6$) δ 8.54 (1H, d, J=5.46 Hz), 7.99 (1H, s), 7.83 (1H, d, J=8.67 Hz), 7.61–7.55 (1H, m), 7.54 (1H, d, J=2.07 Hz), 7.03(1H, dd, J=8.48, 2.07 Hz), 6.64 (1H, d, J=5.27 Hz), 5.10–4.80 (1H, 2m), 4.41–4.16 (1H, 2m), 3.91–3.77 (1H, m), 3.67 (3H, s), 3.64–3.47 (2H, m), 2.80 (3H, d, J=4.52 Hz), 2.60 (3H, s), 2.04–1.81 (4H, m). Anal. Calcd for $C_{25}H_{26}N_4O_4S \cdot 0.4\ H_2O \cdot 0.2$ EtOAc: C, 61.56; H, 5.69.

Example 17

1,2-dimethyl-6-(2-[1-methyl-1H-imidazol-2-yl]thieno[3,2-b]pyridin-7-yloxy)-1H-indole-3-carboxylic acid methylamide

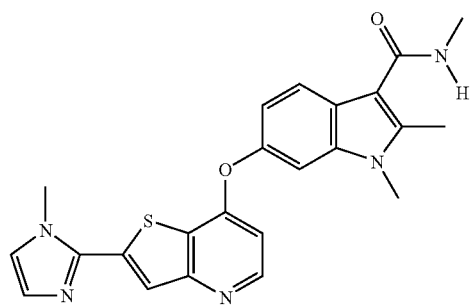

This material was prepared by the reaction of 7-chloro-2-(1-methyl-1H-imidazol-2-yl)thieno[3,2-b]pyridine 1e (76 mg, 0.3 mmole) with 6-hydroxy-1,2-dimethyl-1H-indole-3-carboxylic acid methylamide 16e (100 mg, 0.46 mmole) and $Cs_2CO_3$ (488 mg, 1.5 mmole) in a manner as previously described for example 1 to give 51 mg (39%) of product as an off-white solid. $^1$H NMR (DMSO-$d_6$) δ8.48 (1H, d, J=5.5 Hz), 7.88 (1H, s), 7.83 (1H, d, J=8.6 Hz), 7.61–7.55 (1H, m), 7.53 (1H, t, J=2.3 Hz), 7.41(1H, d, J=1.0 Hz), 7.0–6.99 (2H, m), 6.59 (1H, d, J=5.5 Hz), 3.98 (3H, s), 3.67 (3H, s), 2.80 (3H, d, J=4.6 Hz), 2.60 (3H, s). Anal. Calcd for $C_{23}H_{21}N_5O_2S \cdot 0.3H_2O \cdot 0.1$ EtOAc: C, 63.05; H, 5.07; N, 15.71; S, 7.19. Found: C, 63.06; H, 5.06; N, 15.56; S, 6.96.

Example 18

1,2-dimethyl-6-(2-[3-methoxy-pyrrolidine-1-carbonyl]thieno[3,2-b]pyridin-7-yloxy)-1H-indole-3-carboxylic acid methylamide

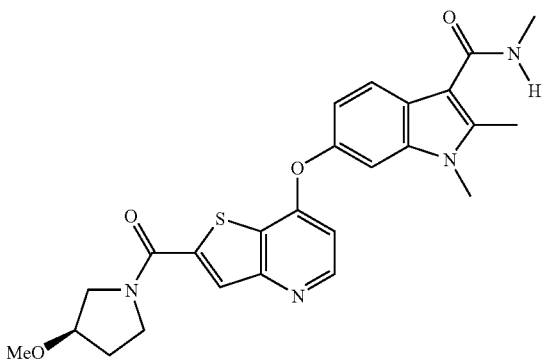

This material was prepared by the reaction of 7-chloro-2-[(R)-3-methoxypyrrolidine-1-carbonyl]thieno[3,2-b]pyridine 4b (157 mg, 0.5 mmole) with 6-hydroxy-1,2-dimethyl-1H-indole-3-carboxylic acid methylamide 16e (150 mg, 0.7 mmole) and $Cs_2CO_3$ (673 mg, 2.1 mmole) in a manner as previously described for example 1 to give 51 mg (39%) of a crisp foam. $^1$H NMR (DMSO-$d_6$) δ 8.54 (1H, dd, J=5.5, 1.13 Hz), 8.05 (1H, s), 7.84 (1H, d, J=8.6 Hz, 7.61–7.55 (1H, m), 7.54 (1H, d, J=2.1 Hz), 7.03(1H, dd, J=2.1, 8.6 Hz), 6.64 (1H, d, J=5.5 Hz), 4.12–3.51 (5H, m), 3.67 (3H, s), 3.27, 3.24 (3H, 2s), 2.80 (3H, d, J=4.5 Hz), 2.60 (3H, s), 2.35–1.95 (2H, m). Anal. Calcd for $C_{25}H_{26}N_4O_4S \cdot 0.9\ H_2O \cdot 0.2$ EtOAc: C, 60.47; H, 5.78; N, 10.93; S, 6.26. Found: C, 60.46; H, 5.56; N, 10.81; S, 6.34.

Example 19

1,2-dimethyl-6-(2-[3-hydroxy-pyrrolidine-1-carbonyl]thieno[3,2-b]pyridin-7-yloxy)-1H-indole-3-carboxylic acid methylamide

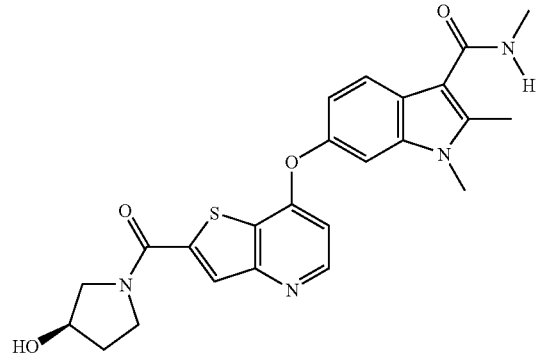

This material was prepared from 1,2-dimethyl-6-(2-[3-methoxy-pyrrolidine-1-carbonyl]thieno[3,2-b]pyridin-7-yloxy)-1H-indole-3-carboxylic acid methylamide 18 (128 mg, 0.27 mmole) by treatment with $BBr_3$ in a manner as previously described for example 1d to give 70 mg (56%) of a white solid. $^1$H NMR (DMSO-$d_6$) δ 8.54 (1H, dd, J=5.3, 1.1 Hz), 8.05, 7.99 (1H, 2s), 7.83 (1H, d, J=8.6 Hz), 7.61–7.55 (1H, m), 7.54 (1H, d, J=2.2 Hz), 7.03(1H, dd, J=2.2, 8.6 Hz), 6.64 (1H, dd, J=5.3, 1.1 Hz), 5.10–5.05 (1H, m), 4.41–4.31 (1H, m), 4.00–3.90 (1H, m), 3.67 (3H, s), 3.66–3.42 (3H, m), 2.80 (3H, d, J=4.5 Hz), 2.60 (3H, s), 2.06–1.92 (2H, m). Anal. Calcd for $C_{24}H_{24}N_4O_4S \cdot 0.9 H_2O$: C, 59.96; H, 5.41; N, 11.65; S, 6.67. Found: C, 59.87; H, 5.19; N, 11.51; S, 6.48.

Example 20(a):

6-Methoxy-1,2-dimethyl-1H-indol-3-carboxylic acid cyclopropylamide

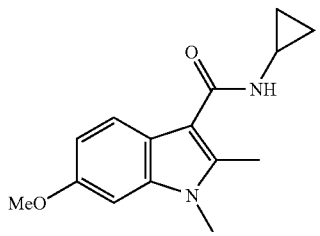

This material was prepared from 1,2-dimethyl-6-methoxy1H-indole-3-carboxylic acid 16c (500 mg, 2.3 mmole), oxalyl chloride (0.4 ml, 4.6 mmole) and cyclopropylamine (1.6 ml, 23 mmole) in a manner as previously described for example 16d to give 480 mg (82%) of a white solid. $^1$H NMR (DMSO-$d_6$) δ 7.57 (1H, d, J=3.8 Hz), 7.50 (1H, d, J=8.8 Hz), 6.99 (1H, d, J=2.3 Hz), 6.71 (1H, dd, J=2.3, 8.8 Hz), 3.78 (3H, s), 3.63 (3H, s), 2.83–2.80 (1H, m), 2.51 (3H, s), 0.68–0.62 (2H, m), 0.57–0.53 (2H, m).

Example 20(b)

6-Hydroxy-1,2-dimethyl-1H-indol-3-carboxylic acid cyclopropylamide

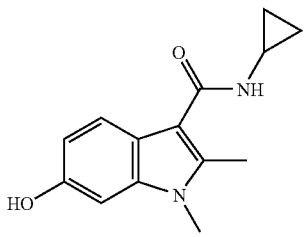

This material was prepared from 6-methoxy-1,2-dimethyl-1H-indole-3-carboxylic acid cyclopropylamide 20a (655 mg, 2.5 mmole) by treatment with $BBr_3$ in a manner as previously described for example 1d to give 130 mg (21%) of a white solid. $^1$H NMR (DMSO-$d_6$) δ 9.06 (1H, s), 7.51 (1H, d, J=4.0 Hz), 7.41 (1H, d, J=8.5 Hz), 6.73 (1H, d, J=1.8 Hz), 6.60 (1H, dd, J=1.8, 8.5 Hz), 3.56 (3H, s), 2.82 (1H, m), 2.50 (3H, s), 0.62 (2H, m), 0.52 (2H, m).

Example 20

1,2-Dimethyl-6-[2-(1-methyl-1H-imidazol-2-yl)-thieno[3,2-b]pyridin-7-yloxy]-1H-indole-3-carboxylic acid cyclopropylamide

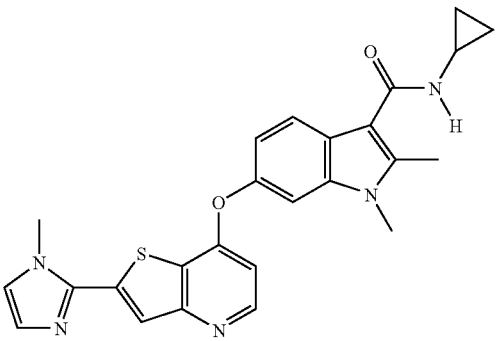

This material was prepared by the reaction of 7-chloro-2-(1-methyl-1H-imidazol-2-yl)thieno[3,2-b]pyridine 1e (79 mg, 0.3 mmole) with 1,2-dimethyl-6-hydroxy-1H-indole-3-carboxylic acid cyclopropylamide 20b (93 mg, 0.4 mmole) and $Cs_2CO_3$ (517 mg, 1.6 mmole) in a manner as previously described for example 1 to give 84 mg (58%) of a white solid. $^1$H NMR (DMSO-$d_6$) δ 8.47 (1H, d, J=4.9 Hz), 7.87 (1H, s), 7.78 (1H, d, J=3.7 Hz), 7.72 (1H, d, J=8.5 Hz), 7.52 (1H, s), 7.40 (1H, s), 7.02 (1H, s), 7.01 (1H, d, J=8.9 Hz), 6.58 (1H, d, J=5.3 Hz), 3.98 (3H, s), 3.67 (3H, s), 2.85 (1H, m), 2.57 (3H, s), 0.68 (2H, m), 0.58 (2H, m).

Anal. Calcd for $C_{25}H_{23}N_5O_2S \cdot 0.5$ MeOH: C, 64.67; H, 5.32; N, 14.79; S, 6.77. Found: C, 64.57; H, 5.24; N, 14.72; S, 6.81.

Example 21(a)

6-methoxy-1-methyl-1H-indole-3-carboxylic acid methylamide

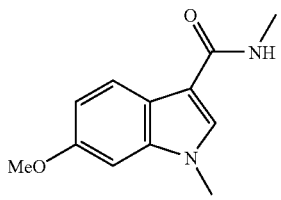

This material was prepared from 6-methoxy-1-methyl-indole-3-carboxylic acid 16b (515 mg, 2.5 mmole), oxalyl chloride (0.9 ml, 12.6 mmole) and methylamine (7.5 mmole) in a manner as previously described for example 16d to give 457 mg of a pale brown solid (83%). $^1$H NMR ($CD_3OD$) δ7.83 (1H, d, J=8.7 Hz), 7.51 (1H, s), 6.81 (1H, d, J=2.3 Hz), 6.72 (1H, dd, J=2.3, 8.7 Hz), 3.75 (3H, s), 3.67 (3H, s), 2.80 (3H, s); ESIMS (MH$^+$): 219.05.

Example 21(b)

6-hydroxy-1-methyl-1H-indole-3-carboxylic acid methylamide

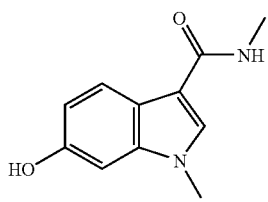

This material was prepared from 6-methoxy-1-methyl-1H-indole-3-carboxylic acid methylamide 21a (453 mg, 2.1 mmol) by treatment with BBr$_3$ in a manner as previously described for example 1d to give 219 mg (51%) of a pale orange solid. $^1$H NMR (CD$_3$OD) δ 7.75 (1H, d, J=8.5 Hz), 7.47 (1H, s), 6.61–6.66 (2H, m), 3.62 (3H, s), 3.24 (1H, s), 2.79 (3H, s). ESIMS (MH$^+$): 205.10.

Example 21

6-{2-[3-(R)-hydroxy-pyrrolidine-1-carbonyl]thieno[3,2-b]pyridin-7-yloxy}-1-methyl-1H-indole-3-carboxylic acid methylamide

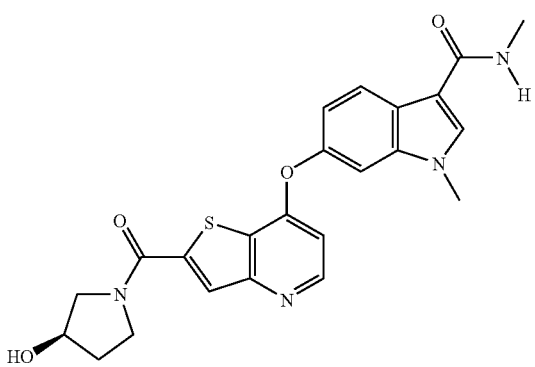

This material was prepared by the reaction of 7-chloro-2-[(R)-3-hydroxypyrrolidine-1-carbonyl]thieno[3,2-b]pyridine 4a (152 mg, 0.5 mmole) with 6-hydroxy-1-methyl-1H-indole-3-carboxylic acid methylamide 21b (110 mg, 0.5 mmole) and Cs$_2$CO$_3$ (176 mg, 0.5 mmole) in a manner as previously described for example 1 to give 65 mg (27%) of a white solid. $^1$H NMR (CD$_3$OD) δ 8.39 (1H, d, J=5.5 Hz), 8.12 (1H, d, J=8.7 Hz), 7.77 (1H, d, J=17.33 Hz, 7.72 (1H, s), 7.32 (2H, m), 6.99 (dd, 1H, J$_1$=6.59 Hz, J$_2$=2.08 Hz), 6.60 (1H, d, J=5.5 Hz), 4.43 (m, 1H), 3.95 (1H, m), 3.73 (3H, s), 3.59–3.69 (3H, m), 2.83 (3H, s), 2.01 (2H, m). ESIMS (MH$^+$): 451.10; Anal. Calcd. For C$_{23}$H$_{22}$N$_4$O$_4$S.0.6 CH$_3$OH.0.2 CH$_2$Cl$_2$: C, 57.91; H, 5.02; N, 11.35. Found: C, 57.68; H, 5.06; N, 11.43.

Example 22

6-[2-(3-methoxypyrrolidine-1-carbonyl)-thieno[3,2-b]pyridin-7-yloxy]-1-methyl-1H-indole-3-carboxylic acid methylamide

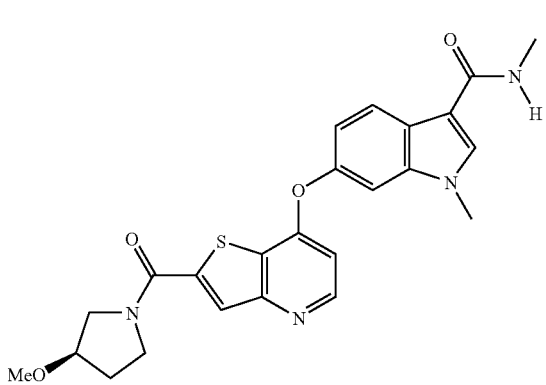

This material was prepared by the reaction of 7-chloro-2-[(R)-3-methoxypyrrolidine-1-carbonyl]thieno[3,2-b]pyridine 4b with 6-hydroxy-1-methyl-1H-indole-3-carboxylic acid methylamide 21b and Cs$_2$CO$_3$ in a manner as previously described for example 1. $^1$H NMR (300 MHz, CD$_3$OD) δ 8.53 (1H, d, J=5.5 Hz), 8.25 (1H, d, J=8.7 Hz), 7.96 (1H, d, J=6.2 Hz), 7.86 (1H, s), 7.46 (1H, d, J=1.9 Hz), 7.12 (1H, d, J=8.5 Hz), 6.74 (1H, d, J=5.5 Hz), 4.19–4.11 (1H, m), 4.05–3.95 (2H, m), 3.38 (3H, s), 3.85–3.72 (2H, m), 3.40 (3H, d, J=13.9 Hz), 2.96 (3H, s), 2.30–2.09 (2H, m). LCMS (ESI+) [M+H]/z Calc'd 465. found 465. Anal. (C$_{24}$H$_{24}$N$_4$O$_4$S.0.4CH$_2$Cl$_2$) C, H, N.

Example 23

1-Methyl-6-[2-(1-methyl-1H-imidazol-2-yl)-thieno[3,2-b]pyridin-7-yloxy]-1H-indole-3-carboxylic acid methylamide

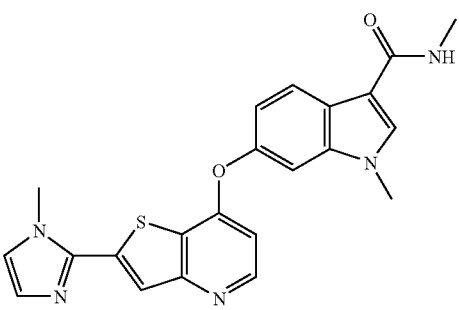

This material was prepared by the reaction of 7-chloro-2-(1-methyl-1H-imidazol-2-yl)thieno[3,2-b]pyridine 1e with 6-hydroxy-1-methyl-1H-indole-3-carboxylic acid methylamide 21b and Cs$_2$CO$_3$ in a manner as previously described for example 1. $^1$H NMR (300 MHz, CDCl$_3$) δ 8.43 (1H, d, J=5.5 Hz), 8.05 (1H, d, J=8.7 Hz), 7.67 (1H, s), 7.61

(1H, s), 7.17 (1H, d, J=2.1 Hz), 7.13 (1H, s), 7.08 (1H, dd, J=2.1, 8.7 Hz), 7.02 (1H, s), 6.54 (1H, d, J=5.5 Hz), 3.95 (3H, s), 3.75 (3H, s), 3.01 (3H, s). LCMS (ESI+) [M+H]/z Calc'd 418. found 418. Anal. (C$_{22}$H$_{19}$N$_5$O$_2$S.0.25EtOAc) C, H, N.

Example 24(a)

6-Methoxy-2-methyl-1H-indol-3-carboxylic acid methylamide

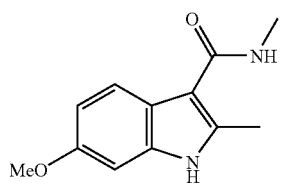

To a stirred solution of 6-methoxy-2-methyl-1H-indole (500 mg, 3.1 mmol) (prepared according to JACS 1988, 110, 2242) in 8 mL anhydrous THF maintained at room temperature was added methylmagnesium bromide (1.13 ml, 3.0 M solution in diethyl ether, 3.41 mmol). After stirring for 1 hour at room temperature, a solution of 0.5M zinc chloride in THF (7.44 ml, 3.72 mmol) was introduced and the mixture was stirred for 1 hour at room temperature before addition of methyl isocyanate (424 mg, 7.44 mmol). The resulting mixture was stirred at ambient temperature overnight, quenched with water, and extracted with EtOAc. The combined organic layer was washed with brine, dried over Na$_2$SO$_4$, filtered and concentrated. The residue was purified by flash column chromatography eluting with 2–5% MeOH in CH$_2$Cl$_2$ to give 200 mg product (30% yield). $^1$H NMR (300 MHz, CD$_3$OD) δ 7.55 (1H, d, J=8.6 Hz), 6.78 (1H, d, J=2.2 Hz), 6.70 (1H, dd, J=2.2, 8.6 Hz), 3.73 (3H, s), 2.90 (3H, s), 2.52 (3H, s). LCMS (ESI+) [M+H]/z Calc'd 219. found 219.

Example 24(b)

6-Hydroxy-2-methyl-1H-indol-3-carboxylic acid methylamide

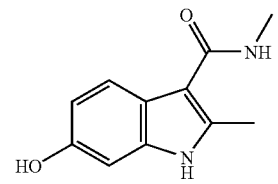

This material was prepared from 6-methoxy-2-methyl-1H-indol-3-carboxylic acid methylamide 24a by treatment with BBr$_3$ in a manner as previously described for example 1d. $^1$H NMR (300 MHz, CD$_3$OD) δ 7.52 (1H, d, J=8.7 Hz), 6.72 (1H, d, J=2.3 Hz), 6.65 (1H, dd, J=2.3, 8.7 Hz), 2.93 (3H, s), 2.55 (3H, s). LCMS (ESI+) [M+H]/z Calc'd 205. found 205.

Example 24

6-[2-(3-Hydroxy-pyrrolidine-1-carbonyl)-thieno[3,2-b]pyridin-7-yloxy]-2-methyl-1H-indole-3-carboxylic acid methylamide This material was prepared by the reaction of 7-chloro-2-[(R)-3-hydroxypyrrolidine-1-carbynyl]thieno[3,2-b]pyridine 4a with 6-hydroxy-2-methyl-1H-indol-3-carboxylic acid methylamide and Cs$_2$CO$_3$ in a manner as previously described for Example 1. $^1$H NMR (300 MHz, CD$_3$OD) δ 8.48 (1H, d, J=5.5 Hz), 7.91 (1H, d, J=17.3 Hz), 7.86 (1H, d, J=8.6 Hz), 7.21 (1H, s), 7.00 (1H, d, J=8.6 Hz), 6.69 (1H, d, J=5.5 Hz), 4.50 (1H, m), 4.05–3.70 (4H, m), 2.97 (3H, s), 2.63 (3H, s), 2.40–1.90 (2H, m). LCMS (ESI+) [M+H]/z Calc'd 451. found 451.

Example 25(a)

2-(Azetidin-1-ylcarbonyl)-7-chlorothieno[3,2-b]pyridine

This material was prepared from lithium 7-chlorothieno[3,2-b]pyridine-2-carboxylate (100 mg, 0.47 mmole) by treatment with thionyl chloride followed by coupling with azetidine, in a manner as previously described for example 9d to afford 98 mg (83%) of a dark yellow solid. $^1$H NMR (DMSO-d$_6$) δ 8.72 (1H, d, J=5.1 Hz), 7.96 (1H, s), 7.70 (1H, d, J=5.1 Hz), 4.62 (2H, t, J=7.4 Hz), 4.12 (2H, t, J=7.7 Hz), 2.34 (2H, tt, J=7.4, 7.7 Hz).

Anal. Calcd for C$_{11}$H$_9$N$_2$OSCl: C, 52.28; H, 3.59; Cl, 14.03; N, 11.09; S, 12.69. Found: C, 52.39; H, 3.63; Cl, 14.29; N, 10.99; S, 12.74.

Example 25

6-[2-(Azetidine-1-carbonyl)-thieno[3,2-b]pyridin-7-yloxy]-1,2-dimethyl-3H-indole-3-carboxylic acid methylamide

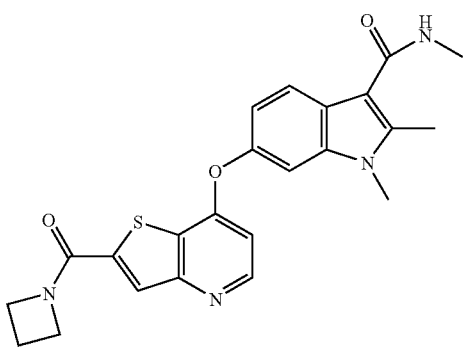

This material was prepared by the reaction of 2-(azetidin-1-ylcarbonyl)-7-chlorothieno[3,2-b]pyridine 25a with 6-hydroxy-1,2-dimethyl-1H-indole-3-carbyxylic acid methylamide 16e and $Cs_2CO_3$ in a manner as previously described for example 1. $^1$H NMR (300 MHz, $CD_3OD$) δ 8.41 (1H, d, J=5.5 Hz), 7.80 (1H, d, J=3.20 Hz), 7.74 (1H, d, J=11.68 Hz), 7.30 (1H, s), 6.94 (1H, d, J=8.66 Hz), 6.62 (1H, d, J=5.5 Hz), 4.64–4.59 (2H, m), 4.20–4.15 (2H, m), 3.63 (3H, s), 2.85 (3H, s), 2.57 (3H, s), 2.44–2.36 (2H, m). LCMS (ESI+) [M+H]/z Calc'd 435. found 435.

Anal. ($C_{23}H_{22}N_4O_3S.0.35CH_2Cl_2$) C, H, N.

Example 26

1,2-Dimethyl-6-(2-[4-(hydroxymethyl)thiazol-2-yl]thieno[3,2-b]pyridin-7-yloxy)-1H-indole-3-carboxylic acid methylamide

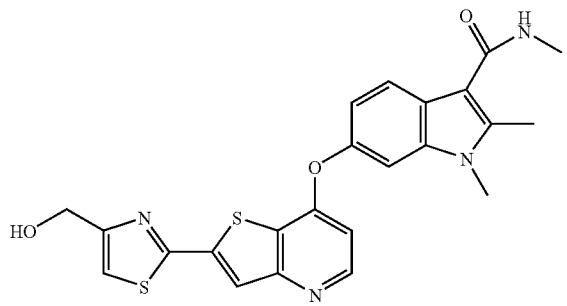

This material was prepared by the reaction of [2-(7-chloro-thieno[3,2-b]pyridin-2-yl)-thiazol-4-yl]-methanol with 6-hydroxy-1,2-dimethyl-1H-indole-3-carboxylic acid methyl amide 16e and $Cs_2CO_3$ in a manner as previously described for example 1. $^1$H NMR (300 MHz, DMSO-$d_6$) δ 8.52 (1H, d, J=5.5 Hz), 8.14 (1H, s), 7.83 (1H, d, J=8.6 Hz), 7.63 (1H, s), 7.58 (1H, d, J=4.7 Hz), 7.54 (1H, d, J=2.0 Hz), 7.04 (1H, dd, J=2.0, 8.6 Hz), 6.64 (1H, d, J=5.5 Hz), 4.60 (2H, s), 3.67 (3H, s), 2.80 (3H, d, J=4.3 Hz), 2.61 (3H, s). LCMS (ESI+) [M+H]/z Calc'd 465. found 465. Anal. ($C_{23}H_{20}N_4O_3S_2.0.6CH_3OH$) C, H, N.

Example 27(a)

(3R)-1-[(7-Chlorothieno[3,2-b]pyridin-2-yl)carbonyl]-N,N-dimethylpyrrolidin-3-amine

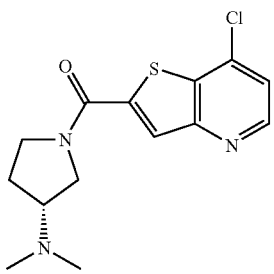

This material was prepared from lithium 7-chlorothieno[3,2-b]pyridine-2-carboxylate (0.214 g, 1.0 mmole) by treatment with thionyl chloride followed by reaction of the resultant acyl chloride with (3R)-N,N-dimethylpyrrolidin-3-amine (0.114 g, 1.0 mmole) and $Et_3N$ (0.139 ml, 1.0 mmole), in a manner as previously described for example 9d to give a brown solid (0.134 g, 43%). $^1$H NMR (300 MHz, $CD_3OD$) δ σ7.24 (1H, d, J=5.1 Hz), 6.57 (1H, d, J=8.48 Hz), 6.15 (1H, d, J=5.1 Hz), 2.70 (1H, m), 2.51 (2H, m), 2.24 (1H, m), 2.04 (1H, m), 1.49 (1H, m), 0.93 (3H, s), 0.90 (3H, s), 0.52 (1H, m); ESIMS (MH$^+$): 310.10.

Example 27

6-[(2-{[(3R)-3-(Dimethylamino)pyrrolidin-1-yl]carbonyl}thieno[3,2-b]pyridin-7-yl)oxy]-N,1,2-trimethyl-1H-indole-3-carboxamide

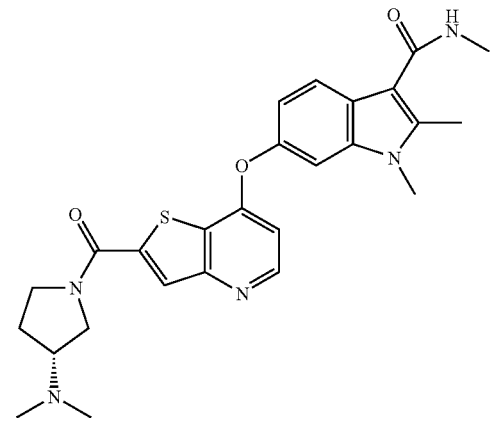

This material was prepared by the reaction (3R)-1-[(7-chlorothieno[3,2-b]pyridin-2-yl)carbonyl]-N,N-dimethylpyrrolidin-3-amine 27a (0.136 g, 0.44 mmole) with 6-hydroxy-N,1,2-trimethyl-1H-indole-3-carboxamide 16e (0.0649, 0.294 mmole) and $Cs_2CO_3$ (0.096 g, 0.29 mmole) in a manner as previously described for example 1 to give a brown colored foam (0.059 g, 17%). $^1$H NMR (300 MHz, $CD_3OD$) δ 8.40 (1H, d, J=5.46 Hz), 7.84 (1H, d, J=6.59 Hz), 7.76 (1H, d, J=8.67 Hz), 7.29 (1H, d, J=2.07 Hz), 6.95 (1H, dd, J=8.57, 2.17 Hz), 6.62 (1H, d, J=5.65 Hz), 4.06 (1H, m), 3.87 (2H, m), 3.63 (3H, s) 3.03 (2H, m), 2.88 (3H, s), 2.57

(3H, s), 2.37 (3H, s), 2.32 (3H, s), 2.23 (1H, m), 1.95 (1H, m); HRMS (MH+): Calcd: 492.2085. Found: 492.2069.

Example 28(a)

(7-Chloro-thieno[3,2-b]pyridin-2-yl)-pyrrolidin-1-yl-methanone

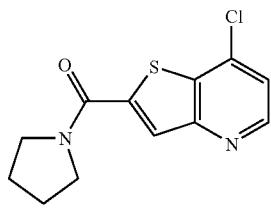

This material was prepared from the coupling of 7-chlorothieno[3,2-b]pyridine-2-carboxylic acid and pyrrolidine in a manner as previously described for example 9d. $^1$H NMR (300 MHz, CD$_3$OD) δ 8.60 (1H, d, J=5.1 Hz), 7.84 (1H, s), 7.32 (1H, d, J=5.1 Hz), 3.82 (2H, t, J=6.4 Hz), 3.70 (2H, t, J=6.6 Hz), 2.02 (4H, m). LCMS (ESI+) [M+H]/z Calc'd 267. found 267.

Example 28

1,2-Dimethyl-6-[2-(pyrrolidine-1-carbonyl)-thieno[3,2-b]pyridin-7-yloxy]-1H-indole-3-carboxylic acid methylamide

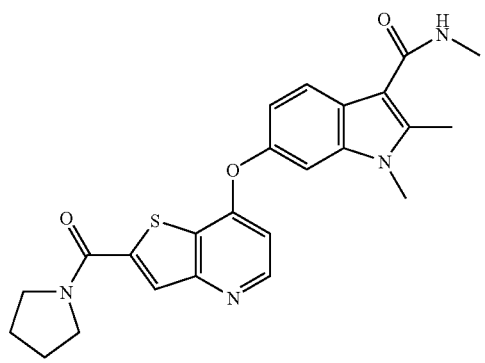

This material was prepared from the reaction of (7-chlorothieno[3,2-b]pyridin-2-yl)-pyrrolidin-1-yl-methanone 28a with 6-hydroxy-1,2-dimethyl-1H-indole-3-carboxylic acid methylamide 16e and Cs$_2$CO$_3$ in a manner as previously described for example 1. $^1$H NMR (300 MHz, CD$_3$OD) δ 8.47 (1H, d, J=5.3 Hz), 7.82 (1H, s), 7.74 (1H, d, J=8.4 Hz), 7.14 (1H, d, J=1.7 Hz), 7.02 (1H, dd, J=1.7, 8.4 Hz), 6.55 (1H, d, J=5.3 Hz) 5.91 (1H, bs), 3.84 (2H, m), 3.70 (2H, m), 3.65 (3H, s), 3.05 (3H, d, J=4.5 Hz), 2.72 (3H, s), 2.02 (4H, m). LCMS (ESI+) [M+H]/z Calc'd 449. found 449.

Anal. (C$_{24}$H$_{24}$N$_4$O$_3$S.0.5CH$_3$OH) C, H, N.

Example 29(a)

7-Chloro-N-[2-(dimethylamino)ethyl]-N-methylthieno[3,2-b]pyridine-2-carboxamide

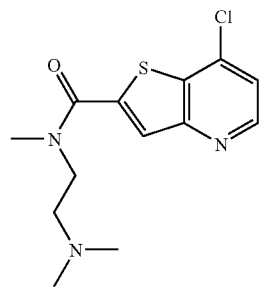

This material was prepared from lithium 7-chlorothieno[3,2-b]pyridine-2-carboxylate (0.957 g, 4.48 mmole) by treatment with thionyl chloride followed by reaction of the resultant acyl chloride with N,N,N-trimethylethane-1,2-diamine (0.640 ml, 4.93 mmole) and Et$_3$N (0.624 ml, 4.48 mmole), in a manner as previously described for example 9d to give a brown solid (0.167 g, 13%). $^1$H NMR (400 MHz, CDCl$_3$) δ 8.60 (1H, d, J=5.1 Hz), 7.74 (1H, s), 7.32 (1H, d, J=5.1 Hz), 3.66 (2H, t, J=6.4 Hz), 3.26 (3H, s), 2.57 (2H, t, J=6.4 Hz), 2.25 (6H, s); ESIMS (MH+): 298.05.

Example 29

N-[2-(Dimethylamino)ethyl]-7-({1,2-dimethyl-3-[(methylamino)carbonyl]-1H-indol-6-yl}oxy)-N-methylthieno[3,2-b]pyridine-2-carboxamide

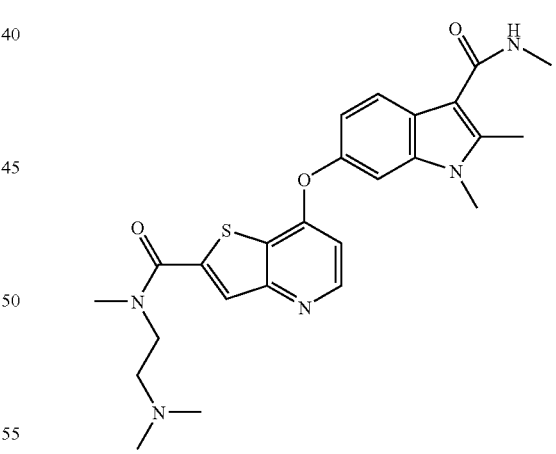

This material was prepared by the reaction of 7-chloro-N-[2-(dimethylamino)ethyl]-N-methylthieno[3,2-b]pyridine-2-carboxamide 29a (0.167 g, 0.56 mmole) with 6-hydroxy-N,1,2-trimethyl-1H-indole-3-carboxamide 16e (0.123 g, 0.56 mmole) and Cs$_2$CO$_3$ (0.182 g, 0.56 mmole) in a manner as previously described for example 1 to give a yellow solid (0.040 g, 13%). $^1$H NMR (400 MHz, CD$_3$OD) δ 8.71 (1H, d, J=6.8 Hz), 8.06 (1H, s), 7.83 (1H, d, J=8.6 Hz), 7.46 (1H, d, J=2.0 Hz), 7.09 (1H, d, J=6.8 Hz), 7.05 (1H, dd, J=2.0, 8.6 Hz), 3.90 (2H, t, J=5.8 Hz), 3.64 (3H, s), 3.42 (2H, t, J=5.8 Hz), 3.23 (6H, s), 2.93 (3H, s), 2.88 (3H, s), 2.58 (3H, s). HRMS (MH+): Calcd: 480.2090. Found: 480.2069.

Example 30

6-[2-(3-Hydroxy-azetidine-1-carbonyl)-thieno[3,2-b]pyridin-7-yloxy]-1,2-dimethyl-1H-indole-3-carboxylic acid methylamide

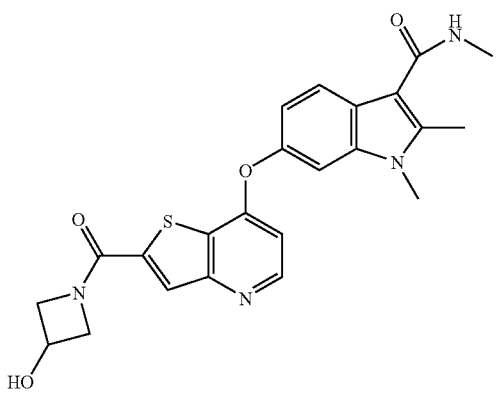

This material was prepared by the reaction of (7-chlorothieno[3,2-b]pyridin-2-yl)-(3-hydroxy-azetidin-1-yl)-methanone 9d with 6-hydroxy-1,2-dimethyl-1H-indole-3-carboxylic acid methylamide 16e and $Cs_2CO_3$ in a manner as previously described for example 1. $^1$H NMR (300 MHz, $CD_3OD$) δ 8.41 (1H, d, J=5.5 Hz), 7.78–7.74 (2H, m), 7.29 (1H, d, J=2.1 Hz), 6.95(1H, dd, J=2.1, 8.6 Hz), 6.62 (1H, d, J=5.5 Hz), 4.76–4.73 (2H, m), 4.63 (1H, bs), 4.35–4.32 (2H, m), 3.9.7–3.94(1H, m), 3.62(3H, s), 2.89(3H, s), 2.57 (3H, s). LCMS (ESI+) [M+H]/z Calc'd 451. found 451.
Anal. ($C_{23}H_{22}N_4O_4S \cdot 1.1CH_2Cl_2$) C, H, N.

Example 31(a)

7-Chloro-N-(2-hydroxyethyl)-N-methylthieno[3,2-b]pyridine-2-carboxamide

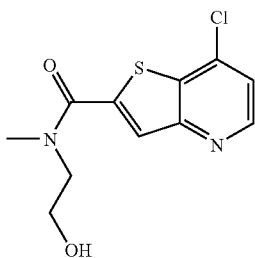

This material was prepared from lithium 7-chlorothieno[3,2-b]pyridine-2-carboxylate (1.0 g, 4.68 mmole) by treatment with thionyl chloride followed by reaction of the resultant acyl chloride with 2-(methylamino)ethanol (0.414 ml, 5.15 mmole) and $Et_3N$ (0.718 ml, 5.15 mmole), in a manner as previously described for example 9d to give a pale brown solid (0.624 g, 49% yield). $^1$H NMR (400 MHz, $CDCl_3$) σ8.61 (1H, d, J=4.8 Hz), 7.80 (1H, s), 7.33 (1H, d, J=4.8 Hz), 3.92 (2H, m), 3.76 (2H, t, J=5.1 Hz), 3.37 (3H, s), 3.19 (1H, s); ESIMS (MH+): 259.10.

Example 31(b)

N-(2-{[tert-Butyl(dimethyl)silyl]oxy}ethyl)-7-chloro-N-methylthieno[3,2-b]pyridine-2-carboxamide

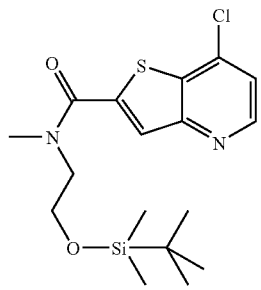

This material was prepared from 7-chloro-N-(2-hydroxyethyl)-N-methylthieno[3,2-b]pyridine-2-carboxamide 31a (1.27 g, 4.68 mmole), t-butyldimethylsilyl chloride (0.705 g, 4.68 mmole) and $Et_3N$ (0.718 ml, 4.68 mmole) in a manner as previously described for 3b to give an orange oil (1.40 g, 78%). $^1$H NMR (300 MHz, $CDCl_3$) ϵ 8.61 (1H, d, J=5.1 Hz), 7.74 (1H, s), 7.32 (1H, d, J=5.1 Hz), 3.89 (2H, m), 3.71 (2H, m), 3.37 (3H, s), 0.89 (9H, m), 0.07 (6H, m); ESIMS (MH+): 385.10.

Example 31

N-({1,2-Dimethyl-3-[(methylamino)carbonyl]-1H-inden-6yl}oxy)-N-(2-hydroxyethyl)-N-methylthieno[3,2-b]pyridine-2-carboxamide

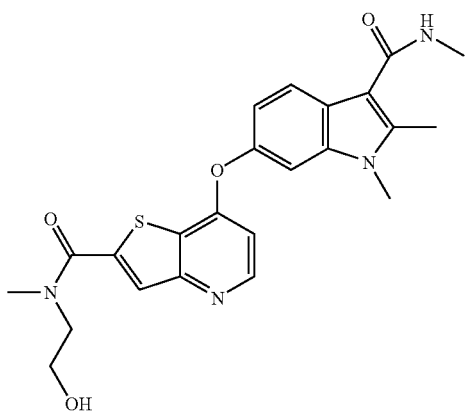

This material was prepared by the reaction of N-(2-{[tert-butyl(dimethyl)silyl]oxy}ethyl)-7-chloro-N-methylthieno[3,2-b]pyridine-2-carboxamide 31b (0.133 g, 0.35 mmole) with 6-hydroxy-N,1,2-trimethyl-1H-indole-3-carboxamide 16e (0.76 g, 0.35 mmole) and $Cs_2CO_3$ (0.114 g, 0.35 mmole) in a manner as previously described for example 1 to give a mixture of N-(2-{[tert-butyl(dimethyl)silyl]oxy}ethyl)-7-({1,2-dimethyl-3-[(methylamino)carbonyl]-1H-indol-6-yl}oxy)-N-methylthieno[3,2-b]pyridine-2-carboxamide and 7-({1,2-dimethyl-3-[(methylamino)carbonyl]-1H-inden-6-yl}oxy)-N-(2-hydroxyethyl)-N-methylthieno[3,2-b]pyridine-2-carboxamide, which was dissolved in THF (10 ml) and treated with TBAF (0.7 ml) for 2 h. The reaction mixture was quenched with $H_2O$ and partitioned between $CH_2Cl_2$ (50×2 ml) and $H_2O$ (50 ml). The combined organic layers were dried over MgSO₄ and concentrated. The residue was purified by flash column chromatography eluting with 5–8% CH₃OH in CH₂Cl₂ to give an off-white solid (0.064 g, 41% yield). ¹H NMR (400 MHz, CD₃OD) δ 8.38 (1H, d, J=5.4 Hz), 7.76 (2H, m), 7.29 (1H, s), 6.95 (1H, dd, J=2.1, 8.7 Hz), 6.61 (1H, d, J=5.4 Hz), 3.72 (2H, m), 3.62 (3H, s), 3.22 (3H, s), 3.12 (2H, m), 2.88 (3H, s), 2.57 (3H, s); HRMS (MH⁺): Calcd: 453.1606. Found: 453.1597.

Example 32(a):

7-Chloro-N-[3-(dimethylamino)propyl]-N-methylthieno[3,2-b]pyridine-2-carboxamide

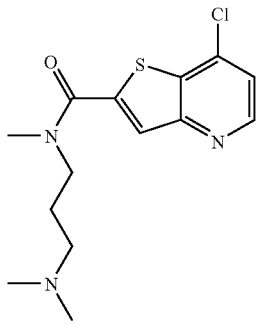

This material was prepared from 7-chlorothieno[3,2-b]pyridine-2-carboxylic acid (1.0 g, 4.68 mmole), SOCl₂ (10 ml), N,N,N-trimethylpropane-1,3-diamine (0.868 ml, 4.68 mmole) and Et₃N (1.96 ml, 14.04 mmole) in a manner as previously described for example 9d to give a white foam (1.07 g, 77%). ¹H NMR (300 MHz, CD₃OD) δ 8.56 (1H, d, J=5.2 Hz), 7.76 (1H, s), 7.46 (1H, d, J=5.2 Hz), 3.51 (2H, m), 3.20 (3H, s), 2.33 (2H, m), 2.18 (6H, s), 1.79 (2H, m); ESIMS (MH⁺): 312.05.

Example 32

N-[3-(Dimethylamino)propyl]-7-({1,2-dimethyl-3-[(methylamino)carbonyl]-1H-indol-6-yl}oxy)-N-methylthieno[3,2-b]pyridine-2-carboxamide

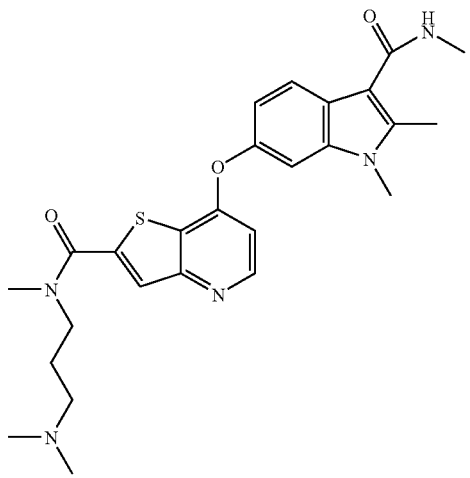

This material was prepared by the reaction of 7-chloro-N-[3-(dimethylamino)propyl]-N-methylthieno[3,2-b]pyridine-2-carboxamide 32a (0.095 g, 0.32 mmole) with 6-hydroxy-N,1,2-trimethyl-1H-indole-3-carboxamide (0.070 g, 0.32 mmole) 16e and Cs₂CO₃ (0.104 g, 0.32 mmole) in a manner as described previously for example 1 to give a white solid (0.098 g, 62%). ¹H NMR (300 MHz, CD₃OD) δ 8.53 (1H, d, J=5.3 Hz), 7.91 (2H, m), 7.38 (1H, s), 7.09 (1H, dd, J=2.1, 8.7 Hz), 6.81(1H, d, J=5.3 Hz), 3.73 (3H, s), 3.66 (2H, m), 3.28 (2H, m), 3.01 (3H, s), 2.68 (9H, m), 2.06 (2H, m), 1.94(3H, s); HRMS (MH⁺): Calcd: 494.2223. Found: 494.2226.

Example 33(a)

7-Chloro-N,N-dimethylthieno[3,2-b]pyridine-2-carboxamide

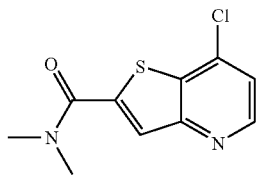

This material was prepared from 7-chlorothieno[3,2-b]pyridine-2-carboxylic acid (0.57 g, 2.67 mmole), SOCl₂ (5 ml), 2.0 M N,N-dimethylamine in THF (1.60 ml, 3.20 mmole) and Et₃N (0.447 ml, 3.20 mmole) in a manner as previously described for example 9d to give a brown solid (0.54 g, 84%). ¹H NMR (300 MHz, CDCl₃) δδδ 1H, d, J=5.0 Hz), 7.74 (1H, s), 7.35 (1H, d, J=5.0 Hz), 3.28 (3H, s), 3.22 (3H, s); ESIMS (MH⁺): 240.95.

Example 33

7-({1,2-Dimethyl-3-[(methylamino)carbonyl]-1H-indol-6-yl}oxy)-N,N-dimethylthieno[3,2-b]pyridine-2-carboxamide

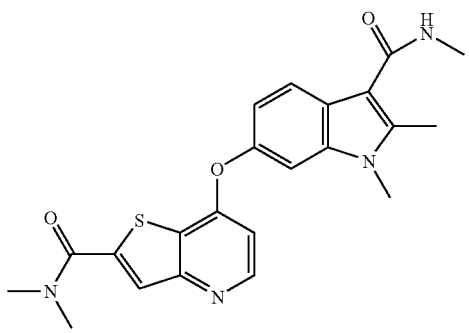

This material was prepared by the reaction 7-chloro-N,N-dimethylthieno[3,2-b]pyridine-2-carboxamide 33a (0.077 g, 0.32 mmole) and 6-hydroxy-N,1,2-trimethyl-1H-indole-3-carboxamide 16e (0.070 g, 0.32 mmole) and Cs₂CO₃ (0.104 g, 0.32 mmole) in a manner as previously described for example 1 to give a pale yellow solid (0.098 g, 73%). ¹H NMR (300 MHz, CD₃OD) δ 8.38 (1H, d, J=5.5 Hz), 7.75 (1H, d, J=8.7 Hz), 7.66 (1H, s), 7.28 (1H, d, J=2.1 Hz), 6.94 (1H, dd, J=2.1, 8.7 Hz), 6.60 (1H, d, J=5.5 Hz), 3.61 (3H, s), 3.21 (6H, m), 2.87 (3H, s), 2.56 (3H, s). ESIMS (MH⁺): 423.05.

Anal. Calcd. For C₂₂H₂₂N₄O₃S·0.6H₂O: C, 59.21; H, 5.28; N, 12.44. Found: C, 59.20; H, 5.28; N, 12.44.

Example 34(a)

Benzyl (3R)-3-[(tert-butoxycarbonyl)(methyl)amino]pyrrolidine-1-carboxylate

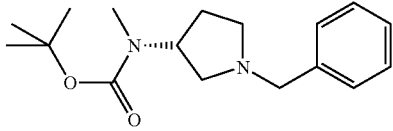

Boc$_2$O (1.26 g, 5.78 mmole) and DMAP (6.4 mg, 0.053 mmole) was added to a solution of tert-butyl methyl[(3R)-pyrrolidin-3-yl]carbamate (1.0 g, 5.26 mmole). The reaction mixture was stirred at room temperature overnight and was partitioned between CH$_2$Cl$_2$ (2×100 ml) and H$_2$O (100 ml). The combined organic layers were dried over MgSO$_4$ and concentrated. The residue was purified by flash column chromatography eluting with 1–2% CH$_3$OH in CH$_2$Cl$_2$ to give a pale yellow oil (1.51 g, 99%). $^1$H NMR (300 MHz, CDCl$_3$) δ 7.30 (5H, m), 3.56 (2H, m), 2.82 (3H, s), 2.76 (2H, m), 2.53 (2H, m), 2.33 (1H, m), 2.09 (1H, m), 1.73 (1H, m), 1.42 (9H, m); ESIMS (MH$^+$): 291.20.

Example 34(b)

tert-Butyl methyl[(3R)-pyrrolidin-3-yl]carbamate

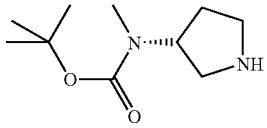

To a stirred solution of benzyl (3R)-3-[(tert-butoxycarbonyl)(methyl)amino]pyrrolidine-1-carboxylate 34a (1.5 g, 5.17 mmole) in MeOH (10 ml) was added Pd(OH)$_2$ on carbon (150 mg). The reaction mixture was under 1 atmosphere of H$_2$ overnight, filtered through celite and concentrated, in vacuo. The residue obtained was used directly in the subsequent reaction without any further purification, vide infra. $^1$H NMR (300 MHz, CD$_3$OD) δ 4.47 (1H, m), 3.20 (1H, m), 2.91 (2H, m), 2.76 (1H, m), 2.69 (3H, s), 1.89 (1H, m), 1.68 (1H, m), 1.35 (9H, s).

Example 34(c)

tert-Butyl (3R)-1-[(7-chlorothieno[3,2-b]pyridin-2-yl)carbonyl]pyrrolidin-3-yl(methyl)carbamate

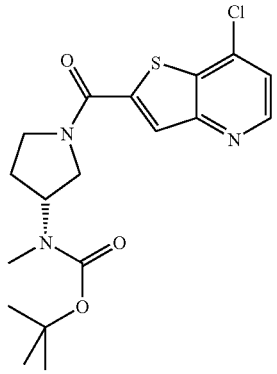

This material was prepared from 7-chlorothieno[3,2-b]pyridine-2-carboxylic acid (1.05 g, 4.94 mmole), SOCl$_2$ (10 ml), tert-butyl methyl[(3R)-pyrrolidin-3-yl]carbamate 34b (0.989 g, 4.94 mmole) and Et$_3$N (0.689 ml, 4.94 mmole) in a manner as previously described for example 9d to give a brown oil (0.723 g, 0.30%). $^1$H NMR (300 MHz, CDCl$_3$) δ 8.62 (1H, d, J=5.1 Hz), 7.85 (1H, s), 7.35 (1H, d, J=5.1 Hz), 4.82 (1H, m), 3.93 (3H, m), 3.63 (1H, m), 2.82 (3H, s), 2.12 (2H, m), 1.47 (9H, s); ESIMS (MH$^+$): 396.05.

Example 34 tert-Butyl-(3R)-1-{[7-({1,2-dimethyl-3-[(methylamino)carbonyl]-1H-indol-6-yl}oxy)thieno[3,2-b]pyridin-2-yl]carbonyl}pyrrolidin-3-yl(methyl)carbamate

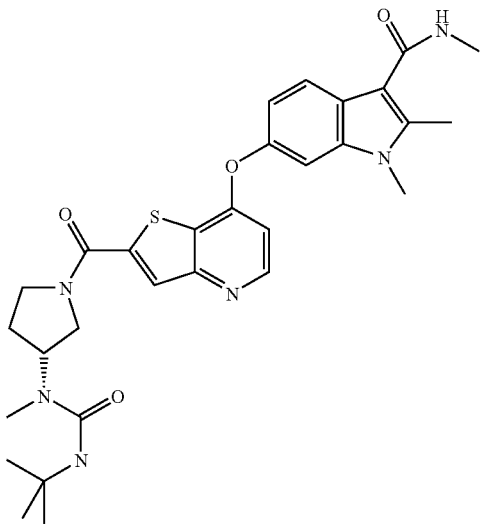

This material was prepared by the reaction of tert-butyl (3R)-1-[(7-chlorothieno[3,2-b]pyridin-2-yl)carbonyl]pyrrolidin-3-yl(methyl)carbamate 34c (0.181 g, 0.46 mmole) with 6-hydroxy-N, 1,2-trimethyl-1H-indole-3-carboxamide 16e (0.10 g, 0.46 mmole) and Cs$_2$CO$_3$ (0.149 g, 0.46 mmole) in a manner as previously described for example 1 to give a yellow solid (0.105 g, 40%). $^1$H NMR (300 MHz, CDCl$_3$) δ 8.48 (1H, d, J=5.4 Hz), 7.82 (1H, s), 7.75 (1H, d, J=8.7 Hz), 7.15 (1H, d, J=2.1 Hz), 7.02 (1H, dd, J=2.1, 8.7 Hz), 6.56 (1H, d, J=5.4 Hz), 5.91 (1H, d, J=4.7 Hz), 4.82 (1H, m), 4.07 (2H, m), 3.87 (1H, m), 3.68 (1H, m), 3.65 (3H, s), 3.05 (3H, d, J=4.7 Hz), 2.84 (3H, s), 2.73 (3H, s), 2.17 (2H, m), 1.45 (9H, s); HRMS (MH$^+$): Calcd: 578.2450. Found: 578.2437.

Example 35

1,2-Dimethyl-6-[2-(3-methylamino-pyrrolidine-1-carbonyl)-thieno[3,2-b]pyridin-7-yloxy]-1H-indole-3-carboxylic acid methylamide

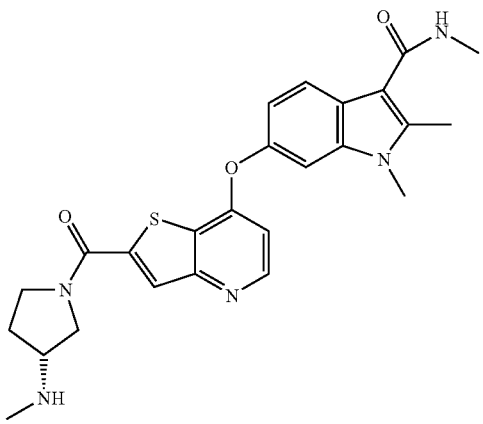

4N HCl in 1,4-dioxane (1.0 ml) was added to a solution of tert-butyl (3R)-1-{[7-({1,2-dimethyl-3-[(methylamino)carbonyl]-1H-indol-6-yl}oxy)thieno[3,2-b]pyridin-2-yl]carbonyl}pyrrolidin-3-yl(methyl)carbamate 34 (0.090 g, 0.16 mmole) in 1,4-dioxane (5 ml). The reaction mixture was stirred at room temperature for 3 hr., then concentrated, in vacuo. The residue was purified by reverse phase chromatography eluting with 10–60% $CH_3CN$ in $H_2O$ to give a white solid (0.020 g, 26%). $^1$H NMR (300 MHz, $CDCl_3$) δ 8.54 (1H, d, J=5.3 Hz), 8.01 (1H, s), 7.83 (1H, d, J=8.7 Hz), 7.53–7.57 (2H, m), 7.03 (1H, dd, J=1.9, 8.7 Hz), 6.63 (1H, d, J=5.3 Hz), 3.88–3.99 (2H, m), 3.67 (3H, s), 3.61 (1H, m), 3.29 (3H, m), 2.80 (3H, d, J=4.50 Hz), 2.61 (3H, s), 2.30 (3H, d, J=10.55 Hz), 1.78–1.83 (1H, m); ESIMS (MH$^+$): 478.10.

Anal. Calcd. For $C_{25}H_{27}N_5O_3S.1.2$ $CH_2Cl_2$: C, 54.30; H, 5.11; N, 12.09. Found: C, 53.95; H, 5.52; N, 11.96.

Example 36

6-[2-(3,4-Dimethoxy-pyrrolidine-1-carbonyl)-thieno[3,2-b]pyridin-7-yloxy]-1,2-dimethyl-1H-indole-3-carboxylic acid methylamide (36).

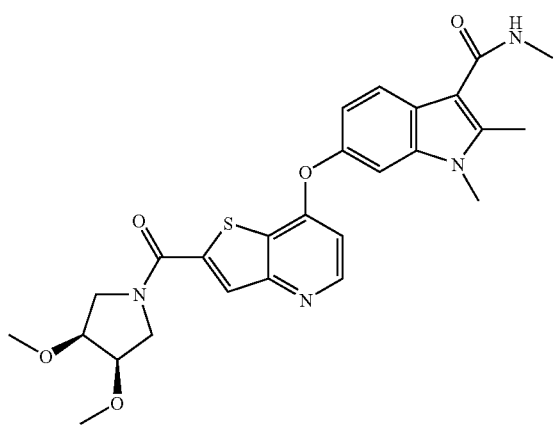

This material was prepared by the reaction of 7-chloro-2-{[(3R,4S)-3,4-dimethoxypyrrolidin-1-yl]carbonyl}thieno[3,2-b]pyridine 5d (0.152 g, 0.47 mmole) with 6-hydroxy-N,1,2-trimethyl-1H-indole-3-carboxamide 16e (0.102 g, 0.47 mmole) and $Cs_2CO_3$ (0.153 g, 0.47 mmole) in a manner as previously described for example 1 to give an off-white solid (0.093 g, 39%). $^1$H NMR (300 MHz, $CDCl_3$) δ 8.42 (1H, d, J=5.3 Hz), 7.84 (1H, s), 7.77 (1H, dd, J=3.8, 8.7 Hz), 7.31 (1H, d, J=2.30 Hz), 3.97 (1H, dd, J=2.3, 8.7 Hz), 6.63 (1H, d, J=5.3 Hz), 4.04 (4H, m), 3.68 (2H, m), 3.64 (3H, s), 3.42 (3H, s), 3.38 (3H, s), 2.90 (3H, s), 2.59 (3H, s); ESIMS (MH$^+$): 409.15.

Anal. Calcd. For $C_{26}H_{28}N_4O_5S.0.2$ $CH_2Cl_2.0.5EtOAc$: C, 59.46; H, 5.73; N, 9.84. Found: C, 59.09; H, 5.95; N, 9.93.

Example 37

6-[2-(3,4-Dihydroxy-pyrrolidine-1-carbonyl)-thieno[3,2-b]pyridin-7-yloxy]-1,2-dimethyl-1H-indole-3-carboxylic acid methylamide (37).

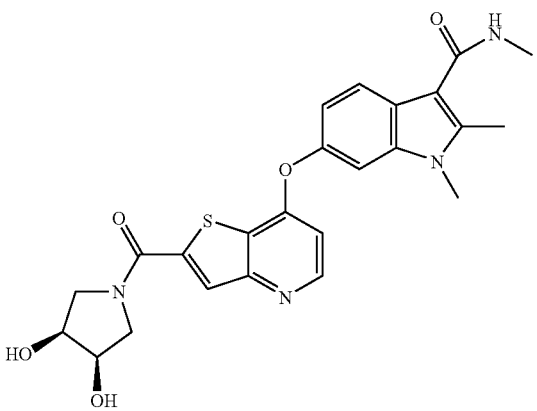

This material was prepared by treating 6-[(2-{[(3R,4S)-3,4-dimethoxypyrrolidin-1-yl]carbonyl}thieno[3,2-b]pyridin-7-yl)oxy]-1,2-dimethyl-1H-indole-3-carboxylic acid methylamide 36 (0.065 g, 0.13 mmole) with 1.0 M $BBr_3$ in $CH_2Cl_2$ (0.070 ml, 0.77 mmole) in a manner as described previously for example 1d to give a white solid (0.017 g, 33%). $^1$H NMR (300 MHz, $CD_3OD$) δ 8.38 (1H, d, J=5.5 Hz), 7.79 (2H, m), 7.28 (1H, d, J=2.1 Hz), 6.94 (1H, dd, J=2.1, 8.7 Hz), 6.60 (1H, d, J=5.5 Hz), 5.07–5.13 (2H, m)., 4.41 (1H, m), 3.95 (2H, m), 3.70 (1H, m), 3.61 (3H, s), 2.55 (3H, m), 1.90 (3H, s); ESIMS (MH$^+$): 481.10.

Anal. Calcd. For $C_{24}H_{24}N_4O_5S.0.2CH_2Cl_2.H_2O$: C, 56.38; H, 5.16; N, 10.87. Found: C, 56.36; H, 5.09; N, 10.60.

Example 38(a)

7-Chloro-2-pyridin-4-ylthieno[3,2-b]pyridine

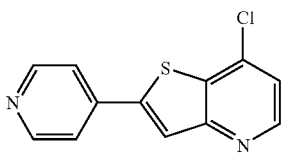

Tereakis(triphenylphosphine)palladium (54 mg, 0.05 mmole) was added to a solution of 4-(tributylstannyl)pyridine (0.432 g, 1.17 mmole) and 7-chloro-2-iodothieno[3,2-b]pyridine (0.347 g, 1.17 mmole) in DMF (5 ml). The reaction mixture was stirred at reflux for 3h, cooled to room temperature. The mixture was filtered, washed with $CH_2Cl_2$ and was partitioned between H₂O (50 ml) and CH₂Cl₂ (2×50 ml). The combined organic layers were dried over MgSO₄ and concentrated. The residue was purified by flash column chromatography eluting with 30–60% EtOAc in hexane to give pale yellow color solid (0.103 g, 36%); ¹H NMR (300 MHz, CDCl₃) δ 8.61 (1H, d, J=5.1 Hz), 7.95 (1H, s), 7.66 (2H, m), 7.44 (2H, m), 7.31 (1H, d, J=5.1 Hz); ESIMS (MH⁺): 481.10.

Example 38

1,2-Dimethyl-6-(2-pyridin-4-yl-thieno[3,2-b]pyridin-7-yloxy)-1H-indole-3-carboxylic acid methylamide

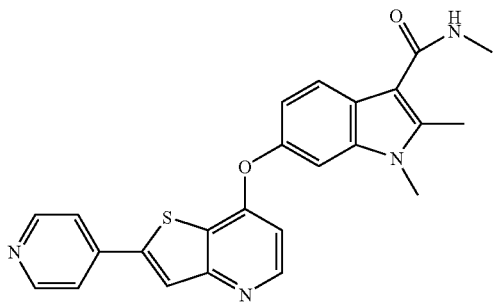

This material was prepared by the reaction 7-chloro-2-pyridin-4-ylthieno[3,2-b]pyridine 38a (0.103 g, 0.42 mmole) with 6-hydroxy-N,1,2-trimethyl-1H-indole-3-carboxamide 16e (0.070 g, 0.32 mmole) and Cs₂CO₃ (0.104 g, 0.32 mmole) in a manner as previously described for example 1 to give an off-white solid (0.055 g, 31%). ¹H NMR (300 MHz, DMSO-d₆) δ 8.70 (2H, m), 8.52 (1H, m), 8.37 (1H, m), 7.87 (3H, m), 7.56 (2H, m), 7.05 (1H, d, J=8.3 Hz), 6.59 (1H, m), 3.68 (3H, s), 2.80 (3H, s), 2.61 (3H, s); ESIMS (MH⁺): 429.05.

Anal. Calcd. For C₂₄H₂₀N₄O₂S.0.5 CH₂Cl₂.0.4 EtOAc: C, 61.92; H, 4.82; N, 11.07. Found: C, 61.93; H, 4.97; N, 10.99.

Example 39(a)

7-Chloro-2-(trimethylstannyl)thieno[3,2-b]pyridine

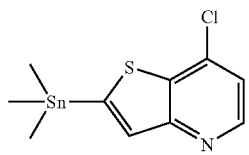

Tereakis(triphenylphosphine)palladium (238 mg, 0.2 mmole) was added to a solution of hexamethyldistannane (1.68 g, 5.1 mmole) and 7-chloro-2-iodothieno[3,2-b]pyridine (1.52 g, 5.1 mmole) in 1,4-dioxane (20 ml). The reaction mixture was stirred at 110° C. for 3 hr. After cooling to room temperature, the mixture was filtered, washed with CH₂Cl₂ and was partitioned between H₂O (100 ml) and CH₂Cl₂ (2×100 ml). The combined organic layers were dried over MgSO₄ and concentrated. The residue was purified by flash column chromatography eluting with 10–15% EtOAc in hexane to give an orange solid (1.09 g, 63%). ¹H NMR (300 MHz, CDCl₃) δ 8.16 (1H, d, J=5.1 Hz), 6.87 (1H, s), 6.82 (1H, d, J=5.1 Hz), 0.08 (9H, m); ESIMS (MH⁺): 333.95.

Example 39(b)

7-Chloro-2-pyrimidin-5-ylthieno[3,2-b]pyridine

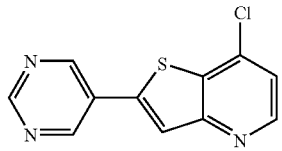

Tereakis(triphenylphosphine)palladium (17 mg) was added to a solution of 5-bromopyrimidine (0.057 g, 0.36 mmole) and 7-chloro-2-(trimethylstannyl)thieno[3,2-b]pyridine 39a (0.119 g, 0.36 mmole) in toluene (10 ml). The reaction mixture was stirred at 90° C. overnight. After cooling to room temperature, the mixture was filtered, washed with CH₂Cl₂ and was partitioned between H₂O (20 ml) and CH₂Cl₂ (2×20 ml). The combined organic layers were dried over MgSO₄ and concentrated. The residue was purified by flash column chromatography eluting with 0–1% MeOH in CH₂Cl₂ to give white solid (0.045 g, 51%); ¹H NMR (300 MHz, C₆D₆) δ 9.25 (1H, s), 9.10 (2H, s), 8.64 (1H, d, J=5.1 Hz), 7.89 (1H, s), 7.34 (1H, d, J=5.1 Hz); ESIMS (MH⁺): 248.00.

Example 39

1,2-Dimethyl-6-(2-pyrimidin-5-yl-thieno[3,2-b]pyridin-7-yloxy)-1H-indole-3-carboxylic acid methylamide

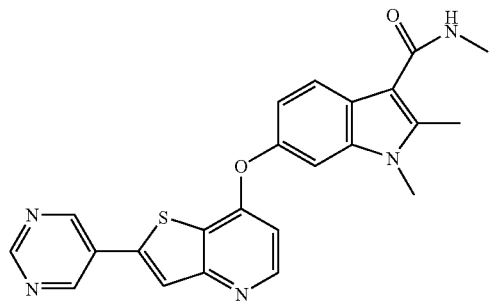

This material was prepared by the reaction of 7-chloro-2-pyrimidin-5-ylthieno[3,2-b]pyridine 39b (0.045 g, 0.18 mmole) with 6-hydroxy-N,1,2-trimethyl-1H-indole-3-carboxamide 16e (0.040 g, 0.18 mmole) and Cs₂CO₃ (0.059 g, 0.18 mmole) in a manner as previously described for example 1 to give an off-white solid (0.018 g, 23%). ¹H NMR (300 MHz, CD₃OD) δ 9.23 (3H, m), 8.63 (1H, d, J=6.2 Hz), 8.11 (1H, s), 7.82 (1H, d, J=8.5 Hz), 7.43 (1H, s), 7.01 (2H, m), 3.63 (3H, s), 2.88 (3H, s), 2.55 (3H, s); ESIMS (MH⁺): 430.10.

Anal. Calcd. For C₂₄H₂₀N₄O₂S.1.0 CH₂Cl₂.1.5 CH₃OH: C, 54.45; H, 4.84; N, 12.45. Found: C, 54.12; H, 4.89; N, 12.30.

Example 40(a)

2-[2-(7-Chlorothieno[3,2-b]pyridin-2-yl)-1,3-thiazol-4-yl]propan-2-ol

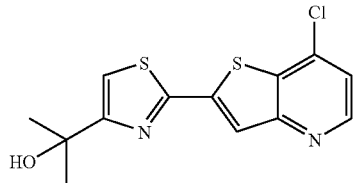

The title compound was prepared by the method described in PC10795A, section A, example 27.

Example 40

6-{2-[4(1-Hydroxy-1-methyl-ethyl)-thiazol-2-yl]-thieno[3,2-b]pyridin-7-yloxy}-1,2-dimethyl-1H-indole-3-carboxylic acid methylamide

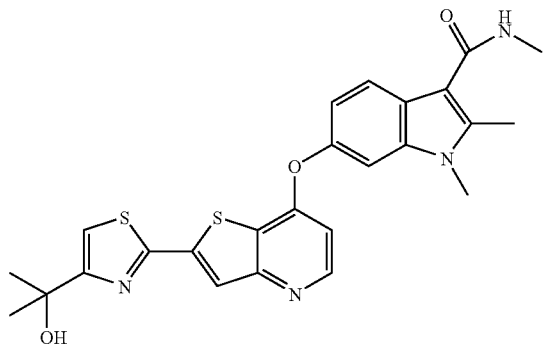

This material was prepared by the reaction of 2-[2-(7-chlorothieno[3,2-b]pyridin-2-yl)-1,3-thiazol-4-yl]propan-2-ol 40a (0.099 g, 0.32 mmole) with 6-hydroxy-N,1,2-trimethyl-1H-indole-3-carboxamide 16e (0.071 g, 0.32 mmole) and Cs$_2$CO$_3$ (0.106 g, 0.32 mmole) in a manner as previously described for example 1 to give a yellow color solid (0.116 g, 73%). $^1$H NMR (300 MHz, DMSO-d$_6$) δ 8.50 (1H, d, J=5.46 Hz), 8.12 (1H, s), 7.84 (1H, d, J=8.67 Hz), 7.58 (2H, m), 7.54 (1H, d, J=2.07 Hz), 7.04 (1H, dd, J=8.67, 2.26 Hz), 6.59 (1H, d, J=5.46 Hz), 3.68 (3H, s), 2.80 (1H, d, J=4.71 Hz), 2.61 (3H, s), 2.53 (3H, s), 1.50 (6H, s).

Anal. Calcd. For C$_{22}$H$_{24}$N$_4$O$_3$S$_2$.0.45 CH$_2$Cl$_2$.1.0 CH$_3$OH: C, 55.64; H, 5.18; N, 9.95. Found: C, 56.37; H, 5.22; N, 9.89.

Example 41(a)

7-Chloro-2-(1,3-thiazol-2-yl)thieno[3,2-b]pyridine

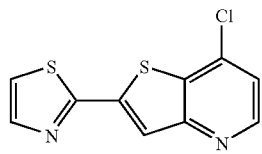

This material was prepared by coupling of 7-chloro-2-(trimethylstannyl)thieno[3,2-b]pyridine 39a (0.140 g, 0.42 mmole) and 2-bromo-1,3-thiazole (0.038 ml, 0.42 mmole) with tereakis(triphenylphosphine)palladium(0) (0.019 g) in a manner as previously described in example 39b to give a yellow solid (0.049 g, 46%). $^1$H NMR (300 MHz, CDCl$_3$) δ 8.59 (1H, d, J=5.1 Hz), 7.93 (1H, s), 7.89 (1H, d, J=3.4 Hz), 7.45 (1H, d, J=3.4 Hz), 7.30 (1H, d, J=5.1 Hz).

Example 41

1,2-Dimethyl-6-(2-thiazol-2-yl-thieno[3,2-b]pyridin-7-yloxy)-1H-indole-3-carboxylic acid methylamide

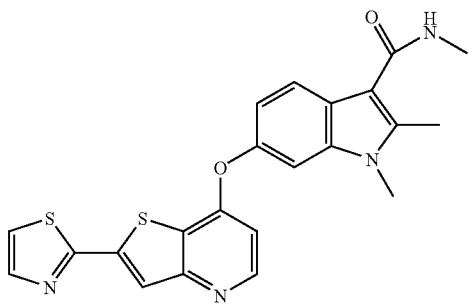

This material was prepared by the reaction of 7-chloro-2-(1,3-thiazol-2-yl)thieno[3,2-b]pyridine 41a (0.049 g, 0.19 mmole) with 6-hydroxy-N,1,2-trimethyl-1H-indole-3-carboxamide 16e (0.043 g, 0.19 mmole) and Cs$_2$CO$_3$ (0.062 g, 0.19 mmole) in a manner as previously described for example 1 to give an off-white solid (0.050 g, 60%). $^1$H NMR (300 MHz, DMSO-d$_6$) δ 8.52 (1H, d, J=5.4 Hz), 8.18 (1H, s), 7.93 (2H, m), 7.84 (1H, d, J=8.9 Hz), 7.56 (2H, m), 7.05 (1H, m), 6.63 (1H, d, J=5.4 Hz), 3.68 (3H, s), 2.80 (3H, d, J=4.5 Hz), 2.61 (3H, s); ESIMS (MH$^+$): 430.10.

Anal. Calcd. For C$_{22}$H$_{18}$N$_4$O$_2$S$_2$.0.45 CH$_2$Cl$_2$.1.0 CH$_3$OH: C, 55.64; H, 5.18; N, 9.95. Found: C, 56.37; H, 5.22; N, 9.89.

Example 42(a)

7-Chloro-2-pyridin-2-ylthieno[3,2-b]pyridine

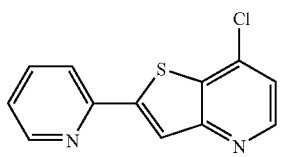

This material was prepared by coupling 7-chloro-2-(trimethylstannyl)thieno[3,2-b]pyridine 39a (0.255 g, 0.77 mmole) with 2-bromopyridine (0.121 g, 0.77 mmole) using tereakis(triphenylphosphine)palladium(0) (0.036 g) as catalyst in a manner as previously described in example 39b to give a white solid (0.058 g, 31%). $^1$H NMR (300 MHz, CDCl$_3$) δ 8.66 (1H, m), 8.57 (1H, d, J=5.1 Hz), 8.00 (1H, s), 7.83 (3H, m), 7.27 (1H, d, J=5.1 Hz); ESIMS (MH$^+$): 246.95.

Example 42

1,2-Dimethyl-6-(2-pyridin-2-yl-thieno[3,2-b]pyridin-7-yloxy)-1H-indole-3-carboxylic acid methylamide

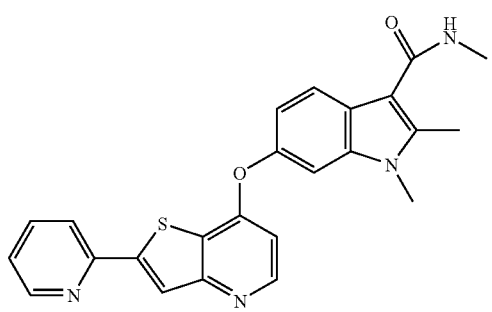

This material was prepared by the reaction of 7-chloro-2-pyridin-2-ylthieno[3,2-b]pyridine (0.100 g, 0.41 mmole) 42a with 6-hydroxy-N,1,2-trimethyl-1H-indole-3-carboxamide 16e (0.089 g, 0.41 mmole) and $Cs_2CO_3$ (0.134 g, 0.41 mmole) in a manner as previously described for example 1 to give an off-white solid (0.048 g, 27%). $^1$H NMR (300 MHz, DMSO-$d_6$) δ 8.63 (1H, d, J=4.5 Hz), 8.49 (1H, d, J=5.5 Hz), 8.35 (1H, s), 8.28 (1H, d, J=7.72 Hz), 7.95 (1H, t, J=8.4 Hz), 7.84 (1H, d, J=8.6 Hz), 7.58 (1H, d, J=4.5 Hz), 7.54 (1H, d, J=1.9 Hz), 7.43 (1H, m), 7.04 (1H, dd, J=1.9, 8.6 Hz), 6.58 (1H, d, J=5.5 Hz), 3.68 (3H, s), 2.80 (3H, s), 2.62 (3H, s); ESIMS (MH$^+$): 429.05.

Anal. Calcd. For $C_{24}H_{20}N_4O_2S \cdot 0.8\ H_2O$: C, 65.08; H, 4.92; N, 12.65. Found: C, 65.16; H, 4.93; N, 12.40.

Example 43(a)

2-(7-Chlorothieno[3,2-b]pyridin-2-yl)-1,3-thiazole-4-carboxylic acid

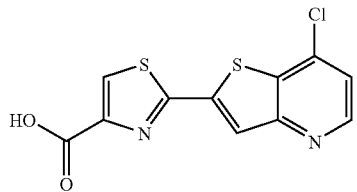

To a solution of methyl 2-(7-chlorothieno[3,2-b]pyridin-2-yl)-1,3-thiazole-4-carboxylate (0.200 g, 0.62 mmole), prepared by the method described in PC10795A, section A, example 26, in EtOAc (5 ml) was added 1N aqueous NaOH solution (1.85 ml, 1.85 mmole). The reaction mixture was stirred at 50° C. for 1 h, cooled to room temperature, diluted with $H_2O$ (10 ml) and acidified with 1N HCl to pH~2. The resulting solution was extracted with 10% MeOH in $CH_2Cl_2$ (5×10 ml), dried over $MgSO_4$ and concentrated and dried under vacuum to give yellow solid (0.181 g, 98%). $^1$H NMR (300 MHz, DMSO-$d_6$) □ 7.67 (1H, d, J=5.09 Hz) 8.41 (1H, s) 8.65 (1H, s) 8.71 (1H, bs); ESIMS (MH$^+$): 309.95.

Example 43(b)

2-(7-Chlorothieno[3,2-b]pyridin-2-yl)-N-methyl-1,3-thiazole-4-carboxamide

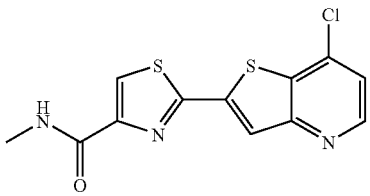

To a solution of 2-(7-chlorothieno[3,2-b]pyridin-2-yl)-1,3-thiazole-4-carboxylic acid 43a (0.123 g, 0.41 mmole) in $CH_2Cl_2$ cooled at 0° C. was added 2.0 M oxalyl chloride in $CH_2Cl_2$ (0.520 ml, 1.04 mmole) and DMF (2 drops). The reaction mixture was stirred at room temperature for 1 h, concentrated and dried. The residue was taken into $CH_2Cl_2$ (10 ml), and 2.0 M methylamine in $CH_2Cl_2$ (0.250 ml, 0.492 mmole) was added. The reaction mixture was stirred at room temperature for 1 h, and then partitioned between $H_2O$ (100 ml) and $CH_2Cl_2$ (2×100 ml). The combined organic layers were dried over $MgSO_4$ and concentrated. The residue was purified by flash column chromatography eluting with 2–8% $CH_3OH$ in $CH_2Cl_2$ to give yellow solid (0.116 g, 91%). $^1$H NMR (300 MHz, CDCl$_3$) δ 8.62 (1H, d, J=5.1 Hz), 8.19 (1H, s), 7.96 (1H, s), 7.33 (1H, d, J=5.1 Hz), 3.06 (3H, d, J=4.9 Hz); ESIMS (MH$^+$): 309.95.

Example 43

1,2-Dimethyl-6-[2-(4-methylcarbamoyl-thiazol-2-yl)-thieno[3,2-b]pyridin-7-yloxy]-1H-indole-3-carboxylic acid methylamide

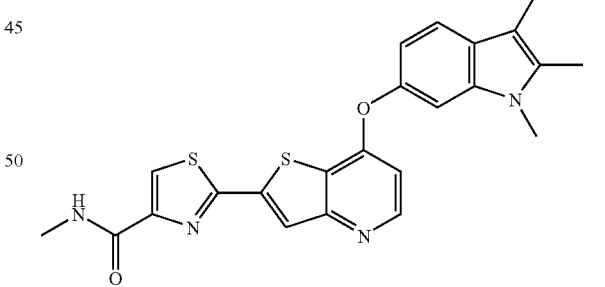

This material was prepared by the reaction of 2-(7-chlorothieno[3,2-b]pyridin-2-yl)-N-methyl-1,3-thiazole-4-carboxamide 43b (0.125 g, 0.403 mmole) with 6-hydroxy-1,2-dimethyl-1H-indole-3-carboxylic acid methylamide 16e (0.092 g, 0.403 mmole) and $Cs_2CO_3$ (0.137 g, 0.42 mmole) in a manner as previously described for example 1 to give an off-white solid (0.015 g, 9%). $^1$H NMR (300 MHz, DMSO-$d_6$) δ 8.54 (1H, d, J=5.3 Hz), 8.43 (1H, d, J=4.7 Hz), 8.40 (1H, s), 8.30 (1H, s), 7.84 (1H, d, J=8.7 Hz), 7.56 (2H, m), 7.05 (1H, dd, J=2.1, 8.7 Hz), 6.63 (1H, d, J=5.3 Hz), 3.68 (3H, s), 2.81 (6H, m), 2.61 (3H, s); ESIMS (MH$^+$): 492.05.

Anal. Calcd. For C$_{24}$H$_{21}$N$_4$O$_3$S$_2$Cl.0.5 CH$_2$Cl$_2$: C, 55.10; H, 4.15; N, 13.11. Found: C, 55.14; H, 4.42; N, 12.99.

Example 44(a)

tert-Butyl pyrrolidin-3-ylmethylcarbamate

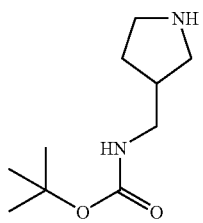

To a solution of tert-butyl (1-benzylpyrrolidin-3-yl)methylcarbamate (3.0 g, 10.33 mmole) in EtOAc (100 ml) was added Pd(OH)$_2$ on carbon (0.3 g). The mixture was stirred under H$_2$ balloon at room temperature for 3 h and filtered through Celite. The filtrate was concentrated to give colorless oil (1.87 g, 90%).

Example 44(b)

tert-Butyl {1-[(7-chlorothieno[3,2-b]pyridin-2-yl)carbonyl]pyrrolidin-3-yl}methylcarbamate

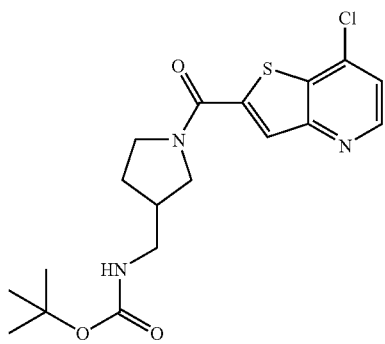

This material was prepared from 7-chlorothieno[3,2-b]pyridine-2-carboxylic acid lithium salt (2.27 g, 10.33 mmole), SOCl$_2$ (10 ml), tert-butyl pyrrolidin-3-ylmethylcarbamate 44a (2.07 g, 10.33 mmole) and Et$_3$N (1.44 ml, 10.33 mmole) in a manner as previously described for example 9d to give a yellow solid (2.44 g, 60%). $^1$H NMR (300 MHz, CDCl$_3$) δ 7.85 (1H, s), 7.34 (1H, d, J=5.1 Hz), 4.73 (1H, s), 3.96 (1H, m), 3.85 (1H, m), 3.70 (1H, m), 3.55 (1H, m), 3.42 (1H, m), 3.22 (2H, m), 2.54 (1H, m), 2.12 (1H, m), 1.43, 1.41 (9H, s); ESIMS (M$^+$): 396.05.

Example 44 tert-Butyl (1-{[7-({1,2-dimethyl-3-[(methylamino)carbonyl]-1H-indol-6-yl}oxy)thieno[3,2-b]pyridin-2-yl]carbonyl}pyrrolidin-3-yl)methylcarbamate

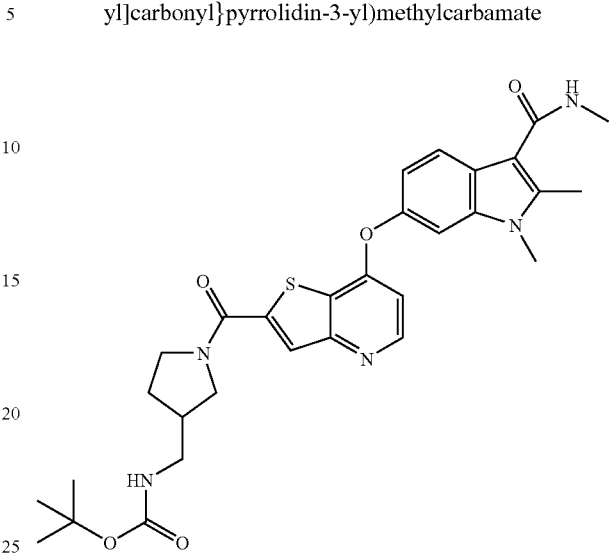

This material was prepared by the reaction of tert-butyl {1-[(7-chlorothieno[3,2-b]pyridin-2-yl)carbonyl]pyrrolidin-3-yl}methylcarbamate 44b (0.206 g, 0.52 mmole) with 6-hydroxy-N,1,2-trimethyl-1H-indole-3-carboxamide 16e (0.113 g, 0.52 mmole) and Cs$_2$CO$_3$ (0.169 g, 0.52 mmole) in a manner as previously described for example 1 to give an off-white solid (0.168 g, 56%). $^1$H NMR (300 MHz, CDCl$_3$) δ 8.48 (1H, d, J=5.3 Hz), 7.82 (1H, s), 7.75 (1H, d, J=8.7 Hz), 7.25 (1H, s), 7.15 (1H, d, J=2.0 Hz), 7.02 (1H, dd, J=2.0, 8.7 Hz), 6.56 (1H, d, J=5.3 Hz), 5.89 (1H, s), 4.74 (1H, s), 3.97 (1H, m), 3.84 (1H, m), 3.65 (3H, s), 3.44 (1H, m), 3.20 (2H, m), 3.06 (3H, d, J=4.71 Hz), 2.72 (3H, s), 1.77 (1H, m), 1.44, 1.42 (9H, s), 0.84 (2H, m).

Anal. Calcd. For C$_{30}$H$_{35}$N$_5$O$_5$S.1.0 H$_2$O.1.2 EtOAc: C, 59.59; H, 6.70; N, 9.98. Found: C, 59.54; H, 6.44; N, 9.85.

Example 45

6-[2-(3-Aminomethyl-pyrrolidine-1-carbonyl)-thieno[3,2-b]pyridin-7-yloxy]-1,2-dimethyl-1H-indole-3-carboxylic acid methylamide

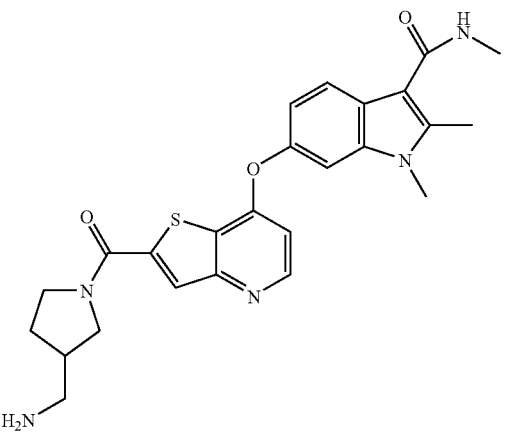

Trifluoroacetic acid (1 ml) was added to a stirred solution of tert-butyl (1-{[7-({1,2-dimethyl-3-[(methylamino)carbonyl]-1H-indol-6-yl}oxy)thieno[3,2-b]pyridin-2-yl]carbonyl}pyrrolidin-3-yl)methyl carbamate 44 (0.148 g, 0.26 mmole). The reaction mixture was stirred at room temperature for 15 min and concentrated. The residue was triturated with Et₂O, filtrated to give a yellow solid (0.050 g, 40%). ¹H NMR (300 MHz, DMSO-d₆) δ 8.56 (1H, d, J=5.5 Hz), 8.05 (1H, s), 7.84 (3H, m), 7.58 (1H, d, J=4.5 Hz), 7.54 (1H, d, J=1.7 Hz), 7.02 (1H, d, J=8.8 Hz), 6.67 (1H, d, J=5.5 Hz), 4.08 (1H, m), 3.92 (1H, m), 3.78 (1H, m), 3.67 (3H, s), 3.54 (1H, m), 3.36 (1H, m), 2.96 (2H, m), 2.80 (3H, d, J=4.33 Hz), 2.61 (3H, s), 2.09 (1H, m), 1.78 (1H, m); ESIMS (MH⁺): 478.10.

Anal. Calcd. For C₂₅H₂₇N₅O₃Se 1.0 CF₃CO₂H.2.7 CH₂Cl₂: C, 46.69; H, 4.41; N, 9.17. Found: C, 46.87; H, 4.27; N, 9.06.

Example 46(a)

N-({1-[(7-chlorothieno[3,2-b]pyridin-2-yl)carbonyl]pyrrolidin-3-yl}methyl)-N-methylamine

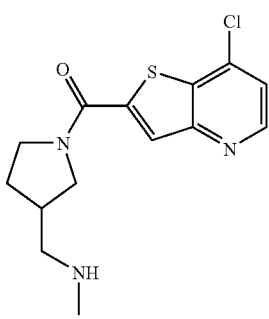

NaH (0.033 g, 0.82 mmole) and CH₃I (0.064 ml, 1.02 mmole) were added to a solution of tert-butyl {1-[(7-chlorothieno[3,2-b]pyridin-2-yl)carbonyl]pyrrolidin-3-yl}methyl-carbamate 43 (0.271 g, 0.68 mmole) in THF at 0° C. The reaction mixture was stirred and warmed to room temperature overnight and partitioned between H₂O (50 ml) and EtOAc (2×50 ml). The combined organic layers were dried over MgSO₄ and concentrated. The residue was purified by flash column chromatography eluting with 0–2% CH₃OH in CH₂Cl₂ to give a yellow solid (0.283 g, 82%). ¹H NMR (300 MHz, CDCl₃) δ 8.62 (1H, d, J=5.1 Hz), 7.85 (1H, s), 7.34 (1H, d, J=5.1 Hz), 4.72 (1H, s), 3.99 (1H, m), 3.77 (2H, m), 3.50 (1H, m), 3.19 (2H, m), 2.88 (3H, d, J=12.06 Hz), 2.62 (1H, m), 2.14 (1H, m), 1.83 (1H, m); ESIMS (MH⁺): 310.10.

Example 46

1,2-Dimethyl-6-[2-(3-methylaminomethyl-pyrrolidine-1-carbonyl)-thieno[3,2-b]pyridin-7-yloxy]-1H-indole-3-carboxylic acid methylamide

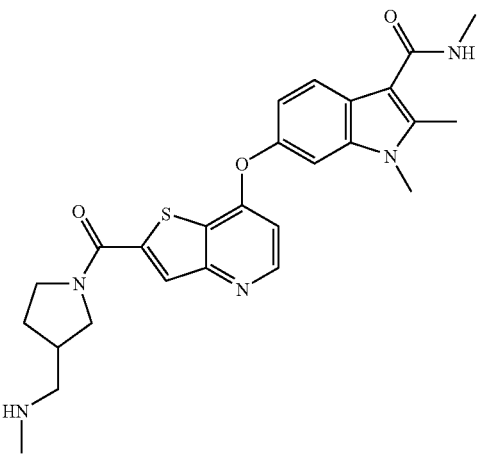

This material was prepared by the reaction of N-({1-[(7-chlorothieno[3,2-b]pyridin-2-yl)carbonyl]pyrrolidin-3-yl}methyl)-N-methylamine 46a (0.115 g, 0.41 mmole) with 6-hydroxy-N,1,2-trimethyl-1H-indole-3-carboxamide 16e (0.090 g, 0.41 mmole) and Cs₂CO₃ (0.147 g, 0.41 mmole) in a manner as previously described for example 1 to give an off-white solid (0.110 g, 54%). ¹H NMR (300 MHz, DMSO-d₆) δ 8.54 (1H, s), 8.01 (1H, s), 7.83 (1H, m), 7.54 (2H, m), 7.02 (1H, s), 6.64 (1H, d, J=5.46 Hz), 3.93 (2H, m), 3.68 (3H, s), 3.54 (2H, m), 3.16 (2H, m), 2.99 (1H, m), 2.80 (3H, s), 2.79 (3H, s), 1.98 (2H, m), 1.65 (1H, m); HRMS (MH⁺): Calcd: 492.2064. Found: 492.2048.

Example 47(a)

Methyl N-[(7-chlorothieno[3,2-b]pyridin-2-yl)carbonyl]-L-serinate

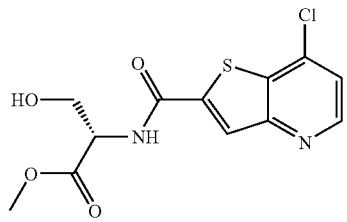

This material was prepared from lithium 7-chlorothieno[3,2-b]pyridine-2-carboxylic acid (2.69 g, 12.25 mmole), SOCl₂ (10 ml), L-serine methyl ester hydrochloride (2.86 g, 18.4 mmole) and Et₃N (5.12 ml, 37.7 mmole) in a manner as previously described for example 9d to give a white solid (2.09 g, 54%). ¹H NMR (300 MHz, CDCl₃) δ 8.61 (1H, d, J=5.1 Hz), 8.02 (1H, s), 7.35 (1H, d, J=5.1 Hz), 4.89 (1H, m), 4.15 (2H, m), 3.84 (3H, m).

Example 47(b)

2-[2-(7-Chlorothieno[3,2-b]pyridin-2-yl)-4,5-dihydro-1,3-oxazol-4-yl]propan-2-ol

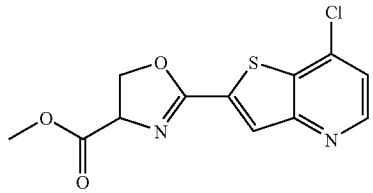

Burgess reagent (0.606 g, 2.54 mmole) was added to a stirred solution of methyl N-[(7-chlorothieno[3,2-b]pyridin-2-yl)carbonyl]-L-serinate 47a (0.728 g, 2.31 mmole) in THF (10 ml). The reaction mixture was stirred at reflux for 2 h, quenched with MeOH (1 ml) and was partitioned between saturated H$_2$O (30 ml) and EtOAc (2×30 ml). The combined organic layers were dried over MgSO$_4$ and concentrated. The residue was purified by flash column chromatography eluting with 20–60% EtOAc in hexane to a white solid (0.314 g, 46%). $^1$H NMR (300 MHz, CDCl$_3$) δ 8.66 (1H, d, J=5.1 Hz), 8.08 (1H, s), 7.37 (1H, d, J=5.1 Hz), 5.03 (1H, m), 4.81 (1H, t, J=8.4 Hz), 4.70 (1H, m), 3.85 (3H, s); ESIMS (MH$^+$): 296.95.

Example 47(c)

Methyl 2-(7-chlorothieno[3,2-b]pyridin-2-yl)-1,3-oxazole-4-carboxylate

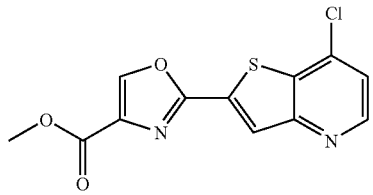

MnO$_2$ (0.628 mg) was added to a solution of 2-[2-(7-chlorothieno[3,2-b]pyridin-2-yl)-4,5-dihydro-1,3-oxazol-4-yl]propan-2-ol 47b (0.314 g, 1.06 mmole) in benzene (15 ml). The reaction mixture was heated to reflux for 2 hr., then filtered through celite. The filtrate was concentrated and the residue was purified by flash column chromatography eluting with 10–60% EtOAc in hexane to give a white solid (0.220 g, 71%). $^1$H NMR (300 MHz, CDCl$_3$) δ 8.65 (1H, d, J=5.0 Hz), 8.35 (1H, s), 8.20 (1H, s), 7.36 (1H, d, J=5.0 Hz), 3.97 (3H, s); ESIMS (MH$^+$): 294.95.

Example 47(d)

2-[2-(7-chlorothieno[3,2-b]pyridin-2-yl)-1,3-oxazol-4yl]propan-2-ol

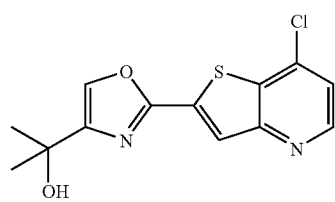

MeMgBr (0.483 ml, 1.45 mmole) was added to a solution of methyl 2-(7-chlorothieno[3,2-b]pyridin-2-yl)-1,3-oxazole-4-carboxylate 47c (0.171 g, 0.58 mmole) in THF (10 ml) at 0° C. The reaction mixture was stirred at 0° C. for 1 h, quenched with saturated NH$_4$Cl (1 ml) and partitioned between saturated NaHCO$_3$ (20 ml) and EtOAc (2×20 ml). The combined organic layers were dried over MgSO$_4$ and concentrated. The residue was purified by flash column chromatography eluting with 0–2% CH$_3$OH in 1:1 EtOAc and CH$_2$Cl$_2$ to give a off-white solid (0.070 g, 41%). $^1$H NMR (300 MHz, CDCl$_3$) δ 8.65 (1H, d, J=5.0 Hz), 8.35 (1H, s), 8.20 (1H, s), 7.36 (1H, d, J=5.0 Hz), 3.97 (6H, s); ESIMS (MH$^+$): 294.95.

Example 47

6-{2-[4-(1-Hydroxy-1-methyl-ethyl)-oxazol-2-yl]-thieno[3,2-b]pyridin-7-yloxy}1,2-dimethyl-1H-indole-3-carboxylic acid methylamide (47)

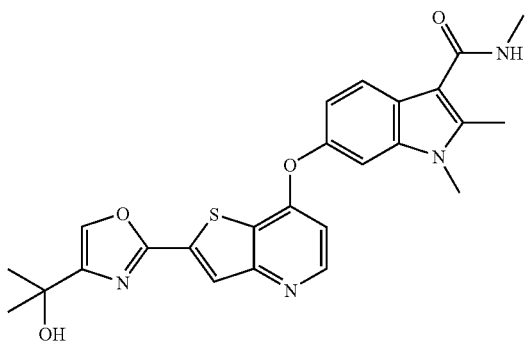

This material was prepared by the reaction of 2-[2-(7-chlorothieno[3,2-b]pyridin-2-yl)-1,3-oxazol-4-yl]propan-2-ol 47d (0.068 g, 0.23 mmole) with 6-hydroxy-N,1,2-trimethyl-1H-indole-3-carboxamide 16e (0.051 g, 0.23 mmole) and Cs$_2$CO$_3$ (0.081 g, 0.23 mmole) in a manner as previously described for example 1 to give a yellow solid (0.046 g, 42%). $^1$H NMR (300 MHz, CD$_3$OD) δ 8.39 (1H, d, J=5.3 Hz), 7.94 (1H, d, J=1.0 Hz), 7.79 (1H, s), 7.77 (1H, s), 7.32 (1H, s), 6.98 (1H, d, J=8.6 Hz), 6.62 (1H, d, J=5.3 Hz), 3.63 (3H, s), 2.90 (3H, s), 2.58 (3H, s), 1.51 (6H, s); ESIMS (MH$^+$): 477.10.

Anal. Calcd. For C$_{25}$H$_{25}$N$_4$O$_4$S.0.25 CH$_2$Cl$_2$: C, 60.80; H, 5.15; N, 11.26. Found: C, 60.84; H, 5.21; N, 10.98.

Example 48(a)

7-Chloro-2-(5-methoxypyridin-2-yl)thieno[3,2-b]pyridine

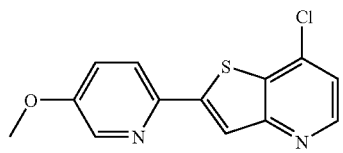

This material was prepared by coupling 7-chloro-2-(trimethylstannyl)thieno[3,2-b]pyridine 39a (0.214 g, 0.64 mmole) with 2-iodo-5-methoxypyridine (0.152 g, 0.64 mmole) using tereakis(triphenylphosphine)palladium(0) (30 mg) as catalyst in a manner as previously described for example 39b to give a yellow solid (0.060 g, 34%). $^1$H NMR (300 MHz, CDCl$_3$) δ 8.55 (1H, d, J=5.1 Hz), 8.43 (1H, s), 8.28 (1H, dd, J=1.3, 4.6 Hz), 7.34 (1H, m), 7.28 (1H, m), 7.24 (1H, d, J=5.8 Hz), 4.04 (3H, s).

Example 48

6-[2-(5-Methoxy-pyridin-2-yl)-thieno[3,2-b]pyridin-7-yloxy]-1,2-dimethyl-1H-indole-3-carboxylic acid methylamide

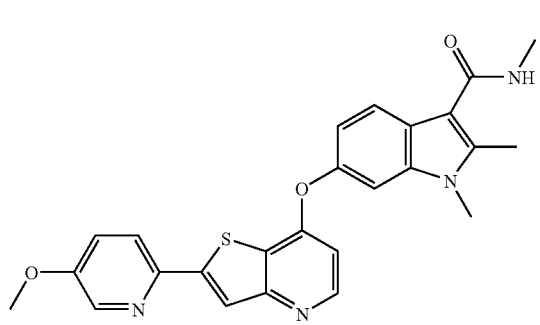

This material was prepared by the reaction 7-chloro-2-(5-methoxypyridin-2-yl)thieno[3,2-b]pyridine 48a (0.058 g, 0.21 mmole) with 6-hydroxy-N,1,2-trimethyl-1H-indole-3-carboxamide 16e (0.046 g, 0.21 mmole) and Cs$_2$CO$_3$ (0.068 g, 0.21 mmole) in a manner as previously described for example 1 to give a pale yellow solid (0.014 g, 15%). $^1$H NMR (300 MHz, CDCl$_3$) δ 8.42 (2H, m), 8.26 (1H, dd, J=1.1, 4.6 Hz), 7.73 (1H, d, J=8.6 Hz), 7.34 (1H, m), 7.27 (1H, d, J=4.6 Hz), 7.15 (1H, d, J=2.0 Hz), 7.05 (1H, dd, J=2.0, 8.6 Hz), 6.49 (1H, d, J=5.31 Hz), 5.91 (1H, bs), 4.03 (3H, s), 3.64 (3H, s), 3.06 (3H, d, J=4.8 Hz), 2.72 (3H, s); ESIMS (MH$^+$): 459.03.

Anal. Calcd. For C$_{25}$H$_{22}$N$_4$O$_3$S.0.7 CH$_3$OH: C, 64.18; H, 5.20; N, 11.65. Found: C, 64.28; H, 5.27; N, 11.47.

Example 49(a)

7-Chloro-2-(6-methoxypyridin-2-yl)thieno[3,2-b]pyridine

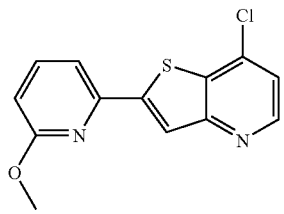

This material was prepared by coupling 7-chloro-2-(trimethylstannyl)thieno[3,2-b]pyridine 39a (0.478 g, 1.44 mmole) with 2-bromo-6-methoxypyridine (0.177 ml, 1.44 mmole) using tereakis(triphenylphosphine)palladium(0) (67 mg) as catalyst in a manner as previously described for example 39b to give a pale yellow solid (0.249 g, 63%). $^1$H NMR (300 MHz, CDCl$_3$) δ 8.56 (1H, d, J=5.1 Hz), 7.98 (1H, s), 7.66 (3H, m), 6.75 (1H, d, J=8.3 Hz), 4.05 (3H, s); ESIMS (MH$^+$): 276.95.

Example 49

6-[2-(6-Methoxy-pyridin-2-yl)-thieno[3,2-b]pyridin-7-yloxy]-1,2-dimethyl-1H-indole-3-carboxylic acid methylamide

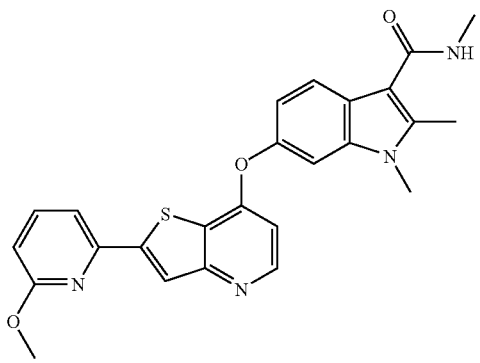

This material was prepared by the reaction of 7-chloro-2-(6-methoxypyridin-2-yl)thieno[3,2-b]pyridine 49a (0.093 g, 0.34 mmole) with 6-hydroxy-N,1,2-trimethyl-1H-indole-3-carboxamide 16e (0.074 g, 0.34 mmole) and Cs$_2$CO$_3$ (0.111 g, 0.34 mmole) in a manner as previously described for example 1 to give a white solid (0.029 g, 19%). $^1$H NMR (300 MHz, CDCl$_3$) δ 8.43 (1H, d, J=5.46 Hz), 7.99 (1H, s), 7.76 (1H, d, J=8.7 Hz), 7.65 (1H, m), 7.45 (1H, d, J=7.4 Hz), 7.18 (1H, d, J=2.0 Hz), 7.07 (1H, dd, J=2.0, 8.7 Hz), 6.73 (1H, d, J=8.1 Hz), 6.47 (1H, m), 5.87 (1H, s), 4.03 (3H, s), 3.66 (3H, s), 3.07 (3H, d, J=4.9 Hz), 2.74 (3H, s); ESIMS (MH$^+$): 459.20.

Anal. Calcd. For C$_{25}$H$_{22}$N$_4$O$_3$S.0.85 H$_2$O: C, 63.37; H, 5.04; N, 11.82. Found: C, 63.48; H, 4.98; N, 11.43.

Example 50(a)

7-Chloro-2-pyrimidin-2-ylthieno[3,2-b]pyridine

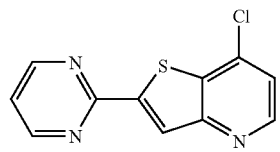

This material was prepared by coupling 7-chloro-2-(trimethylstannyl)thieno[3,2-b]pyridine 39a (0.218 g, 0.66 mmole) with 2-bromopyrimidine (0.104 g, 0.66 mmole) using tereakis(triphenylphosphine) palladium(0) (31 mg) as catalyst in a manner as previously described for example 39b to give a white solid (0.066 g, 40%). $^1$H NMR (300 MHz, CDCl$_3$) δ 8.76 (2H, d, J=4.90 Hz), 8.57 (1H, d, J=5.1 Hz), 8.41 (1H, s), 7.26 (1H, d, J=5.1 Hz), 7.20 (1H, m); ESIMS (MH$^+$): 248.00.

Example 50

1,2-Dimethyl-6-(2-pyrimidin-2-yl-thieno[3,2-b]pyridin-7-yloxy)-1H-indole-3-carboxylic acid methylamide

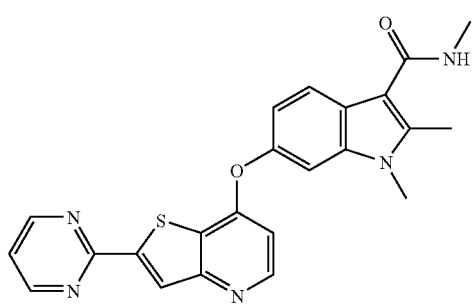

This material was prepared by the reaction of 7-chloro-2-pyrimidin-2-ylthieno[3,2-b]pyridine 50a (0.066 g, 0.23 mmole) with 6-hydroxy-N,1,2-trimethyl-1H-indole-3-carboxamide 16e (0.050 g, 0.23 mmole) and $Cs_2CO_3$ (0.075 g, 0.23 mmole) in a manner as previously described for example 1 to give a white solid (0.041 g, 41%). $^1$H NMR (300 MHz, DMSO-$d_6$) δ 8.90 (2H, d, J=4.9 Hz), 8.50 (1H, d, J=5.3 Hz), 8.29 (1H, s), 7.81 (1H, d, J=8.5 Hz), 7.50 (3H, m), 7.01 (1H, dd, J=2.2, 8.5 Hz), 6.60 (1H, d, J=5.3 Hz), 3.64 (3H, s), 2.76 (3H, d, J=4.5 Hz), 2.57 (3H, s); ESIMS (MH$^+$): 430.10.

Anal. Calcd. For $C_{23}H_{19}N_5O_2S \cdot 0.75\ CH_3OH$: C, 62.90; H, 4.89; N, 15.44. Found: C, 62.92; H, 4.61; N, 15.39.

Example 51(a)

1-(7-Chlorothieno[3,2-b]pyridin-2-yl)propan-1-one

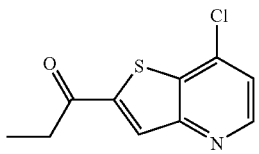

2.5 M nBuLi in hexane (0.619 ml, 1.55 mmole) was added to a solution of 7-chlorothieno[3,2-b]pyridine (0.250 g, 1.47 mmole) in THF (5 ml) at −78° C. The reaction mixture was stirred at −78° C. for 30 min, and then propanoyl chloride (0.162 ml, 1.76 mmole) was added. The reaction mixture stirred at −78° C. and slowly warmed to 0° C. and quenched with $H_2O$ (10 ml), extracted with EtOAc (2×10 ml). The organic layer was dried over $MgSO_4$ and concentrated. The residue was purified by flash column chromatography eluting with 10–70% EtOAc in hexane to a off-white solid (0.084 g, 25%). $^1$H NMR (300 MHz, CDCl$_3$) δ 8.66 (1H, d, J=4.9 Hz), 8.12 (1H, s), 7.38 (1H, d, J=4.9 Hz), 3.09 (2H, q, J=7.3 Hz), 1.29 (3H, t, J=7.3 Hz,); ESIMS (MH$^+$): 225.95.

Example 51

1,2-Dimethyl-6-(2-propionyl-thieno[3,2-b]pyridin-7-yloxy)-1H-indole-3-carboxylic acid methylamide

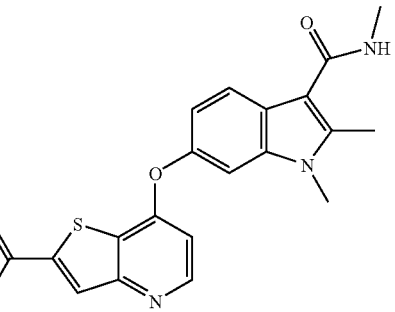

This material was prepared by the reaction of 1-(7-chlorothieno[3,2-b]pyridin-2-yl)propan-1-one 51a (0.062 g, 0.28 mmole) with 6-hydroxy-N,1,2-trimethyl-1H-indole-3-carboxamide 16e (0.061 g, 0.28 mmole) and $Cs_2CO_3$ (0.091 g, 0.28 mmole) in a manner as previously described for example 1 to give an off-white solid (0.035 g, 31%). $^1$H NMR (300 MHz, CDCl$_3$) δ 8.51 (1H, d, J=5.5 Hz), 8.11 (1H, s), 7.76 (1H, d, J=8.6 Hz), 7.15 (1H, d, J=2.1 Hz), 7.02 (1H, dd, J=2.1, 8.6 Hz), 6.58 (1H, d, J=5.5 Hz), 5.87 (1H, d, J=4.3 Hz), 3.66 (3H, s), 3.10 (2H, m), 3.06 (3H, d, J=4.9 Hz), 2.73 (3H, s), 1.31 (3H, t, J=7.3 Hz); ESIMS (MH$^+$): 408.05.

Anal. Calcd. For $C_{22}H_{21}N_3O_3S \cdot 0.15\ CH_2Cl_2$: C, 63.31; H, 5.11; N, 10.00. Found: C, 63.42; H, 5.03; N, 9.83.

Example 52(a)

6-(7-Chlorothieno[3,2-b]pyridin-2-yl)pyridine-2-carbaldehyde

This material was prepared by coupling 7-chloro-2-(trimethylstannyl)thieno[3,2-b]pyridine 39a (0.707 g, 2.17 mmole) with 6-bromopyridine-2-carbaldehyde (0.396 g, 2.17 mmole) using tereakis(triphenylphosphine)palladium (0) (100 mg) as catalyst in a manner as previously described for example 39b to give a white solid (0.161 g, 27%). $^1$H NMR (300 MHz, CDCl$_3$) δ 10.15 (1H, s), 8.61 (1H, d, J=5.1 Hz), 7.93–8.09 (4H, m) 7.31 (1H, d, J=5.1 Hz); ESIMS (MH$^+$): 275.00.

Example 52(b)

N-{[6-(7-Chlorothieno[3,2-b]pyridin-2-yl)pyridin-2-yl]methyl}-N,N-dimethylamine

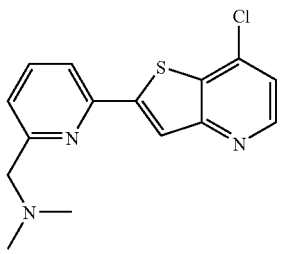

To a solution of 6-(7-chlorothieno[3,2-b]pyridin-2-yl)pyridine-2-carbaldehyde 52a (0.127 g, 0.46 mmole) in THF (20 ml) was added 2.0 M dimethylamine in THF (1.5 ml, 2.3 mmole), NaCNBH$_3$ (0.063 g, 0.92 mmole) and NaOAc (0.076 g, 0.92 mmole). The reaction mixture was stirred at room temperature overnight and concentrated. The residue was purified by flash column chromatography eluting with 2–10% CH$_3$OH in CHCl$_3$ to give a yellow solid (0.086 g, 61%). $^1$H NMR (300 MHz, CD$_3$OD) δ 8.50 (1H, d, J=5.3 Hz), 8.11 (1H, s), 8.03 (1H, d, J=7.9 Hz), 7.90 (1H, t, J=7.9 Hz), 7.41 (2H, m), 4.16 (2H, s), 2.71 (6H, s).

Example 52

6-[2-(6-Dimethylaminomethyl-pyridin-2-yl)-thieno[3,2-b]pyridin-7-yloxy]-1,2-dimethyl-1H-indole-3-carboxyllc acid methylamide

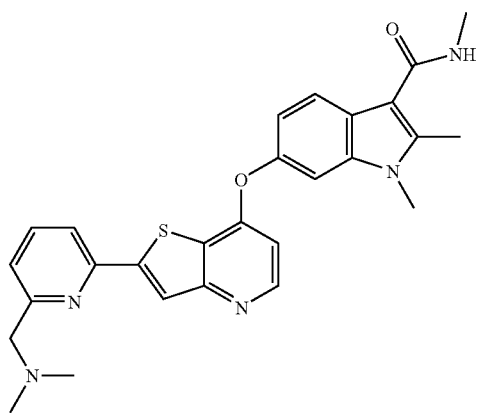

This material was prepared by the reaction of N-{[6-(7-chlorothieno[3,2-b]pyridin-2-yl)pyridin-2-yl]methyl)-N,N-dimethylamine 52b (0.080 0.26 mmole) with 6-hydroxy-N,1,2-trimethyl-1H-indole-3-carboxamide 16e (0.058 g, 0.26 mmole) and Cs$_2$CO$_3$ (0.085 g, 0.26 mmole) in a manner as previously described for example 1 to give a white solid (0.016 g, 13%). $^1$H NMR (300 MHz, CD$_3$OD) δ 8.27 (1H, d, J=5.5 Hz), 7.91 (1H, s), 7.77 (3H, m), 7.31 (1H, d, J=7.0 Hz), 7.24 (1H, d, J=2.0 Hz), 6.93 (1H, dd, J=2.0, 8.6 Hz), 6.49 (1H, d, J=5.5 Hz), 3.57 (5H, m), 2.88 (3H, s), 2.54 (3H, s), 2.26 (6H, s).

Anal. Calcd. For C$_{27}$H$_{27}$N$_5$O$_2$S.1.5 CH$_2$Cl$_2$: C, 55.84; H, 4.93; N, 11.43. Found: C, 55.75; H, 5.15; N, 11.01.

Example 53

6-[2-((R)-3-Hydroxy-pyrrolidine-1-carbonyl)-thieno[3,2-b]pyridin-7-yloxy]-1,2-dimethyl-1H-indole-3-carboxylic acid cyclopropylamide

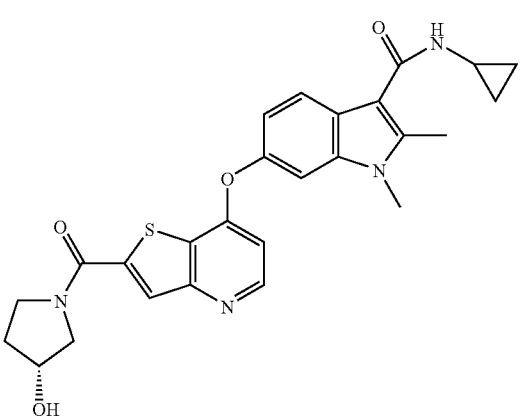

This material was prepared by the reaction of (7-chlorothieno[3,2-b]pyridin-2-yl)-((R)-3-hydroxy-pyrrolidin-1-yl)-methanone 4a with 6-hydroxy-1,2-dimethyl-1H-indole-3-carboxylic acid cyclopropylamide 20b and Cs$_2$CO$_3$ in a manner as previously described for example 1. $^1$H NMR (300 MHz, CD$_3$OD) δ 8.50 (1H, d, J=5.5 Hz), 7.93 (1H, d, J=17.33 Hz), 7.80 (1H, d, J=8.6 Hz), 7.39 (1H, d, J=2.1 Hz), 7.05 (1H, dd, J=2.1, 8.6 Hz), 6.71 (1H, d, J=5.5 Hz), 4.54 (1H, bs), 4.11–4.00 (2H, m), 3.85–3.72(6H, m), 2.93–2.86 (1H, m), 2.66 (3H, s), 2.19–2.07 (2H, m), 0.90–0.84 (2H, m), 0.76–0.68 (2H, m). LCMS (ESI+) [M+H]/z Calc'd 491. found 491.

Anal. (C$_{26}$H$_{26}$N$_4$O$_4$S.0.2CH$_2$Cl$_2$) C, H, N.

Example 54

N-Cyclopropyl-6-[(2-{[(2S)-2-(hydroxymethyl)pyrrolidin-1-yl]carbonyl}thieno[3,2-b]pyridin-7-yl)oxy]-1,2-dimethyl-1H-indole-3-carboxamide

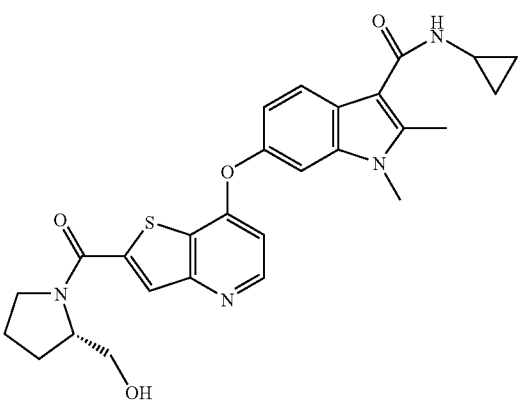

This material was prepared by the reaction of {(2S)-1-[(7-chlorothieno[3,2-b]pyridin-2-yl)carbonyl]pyrrolidin-2-yl}methanol 3b (0.107 g, 0.345 mmole) with N-cyclopropyl-6-hydroxy-1,2-dimethyl-1H-indole-3-carboxamide 20b (0.055 g, 0.23 mmole) and Cs$_2$CO$_3$ (0.073 g, 0.23 mmole) in a manner as previously described for example 1 to give brown solid (0.0599, 51%). $^1$H NMR (300 MHz, CD$_3$OD) δ 8.37 (1H, d, J=5.6 Hz), 7.81 (1H, s), 7.67 (1H, d, J=8.6 Hz), 7.27 (1H, d, J=2.1 Hz), 6.92 (1H, dd, J=2.1, 8.6 Hz), 6.59 (1H, d, J=5.6 Hz), 4.25 (1H, m), 3.82 (3H, m), 3.61 (3H, s), 2.76 (1H, m), 2.54 (3H, s), 2.00 (4H, m), 1.84 (1H, m), 1.14 (2H, m), 0.77 (2H, m). ESIMS (MH$^+$): 505.15.

Anal. Calcd. for C$_{27}$H$_{28}$N$_4$O$_4$S.0.45 CH$_2$Cl$_2$: C, 60.74; H, 5.37; N, 10.32. Found: C, 60.40; H, 5.56; N, 10.06.

Example 55(a)

N-(Cyclopropylmethyl)-6-methoxy-1,2-dimethyl-1H-indole-3-carboxamide

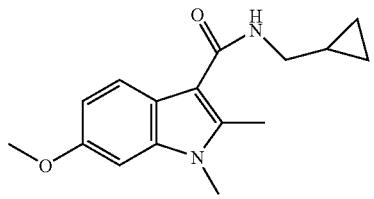

This material was prepared from 6-methoxy-1,2-dimethyl-1H-indole-3-carboxylic acid 16c (0.80, 3.65 mmole) with SOCl$_2$ (0.799 ml, 10.95 mmole) and cyclopropylmethylamine (0.38 ml, 4.38 mmole) in a manner as previously described for example 9d to give a pale yellow solid (0.382 g, 38%). $^1$H NMR (300 MHz, CD$_3$OD) δ 7.50 (1H, d, J=8.7 Hz), 6.81 (1H, d, J=2.2 Hz), 6.69 (1H, dd, J=2.2, 8.7 Hz), 3.74 (3H, s), 3.56 (3H, s), 3.20 (2H, m), 2.50 (3H, m), 1.07 (1H, m), 0.44 (2H, m}, 0.21 (2H, m); ESIMS (MH$^+$): 273.10.

Example 55(b)

N-(Cyclopropylmethyl)-6-hydroxy-1,2-dimethyl-1H-indole-3-carboxamide

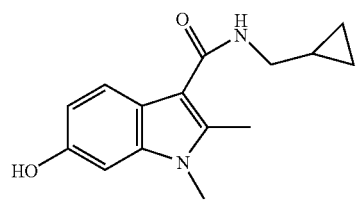

This material was prepared by reaction of N-(cyclopropylmethyl)-6-methoxy-1,2-dimethyl-1H-indole-3-carboxamide 55a (0.38 g, 1.4 mmole) with 1.0 M BBr$_3$ in CH$_2$Cl$_2$ (4.19 ml, 4.19 mmole) in a manner as previously described for example 1d to give a pale yellow solid (0.278 g, 77%). $^1$H NMR (400 MHz, CD$_3$OD) δ 7.55 (1H, d, J=8.5 Hz), 6.77 (1H, s), 6.71 (1H, d, J=8.5 Hz), 3.63 (3H, s), 3.28 (2H, m), 2.61 (3H, s), 1.18 (1H, m), 0.56 (2H, m); ESIMS (MH$^+$): 259.10.

Example 55

N-(Cyclopropylmethyl)-1,2-dimethyl-6-{[2-(1-methyl-1H-imidazol-2-yl)thieno[3,2-b]pyridin-7-yl]oxy}-1H-indole-3-carboxamide

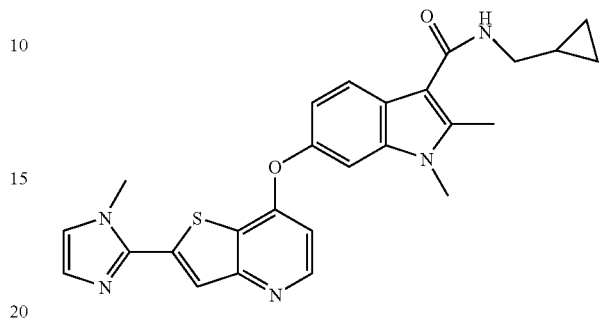

This material was prepared by the reaction of 7-chloro-2-(1-methyl-1H-imidazol-2-yl)thieno[3,2-b]pyridine 1e (0.76 g, 0.32 mmole) with 6-hydroxy-N,1,2-trimethyl-1H-indole-3-carboxamide 55b (0.074 g, 0.32 mmole) and Cs$_2$CO$_3$ (0.098 g, 0.30 mmole) in a manner as previously described for example 1 to give a pale yellow solid (0.060 g, 40%). $^1$H NMR (400 MHz, CD$_3$OD) δ 8.33 (1H, d, J=5.6 Hz), 7.75 (1H, d, J=8.6 Hz), 7.67 (1H, s), 7.28 (1H, d, J=2.2 Hz), 7.21 (1H, d, J=1.1 Hz), 6.99 (1H, d, J=1.1 Hz), 6.95 (1H, dd, J=2.2, 8.6 Hz), 6.57 (1H, d, J=5.6 Hz), 3.92 (3H, s), 3.61 (3H, s), 2.55 (3H, s), 1.06 (1H, m), 0.46 (2H, m), 0.23 (2H, m). ESIMS (MH$^+$): 472.10.

Anal. Calcd. For C$_{26}$H$_{25}$N$_5$O$_2$S.0.5 CH$_3$OH: C, 65.27; H, 5.58; N, 14.36. Found: C, 65.52; H, 5.58; N, 14.12.

Example 56

N-(Cyclopropylmethyl)-6-[(2-{[(3R)-3-hydroxypyrrolidin-1-yl]carbonyl}thieno[3,2-b]pyridin-7-yl)oxy-1,2-dimethyl-1H-indole-3-carboxamide

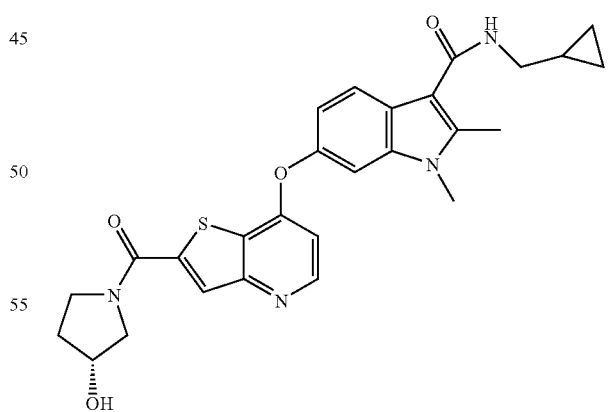

This material was prepared by the reaction of (3R)-1-[(7-chlorothieno[3,2-b]pyridin-2-yl)carbonyl]pyrrolidin-3-ol 4a (0.083 g, 0.29 mmole) with 6-hydroxy-N,1,2-trimethyl-1H-indole-3-carboxamide 55b (0.075 g, 0.29 mmole) and Cs$_2$CO$_3$ (0.094 g, 0.29 mmole) in a manner as previously described for example 1 to give a pale yellow solid (0.050 g, 34%). $^1$H NMR (300 MHz, CD$_3$OD) δ 8.50 (1H, d, J=5.3

Hz), 7.83 (1H, s), 7.73 (1H, d, J=8.7 Hz), 7.50 (1H, d, J=4.7 Hz), 7.42 (1H, d, J=2.1 Hz), 6.99 (1H, d, J=2.1, 8.7 Hz), 4.53 (1H, m), 3.96 (2H, m), 3.65 (2H, m), 3.61 (3H, s), 3.10 (4H, m), 2.35 (3H, s),1.09 (1H, m), 0.88 (2H, m), 0.45 (2H, m); ESIMS (MH+): 505.20.

Anal. Calcd. For $C_{27}H_{28}N_4O_4S \cdot 0.25 \, CH_2Cl_2$: C, 62.24; H, 5.46; N, 10.66. Found: C, 62.10; H, 5.74; N, 10.33.

Example 57

6-{2-[4(1-Hydroxy-1-methyl-ethyl)-thiazol-2-yl]-thieno[3,2-b]pyridin-7-yloxy)-1,2-dimethyl-1H-indole-3-carboxylic acid cyclopropylmethyl-amide

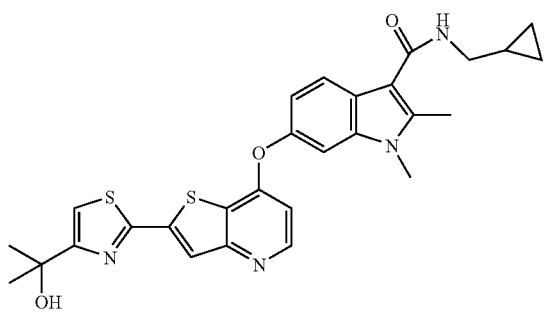

This material was prepared by the reaction of 2-[2-(7-chlorothieno[3,2-b]pyridin-2-yl)-1,3-thiazol-4-yl]propan-2-ol 40a (0.102 g, 0.33 mmole) with N-(cyclopropylmethyl)-6-hydroxy-1,2-dimethyl-1H-indole-3-carboxamide 55b (0.085 g, 0.33 mmole) and $Cs_2CO_3$ (0.1089, 0.33 mmole) in a manner as previously described for example 1. $^1$H NMR (300 MHz, DMSO-$d_6$) δ 8.50 (1H, d, J=5.5 Hz), 8.12 (1H, s), 7.83 (1H, d, J=8.6 Hz), 7.73 (1H, t, J=5.8 Hz), 7.58 (1H, s), 7.54 (1H, d, J=2.1 Hz), 7.05 (1H, dd, J=2.1, 8.6 Hz), 6.59 (1H, d, J=5.5 Hz), 3.68 (3H, s), 3.17 (2H, t, J=6.1 Hz), 2.61 (3H, s), 1.50 (6H, s), 1.08 (2H, m), 0.43 (2H, m), 0.25 (2H, m); ESIMS (MH+): 533.15.

Anal. Calcd. For $C_{28}H_{28}N_4O_3S_2 \cdot 0.25H_2O$: C, 62.60; H, 5.35; N, 10.43. Found: C, 62.65; H, 5.37; N, 10.20.

Example 58(a)

6-Methoxy-1,2-dimethyl-1H-indol-3-carboxylic acid propylamide

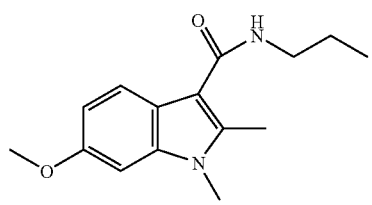

This material was prepared from 1,2-dimethyl-6-methoxy-1H-indole-3-carboxylic acid 16c, thionyl chloride and propylamine in a manner as previously described for example 9d. $^1$H NMR (300 MHz, CDCl$_3$) δ 7.55 (1H, d, J=8.6 Hz), 6.84 (1H, dd, J=2.2, 8.6 Hz), 6.78 (1H, d, J=2.2 Hz), 5.87 (1H, bs), 3.87 (3H, s), 3.63 (3H, s), 3.45 (2H, m), 2.69 (3H, s), 1.67 (2H, m), 1.02 (3H, t, J=7.4 Hz). LCMS (ESI+) [M+H]/z Calc'd 261. found 261.

Example 58(b)

6Hydroxy-1,2-dimethyl-1H-indol-3-carboxylic acid propylamide

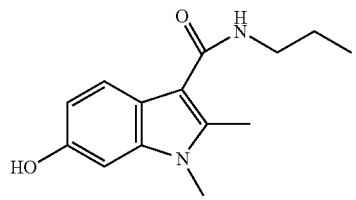

This material was prepared from 6-methoxy-1,2-dimethyl-1H-indol-3-carboxylic acid propylamide 58a by treatment with BBr$_3$ in a manner as previously described for example 1d. $^1$H NMR (300 MHz, CD$_3$OD) δ 7.50 (1H, d, J=8.7 Hz), 6.74 (1H, d, J=1.9 Hz), 6.68 (1H, dd, J=1.9, 8.7 Hz), 3.61 (3H, s), 3.32 (2H, m), 2.58 (3H, s), 1.66 (2H, m), 1.01 (3H, t, J=7.4 Hz). LCMS (ESI+) [M+H]/z Calc'd 247. found 247.

Example 58

6-(2-[2-(S)Hydroxymethyl-pyrrolidine-1-carbonyl]thieno[3,2-b]pyridin-7-yloxy)-1,2-dimethyl-1H-indole-3-carboxylic acid propylamide

This material was prepared by the reaction of (7-chlorothieno[3,2-b]pyridin-2-yl)-(3-hydroxymethyl-pyrrolidin-1-yl)-methanone 3a (0.127 g, 0.43 mmole) with 6-hydroxy-1,2-dimethyl-1H-indole-3-carboxylic acid propylamide 58b (0.070 g, 0.285 mmole) and Cs$_2$CO$_3$ (0.099 g, 0.35 mmole) in a manner as previously described for example 1 to give 30 mg (14% yield) of pale yellow solid. $^1$H NMR (CD$_3$OD) δ 8.33 (1H, d, J=5.1 Hz), 7.69–7.75 (2H, m), 7.24 (1H, s), 6.9 (1H, d, J=8.1 Hz), 6.56 (1H, d, J=5.1 Hz), 4.22 (1H, m), 3.64–3.78 (4H, m), 3.56 (3H, s), 3.20–3.31 (2H, m), 2.52 (3H, s), 1.90–1.98 (4H, m), 1.62–1.55 (2H, m), 0.95–0.90 (3H, m). ESIMS (MH+): 507.20.

Anal. Calcd. For $C_{27}H_{30}N_4O_4S \cdot 1.0 \, CH_3OH$: C, 62.43; H, 6.36; N, 10.40. Found: C, 62.44; H, 6.13; N, 10.13.

Example 59

6-[2-(3-Hydroxy-pyrrolidine-1-carbonyl)-thieno[3,2-b]pyridin-7-yloxy]-1,2-dimethyl-3H-indole-3-carboxylic acid propylamide

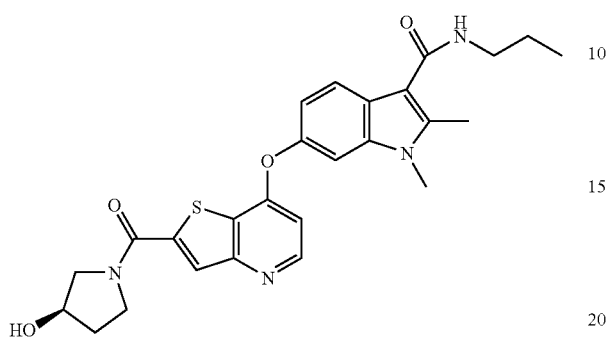

This material was prepared by the reaction of 7-chloro-2-[(R)-3-hydroxypyrrolidine-1-carbynyl]thieno[3,2,-b]pyridine 4a with 6-hydroxy-1,2-dimethyl-1H-indol-3-carboxylic acid propylamide 58b and $Cs_2CO_3$ in a manner as previously described for example 1. $^1$H NMR (300 MHz, $CD_3OD$) δ 8.50 (1H, d, J=5.6 Hz), 7.96 (1H, d, J=17.3 Hz), 7.86 (1H, d, J=8.7 Hz), 7.40 (1H, s), 7.06 (1H, d, J=10.7 Hz), 6.72 (1H, d, J=5.6 Hz), 4.61–4.53 (1H, m), 4.15–4.00 (2H, m), 3.91–3.73 (3H, m), 3.73 (3H, s), 3.53–3.40 (2H, m), 2.67 (3H, s), 2.28–2.07 (2H, m), 1.78–1.69 (2H, m), 1,18–1.04 (3H, m). LCMS (ESI+) [M+H]1z Calc'd 493. found 493.

Anal. ($C_{26}H_{28}N_4O_4S.0.3CH_2Cl_2$) C, H, N.

Example 60

1,2-Dimethyl-6-(2-thiazol-2-yl-thieno[3,2-b]pyridin-7-yloxy)1H-indole-3-carboxylic acid propylamide

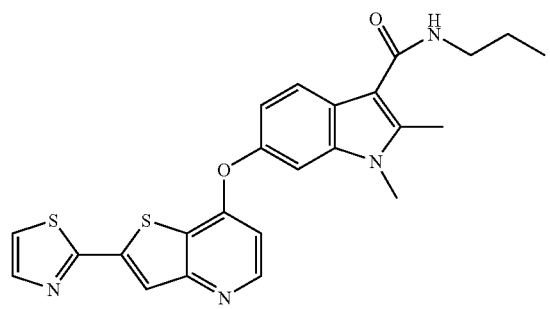

This material was prepared by the reaction of 7-chloro-2-(1,3-thiazol-2-yl)thieno[3,2-b]pyridine 41a (0.078 g, 0.314 mmole) with 6-hydroxy-1,2-dimethyl-N-propyl-1H-indole-3-carboxamide 58b (0.076 g, 0.31 mmole) and $Cs_2CO_3$ (0.101 g, 0.31 mmole) in a manner as previously described for example 1 to give a yellow solid (0.035 g, 24%). $^1$H NMR (300 MHz, $CDCl_3$) δ 8.46 (1H, d, J=5.3 Hz), 7.92 (1H, s), 7.88 (1H, d, J=3.2 Hz), 7.74 (1H, d, J=8.7 Hz), 7.42 (1H, d, J=3.2 Hz), 7.17 (1H, d, J=1.7 Hz), 7.05 (1H, dd, J=1.7, 8.7 Hz), 6.55 (1H, d, J=5.3 Hz), 5.90 (1H, m), 3.66 (3H, s), 3.47 (2H, m), 2.73 (3H, s), 1.69 (2H, m), 1.03 (3H, t, J=7.4 Hz); ESIMS (MH+): 463.10.

Anal. Calcd. For $C_{24}H_{22}N_4O_2S_2.0.05$ $CH_2Cl_2$: C, 61.87; H, 4.77; N, 12.00. Found: C, 61.90; H, 4.77; N, 11.90.

Example 61

1,2-Dimethyl-6-[2-(1-methyl-1H-imidazol-2-yl)thieno[3,2-b]pyridin-7-yloxy]-1H-indole-3-carboxylic acid propylamide

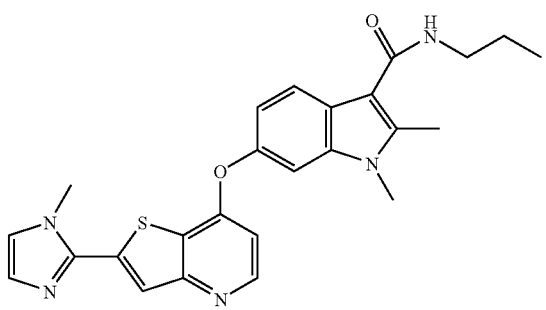

This material was prepared from 7-chloro-2-(1-methyl-1H-imidazol-2-yl]thieno[3,2-b]pyridine 1e with 6-hydroxy-1,2-dimethyl-1H-indole-3-carboxylic acid propylamide 58b and $Cs_2CO_3$ in a manner as previously described for example 1. $^1$H NMR (300 MHz, $CDCl_3$) δ 8.42 (1H, d, J=5.5 Hz), 7.82 (1H, d, J=8.7 Hz), 7.76 (1H, s), 7.37 (1H, d, J=1.8 Hz), 7.30 (1H, s), 7.08 (1H, s), 7.03 (1H, dd, J=1.8, 8.7 Hz), 6.65 (1H, d, J=5.5 Hz), 4.01 (3H, s), 3.70 (3H, s), 3.39 (2H, m), 2.64 (3H, s), 1.70 (2H, m), 1.03 (3H, m). LCMS (ESI+) [M+H]/z Calc'd 460. found 460.

Anal. ($C_{25}H_{25}N_5O_2S.1.0CH_3OH$)C, H, N.

Example 62(a)

6-Methoxy-1,2-dimethyl-1H-indole-3-carboxylic acid butylamide

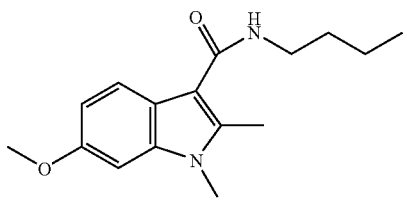

This material was prepared from the reaction of 6-methoxy-1,2-dimethyl-1H-indole-3-carboxylic acid (1.12 g, 5.11 mmole) 16c with oxalyl chloride (0.682 ml, 13.6 mmole) and butan-1-amine (1.51 ml, 15.33 mmole) in a manner as previously described for example 16d to give a yellow solid (0.990 g, 71%). $^1$H NMR (300 MHz, $CDCl_3$) δ 8.01 (1H, d, J=8.6 Hz), 7.31 (1H, dd, J=2.3, 8.6 Hz), 7.25 (1H, d, J=2.3 Hz), 6.32 (1H, s), 4.34 (3H, s), 4.09 (3H, s), 3.95 (2H, m), 3.16 (3H, s), 2.10 (2H, m), 1.92 (2H, m), 1.44 (3H, t, J=7.4 Hz); ESIMS (MH+): 275.15.

Example 62(b)

6-Hydroxy-1,2-dimethyl-1H-indole-3-carboxylic acid butylamide

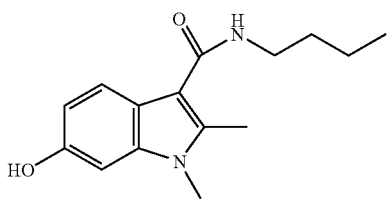

This material was prepared by the reaction of 6-methoxy-1,2-dimethyl-1H-indole-3-carboxylic acid butylamide 62a (0.78 g, 2.84 mmole) with 1.0 M BBr$_3$ in CH$_2$Cl$_2$ (8.53 ml, 8.53 mmole) in a manner as previously described for example 1d to give an off-white solid (0.623 g, 96%). $^1$H NMR (300 MHz, CD$_3$OD) δ 7.40 (1H, d, J=8.5 Hz), 6.64 (1H, d, J=2.1 Hz), 6.59 (1H, dd, J=2.1, 8.5 Hz), 3.50 (3H, s), 3.29 (2H, m), 2.48 (3H, s), 1.54 (2H, m), 1.36 (2H, m), 0.90 (3H, t, J=7.3 Hz); ESIMS (MH$^+$): 261.15.

Example 62

1,2-Dimethyl-6-(2-thiazol-2-yl-thieno[3,2-b]pyridin-7-yloxy)-1H-indole-3-carboxylic acid butylamide

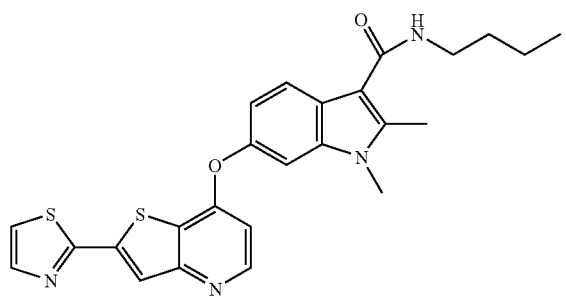

This material was prepared by the reaction of 7-chloro-2-(1,3-thiazol-2-yl)thieno[3,2-b]pyridine 41a (0.085 g, 0.33 mmole) with 6-Hydroxy-1,2-dimethyl-1H-indole-3-carboxylic acid butylamide 62b (0.087 g, 0.33 mmole) and Cs$_2$CO$_3$ (0.108 g, 0.33 mmole) in a manner as previously described for example 1 to give a yellow solid (0.090 g, 57%). $^1$H NMR (300 MHz, CD$_3$OD) δ 8.32 (1H, d, J=5.5 Hz), 7.83 (1H, s), 7.78 (1H, d, J=3.2 Hz), 7.72 (1H, d, J=8.7 Hz), 7.63 (1H, d, J=3.2 Hz), 7.28 (1H, d, J=2.0 Hz), 6.94 (1H, dd, J=2.0, 8.7 Hz), 6.56 (1H, d, J=5.5 Hz), 3.59 (3H, s), 3.34 (2H, m), 2.54 (3H, s), 1.57 (2H, m), 1.38 (2H, m), 0.90 (3H, t, J=7.4 Hz); ESIMS (MH$^+$): 477.05.

Anal. Calcd. For C$_{25}$H$_{24}$N$_4$O$_2$S$_2$.0.7 H$_2$O: C, 61.37; H, 5.23; N, 11.45. Found: C, 61.34; H, 5.22; N, 11.11.

Example 63(a)

6-Methoxy-1,2-dimethyl-1H-indole-3-carboxylic acid (3-hydroxy-propyl)-amide

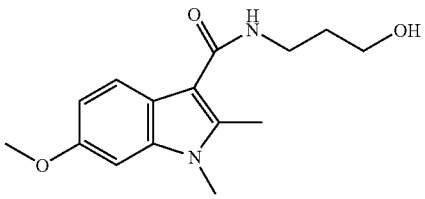

This material was prepared by the reaction of 1,2-dimethyl-6-methoxy-1H-indole-3-carboxylic acid 16c with 3-hydroxy-propyl amine and oxalyl chloride in a manner as previously described for 16d. $^1$H NMR (300 MHz, CD$_3$OD) δ 7.52 (1H, d, J=8.6 Hz), 6.73 (1H, d, J=2.1 Hz), 6.68 (1H, dd, J=2.1, 8.6 Hz), 3.69 (2H, t, J=6.1 Hz), 3.79 (3H, s), 3.63 (3H, s), 3.51 (2H, m), 2.57 (3H, s), 1.85 (2H, m). LCMS (ESI+) [M+H]/z Calc'd 291. found 291.

Example 63(b)

6-Hydroxy-1,2-dimethyl-1H-indole-3-carboxylic acid (3-hydroxy-propyl)-amide

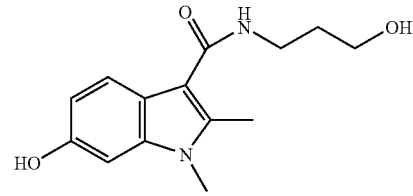

This material was prepared from 6-methoxy-1,2-dimethyl-1H-indole-3-carboxylic acid (3-methoxy-propyl)-amide 63a by treatment with BBr$_3$ in a manner as previously described for example 1d. $^1$H NMR (300 MHz, CD$_3$OD) δ 7.52 (1H, d, J=8.6 Hz), 6.73 (1H, d, J=2.1 Hz), 6.68 (1H, dd, J=2.1, 8.6 Hz), 3.69 (2H, t, J=6.1 Hz), 3.57 (3H, s), 3.51 (2H, m), 2.57 (3H, s), 1.85 (2H, m). LCMS (ESI+) [M+H]/z Calc'd 263. found 263.

Example 63

6-[2-(Azetidine-1-carbonyl)-thieno[3,2-b]pyridin-7-yloxy}-1,2-dimethyl-1H-indole-3-carboxylic acid (3-hydroxy-propyl)-amide

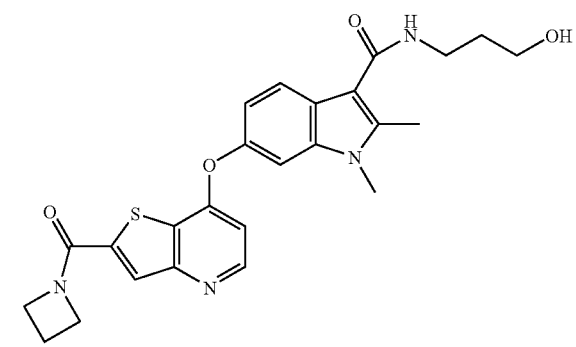

This material was prepared by the reaction of 2-(azetidin-1-ylcarbonyl)-7-chlorothieno[3,2-b]pyridine 25a with 6-hydroxy-1,2-dimethyl-1H-indole-3-carboxylic acid (3-hydroxy-propyl)-amide 63b and Cs$_2$CO$_3$ in a manner as previously described for example 1. $^1$H NMR (300 MHz, CD$_3$OD) δ 8.50 (1H, d, J=5.5 Hz), 7.89 (1H, d, J=8.7 Hz), 7.82 (1H, s), 7.40 (1H, s), 7.06, (1H, d, J=6.6 Hz), 6.72 (1H, d, J=5.5 Hz), 4.74–4.65 (2H, m), 4.31–3.68 (5H, m), 3.60–3.55(2H, m), 2.68 (3H, s), 2.54–2.46 (2H, m), 1.95–1.87 (2H, m). LCMS (ESI+) [M+H]/z Calc'd 478. found 478.

Anal. (C$_{25}$H$_{26}$N$_4$O$_3$S.0.9CH$_2$Cl$_2$) C, H, N.

Example 64

6-[2-((R)-3-Hydroxy-pyrrolidine-1-carbonyl)-thieno[3,2-b]pyridin-7-yloxy]-1,2-dimethyl-1H-indole-3-carboxylic acid (3-hydroxy-propyl)-amide

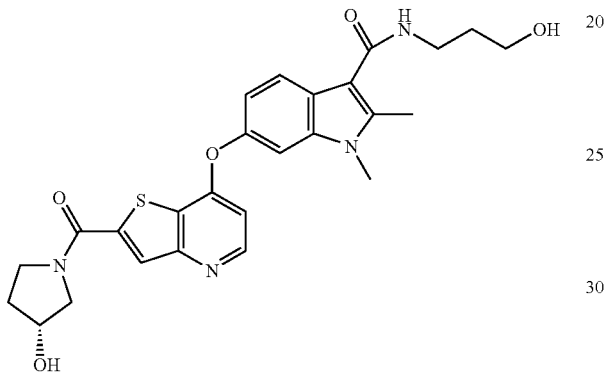

This material was prepared by the reaction of (7-chlorothieno[3,2-b]-pyridin-2-yl)-((R)-3-hydroxy-pyrrolidin-1-yl)-methanone 4a with 6-hydroxy-1,2-dimethyl-1H-indole-3-carboxylic acid (3-hydroxy-propyl)-amide 63b and Cs$_2$CO$_3$ in a manner as previously described for example 1. $^1$H NMR (300 MHz, CD$_3$OD) δ 8.38 (1H, d, J=5.5 Hz), 7.84–7.74 (2H,m), 7.28 (1H, d, J=2.1 Hz), 6.94 (1H, dd, J=2.1, 8.6 Hz), 6.60 (1H, d, J=5.5 Hz), 4.45–4.42 (1H, m), 3.93–3.91 (2H, m), 3.71–3.60 (8H, m), 3.45 (2H, m), 2.56 (3H, s), 2.02–1.98 (2H, m), 1.72–1.68 (2H, m). LCMS (ESI+) [M+H]/z Calc'd 509. found 509.

Anal. (C$_{26}$H$_{28}$N$_4$O$_5$.0.6CH$_2$Cl$_2$) C, H, N.

Example 65

1,2-Dimethyl-6-[2-(pyrrolidine-1-carbonyl)-thieno[3,2-b]pyridin-7-yloxy]-1H-indole-3-carboxylic acid (3-hydroxy-propyl)-amide

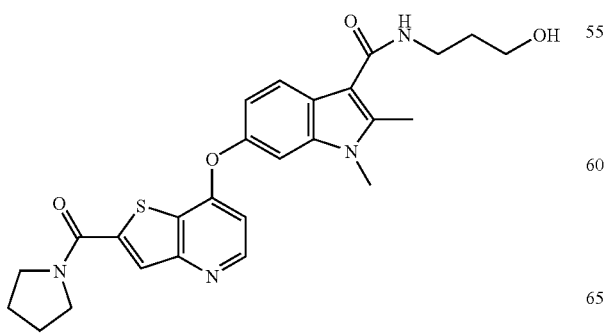

This material was prepared from the reaction of (7-chlorothieno[3,2-b]pyridin-2-yl)-pyrrolidin-1-yl-methanone with 6-hydroxy-1,2-dimethyl-1H-indole-3-carboxylic acid (3-hydroxy-propyl)-amide 63b and Cs$_2$CO$_3$ in a manner as previously described for example 1. $^1$H NMR (300 MHz, CD$_3$OD) δ 8.44 (1H, d, J=5.5 Hz), 7.85 (1H, s), 7.83 (1H, d, J=10.0 Hz), z 7.35 (1H, d, J=1.9 Hz), 7.01 (1H, dd, J=1.9, 8.5 Hz), 6.66 (1H, d, J=5.5 Hz), 3.88 (2H, m), 3.67 (7H, m), 3.54 (2H, m), 2.63 (3H, s), 1.83–2.10 (6H, m). LCMS (ESI+) [M+H]/z Calc'd 493. found 493.

Anal. (C$_{26}$H$_{28}$N$_4$O$_4$S.0.5CH$_3$OH)C, H, N.

Example 66(a)

6-Methoxy-1,2-dimethyl-1H-indole-3-carboxylic acid isopropylamide

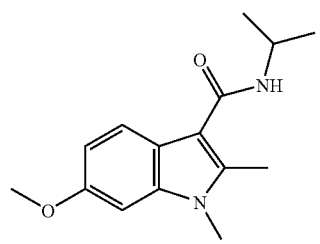

This material was prepared from 1,2-dimethyl-6-methoxy-1H-indole-3-carboxylic acid 16c, oxalyl chloride and isopropylamine in a manner as previously described for example 16d. $^1$H NMR (300 MHz, CDCl$_3$) δ 7.53 (1H, d, J=8.7 Hz), 6.85 (1H, dd, J=2.3, 8.7 Hz), 6.77 (1H, d, J=2.3 Hz), 4.35 (1H, m), 3.87 (3H, s), 3.63 (3H, s), 2.69 (3H, s), 1.30 (3H, s), 1.27 (3H, s). LCMS (ESI+) [M+H]/z Calc'd 261. found 261.

Example 66(b)

6-Hydroxy-1,2-dimethyl-1H-indole-3-carboxylic acid isopropylamide

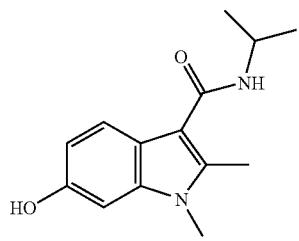

This material was prepared from 6-methoxy-1,2-dimethyl-1H-indol-3-carboxylic acid isopyropylamide 66a by treatment with BBr$_3$ in a manner as previously described for example 1d. $^1$H NMR (300 MHz, CD$_3$OD) δ 7.47 (1H, d, J=8.5 Hz), 6.74 (1H, d, J=2.1 Hz), 6.67 (1H, dd, J=2.1, 8.5 Hz), 4.22 (1H, m), 3.61 (3H, s), 2.56 (3H, s), 1.28 (3H, s), 1.26 (3H, s). LCMS (ESI+) [M+H]/z Calc'd 247. found 247.

Example 66

1,2-Dimethyl-6-(2-thiazol-2-yl-thieno[3,2-b]pyridin-7-yloxy)-1H-indole-3-carboxylic acid isopropylamide

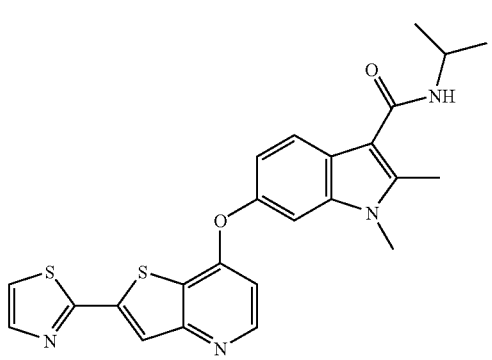

This material was prepared by the reaction 7-chloro-2-(1,3-thiazol-2-yl)thieno[3,2-b]pyridine 41a (0.084 g, 0.33 mmole) with 6-hydroxy-N-isopropyl-1,2-dimethyl-1H-indole-3-carboxamide 66b (0.082 g, 0.33 mmole) and $Cs_2CO_3$ (0.116 g, 0.33 mmole) to give a off-white solid (0.058 g, 38%). $^1$H NMR (300 MHz, $CDCl_3$) δ 8.46 (1H, d, J=5.4 Hz), 7.93 (1H, s), 7.88 (1H, d, J=3.2Hz), 7.73 (1H, d, J=8.6 Hz), 7.42 (1H, d, J=3.2 Hz), 7.17 (1H, d, J=2.1 Hz), 7.07 (1H, dd, J=2.1, 8.6 Hz), 6.54 (1H, d, J=5.4 Hz), 5.71 (1H, d, J=7.7 Hz), 4.36 (1H, m), 3.66 (3H, s), 2.72 (3H, s), 1.31 (6H, d, J=6.6 Hz); ESIMS (MH$^+$): 463.10.

Anal. Calcd. For $C_{24}H_{22}N_4O_2S_2 \cdot 0.3H_2O$: C, 61.59; H, 4.87; N, 11.97. Found: C, 61.48; H, 4.67; N, 11.86.

Example 67(a)

6-Methoxy-1,2-dimethyl-1H-indole-3-carboxylic acid isobutyl-amide

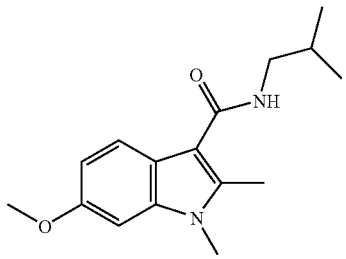

This material was prepared from 1,2-dimethyl-6-methoxy-1H-indole-3-carboxylic acid 16c, oxalyl chloride and isobutylamine in a manner as previously described for example 16d. $^1$H NMR (300 MHz, $CDCl_3$) δ 7.56 (1H, d, J=8.6 Hz), 6.85 (1H, dd, J=2.2, 8.6 Hz), 6.78 (1H, d, J=2.2 Hz), 3.87 (3H, s), 3.63 (3H, s), 3.32 (2H, m), 2.69 (3H, s), 1.93 (1H, m), 1.02 (3H, s), 1.00 (3H, s). LCMS (ESI+) [M+H]/z Calc'd 275. found 275.

Example 67(b)

6-Hydroxy-1,2-dimethyl-1H-indole-3-carboxylic acid isobutyl-amide

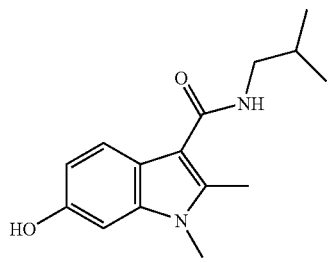

This material was prepared from 6-methoxy-1,2-dimethyl-1H-indol-3-carboxylic acid isobutyl-amide 67a by treatment with $BBr_3$ in a manner as previously described for example 1d. $^1$H NMR (300 MHz, $CD_3OD$) δ 7.52(1H, d, J=8.5 Hz),6.74(1H, d, J=2.3 Hz),6.68(1H, dd, J=2.3, 8.5 Hz), 3.61 (3H, s), 3.22 (2H, m), 2.58 (3H, s), 1.95 (1H, m), 1.02 (3H, s), 1.00 (3H, s). LCMS (ESI+) [M+H]/z Calc'd 261. found 261.

Example 67

1,2-Dimethyl-4(2-thiazol-2-yl-thieno[3,2-b]pyridin-7-yloxy)-1 indole-3-carboxylic acid isobutyl-amide

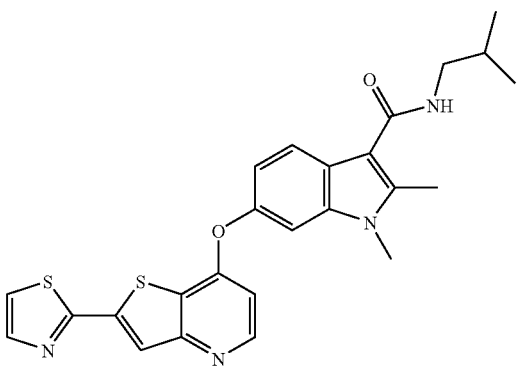

This material was prepared by the reaction tert-butyl 7-chloro-2-(1,3-thiazol-2-yl)thieno[3,2-b]pyridine 41a (0.086 g, 0.34 mmole) with 6-hydroxy-N-isobutyl-1,2-dimethyl-1H-indole-3-carboxamide 67b (0.087 g, 0.34 mmole) and $Cs_2CO_3$ (0.120 g, 0.34 mmole) to give a pale yellow solid (0.065 g, 40%). $^1$H NMR (300 MHz, $CDCl_3$) δ 8.46 (1H, d, J=5.5 Hz), 7.93 (1H, s), 7.88 (1H, d, J=3.2 Hz), 7.75 (1H, d, J=8.6 Hz), 7.42 (1H, d, J=3.2 Hz), 7.18 (1H, d, J=2.1 Hz), 7.06 (1H, dd, J=2.1, 8.6 Hz), 6.55 (1H, d, J=5.5 Hz), 5.95 (1H, s), 3.66 (3H, s), 3.35 (1H, t, J=6.4 Hz), 2.73 (3H, s), 1.95 (1H, m),1.03 (6H, d, J=6.8 Hz); ESIMS (MH$^+$): 477.05.

Anal. Calcd. For $C_{25}H_{24}N_4O_2S_2 \cdot 0.4H_2O$: C, 62.06; H, 5.17; N, 11.58. Found: C, 61.97; H, 5.00; N, 11.47.

Example 68(a)

6-Methoxy-1,2-dimethyl-N-(3-morpholin-4-ylpropyl)-1H-indole-3-carboxamide

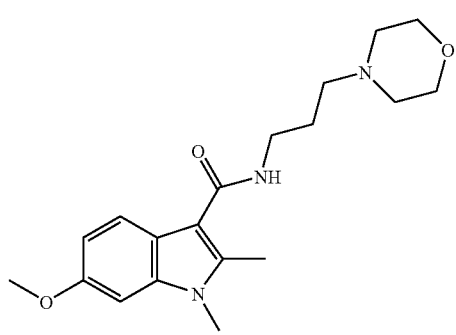

This material was prepared from 6-methoxy-1,2-dimethyl-1H-indole-3-carboxylic acid 16c (0.483 g, 2.20 mmole) with 2.0 M oxalyl chloride in $CH_2Cl_2$ (2.2 ml, 4.4 mmole) and 3-morpholin-4-ylpropylamine in a manner as previously described for example 16d to give a white solid (0.445 g, 59%). $^1$H NMR (300 MHz, $CDCl_3$) δ 7.60 (1H, d, J=8.6 Hz), 6.82 (1H, dd, J=2.3, 8.6 Hz), 6.77 (1H, d, J=2.3 Hz), 6.71 (1H, s), 3.87 (3H, s), 3.62 (3H, s), 3.57 (6H, m), 2.69 (3H, s), 2.50 (2H, t, J=6.6 Hz), 2.43 (4H, m), 1.81 (2H, m); ESIMS ($MH^+$): 346.20.

Example 68(b)

6-Hydroxy-1,2-dimethyl-N-(3-morpholin-4-ylpropyl)-1H-indole-3-carboxamide

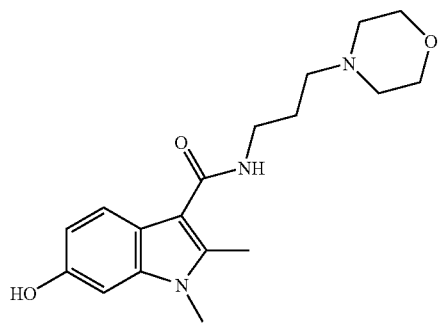

This material was prepared from 6-methoxy-1,2-dimethyl-N-(3-morpholin-4-ylpropyl)-1H-indole-3-carboxamide 68a (0.445 g, 1.29 mmole) by treatment with 1.0 M $BBr_3$ in $CH_2Cl_2$ (3.86 ml, 3.86 mmole) in a manner as described previously for example 1d to give a white solid (0.445 g, 59%). $^1$H NMR (300 MHz, $CD_3OD$) δ 7.49 (1H, d, J=8.6 Hz), 6.71 (1H, s), 6.64 (1H, dd, J=2.2, 8.6 Hz), 3.87 (4H, m), 3.56 (3H, s), 3.47 (2H, t, J=6.4 Hz), 3.10–3.24 (6H, m), 2.55 (3H, s), 2.00 (2H, m); ESIMS ($MH^+$): 332.15.

Example 68

1,2-Dimethyl-6-(2-propionyl-thieno[3,2-b]pyridin-7-yloxy)-1H-indole-3-carboxylic acid (3-morpholin-4-yl-propyl)-amide

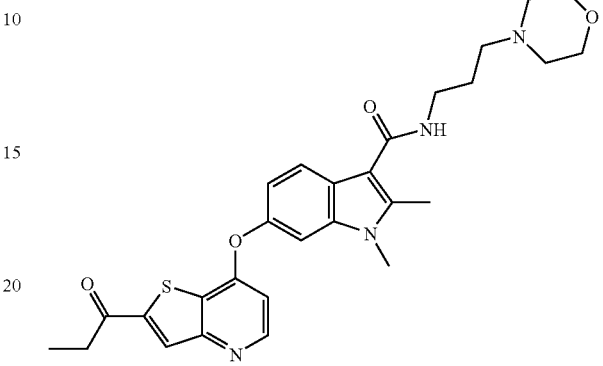

This material was prepared by the reaction of 1-(7-Chlorothieno[3,2-b]pyridin-2-yl)propan-1-one 51a (0.074 g, 0.33 mmole) with 6-hydroxy-1,2-dimethyl-N-(3-morpholin-4-ylpropyl)-1H-indole-3-carboxamide 68b (0.110 g, 0.33 mmole) and $Cs_2CO_3$ (0.108 g, 0.33 mmole) in a manner as previously described for example 1 to give a white solid (0.019 g, 11%). $^1$H NMR (300 MHz, DMSO-$d_6$) δ 8.58 (1H, d, J=5.5 Hz), 8.47 (1H, s), 7.82 (1H, d, J=8.5 Hz), 7.69 (1H, t, J=5.6 Hz), 7.55 (1H, d, J=2.1 Hz), 7.04 (1H, dd, J=2.1, 8.5 Hz), 6.67 (1H, d, J=5.5 Hz), 3.67 (3H, s), 3.54 (4H, m), 3.20 (2H, q, J=7.2 Hz), 2.60 (3H, s), 2.36 (8H, m), 1.71 (2H, m), 1.13 (3H, t, J=7.2 Hz); ESIMS ($MH^+$): 521.15.

Anal. Calcd. For $C_{28}H_{32}N_4O_4S \cdot 1.5\ H_2O$: C, 61.40; H, 6.44; N, 10.23. Found: C, 61.40; H, 6.13; N, 10.09.

Example 69(a)

6-Methoxy-1,2-dimethyl-1H-indole-3-carboxylic acid pyridin-2-ylamide

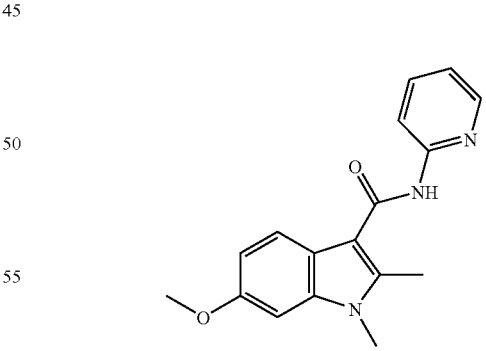

This material was prepared from 1,2-dimethyl-6-methoxy-1H-indole-3-carboxylic acid 16c, oxalyl chloride and propylamine in a manner as previously described for example 16d. $^1$H NMR (300 MHz, $CDCl_3$) δ 8.34–8.37 (2H, m), 8.30 (1H, d, J=5.0 Hz), 7.78 (1H, d, J=8.7 Hz), 7.71 (1H, d, J=8.9 Hz), 7.03 (1H, m), 6.92 (1H, dd, J=2.3, 8.9 Hz), 6.82 (1H, d, J=2.3 Hz), 3.89 (3H, s), 3.68 (3H, s), 2.76 (3H, s). LCMS (ESI+) [M+H]/z Calc'd 296, found 296.

Example 69(b)

6-Hydroxy-1,2-dimethyl-1H-indole-3-carboxylic acid pyridin-2-ylamide

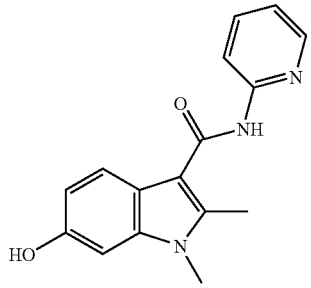

This material was prepared from 6-methoxy-1,2-dimethyl-1H-indol-3-carboxylic acid pyridin-2-ylamide 69a by treatment with BBr$_3$ in a manner as previously described for example 1d. $^1$H NMR (300 MHz, CD$_3$OD) δ 8.29 (1H, m), 8.24 (1H, d, J=8.3 Hz), 7.82 (1H, m), 7.64 (1H, d, J=8.7 Hz), 7.12 (1H, m), 6.82 (1H, d, J=2.2 Hz), 6.76 (1H, dd, J=2.2, 8.7 Hz), 3.66 (3H, s), 2.69 (3H, s). LCMS (ESI+) [M+H]/z Calc'd 282. found 282.

Example 69

1,2-Dimethyl-6-[2-(1-methyl-1H-imidazol-2-yl)-thieno[3,2-b]pyridin-7-yloxy]-1H-indole-3-carboxylic acid pyridin-2-ylamide

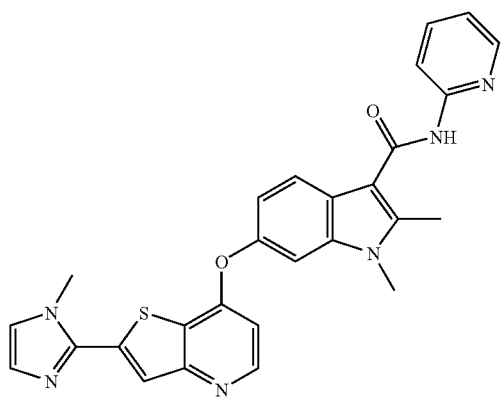

This material was prepared by the reaction of 7-chloro-2-(1-methyl-1H-imidazol-2-yl)thieno[3,2-b]pyridine 1e with 6-hydroxy-1,2-dimethyl-1H-indole-3-carboxylic acid pyridin-2-ylamide 69b and Cs$_2$CO$_3$ in a manner as previously described for example 1. $^1$H NMR (300 MHz, DMSO-d6) δ 8.43 (1H, d, J=5.5 Hz), 8.33 (1H, s), 8.20 (1H, d, J=3.8 Hz), 7.75–7.95 (3H, m), 7.61 (1H, s), 7.40 (1H, s), 7.11 (2H, m), 7.03 (1H, s), 6.60 (1H, d, J=5.5 Hz), 4.05 (3H, s), 3.73 (3H, s), 2.68 (3H, s). LCMS (ESI+) [M+H]/z Calc'd 495, found 495.

Anal. (C$_{27}$H$_{22}$N$_6$O$_2$S.1.0H$_2$O)C, H, N.

Example 70

1,2-Dimethyl-6-(2-thiazol-2-yl-thieno[3,2-b]pyridin-7-yloxy)-1H-indole-3-carboxylic acid pyridin-2-ylamide

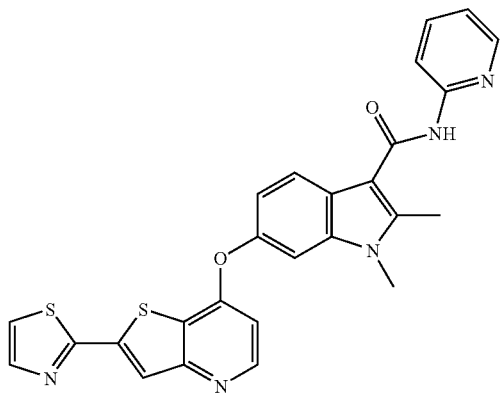

This material was prepared by the reaction of 7-chloro-2-(1,3-thiazol-2-yl)thieno[3,2-b]pyridine 41a (0.117 g, 0.46 mmole) with 6-hydroxy-1,2-dimethyl-N-pyridin-2-yl-1H-indole-3-carboxamide 69b (0.130 g, 0.46 mmole) and Cs$_2$CO$_3$ (0.150 g, 0.46 mmole) in a manner as previously described for example 1 to give a yellow solid (0.051 g, 22%). $^1$H NMR (300 MHz, CDCl$_3$) δ 8.48 (1H, d, J=5.5 Hz), 8.38 (1H, s), 8.35 (1H, s), 8.30 (1H, d, J=3.77 Hz), 7.95 (2H, s), 7.88 (1H, d, J=3.2 Hz), 7.75 (1H, m), 7.42 (1H, d, J=3.39 Hz), 7.22 (1H, d, J=1.9 Hz), 7.12 (1H, dd, J=1.9, 8.6 Hz), 7.04 (1H, dd, J=5.1, 6.6 Hz), 6.56 (1H, d, J=5.5 Hz), 3.70 (3H, m), 2.80 (3H, m); ESIMS (MH$^+$): 498.05.

Anal. Calcd. For C$_{26}$H$_{19}$N$_5$O$_2$S$_2$.0.1 H$_2$O: C, 62.53; H, 3.88; N, 14.02. Found: C, 62.44; H, 3.96; N, 13.83.

Example 71(a)

2,2,2-Trifluoro-1-(6methoxy-2-methyl-1H-indol-3-yl)-ethanone

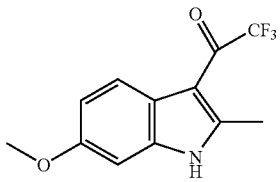

To a solution of 6-methoxy-2-methyl-1H-indole (1 g, 6.2 mmole) (prepared according to JACS 1998, 110, 2242) in 25 ml of THF was added TFAA (1.56 g, 7.44 mmole) with ice bath cooling. The mixture was warmed to room temperature and stirred for two hours and concentrated in vacuo. The residue was further purified by column chromatography (eluting with CH2Cl2) to give 1.34 g product as pale yellow solid (82% yield). $^1$H NMR (300 MHz, CDCl$_3$) δ 7.90 (1H, d, J=8.9 Hz), 6.87 (1H, dd, J=2.2, 8.9 Hz), 6.80 (1H, d, J=2.2 Hz), 3.82 (3H, s), 2.69 (3H, s).

Example 71(b)

1-(1-Ethyl-6-methoxy-2-methyl-1H-indol-3-yl)-2,2,2-trifluoro-ethanone

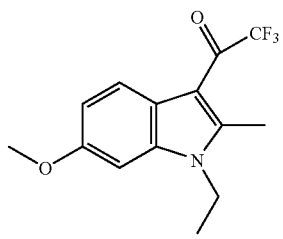

To a solution of 2,2,2-trifluoro-1-(6-methoxy-2-methyl-1H-indol-3-yl)-ethanone 71a (1.3 g, 5.05 mmole) in 20 ml anhydrous THF was added ethyl iodide (2.36 g, 15.15 mmole) and sodium hydride (404 mg, 60% in mineral oil, 10.1 mmole) with ice bath cooling. The mixture was warmed slowly to room temperature and stirred for an additional four hours. The reaction was quenched with water and extracted with EtOAc. The combined organic layer was dried over $Na_2SO_4$, filtered and concentrated under rot vap. The residue was purified by column chromatography (eluting with 20–30% EtOAc in hexanes) to give a brown oil (580 mg, 40% yield). $^1$H NMR (300 MHz, CDCl$_3$) δ 7.91 (1H, d, J=8.9 Hz), 6.93 (1H, dd, J=2.3, 8.9 Hz), 6.82 (1H, d, J=2.3 Hz), 4.18 (2H, m), 3.88 (3H, s), 2.76 (3H, s), 1.40 (3H, m).

Example 71(c)

1-Ethyl-6-methoxy-2-methyl-1H-indole-3-carboxylic acid

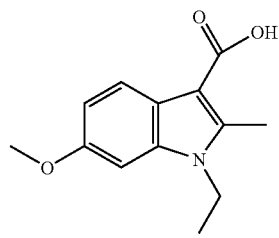

To a solution of 1-(1-ethyl-6-methoxy-2-methyl-1H-indol-3-yl)-2,2,2-trifluoro-ethanone 71b (580 mg, 2.03 mmole) in 10 ml ethanol was added a solution of KOH (1.1 g, 20 mmole) in 10 ml water. The mixture was heated to reflux for 1 hour and cooled to room temperature. Concentrated HCl was added to adjust pH to 1. The mixture was extracted with EtOAc and the combined organic layer was dried over $Na_2SO_4$, filtered and concentrated in vacuo. The residue was further purified by column chromatography (eluting with 1–2% MeOH in $CH_2Cl_2$) to give 350 mg product as brown solid (74% yield). $^1$H NMR (400 MHz, CDCl$_3$) δ 8.07 (1H, d, J=8.7 Hz), 6.90 (1H, dd, J=2.2, 8.7 Hz), 6.80 (1H, d, J=2.2 Hz), 4.14 (2H, q, J=7.2 Hz), 3.88 (3H, s), 2.77 (3H, s), 1.37 (3H, t, J=7.2 Hz).

Example 71(d)

1-Ethyl-6-methoxy-2-methyl-1H-indole-3-carboxylic acid methylamide

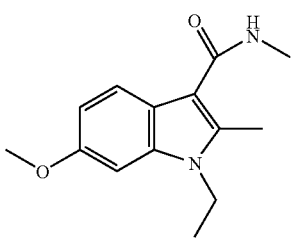

This material was prepared from the reaction of 1-ethyl-6-methoxy-2-methyl-1H-indole-3-carboxylic acid 71c (350 mg, 1.5 mmole), oxalyl chloride (1.1 ml, 2.0M solution) and methylamine (1.5 ml, 2.0M solution) in a manner as previously described for example 16d to give 350 mg product as beige solid (95% yield). $^1$H NMR (300 MHz, CDCl$_3$) δ 7.56 (1H, d, J=8.7 Hz), 6.84 (1H, dd, J=2.3, 8.7 Hz), 6.80 (1H, d, J=2.3 Hz), 5.84 (1H, bs), 4.10 (2H, q, J=7.2 Hz), 3.87 (3H, s), 3.03 (3H, d, J=4.9 Hz), 2.70 (3H, s), 1.33 (3H, t, J=7.2 Hz).

Example 71(e)

1-Ethyl-6-hydroxy-2-methyl-1H-indole-3-carboxylic acid methylamide

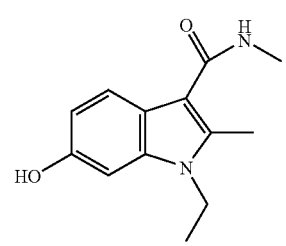

This material was prepared from 1-ethyl-6-methoxy-2-methyl-1H-indole-3-carboxylic acid methylamide 71d (350 mg, 1.42 mmole) by treatment with BBr$_3$ in a manner as previously described for example 1d to give 280 mg product as white solid (85% yield). $^1$H NMR (400 MHz, CDCl$_3$) δ 7.48 (1H, d, J=8.3 Hz), 6.73–6.77 (2H, m), 6.01 (1H, bs), 4.04 (2H, q, J=7.2 Hz, 3.03 (3H, d, J=4.9 Hz), 2.66 (3H, s), 1.31 (3H, t, J=7.2 Hz).

Example 71

6-[2-(Azetidine-1-carbonyl)thieno[3,2-b]pyridin-7-yloxy]-1-ethyl-2-methyl-1H-indole-3-carboxylic acid methylamide

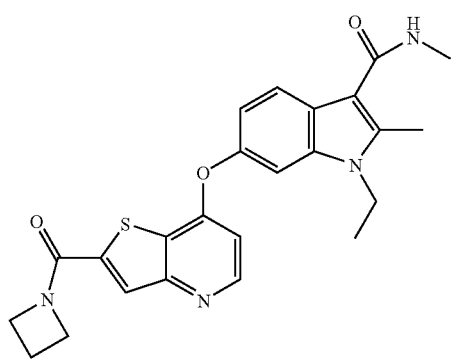

This material was prepared by the reaction of 2-(azetidin-1-ylcarbonyl)-7-chlorothieno[3,2-b]pyridine 25a with 1-ethyl-6-hydroxy-2-methyl-1H-indole-3-carboxylic acid methylamide 71e and $Cs_2CO_3$ in a manner as previously described for example 1. $^1$H NMR (300 MHz, $CDCl_3$) δ 8.47 (1H, d, J=5.5 Hz), 7.75 (2H, m), 7.16 (1H, d, J=1.7 Hz), 7.01 (1H, dd, J=1.7, 8.4 Hz), 6.56 (1H, d, J=5.5 Hz), 5.91 (1H, bs), 4.59 (2H, m), 4.28 (2H, m), 4.11 (2H, m), 3.05 (3H, d, J=4.0 Hz), 2.72 (3H, s), 2.45 (2H, m), 1.33 (3H, m). LCMS (ESI+) [M+H]/z Calc'd 449, found 449.

Anal. ($C_{24}H_{24}N_4O_3S \cdot 0.5H_2O \cdot 0.25MeOH$) C, H, N.

Example 72

1-Ethyl-2-methyl-6-[2-(1-methyl-1H-imidazol-2-yl)-thieno[3,2-b]pyridin-7-yloxy]-1H-indole-3-carboxylic acid methylamide

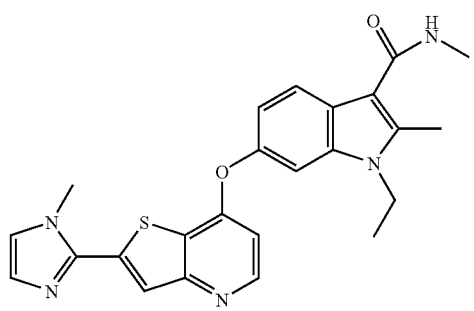

This material was prepared by the reaction of 7-chloro-2-(1-methyl-1H-imidazol-2-yl)thieno[3,2-b]pyridine 1e with 1-ethyl-6-hydroxy-2-methyl-1H-indole-3-carboxylic acid methylamide 71e and $Cs_2CO_3$ in a manner as previously described for example 1. $^1$H NMR (300 MHz, $CDCl_3$) δ 8.44 (1H, d, J=5.4 Hz), 7.74 (1H, d, J=8.7 Hz), 7.68 (1H, s), 7.18 (1H, d, J=1.9 Hz), 7.14 (1H, s), 7.05 (1H, d, J=1.9 Hz), 7.02 (1H, s), 6.54 (1H, d, J=5.4 Hz), 5.92 (1H, bs), 4.11 (2H, m), 3.96 (3H, s), 3.05 (3H, d, J=4.7 Hz), 2.72 (3H, s), 1.33 (3H, m). LCMS (ESI+) [M+H]/z Calc'd 446, found 446.

Anal. ($C_{24}H_{23}N_5O_2S \cdot 0.5 H_2O \cdot 0.5 MeOH$) C, H, N.

Example 73(a)

[2-(2-Hydroxy-butyl)-5-methoxy-phenyl]-carbamic acid t-butyl ester

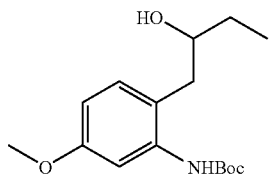

To a solution of (5-methoxy-2-methyl-phenyl)-carbamic acid t-butyl ester (6.95 g, 29.3 mmole) in 100 ml THF cooled at −45° C. was added sec-BuLi (45 ml, 58.5 mmole) slowly to keep temperatue lower than −45° C. The reaction mixture was stirred and warmed to −20° C., then cooled to −45° C. and propionaldehyde (2.67 ml, 36.63 mmole) was added. The reaction mixture was stirred and warmed to room temperature for 1 h, quenched with 1N HCl and extracted with EtOAc, dried over $MgSO_4$ and concentrated. The residue was purified by flash column chromatography (10–15% EtOAc in hexane) to give colorless oil (3.40 g, 39%). $^1$H NMR ($CDCl_3$) δ 7.96 (1H, s), 7.44 (1H, s), 6.96–7.00 (1H, m), 6.55 (1H, m), 3.80 (3H, s), 2.60–2.76 (2H, m), 1.93–1.95 (2H, m), 1.50 (9H, s), 0.93–1.01 (4H, m). ESIMS ($MNa^+$): 318.20.

Example 73(b)

[5-Methoxy-2-(2-oxo-butyl)-phenyl]-carbamic acid t-butyl ester

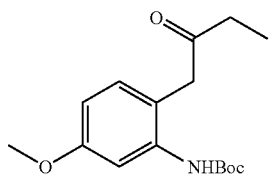

To a solution of Dess-Martin reagent (2.82 g, 6.68 mmole) in 80 ml THF cooled at 0° C. was added [2-(2-hydroxy-butyl)-5-methoxy-phenyl]-carbamic acid t-butyl ester 73a (1.64 g, 5.57 mmole) in 20 ml THF. The reaction mixture was stirred and warmed to room temperature for 2 h, quenched with half saturated $NaHCO_3$, extracted with EtOAc. The organic layer was dried over $MgSO_4$ and concentrated. The residue was purified by flash column chromatography (10–15% EtOAc in hexane) to give colorless oil (1.36 g, 84%). $^1$H NMR ($CDCl_3$) δ 7.67 (1H, bs), 7.48 (1H, s), 6.99–7.03 (1H, m), 6.56–6.60 (1H, m), 3.79 (3H, s), 3.59 (2H, s), 2.53–2.61 (2H, q, J=7.2 Hz), 1.51 (9H, s), 1.02 (3H, t, J=7.2 Hz). ESIMS ($MNa^+$): 316.10.

Example 73(c)

2-Ethyl-4-methoxy-1H-indole

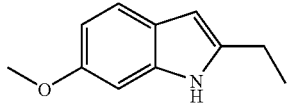

To a solution of [5-methoxy-2-(2-oxo-butyl)-phenyl]-carbamic acid t-butyl ester 73b (1.36 g, 4.65 mmole) in 10 ml THF was added 4 ml TFA. The reaction mixture was stirred at room temperature for 5 h, quenched with 50 ml $H_2O$ and extracted with EtOAc. The organic layer was dried over $MgSO_4$ and concentrated. The residue was purified by flash column chromatography (10–15% EtOAc in hexane) to give pale yellow solid (1.36 g, 73%). $^1$H NMR (CDCl$_3$) δ 7.75 (1H, bs), 7.49 (1H, d, J=8.6 Hz), 6.81 (1H, s), 6.73 (1H, d, J=8.6 Hz), 3.83 (3H, s), 2.75 (2H, q, J=7.5 Hz), 1.32 (3H, t, J=7.5 Hz). ESIMS (MH$^+$): 272.10.

Example 73(d)

1-(2-Ethyl-6-methoxy-1-methyl-1H-indol-3-yl)-2,2,2-trifluoro-ethanone

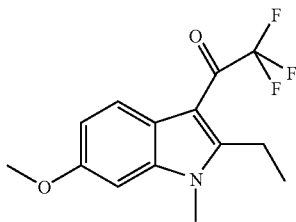

To a solution of 2-ethyl-6-methoxy-1H-indole 73c (1.79 g, 10.2 mmole) in 50 ml THF at 0° C. was added TFAA (1.58 ml, 11.22 mmole). The reaction mixture was stirred at 0° C. for 1 h, then concentrated and dried under vacuum, which was used without purification. ESIMS (MH$^+$): 272.10. The above residue was dissolved in 25 ml THF and cooled to 0° C., MeI (1.59 ml, 25.5 ml) and NaH (60%, 0.816 g, 20.4 mmole) was added. The reaction was stirred at room temperature for 1 h, quenched with $H_2O$ and extracted with EtOAc. The organic layer was dried over $MgSO_4$, and concentrated. The residue was purified by flash column chromatography (25% EtOAc in hexane) to give yellow color solid (2.42 g, 73%). $^1$H NMR (CDCl$_3$) δ 7.88 (1H, d, J=8.9 Hz), 6.94 (1H, dd, J=2.4, 8.9 Hz), 6.81 (1H, s), 3.88 (3H, s), 3.72 (3H, s), 3.20 (2H, q, J=7.5 Hz), 1.27 (3H, t, J=7.5 Hz). ESIMS (MH$^+$): 286.10

Example 73(e)

2-Ethyl-6-methoxy-1-methyl-1H-indole-3-carboxylic acid

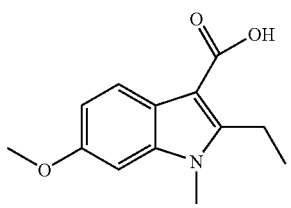

KOH (1.9 g, 33.49 mmole) in 20 ml $H_2O$ was added to a solution of 1-(2-ethyl-6-methoxy-1-methyl-1H-indol-3-yl)-2,2,2-trifluoro-ethanone 73d (2.42 g, 8.47 mmole) in 20 ml EtOH. The reaction mixture was heated to reflux for 8 h and concentrated. The residue was dissolved in $H_2O$, acidified with 1N HCl to pH~1 and filtrated. The solid was purified by flash column chromatography (2–5% $CH_3OH$ in $CH_2Cl_2$) to give yellow color solid (1.3 g, 72%). $^1$H NMR (CDCl$_3$) δ 11.88 (1H, bs), 7.82 (1H, d, J=8.7 Hz), 7.04 (1H, s), 6.77 (1H, d, J=8.7 Hz), 3.80 (3H, s), 3.70 (3H, s), 3.51 (2H, q, J=7.4 Hz), 1.15 (3H, t, J=7.4 Hz). ESIMS (MH$^+$): 234.05.

Example 73(f)

2-Ethyl-6-methoxy-1-methyl-1H-indole-3-carboxylic acid methylamide

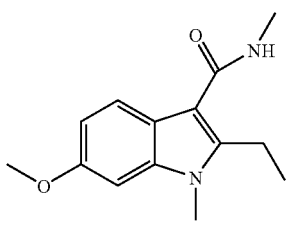

Thionyl chloride (0.383 ml, 4.45 mmole) was added to a solution of 2-ethyl-6-methoxy-1-methyl-1H-indole-3-carboxylic acid 73e (0.347 g, 1.48 mmole). The reaction mixture was heated to reflux for 30 min and concentrated. The residue was dissolved in 5 ml $CH_2Cl_2$ and added methylamine (2.0 M in THF, 2.22 ml, 4.44 mmole). The reaction mixture was stirred at room temperature for 1 hr, then concentrated. The residue was purified by flash column chromatography (2–5% $CH_3OH$ in $CH_2Cl_2$) to give yellow color solid (0.267 g, 73%). $^1$H NMR (CDCl$_3$) δ 7.47 (1H, d, J=8.7 Hz), 6.80 (1H, s), 6.69 (1H, d, J=8.7 Hz), 3.47 (3H, s), 3.58 (3H, s), 3.00 (2H, q, J=7.4 Hz), 2.83 (3H, s), 1.14 (3H, t, J=7.4 Hz). ESIMS (MH$^+$): 247.10.

Example 73(g)

2-Ethyl-6-hydroxy-1-methyl-1H-indole-3-carboxylic acid methylamide

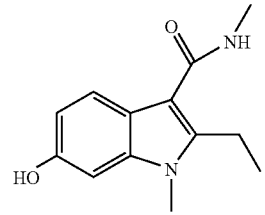

To a solution of 2-ethyl-6-methoxy-1-methyl-1H-indole-3-carboxylic acid methylamide 73f (0.267 g, 1.08 mmole) in 15 ml $CH_2Cl_2$ at 0° C. was added $BBr_3$ (1.0 M in $CH_2Cl_2$, 3.25 ml, 3.25 mmole). The reaction mixture was stirred at room temperature for 2 h, quenched with saturated $NH_4OH$ to make pH~10. The mixture was diluted with $H_2O$ and extracted with 10% $CH_3OH$ in $CH_2Cl_2$. The organic layer was dried over $MgSO_4$ and concentrated. The residue purified by flash column chromatography (3–5% $CH_3OH$ in $CH_2Cl_2$) to give pale yellow color solid (0.170 g, 68%). $^1$H NMR (CDCl$_3$) δ 7.40 (1H, d, J=8.5 Hz), 6.65 (1H, s), 6.59 (1H, d, J=8.5 Hz), 3.53 (3H, s), 3.28 (2H, q, J=7.5 Hz), 2.82 (3H, s), 1.13 (3H, t, J=7.5 Hz). ESIMS (MH$^+$): 233.15.

Example 73

2-Ethyl-6-[2-(3-hydroxy-pyrrolidine-1-carbonyl)-thieno[3,2-b]pyridin-7-yloxy]-1-methyl-1H-indole-3-carboxylic acid methylamide

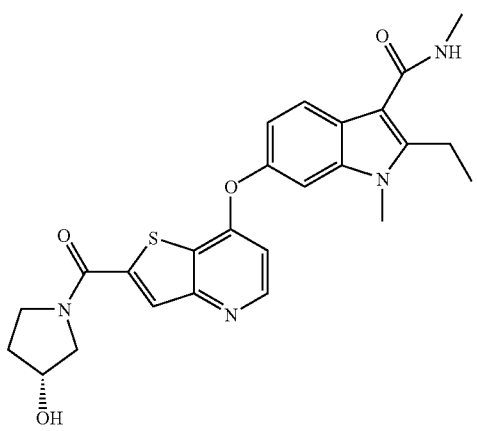

The material was prepared by the reaction of (7-chloro-thieno[3,2-b]pyridin-2-yl)-(3-hydroxy-pyrrolidin-1-yl)-methanone 4a (0.146 g, 0.517 mmole) with 2-ethyl-6-hydroxy-1-methyl-1H-indole-3-carboxylic acid methylamide 73g (0.080 g, 0.344 mmole) and $Cs_2CO_3$ (0.112 g, 0.344 mmole) in a manner as previously described for example 1 to give 30 mg (18% yield) of pale yellow solid. $^1$H NMR (CD$_3$OD) δ 8.34 (1H, d, J=5.5 Hz), 7.69–7.70 (2H, m), 7.26 (1H, s), 6.91 (1H, d, J=6.8 Hz), 6.65 (1H, d, J=5.5 Hz), 4.39 (1H, m), 3.90 (2H, m), 3.67–3.61 (5H, m), 2.99 (2H, m), 2.86 (3H, m), 2.00 (2H, m), 1.14–1.19 (3H, m). ESIMS (MH$^+$): 479.10.

Anal. Calcd. For $C_{25}H_{26}N_4O_4S \cdot 0.55\ CH_2Cl_2$: C, 58.42; H, 5.20; N, 10.67. Found: C, 58.47; H, 5.43; N, 11.31.

Example 74

2-Ethyl-1-methyl-6-[2-(1-methyl-1H-imidazol-2-yl)-thieno[3,2-b]pyridin-7-yloxy]-1H-indole-3-carboxylic acid methylamide

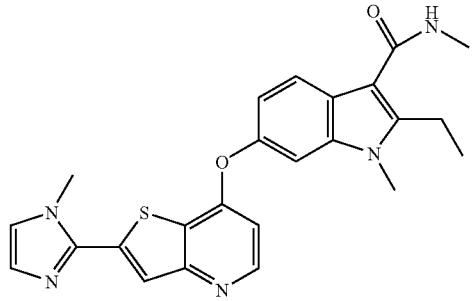

This material was prepared by the reaction 7-chloro-2-(1-methyl-1H-imidazol-2-yl)thieno[3,2-b]pyridine 1e (0.084 g, 0.34 mmole) with 2-ethyl-6-hydroxy-N,1-dimethyl-1H-indole-3-carboxamide 73g (0.078 g, 0.33 mmole) and $Cs_2CO_3$ (0.111 g, 0.34 mmole) in a manner as previously described for example 1 to give an off-white solid (0.058 g, 40%). $^1$H NMR (300 MHz, CD$_3$OD) δ 8.27 (1H, d, J=5.4 Hz), 7.68 (1H, d, J=8.6 Hz), 7.59 (1H, s), 7.24 (1H, d, J=1.9 Hz), 7.17 (1H, s), 6.96 (1H, s), 6.90 (1H, dd, J=1.9, 8.6 Hz), 6.50 (1H, d, J=5.4 Hz), 3.87 (3H, s), 3.58 (3H, s), 3.01 (2H, m), 2.85 (3H, s), 1.14 (3H, m). HRMS (MH$^+$): Calcd: 446.1655. Found: 446.1651.

Example 75(a)

6-Methoxy-1-methyl-1H-indole-3-carboxylic acid methylamide

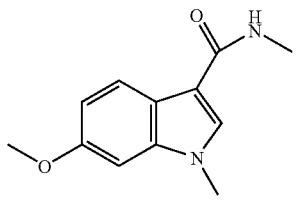

This material was prepared from 6-methoxy-1-methyl-1H-indole-3-carboxylic acid 16b (2.39 g, 10.9 mmole), oxalyl chloride and methylamine in a manner as previously described for example 16d to give a brown solid (1.08 g, 45%). $^1$H NMR (300 MHz, DMSO-d$_6$) δ 7.97 (1H, d, J=8.7 Hz), 7.76 (2H, m), 6.99 (1H, d, J=2.3 Hz), 6.77 (1H, dd, J=2.3, 8.7 Hz), 3.80 (3H, s), 3.76 (3H, s), 2.74 (3H, s); ESIMS (MH$^+$): 219.05.

Example 75(b)

2-Chloro-6-methoxy-1-methyl-1H-indole-3-carboxylic acid methylamide

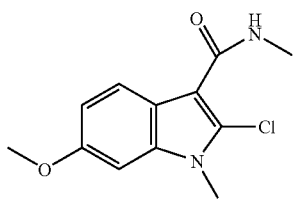

N-Chlorosuccinimide (0.150 g, 1.12 mmole) was added to a solution of 6-methoxy-N,1-dimethyl-1H-indole-3-carboxamide 75a (0.243 g, 1.11 mmole) in CCl$_4$ (10 ml) and DMF (3 ml). The reaction mixture was heated to 60° C. for 3 h and concentrated. The residue was purified by reverse phase chromatography eluting with 0–1% CH$_3$OH in 1:1 EtOAc and CH$_2$Cl$_2$ to give a brown colored oil (0.243 g, 87% yield); $^1$H NMR (300 MHz, CDCl$_3$) δ 7.61 (1H, d, J=8.6 Hz), 6.38 (1H, d, J=8.6 Hz), 6.19 (1H, s), 3.35 (3H, s), 2.96 (3H, s), 2.52 (3H, s); ESIMS (MH$^+$): 253.05.

Example 75(c)

2-Chloro-6-hydroxy-1-methyl-1H-indole-3-carboxylic acid methylamide

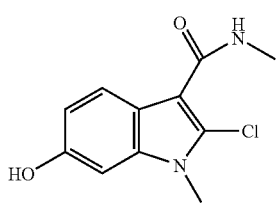

This material was prepared by reaction of 2-chloro-6-methoxy-N,1-dimethyl-1H-indole-3-carboxamide 75b (0.38 g, 1.4 mmole) with 1.0 M BBr$_3$ in CH$_2$Cl$_2$ (4.19 ml, 4.19 mmole) in a manner as previously described for example 1d to give an off-white solid (0.195 g, 85%). $^1$NMR (300 MHz, CD$_3$OD) δ 7.61 (1H, d, J=8.3 Hz), 6.65 (1H, s), 6.62 (1H, d, J=2.1 Hz), 3.56 (3H, s) 2.85 (3H, s); ESIMS (MH$^+$): 239.00.

Example 75

2-Chloro-6-{2-[4-(1-hydroxy-1-methyl-ethyl)thiazol-2-yl]-thieno[3,2-b]pyridin-7-yloxy}-1-methyl-1H-indole-3-carboxyllc acid methylamide

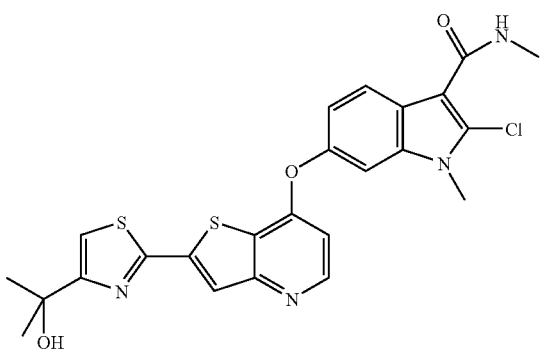

This material was prepared by the reaction of 2-[2-(7-chlorothieno[3,2-b]pyridin-2-yl)-1,3-thiazol-4-yl]propan-2-ol 40a (0.102 g, 0.33 mmole) with 2-chloro-6-hydroxy-N,1-dimethyl-1H-indole-3-carboxamide 75c (0.085 g, 0.33 mmole) and Cs$_2$CO$_3$ (0.108 g, 0.33 mmole) in a manner as previously described for example 1 to give an off-white solid (0.039 g, 21%). $^1$H NMR (300 MHz, CDCl$_3$) δ 8.40 (1H, d, J=5.5 Hz), 8.31 (1H, d, J=8.3 Hz), 7.82 (1H, m), 7.20 (1H, s), 7.14 (1H, s), 7.07 (2H, m), 6.47 (1H, d, J=5.5 Hz), 6.34 (1H, m), 3.69 (3H, s), 3.01 (3H, d, J=4.7 Hz), 1.60 (6H, s).

Anal. Calcd. For C$_{24}$H$_{21}$N$_4$O$_3$S$_2$Cl.0.6 H$_2$O.1.0 CH$_3$OH: C, 54.71; H, 4.53; N, 10.36. Found: C, 54.56; H, 4.45; N, 10.17.

Example 76(a)

2-Iodo-5-methoxy-phenylamine

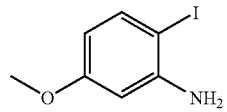

To a solution of 4-iodo-3-nitroanisole (5 g, 17.9 mmole) in 100 ml methanol was added FeCl$_3$ (50 mg, 0.3 mmole) and activated carbon (40 mg). The mixture was heated to reflux and hydrazine hydrate (1.75 g, 35 mmole) was added dropwise. The mixture was refluxed for an additional 8 hours and cooled to room temperature, filtered through Celite. The filtrate was concentrated and purified by column chromatography (eluting with 10% EtOAc in hexanes) to give 4.05 g product as pale yellow oil (91% yield). $^1$H NMR (300 MHz, CDCl$_3$) δ 7.47 (1H, d, J=8.7 Hz), 6.31 (1H, d, J=2.8 Hz), 6.13 (1H, dd, J=2.8, 8.7 Hz), 3.73 (3H, s).

Example 76(b)

2,2,2-Trifluoro-N-(2-iodo-5-methoxy-phenyl)-acetamide

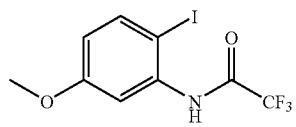

To a solution of 2-iodo-5-methoxy-phenylamine 76a (4.05 g, 16.3 mmole) in 10 ml anhydrous CH$_2$Cl$_2$ was added TFAA (4.1 g, 19.5 mmole). The mixture was stirred at 36° C. overnight, TLC indicated some starting material remained. Additional TFAA (4.1 g, 19.5 mmole) was added and stirred at 38° C. for another 24 hours. The mixture was concentrated under rot vap and purified by column chromatography (eluting with 5–10% EtOAc in hexanes) to give 4.6 g product (81% yield). $^1$H NMR (300 MHz, CDCl$_3$) δ 7.92 (1H, d, J=2.8 Hz), 7.66 (1H, d, J=8.9 Hz), 6.59 (1H, dd, J=2.8, 8.9 Hz), 3.82 (3H, s).

Example 76(c)

4,4,4-Trifluoro-3-(2-iodo-5-methoxy-phenylamino)-but-2-enoic acid ethyl ester

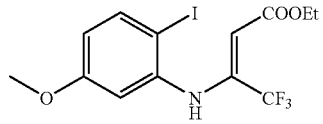

A solution of 2,2,2-trifluoro-N-(2-iodo-5-methoxy-phenyl)-acetamide 76b (4.6 g, 13.3 mmole) and methyl (triphenylphosphoranylidene)acetate (8.7 g, 25 mmole) in 50 ml toluene was brought to reflux for 5 hours and cooled to room temperature. The solution was concentrated, in vacuo and purified by column chromatography (eluting with 2–6% EtOAc in hexanes) to give 4.8 g product (87% yield). $^1$H NMR (300 MHz, CDCl$_3$) δ 9.57 (1H, s), 7.68 (1H, d, J=8.8

Hz), 6.83 (1H, d, J=2.8 Hz), 6.57 (1H, dd, J=2.8, 8.8 Hz), 5.43 (1H, s), 4.23 (2H, m), 3.76 (3H, s),1.55 (3H, s), 1.31 (3H, m).

Example 76(d)

6-Methoxy-2-trifluoromethyl-1H-indole-3-carboxylic acid ethyl ester

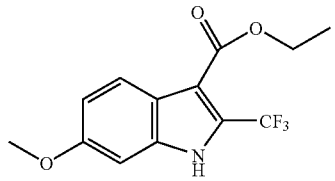

A mixture of 4,4,4-trifluoro-3-(2-iodo-5-methoxy-phenylamino)-but-2-enoic acid ethyl ester 76c (0.5 g, 1.2 mmole), Pd(OAc)$_2$ (22.4 mg, 0.1 mmole), PPh$_3$ (52.5 mg, 0.2 mmole) and NaHCO$_3$ (505 mg, 6 mmole) in 5 ml DMF was heated at 120° C. under argon for 24 hours and cooled to room temperature. The mixture was poured into EtOAc/water and washed with brine. The organic layer was dried over Na$_2$SO$_4$ and concentrated under rot vap. The residue was purified by column chromatography to give 217 mg product (63% yield). $^1$H NMR. (300 MHz, CD$_3$OD) δ 8.00 (1H, d, J=9.0 Hz), 6.96 (1H, d, J=2.0 Hz), 6.90 (1H, dd, J=2.0, 9.0 Hz), 4.37 (2H, m), 3.84 (3H, s), 1.40 (3H, m).

Example 76(e)

6-Methoxy-1-methyl-2-trifluoromethyl-1H-indole-3-carboxylic acid ethyl ester

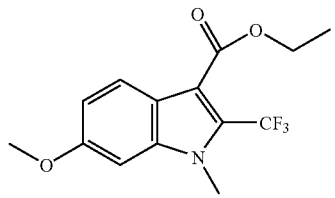

This material was prepared from 6-methoxy-2-trifluoromethyl-1H-indole-3-carboxylic acid ethyl ester 76d (1.64 g, 5.7 mmole) by treatment with NaH (274 mg, 60% in mineral oil, 6.84 mmole) and methyl iodide (1.21 g, 8.55 mmole) and NaH in a manner as previously described for example 16b to give 1.5 g product (87% yield). $^1$H NMR (300 MHz, CDCl$_3$) δ 7.96 (1H, dd, J=3.7, 8.8 Hz), 6.94 (1H, dd, J=2.3, 9.1 Hz), 6.77 (1H, d, J=2.1 Hz), 4.40 (2H, m), 3.89 (3H, s), 3.86 (3H, s), 1.41 (3H, m).

Example 76(f)

6-Methoxy-1-methyl-2-trifluoromethyl-1H-indole-3-carboxylic acid

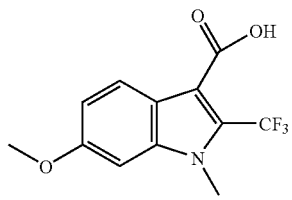

To a solution of 6-methoxy-1-methyl-2-trifluoromethyl-1H-indole-3-carboxylic acid ethyl ester 76e (1.5 g, 4.98 mmole) in 10 ml THF and 5 ml MeOH was added a solution of KOH (2.8 g, 50 mmole) in 5 ml water with ice bath cooling. The mixture was warmed to room temperature and stirred overnight. Concentrated aqueous HCl solution was added to adjust the pH to 1. The mixture was extracted with EtOAc and the combined organic layer was dried over Na$_2$SO$_4$, filtered and concentrated. The residue was further purified by column chromatography (eluting with 1–5% MeOH in CH$_2$Cl$_2$) to give 880 mg product (65% yield). $^1$H NMR (300 MHz, CD$_3$OD) δ 7.90 (1H, d, J=9.0 Hz), 7.01 (1H, d, J=2.1 Hz), 6.91 (1H, dd, J=2.1, 9.0 Hz), 3.90 (3H, s), 3.88 (3H, s).

Example 76(g)

6-Methoxy-1-methyl-2-trifluoromethyl-1H-indole-3-carboxylic acid methylamide

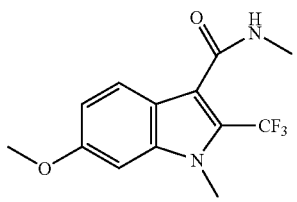

This material was prepared from 6-methoxy-1-methyl-2-trifluoromethyl-1H-indole-3-carboxylic acid 76f (880 mg, 3.22 mmole), oxalyl chloride (3 ml, 2.0M solution) and methylamine (5 ml, 2.0M solution) in a manner as previously described for example 16d to give 900 mg product as white solid (98% yield). $^1$H NMR (300 MHz, CDCl$_3$) δ 7.62 (1H, d, J=8.9 Hz), 6.88 (1H, dd, J=2.1, 8.9 Hz), 6.73 (1H, d, J=2.1 Hz), 5.80 (1H, bs), 3.88 (3H, s), 3.79 (3H, s), 3.04 (3H, d, J=4.9 Hz).

Example 76(h)

6-Hydroxy-1-methyl-2-trifluoromethyl-1H-indole-3-carboxylic acid methylamide

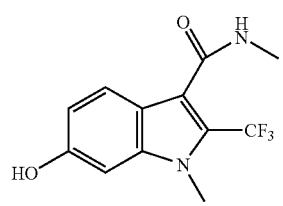

This material was prepared from 6-hydroxy-1-methyl-2-trifluoromethyl-1H-indole-3-carboxylic acid methylamide 76g (900 mg, 3.14 mmole) by treatment with BBr$_3$ in a manner as previously described for example 1d to give 780 mg product as white solid (89% yield). $^1$H NMR (300 MHz, CD$_3$OD) δ 7.44 (1H, d, J=8.7 Hz), 6.76–6.81 (2H, m), 3.77 (1H, s), 2.93 (3H, s).

Example 76

1-Methyl-6-[2-(1-methyl-1H-imidazol-2-yl)-thieno[3,2-b]pyridin-7-yloxy]-2-trifluoromethyl-1H-indole-3-carboxylic acid methylamide

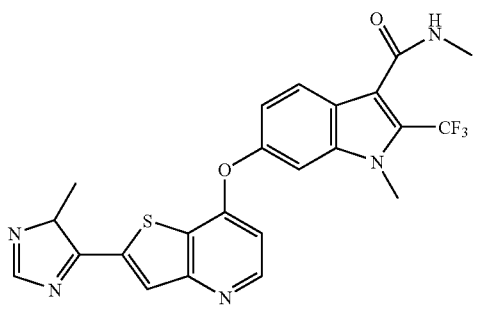

The material was prepared by the reaction of 7-chloro-2-(1-methyl-1H-imidazol-2-yl)thieno[3,2,-b]pyridine 1e with 6-hydroxy-1-methyl-2-trifluoromethyl-1H-indole-3-carboxylic acid methylamide 76 h and $Cs_2CO_3$ in a manner as previously described for example 1. $^1$H NMR (300 MHz, DMSO-$d_6$) δ 8.51 (1H, d, J=5.5 Hz), 7.89 (1H, s), 7.78 (1H, s), 7.72 (1H, d, J=8.6 Hz), 7.41 (1H, s), 7.18 (1H, d, J=9.8 Hz), 7.03 (1H, s), 6.66 (1H, d, J=5.4 Hz), 3.99 (3H, s), 3.86 (3H, s), 2.81 (3H, s). LCMS (ESI+) [M+H]/z Calc'd 486, found 486.

Anal. ($C_{23}H_{18}F_3N_5O_2S\cdot1.3H_2O$)C, H, N.

Example 77

6[2-(Azetidine-1-carbonyl)-thieno[3,2-b]pyridin-7-yloxy]-2-methyl-benzofuran-3-carboxylic acid methylamide

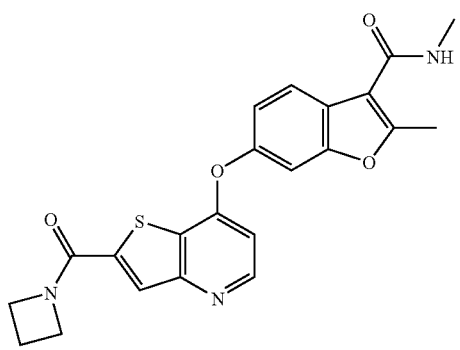

This material was prepared by the reaction 2-(azetidin-1-ylcarbonyl)-7-chlorothieno[3,2-b]pyridine 25a (100 mg, 0.40 mmole) with 6-hydroxy-2-methylbenzofuran-3-carboxylic acid methylamide (100 mg, 0.49 mmole) and $Cs_2CO_3$ (257 mg, 0.79 mmole) in a manner as previously described for example 1 to give 124 mg (74%) of a tan solid. $^1$H NMR (DMSO-$d_6$) δ 8.56 (1H, d, J=5.6 Hz), 7.99 (1H, d, J=4.6 Hz), 7.89 (1H, s), 7.83 (1H, d, J=8.6 Hz), 7.66 (1H, d, J=2.0 Hz), 7.24 (1H, dd, J=8.6, 2.3 Hz), 6.70 (1H, d, J=5.3 Hz), 4.61 (2H, t, J=7.6 Hz), 4.10 (2H, t, J=7.3 Hz), 2.81 (3H, d, J=4.6 Hz), 2.63 (3H, s), 2.35 (2H, p, J=7.7 Hz).

Anal. Calcd for $C_{22}H_{19}N_3O_4S\cdot0.5\ H_2O$: C, 62.03; H, 4.61; N, 9.86; S, 7.53. Found: C, 62.31; H, 4.65; N, 9.60; S, 7.34.

Example 78(a)

1-Benzhydryl-3-methoxy-azetidine

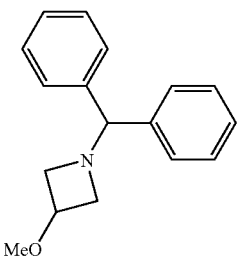

To an ice cold solution of 1-benzhydrylazetidin-3-ol 9a (1.0 g, 4.2 mmole) in DMF (10 ml) was added 60% dispersion NaH in mineral oil (0.25 g, 6.3 mmole). After 30 min at 0° C., 5 ml more DMF was added along with methyl iodide (0.39 ml, 6.3 mmole). The ice bath was removed, and the reaction was stirred at room temperature (rt). After 1.5 hr, the reaction was poured into brine and extracted with $Et_2O$ (2×). The combined organic layers were washed with brine, dried ($MgSO_4$) and concentrated under reduced pressure. The residue was flash chromatographed on silica gel eluting Hexanes/EtOAc (1:1) to give 919 mg (92%) of a colorless oil which crystallized on standing. $^1$H NMR (DMSO-$d_6$) δ 7.42 (4H, d, J=7.3 Hz), 7.27 (4H, t, J=7.3 Hz), 7.13 (2H, t, J=7.3 Hz), 4.39 (1H, s), 3.95 (1H, p, J=5.8 Hz), 3.35 (2H, t, J=6.3 Hz), 3.11 (3H, s), 2.75 (2H, t, J=5.6 Hz).

Example 78(b)

(7-Chloro-thieno[3,2-b]pyridin-2-yl)-(3-methoxy-azetidin-1-yl)-methanone

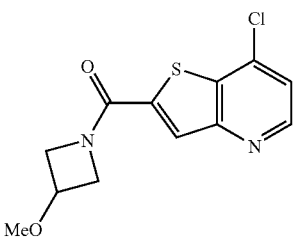

A 100 ml round bottom flask was charged with 1-benzhydryl-3-methoxy-azetidine 78a (447 mg, 1.77 mmole), 10% Pd/C (300 mg), trifluoroacetic acid (0.15 ml, 1.94 mmole) and EtOH (30 ml) and placed under 1 atm $H_2$ and vigorously stirred at rt. After 2 hr, the catalyst was removed and washed with MeOH. The filtrate was concentrated under reduced pressure to give the crude azetidine which was dissolved in $CH_2Cl_2$. To this solution were added triethylamine (0.6 ml, 4.41 mmole) and 7-chloro-thieno[3,2-b]pyridine-2-carbonyl chloride, prepared as previously described in example 25a. After stirring at ambient temperature overnight, the reaction mixture was diluted with more $CH_2Cl_2$, then washed sequentially with 0.5N HCl, satd. $NaHCO_3$ (aq), and brine. The organic layer was dried ($MgSO_4$) and concentrated to near dryness under reduced pressure, then triturated with hexanes to give 278 mg (56%) of the desired product as a light yellow solid. $^1$H NMR (DMSO-$d_6$) δ 8.73(1H, d, J=5.1 Hz), 8.00 (1H, s), 7.70 (1H, d, J=5.1 Hz), 4.77 (1H, m), 4.49 (1H, m), 4.31 (2H, m), 3.90 (1H, m), 3.24 (3H, s). APCl m/z 283/285 (M+H)$^+$.

Example 78

Methoxy-azetidine-1-carbonyl)-thieno[3,2-b]pyridin-7-yloxy]-2-methyl-benzofuran-3-carboxylic acid methylamide

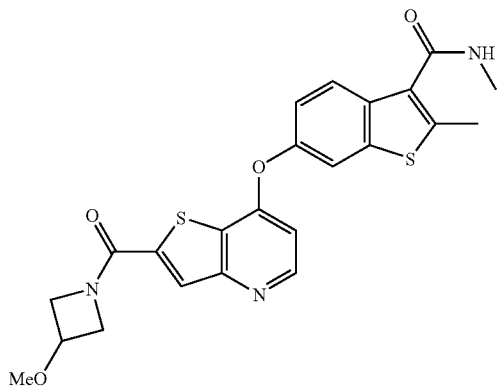

This material was prepared by the reaction of (7-Chloro-thieno[3,2-b]pyridin-2-yl)-(3-methoxy-azetidin-1-yl)-methanone 78b (241 mg, 0.85 mmole) with 6-hydroxy-2-methylbenzo[b]furan-3-carboxylic acid methylamide 12c (210 mg, 1.02 mmole) and $Cs_2CO_3$ (833 mg, 2.56 mmole) in a manner as previously described in example 1 to give 298 mg (77%) of a yellow solid. $^1$H NMR (DMSO-$d_6$) δ 8.57 (1H, d, J=5.3 Hz), 7.99 (1H, d, J=4.7 Hz), 7.94 (1H, s), 7.82 (1H, d, J=8.5 Hz), 7.66 (1H, d, J=2.3 Hz), 7.24 (1H, dd, J=8.5, 2.3 Hz), 6.72 (1H, d, J=5.5 Hz), 4.76 (1H, m), 4.47 (1H, m), 4.30 (2H, m), 3.90 (1H, m), 3.25 (3H, s), 2.82 (3H, d, J=4.5 Hz), 2.63 (3H, s).

Anal. Calcd for $C_{23}H_{21}N_3O_5S.0.4 H_2O$: C, 60.22; H, 4.79; N, 9.16; S, 6.99. Found: C, 60.33; H, 4.78; N, 9.13; S, 6.79.

Example 79

6-(2-[(S)-2-(methoxymethyl)pyrrolidine-1-carbonyl]thieno[3,2-b]pyridin-7-yloxy)-2-methyl-benzofuran-3-carboxylic acid methyl amide

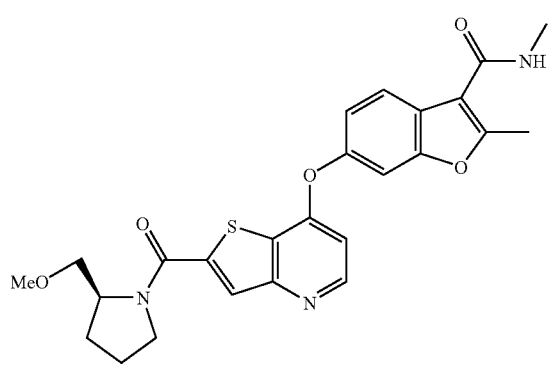

This material was prepared by the reaction of 7-chloro-2-[(R)-2-methoxymethylpyrrolidine-1-carbonyl]thieno[3,2-b]pyridine 2a with 6-Hydroxy-2-methyl-benzofuran-3-carboxylic acid methyl amide 12c and $Cs_2CO_3$ in a manner as previously described for example 1. $^1$H NMR (DMSO-$d_6$) δ 8.57 (1H,d, J=5.3 Hz), 8.02 (1H, s),7.98 (1H, m), 7.83 (1H, d, J=8.6 Hz), 7.66 (1H, d, J=2.0 Hz), 7.25 (1H, dd, J=8.6, 2.0 Hz), 6.72 (1H, d, J=5.3 Hz), 4.31 (1H,m), 3.94–3.80 (2H, m), 3.60–3.39 (2H, m), 3.28 (3H, s), 2.82 (3H, d, J=4.6 Hz), 2.63 (3H, s), 2.06–1.85 (4H,m).

Anal. Calcd for $C_{25}H_{25}N_3O_5S.0.6H_2O.0.2$ Hexanes: C, 61.99; H, 5.76; N, 8.28; S, 6.32. Found: C, 61.94; H, 5.74; N, 8.12; S, 6.32.

Example 80

6-(2-[(S)-2-(hydroxymethyl)pyrrolidine-1-carbonyl]thieno[3,2-b]pyridin-7-yloxy)-2-methyl-benzofuran-3-carboxylic acid methylamide

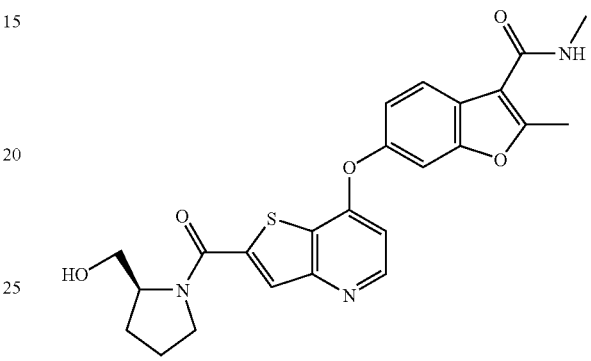

This material was prepared from 2-methyl-6-[2-(2-methoxymethyl-pyrrolidine-1-carbonyl)-thieno[3,2-b]pyridin-7-yloxy]-benzofuran-3-carboxylic acid methylamide 79 by treatment with $BBr_3$ in a manner as previously described for example 1d. $^1$H NMR (DMSO-$d_6$) δ 8.56 (1H, d, J=5.1 Hz), 8.00–7.98 (2H, m), 7.83 (1H, d, J=8.6 Hz), 7.66 (1H, d, J=2.0 Hz), 7.25 (1H, dd, J=8.6, 2.0 Hz), 6.73 (1H, d, J=5.1 Hz), 4.81 (1H, m), 4.18 (1H, m), 3.91–3.32 (4H, m), 2.81 (3H, d, J=4.5 Hz), 2.63 (3H, s), 2.05–1.83 (4H, m).

Anal. Calcd for $C_{24}H_{23}N_3O_5S.2H_2O.0.2$ EtOAc: C, 57.37; H, 5.55; N, 8.09; S, 6.18. Found: C, 57.15; H, 5.24; N, 7.71; S, 6.01.

Example 81

6-[2-(4-Hydroxymethyl-thiazol-2-yl)-thieno[3,2-b]pyridin-7-yloxy]-2-methyl-benzofuran-3-carboxylic acid methylamide

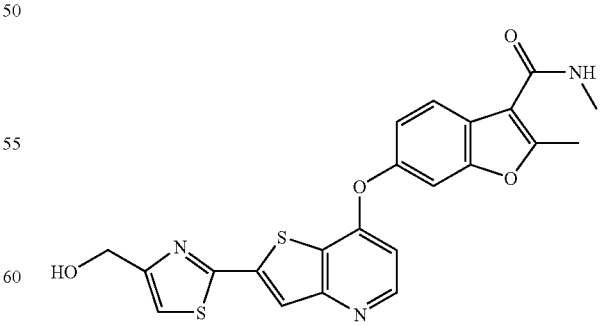

This material was prepared by the reaction of [2-(7-Chloro-thieno[3,2-b]pyridin-2-yl)-thiazol-4-yl]-methanol with 6-hydroxy-2-methyl-benzofuran-3-carboxylic acid methyl amide 12c and $Cs_2CO_3$ in a manner as previously described for example 1. ¹H NMR (DMSO-d₆) δ 8.55 (1H, d, J=5.6 Hz), 8.16 (1H, s), 7.98 (1H, m), 7.84 (1H, d, J=8.6 Hz), 7.67 (1H, d, J=2.0 Hz), 7.63 (1H, s), 7.26 (1H, dd, J=8.6, 2.0 Hz), 6.73 (1H, d, J=5.6 Hz), 5.43 (1H, m), 4.61 (2H,s), 2.82 (3H, d, J=4.6 Hz), 2.64 (3H, s).

Anal. Calcd for $C_{22}H_{17}N_3O_4S_2 \cdot 0.6\ H_2O$: C, 57.15; H, 3.97; N, 9.09; S, 13.87. Found: C, 57.13; H, 4.07; N, 8.95; S, 13.87.

Example 82(a)

6-Methoxy-2-methyl-benzofuran-3-carboxylic acid isopropyl amide

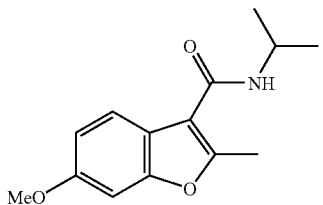

This material was prepared from 6-methoxy-2-methyl-benzofuran 12a (500 mg, 3.1 mmole) by acylation with oxalyl chloride in the presence of $AlCl_3$, followed by treatment with isopropylamine in a manner as previously described for example 1c to give 540 mg (71%) of an off-white solid. ¹H NMR (DMSO-d₆) δ 7.80 (1H, d, J=7.8 Hz), 7.50 (1H, d, J=8.6 Hz), 7.14 (1H, d, J=2.2 Hz), 6.89 (1H, dd, J=8.6, 2.2 Hz), 4.09 (1H, m), 3.76 (3H, s), 2.56 (3H, s), 1.16 (6H, d, J=6.6 Hz).

Anal. Calcd for $C_{14}H_{17}NO_3$: C, 67.99; H, 6.93; N, 5.66. Found: C, 67.86; H, 6.87; N, 5.60.

Example 82(b)

6-Hydroxy-2-methyl-benzofuran-3-carboxylic acid isopropyl amide

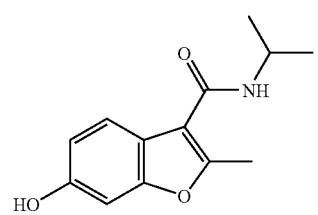

This material was prepared from 6-methoxy-2-methyl-benzofuran-3-carboxylic acid isopropylamide 82a (507 mg, 2.05 mmole) by treatment with $BBr_3$ in a manner as previously described for example 1d to give 425 mg (89%) of lt. tan solid. ¹H NMR (DMSO-d₆) δ 9.54 (1H, s), 7.71 (1H, d, J=8.1 Hz), 7.38 (1H, d, J=8.6 Hz), 6.87 (1H, s), 6.70 (1H, d, J=8.6 Hz), 4.07 (1H, m), 2.51 (3H, s),1.17 (6H, d, J=6.8 Hz).

Anal. Calcd for $C_{13}H_{15}NO_3 \cdot 0.1$ MeOH: C, 66.54; H, 6.56; N, 5.92. Found: C, 66.38; H, 6.48; N, 5.93.

Example 82

6-(2-[(S)-2-(methoxymethyl)pyrrolidine-1-carbonyl] thieno[3,2-b]pyridin-7-yloxy)-2-methyl-benzofuran-3-carboxylic acid isopropylamide This material was prepared by the reaction of 7-chloro-2-[(S)-2-(methoxymethyl)pyrrolidine-1-carbonyl]thieno[3,2-b]pyridine 2a (133 mg, 0.43 mmole) 6-hydroxy- 2-methyl-benzofuran-3-carboxylic acid isopropy amide 82b (120 mg, 0.51 mmole) and $CS_2CO_3$ (279 mg, 0.86 mmole) in a manner as previously described to give 150 mg (69%) of an off-white brittle foam. ¹H NMR (DMSO-d₆): δ 8.56 (1H, d, J=5.3 Hz), 8.03 (1H, s), 7.96 (1H, d, J=8.1 Hz), 7.75 (1H, d, J=8.3 Hz), 7.65 (1H, d, J=2.3 Hz), 7.24 (1H, dd, J=8.6, 2.3 Hz), 6.72 (1H, d, J=5.3 Hz), 4.30 (1H, m), 4.12 (1H, m), 3.85 (2H, m), 3.56 (1H, m), 3.42 (1H, m), 3.25 (3H, s), 2.59 (3H, s), 2.08–1.81 (4H, m), 1.20 (6H, d, J=6.6 Hz). Anal. Calcd for $C_{27}H_{29}N_3O_5S \cdot 0.3$ EtOAc: C, 63.42; H, 5.93; N, 7.87; S, 6.00. Found: C, 63.20; H, 5.90; N, 7.85; S, 6.03.

Example 83

2-Methyl-6-[2-(1-methyl-1H-imidazol-2-yl)-thieno [3,2-b]pyridin-7-yloxy]-benzofuran-3-carboxylic acid isopropyl amide This material was prepared by the reaction of 7-chloro-2-(1-methyl-1H-imidazol-2-yl)thieno[3,2-b]pyridine 1e (89 mg, 0.36 mmole) with 6-hydroxy-2-methylbenzo[b]furan-3-carboxylic acid isopropylamide 82a (100 mg, 0.43 mmole) and $Cs_2CO_3$ (233 mg, 0.72 mmole) in a manner as previously described for example 1 to give a 37% yield of a light yellow solid. ¹H NMR (DMSO-d₆) δ 8.51 (1H, d, J=5.3 Hz), 7.97 (1H, d, J=7.8 Hz), 7.88 (1H, s), 7.74 (1H, d, J=8.6 Hz), 7.65 (1H, d, J=2.3 Hz), 7.40 (1H, s), 7.24 (1H, dd, J=8.3, 2.0 Hz), 7.01 (1H, s), 6.65 (1H, d, J=5.6 Hz), 4.12 (1H, m), 3.98 (3H, s), 2.60 (3H, s),1.20 (6H,d, J=6.6 Hz).

Anal. Calcd for $C_{24}H_{22}N_4O_3S \cdot 0.9$ EtOAc: C, 63.04; H, 5.60; N, 10.66; S, 6.10. Found: C, 62.85; H, 5.52; N, 10.76; S, 6.24.

Example 84(a)

6Methoxy-2-methyl-benzofuran-3-carboxylic acid isobutyl-amide

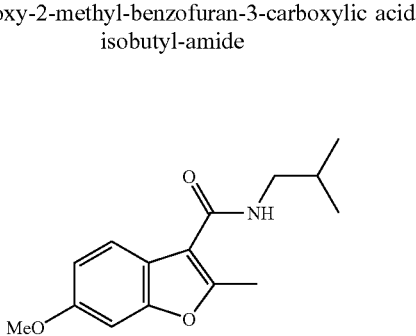

This material was prepared from 6-methoxy-2-methyl-benzofuran 12a (500 mg, 3.1 mmole) by acylation with oxalyl chloride in the presence of $AlCl_3$, followed by treatment with isobutylamine in a manner as previously described for example 1c to give 585 mg (73%) of an off-white solid. $^1H$ NMR (DMSO-$d_6$) δ 7.95 (1H, t, J=5.8 Hz), 7.56 (1H, d, J=8.6 Hz), 7.15(1H, d, J=2.3 Hz), 6.91 (1H, dd, J=8.6, 2.3 Hz), 3.76 (3H, s), 3.07 (2H, m), 2.57 (3H, s), 1.83 (1H, m), 0.88 (6H, d, J=6.8 Hz).

Anal. Calcd for $C_{15}H_{19}NO_3$: C, 68.94; H, 7.33; N, 5.36. Found: C, 68.75; H, 7.27; N, 5.38.

Example 84(b)

6-Hydroxy-2-methyl-benzofuran-3-carboxylic acid isobutyl amide

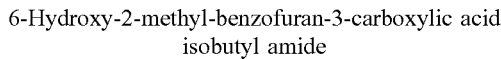

This material was prepared from 6-methoxy-2-methyl-benzofuran-3-carboxylic acid isobutyl amide 84a by treatment with $BBr_3$ in a manner as previously described for example 1d. $^1H$ NMR (DMSO-$d_6$) δ 9.53 (1H, s), 7.90 (1H, t, J=6.1 Hz), 7.44 (1H, d, J=8.3 Hz), 6.86 (1H, s), 6.74 (1H, dd, J=8.6, 1.8 Hz), 3.07 (2H, t, J=6.1 Hz), 2.52 (3H, s), 1.81 (1H, m). 0.90 (6H, d, J=6.8 Hz).

Example 84

2-Methyl-6-[2-(1-methyl-1H-imidazol-2-yl)-thieno[3,2-b]pyridin-7-yloxy]-benzofuran-3-carboxylic acid isobutyl amide

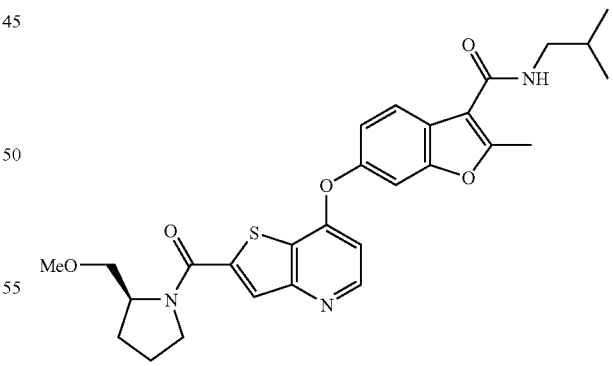

This material was prepared by the reaction of 7-chloro-2-(1-methyl-1H-imidazol-2-yl)thieno[3,2-b]pyridine 1e with 6-hydroxy-2-methyl-benzofuran-3-carboxylic acid isobutyl amide 84b and $Cs_2CO_3$ in a manner as previously described for example 1. $^1H$ NMR (CD$_3$CN) δ 8.48 (1H,d, J=5.6 Hz), 7.81 (1H, d, J=8.3 Hz), 7.74 (1H, s), 7.43 (1H, d, J=2.0 Hz), 7.21 (1H, dd, J=8.6, 2.3 Hz), 7.17 (1H, s), 7.04 (1H, s), 6.70 (1H,m), 6.67 (1H, d, J=5.6 Hz), 3.97 (3H, s), 3.23 (2H, t, J=6.6 Hz), 2.66 (3H, s),1.78 (1H,m), 0.98 (6H, d, J=6.6 Hz).

Anal. Calcd for $C_{25}H_{24}N_4O_3S \cdot 0.3H_2O$: C, 64.44; H, 5.32; N, 12.02; S, 6.88. Found: C, 64.40; H, 5.38; N, 11.76; S, 6.72.

Example 85

6[2-(2-Methoxymethyl-pyrrolidine-1-carbonyl)-thieno[3,2-b]pyridin-7-yloxy]-2-methyl-benzofuran-3-carboxylic acid isobutyl amide This material was prepared by the reaction of 7-chloro-2-[(R)-2-methoxymethylpyrrolidine-1-carbonyl]thieno[3,2-b]pyridine 2a with 6-hydroxy-2-methyl-benzofuran-3-carboxylic acid isobutyl amide 84b and $Cs_2CO_3$ in a manner as previously described for example 1. $^1H$ NMR (CD$_3$CN) δ 8.53 (1H,d, J=5.3 Hz), 7.87 (1H, s), 7.82 (1H, d, J=8.5 Hz), 7.41 (1H, d, J=1.9 Hz), 7.20 (1H, dd, J=8.5, 1.9 Hz), 6.70 (1H, d, J=5.5 Hz), 4.38 (1H, m), 3.85 (2H, m), 3.65–3.41

(2H, m), 3.32 (3H, s), 3.23 (2H, t, J=6.4 Hz), 2.65 (3H, s), 2.15–1.94 (4H,m, partially obscured by CD₃CN), 1.73 (1H, m), Anal. Calcd for C₂₈H₃₁N₃O₅S.0.2H₂O: C, 64.03; H, 6.03; N, 8.00; S, 6.10. Found: C, 64.02; H, 6.11; N, 7.79; S, 5.89.

Example 86

2-Methyl-6-[2-(2-hydroxymethyl-pyrrolidine-1-carbonyl)-thieno[3,2-b]pyridin-7-yloxy]-benzofuran-3-carboxylic acid isobutyl amide

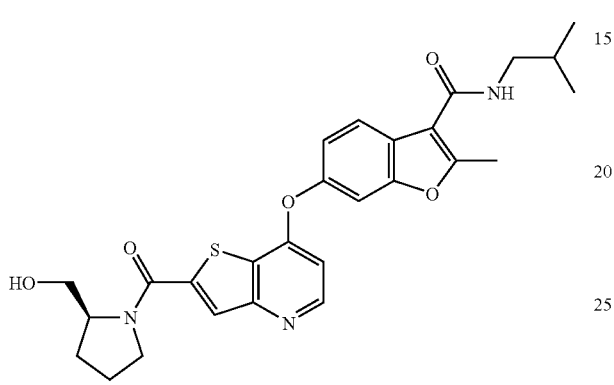

This material was prepared from 2-methyl-6-[2-(2-methoxymethyl-pyrrolidine-1-carbonyl)-thieno[3,2-b]pyridin-7-yloxy]-benzofuran-3-carboxylic acid isobutyl amide 85 by treatment with BBr₃ in a manner as previously described for example 1d. ¹H NMR (CD₃CN) δ 8.52 (1H, d, J=5.5 Hz), 7.89 (1H, s), 7.81 (1H, d, J=8.5 Hz), 7.42 (1H, d, J=2.1 Hz), 7.20 (1H, dd, J=8.5, 2.1 Hz), 6.78 (1H, m), 6.71 (1H, d, J=5.3 Hz), 4.29 (1H, m), 3.94–3.63 (4H, m), 3.22 (2H, t, J=6.4 Hz), 2.65 (3H, s), 2.22–1.95 (4H, m), 0.98 (6H, d, J=6.8 Hz).

Anal. Calcd for C₂₇H₂₉N₃O₅S: C, 63.89; H, 5.76; N, 8.28; S, 6.32. Found: C, 63.56; H, 5.95; N, 8.01; S, 6.07.

Example 87

6-[2-(3-Methoxy-pyrrolidine-1-carbonyl)-thieno[3,2-b]pyridin-7-yloxy]-2-methyl-benzofuran-3-carboxylic acid isobutyl amide

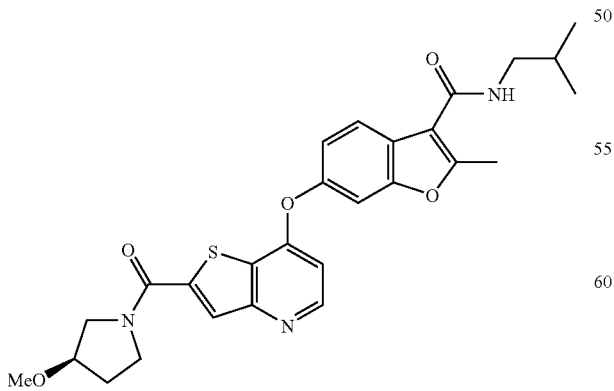

This material was prepared by the reaction of 7-chloro-2-[(R)-3-methoxypyrrolidine-1-carbonyl]thieno[3,2-b]pyridine 4b with 6-hydroxy-2-methyl-benzofuran-3-carboxylic acid isobutyl amide 83b and Cs₂CO₃ in a manner as previously described for example 1. ¹H NMR (CD₃CN) δ 8.53 (1H,d, J=5.5 Hz), 7.88 (1H, d, J=3.0 Hz), 7.82 (1H, d, J=8.5 Hz), 7.41 (1H, d, J=2.3 Hz), 7.20 (1H, dd, J=8.5, 2.3 Hz), 6.70 (2H, d, J=5.5 Hz), 4.10–3.83 (3H, m), 3.73–3.58 (2H, m), 3.33, 3.29 (3H, 2s), 3.23 (2H, t, J=6.8 Hz), 2.65 (3H, s), 2.10–1.95 (2H,m), 0.98 (6H, d, J=6.6 Hz).

Anal. Calcd for C₂₇H₂₉N₃O₅S: C, 63.89; H, 5.76; N, 8.28; S, 6.32. Found: C, 63.83; H, 5.95; N, 8.08; S, 6.10.

Example 88

2-Methyl-6[2-(3-hydroxy-pyrrolidine-1-carbonyl)-thieno[3,2-b]pyridin-7-yloxy]-benzofuran-3-carboxylic acid isobutyl amide

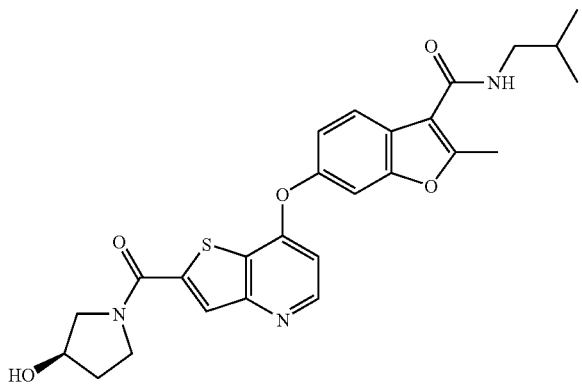

This material was prepared from 2-methyl-6-[2-(3-methoxy-pyrrolidine-1-carbonyl)-thieno[3,2-b]pyridin-7-yloxy]-benzofuran-3-carboxylic acid isobutyl amide 87 by treatment with BBr₃ in a manner as previously described for 1d. ¹H NMR (CD₃CN/DMSO-d₆) δ 8.55 (1H, d, J=5.6 Hz), 7.94, 7.88 (1H, 2s), 7.81 (1H, d, J=8.5 Hz), 7.46 (1H, d, J=2.1 Hz), 7.38 (1H, m), 7.20 (1H, dd, J=8.5, 2.1 Hz), 6.76 (1H, d, J=5.7 Hz), 4.39 (1H, m), 3.94 (1H, m), 3.74–3.51 (3H, m), 3.18 (2H, t, J=6.5 Hz), 2.63 (3H, s), 2.07–1.86 (2H, m, partially obscured by CD₃CN), 0.96 (6H, d, J=6.6 Hz).

Anal. Calcd for C₂₆H₂₇N₃O₅S.0.5 CH₂Cl₂: C, 59.37; H, 5.27; N, 7.84; S, 5.96. Found: C, 59.42; H, 5.44; N, 7.86; S, 5.99.

Example 89(a)

6Hydroxy-2-methylbenzofuran

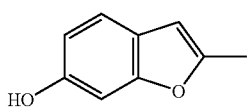

This material was prepared from 6-methoxy-2-methylbenzofuran (1.00 g, 6.17 mmole) by treatment with BBr₃ in a manner as previously described for 1d to give a colorless oil (690 mg, 75%) which solidified on standing. ¹H NMR (DMSO-d₆) δ 9.32 (1H, s), 7.23 (1H, d, J=8.3 Hz), 6.80 (1H, s),6.64 (1H, d, J=8.3 Hz), 6.37 (1H, s), 2.35 (3H, s).

Anal. Calcd for C₉H₈O₂: C, 72.96; H, 5.44. Found: C, 72.72; H, 5.43.

Example 89(b)

6-Acetoxy-2-methylbenzofuran

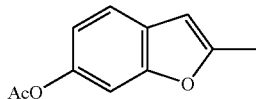

This material was prepared from 6-hydroxy-2-methylbenzofuran (654 mg, 4.41 mmole) by treatment with acetyl chloride (0.41 ml, 5.74 mmole) and triethylamine (0.74 ml, 5.30 mmole) in a manner as previously described for 8b to give the desired product as an oil (850 mg, ~quant). $^1$H NMR (CDCl$_3$) δ 7.41 (1H, d, J=8.3 Hz), 7.13 (1H, s), 6.88 (1H, dd, J=8.3, 1.9 Hz), 6.32 (1H, s), 2.42 (3H, s), 2.30 (3H, s).

Anal. Calcd for $C_{11}H_{10}O_3$: C, 69.46; H, 5.30. Found: C, 69.02; H, 5.44.

Example 89(c)

Methyl 6-Hydroxy-2-methylbenzofuran-3-carboxylate

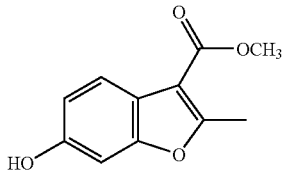

This material was prepared from 6-acetoxy-2-methylbenzofuran 89b (0.81 g, 4.3 mmole) by acylation with oxalyl chloride in the presence of AlCl$_3$, followed by treatment with methanol and K$_2$CO$_3$ in a manner as previously described for example 11a to give a beige solid (607 mg, 69%). $^1$H NMR (DMSO-d$_6$) δ 9.64 (1H, s), 7.62 (1H, d, J=8.5 Hz, 6.93 (1H, d, J=1.9 Hz), 6.78 (1H, dd, J=8.5, 2.0 Hz), 3.79 (3H, s), 2.66 (3H, s).

Anal. Calcd for $C_{11}H_{10}O_4$: C, 64.07; H, 4.89. Found: C, 64.06; H, 4.89.

Example 89(d)

Methyl 6-[2-(3-methoxypyrrolidine-1-carbonyl)-thieno[3,2-b]pyridin-7-yloxy]-2-methyl-benzofuran-3-carboxylate

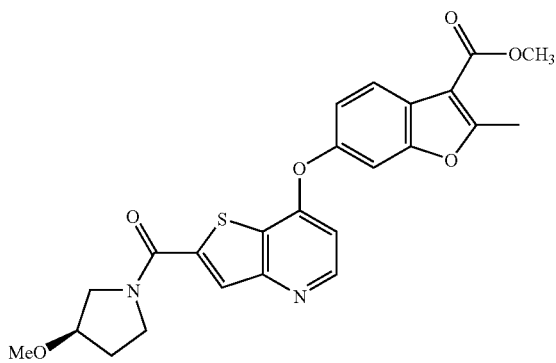

This material was prepared by the reaction of 7-chloro-2-[(R)-3-methoxypyrrolidine-1-carbonyl]thieno[3,2-b]pyridine 4b (707 mg, 2.38 mmole) with methyl 6-hydroxy-2-methyl-benzofuran-3-carboxylate 89c (565 mg, 2.74 mmole) and Cs$_2$CO$_3$ (3.109, 9.53 mmole) in a manner as previously described for example to give 650 mg (58%) of an off-white solid. $^1$H NMR (DMSO-d$_6$) δ 8.57 (1H,d, J=5.3 Hz), 8.07 (1H, s), 7.96 (1H, d, J=8.6 Hz), 7.75 (1H, d, J=2.0 Hz), 7.31 (1H, dd, J=8.6, 2.0 Hz), 6.74 (1H, d, J=5.6 Hz), 4.10–3.85 (3H, m), 3.90 (3H, s), 3.65–3.45 (2H, m), 3.25 (3H, d, J=12.6 Hz), 2.77 (3H, s), 2.15–1.95 (2H,m).

Anal. Calcd for $C_{24}H_{22}N_2O_6S.0.2H_2O$: C, 61.31; H, 4.80; N, 5.96; S, 6.82. Found: C, 61.21; H, 4.99; N, 5.90; S, 6.68.

Example 89(e)

6-[2-(3-Methoxypyrrolidine-1-carbonyl)-thieno[3,2-b]pyridin-7-yloxy]-2-methyl-benzofuran-3-carboxylic acid

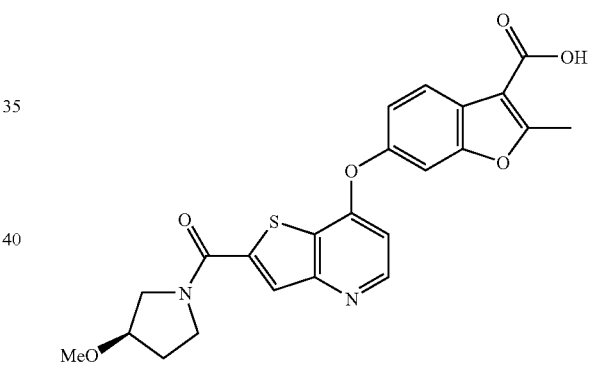

To a stirred solution of methyl 6-[2-(3-methoxypyrrolidine-1-carbonyl)-thieno[3,2-b]pyridin-7-yloxy]-2-methyl-benzofuran-3-carboxylate 89d (540 mg, 1.16 mmole) in THF/MeOH/MeOH (6 ml, 1:1:1) was added lithium hydroxide monohydrate (54 mg, 1.29 mmole). When the ester disappeared by thin layer chromatography (tlc), the organic solvents removed under reduced pressure, and the aqueous residue was neutralized with 2N HCl. The white solid which precipitated was collected by filtration and dried under vacuum to give the desired acid (411 mg, 83%). $^1$H NMR (DMSO-d$_6$) δ 13.02 (1H, bs), 8.57 (1H,d, J=5.3 Hz), 8.05 (1H, s), 7.94 (1H, d, J=8.5 Hz), 7.68 (1H, s), 7.25 (1H, d, J=8.5 Hz), 6.75 (1H, d, J=5.5 Hz), 4.10–3.85 (3H, m), 3.65–3.45 (2H, m), 3.25 (3H, d, J=9.4 Hz), 2.74 (3H, s), 2.15–1.95 (2H,m).

Example 89

6-[2-(3-Methoxypyrrolidine-1-carbonyl)-thieno[3,2-b]pyridin-7-yloxy]-2-methyl-benzofuran-3-carboxylic acid cyclopropylamide

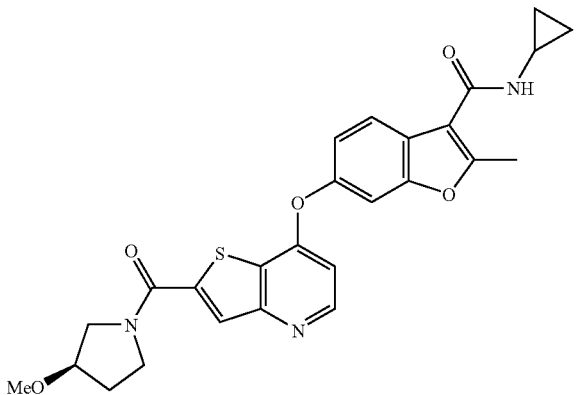

This material was prepared from 6-[2-(3-methoxypyrrolidine-1-carbonyl)-thieno[3,2-b]pyridin-7-yloxy]-2-methyl-benzofuran-3-carboxylic acid 89e (37 mg, 0.08 mmole) by treatment with oxalyl chloride (15 μl, 0.17 mmole) and cyclopropylamine (56 μl, 0.81 mmole) in a manner as previously described for example 16d to give a white solid (13 mg, 33%). $^1$H NMR (DMSO-$d_6$) δ 8.57 (1H, d, J=5.1 Hz), 8.19 (1H,s), 8.06 (1H, bs), 7.74 (1H, d, J=6.1 Hz), 7.65 (1H, s), 7.24 (1H, d, J=6.1 Hz), 6.71 (1H, d, J=1.8 Hz), 4.10–3.80 (3H, m), 3.70–3.35 (2H, m), 3.25 (3H, d, J=13.1 Hz), 2.86 (1H, m), 2.59 (3H, s), 2.25–1.95 (2H, m), 0.71 (2H, m), 0.60 (2H, m).

Anal. Calcd for $C_{26}H_{25}N_3O_5S\cdot0.1$ Hexanes: C, 63.87; H, 5.32; N, 8.40; S, 6.41. Found: C, 63.61; H, 5.51; N, 8.31; S, 6.23.

Example 90

6-[2-(3-Methoxy-pyrrolidine-1-carbonyl)-thieno[3,2-b]pyridin-7-yloxy]-2-methyl-benzofuran-3-carboxylic acid (2-morpholin-4-yl-ethyl)-amide

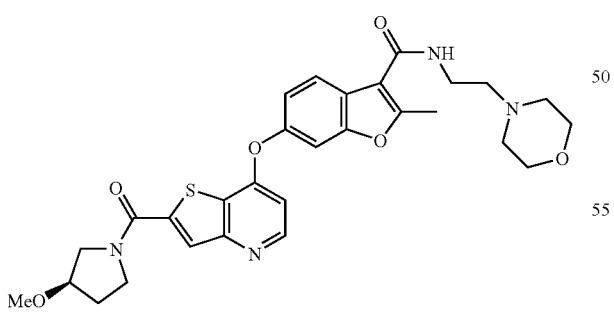

This material was prepared from 6-[2-(3-methoxypyrrolidine-1-carbonyl)-thieno[3,2-b]pyridin-7-yloxy]-2-methyl-benzofuran-3-carboxylic acid 89e by treatment with oxalyl chloride and 2-(morpholin-4-yl)ethylamine in a manner as previously described for example 16d. $^1$H NMR (DMSO-$d_6$) δ 8.57 (1H, d, J=5.1 Hz), 8.06 (1H,s), 7.97 (1H, bs), 7.83 (1H, d, J=8.6 Hz), 7.66 (1H, s), 7.27 (1H, d, J=8.3 Hz), 6.71 (1H, d, J=5.3 Hz), 4.20–3.95 (4H, m), 3.70–3.35 (10H, m), 3.25 (3H, d, J=12.6 Hz), 2.64 (3H, s), 2.41 (3H, s), 2.06 (2H, m).

Anal. Calcd for $C_{29}H_{32}N_4O_6S\cdot0.7H_2O$: C, 60.34; H, 5.83; N, 9.71; S, 5.55. Found: C, 60.67; H, 5.92; N, 9.71; S, 5.39.

Example 91

6-[2-(q-Methoxy-pyrrolidine-1-carbonyl)-thieno[3,2-b]pyridin-7-yloxy]-2-methyl-benzofuran-3-carboxylic acid cyclopropylmethyl-amide

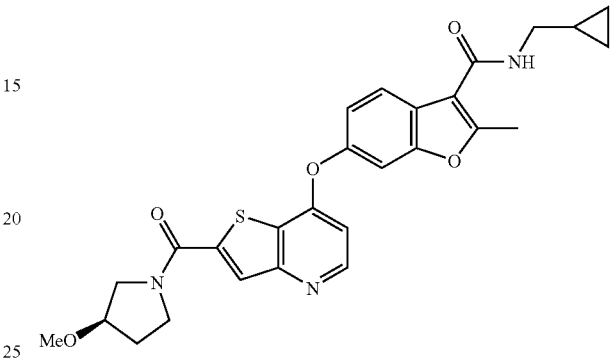

This material was prepared from 6-[2-(3-methoxypyrrolidine-1-carbonyl)-thieno[3,2-b]pyridin-7-yloxy]-2-methyl-benzofuran-3-carboxylic acid 89e by treatment with oxalyl chloride and (aminomethyl)cyclopropane in a manner as previously described for example 16d. $^1$H NMR (DMSO-$d_6$) δ 8.55 (1H, d, J=5.1 Hz), 8.20 (1H,s), 8.05 (1H, s), 7.80 (1H, d, J=8.6 Hz), 7.64 (1H, s, 7.22 (1H, d, J=8.3 Hz), 6.69 (1H, d, J=5.3 Hz), 4.10–3.80 (3H, m), 3.70–3.50 (2H, m), 3.26 (3H, d, J=12.6 Hz), 3.15 (2H, m), 2.63 (3H, s), 2.20–1.95 (2H, m), 1.08 (1H,m), 0.45 (2H, d, J=7.1 Hz), 0.25 (2H, d, J=4.3 Hz).

Anal. Calcd for $C_{27}H_{27}N_3O_5S\cdot0.2$ Hexanes$\cdot0.6H_2O$: C, 63.47; H, 5.86; N, 8.87; S, 6.01. Found: C, 63.54; H, 5.88; N, 7.74; S, 5.91.

Example 92

6-[2-(3-Methoxy-pyrrolidine-1-carbonyl)-thieno[3,2-b]pyridin-7-yloxy]-2-methyl-benzofuran-3-carboxylic acid propyl amide

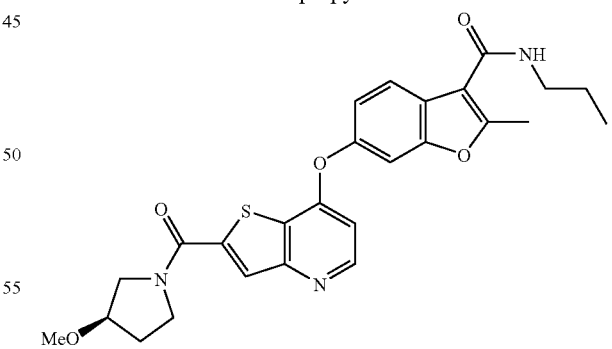

This material was prepared from 6-[2-(3-methoxypyrrolidine-1-carbonyl)-thieno[3,2-b]pyridin-7-yloxy]-2-methyl-benzofuran-3-carboxylic acid 89e by treatment with oxalyl chloride and 1-aminopropane in a manner as previously described for example 16d. $^1$H NMR (DMSO-$d_6$) δ 8.57 (1H, dd, J=5.6, 1.3 Hz), 8.09 (1H, m), 8.06 (1H,s), 7.79 (1H, d, J=8.6 Hz), 7.66 (1H, d, J=2.0 Hz), 7.26 (1H, dd, J=8.6, 2.0 Hz), 6.72 (1H, d, J=5.6 Hz), 4.08–3.82 (3H, m), 3.70–3.44 (2H, m), 3.27–3.22 (5H, m), 2.62 (3H, s), 2.15–1.92 (2H, m), 1.56–1.54 (2H, m), 0.92 (3H, t, J=7.3 Hz).

Anal. Calcd for C$_{26}$H$_{27}$N$_3$O$_5$S.0.7H$_2$O.0.3 MTBE: C, 62.01; H, 6.06; N, 7.89; S, 6.02. Found: C, 61.82; H, 6.07; N, 7.87; S, 5.97.

Example 93

6-[2-(3-Methoxy-pyrrolidine-1-carbonyl)-thieno[3,2-b]pyridin-7-yloxy]-2-methyl-benzofuran-3-carboxylic acid 2-hydroxyethyl amide

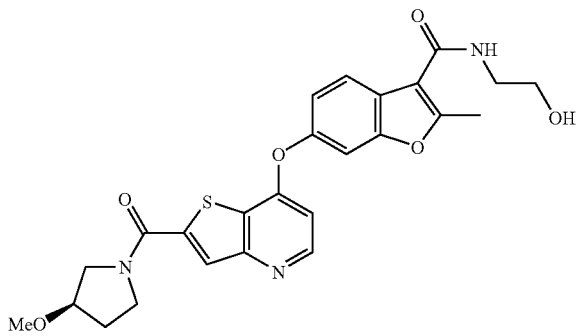

This material was prepared from 6-[2-(3-methoxypyrrolidine-1-carbonyl)-thieno[3,2-b]pyridin-7-yloxy]-2-methylbenzofuran-3-carboxylic acid 89e by treatment with oxalyl chloride and 2-aminoethanol in a manner as previously described for example 16d. $^1$H NMR (DMSO-d$_6$) δ 8.57 (1H, d, J=5.6 Hz), 8.06 (1H,s), 8.00 (1H, t, J=5.3 Hz), 7.82 (1H, d, J=8.6 Hz), 7.66 (1H, d, J=2.3 Hz), 7.26 (1H, dd, J=8.3, 2.3 Hz), 6.72 (1H, d, J=5.3 Hz), 4.76(1H, m), 4.10–3.82 (3H, m), 3.67–3.59 (2H, m), 3.55 (2H, t, J=6.1 Hz), 3.37 (2H, t, J=6.1 Hz), 3.27, 3.24 (3H, 2s), 2.63 (3H, s), 2.06 (2H, m).

Example 94

2-Ethyl-6[2-(1-methyl-1H-imidazol-2-yl)-thieno[3,2-b]pyridin-7-yloxy]-benzofuran-3-carboxylic acid methylamide

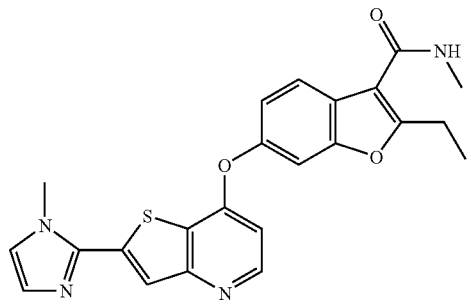

This material was prepared by the reaction of 7-chloro-2-(1-methyl-1H-imidazol-2-yl)thieno[3,2-b]pyridine 1e (114 mg, 0.46 mmole) with 6-hydroxy-2-ethylbenzofuran-3-carboxylic acid methylamide 14c (120 mg, 0.55 mmole) and Cs$_2$CO$_3$ (594 mg, 1.82 mmole) in a manner as previously described for example 1 to give 60 mg (30%) of a tan solid. $^1$H NMR (DMSO-d$_6$) δ 8.49 (1H,d, J=5.6 Hz), 8.00 (1H, d, J=4.6 Hz), 7.89 (1H, s), 7.82 (1H, d, J=8.6 Hz), 7.67 (1H, s), 7.41 (1H, s), 7.26 (1H, d, J=8.6 Hz), 7.03 (1H, s), 6.68 (1H, d, J=5.6 Hz), 3.99 (3H, s), 3.04 (2H, q, J=7.6 Hz), 2.81 (3H, d, J=4.6 Hz), 1.28 (3H, t, J=7.3 Hz).
Anal. Calcd for C$_{23}$H$_{20}$N$_4$O$_3$S.0.1 Hexanes.0.3H$_2$O: C, 63.48; H, 4.97; N, 12.55; S, 7.18. Found: C, 63.40; H, 5.07; N, 12.28; S, 7.15.

Example 95

2-Ethyl-6-[2-(3-hydroxy-pyrrolidine-1-carbonyl)-thieno[3,2-b]pyridin-7-yloxy]-benzofuran-3-carboxylic acid methylamide

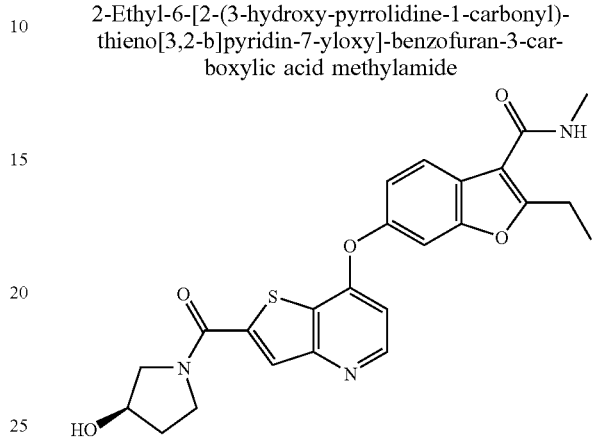

This material was prepared from 2-ethyl-6-[2-(3-methoxypyrrolidine-1-carbonyl)-thieno[3,2-b]pyridin-7-yloxy]benzofuran-3-carboxylic acid methylamide 14 by treatment with BBr$_3$ in a manner as previously described for 1d. $^1$H NMR (DMSO-d$_6$) δ 8.56 (1H, d, J=5.3 Hz), 8.07(1H, s), 8.00 (1H, d, J=4.1 Hz), 7.82 (1H, d, J=8.6 Hz), 7.68 (1H, d, J=2.0 Hz), 7.25 (1H, dd, J=8.6, 2.0 Hz), 6.73 (1H, d, J=5.3 Hz), 5.07 (1H, t, J=3.5 Hz), 4.35 (1H, m), 3.97 (1H, m), 3.86–3.46 (3H, m), 3.03 (2H, q, J=7.6 Hz), 2.80 (3H, d, J=4.5 Hz), 2.10–1.80 (2H, m), 1.27 (3H, t, J=7.6 Hz).
Anal. Calcd for C$_{24}$H$_{23}$N$_3$O$_5$S.0.5H$_2$O: C, 60.74; H, 5.10; N, 8.86; S, 6.76. Found: C, 60.79; H, 5.24; N, 8.61; S, 6.69.

Example 96

2-ethyl-6-(2-[(S)-2-(methoxymethyl)pyrrolidine-1-carbonyl]thieno[3,2-b]pyridin-7-yloxy)-benzofuran-3-carboxylic acid methyl amide

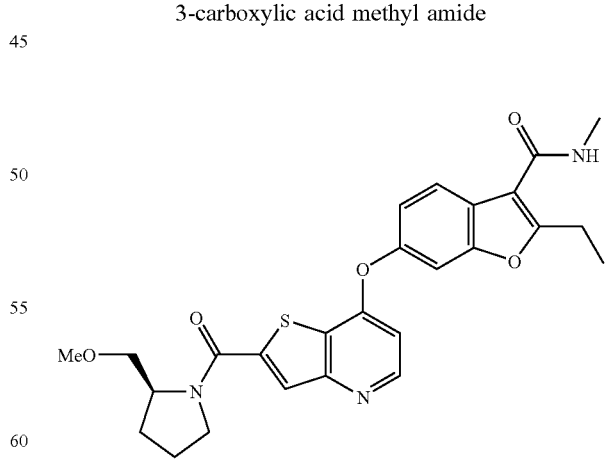

This material was prepared by the reaction of 7-chloro-2-[(R)-2-methoxymethylpyrrolidine-1-carbonyl]thieno[3,2-b]pyridine 2a with 6-hydroxy-2-ethylbenzofuran-3-carboxylic acid methyl amide 14c and Cs$_2$CO$_3$ in a manner as previously described. $^1$H NMR (DMSO-d$_6$) δ 8.57 (1H,d, J=5.5 Hz), 8.03 (1H, s), 8.01 (1H, m), 7.83 (1H, d, J=8.6 Hz), 7.67 (1H, d, J=2.1 Hz), 7.25 (1H, dd, J=8.7, 2.1 Hz), 6.73 (1H, d, J=5.5 Hz), 4.31 (1H, m), 3.92–3.77 (2H, m), 3.58–3.45 (2H, m), 3.27 (3H, s), 3.04 (2H, q, J=7.5 Hz), 2.82 (3H, d, J=4.5 Hz), 2.06–1.85 (4H,m), 1.26 (3H, t, J=7.5 Hz).

Anal. Calcd for $C_{26}H_{27}N_3O_5S.0.5H_2O.0.2$ MTBE C, 62.34; H, 5.89; N, 8.08; S, 6.16. Found: C, 62.38; H, 5.86; N, 7.97; S, 6.15.

Example 97

2-ethyl-6(2-[(S)-2-(hydroxymethyl)pyrrolidine-1-carbonyl]thieno[3,2-b]pyridin-7-yloxy)-benzofuran-3-carboxylic acid methylamide

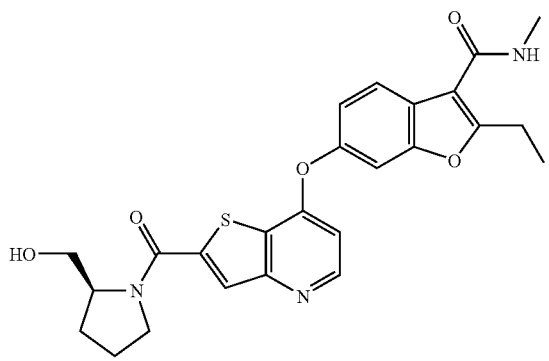

This material was prepared from 2-ethyl-6-[2-(2-methoxymethyl-pyrrolidine-1-carbonyl)-thieno[3,2-b]pyridin-7-yloxy]-benzofuran-3-carboxylic acid methylamide 95 by treatment with BBr$_3$ in a manner as previously described for 1 d. $^1$H NMR (DMSO-d$_6$) δ 8.56 (1H, d, J=5.3 Hz), 8.01 (2H, m), 7.82 (1H, d, J=8.6 Hz), 7.68 (1H, s), 7.25 (1H, dd, J=8.3, 2.0 Hz), 6.73 (1H, d, J=5.1 Hz), 4.82 (1H, m), 4.20 (1H, m), 3.92–3.47 (4H, m), 3.04 (2H, q, J=7.6 Hz), 2.81 (3H, d, J=4.5 Hz), 2.08–1.83 (4H, m), 1.26 (3H, t, J=7.6 Hz).

Anal. Calcd for $C_{25}H_{25}N_3O_5S.1$ $H_2O$: C, 60.35; H, 5.47; N, 8.45; S, 6.44. Found: C, 60.59; H, 5.47; N, 8.28; S, 6.20.

Example 98

6-[2-(Azetidine-1-carbonyl)-thieno[3,2-b]pyridin-7-yloxy]-2-ethyl-benzofuran-3-carboxylic acid methylamide

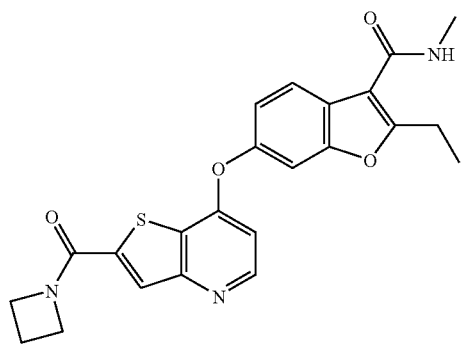

This material was prepared by the reaction of 2-(azetidin-1-ylcarbonyl)-7-chlorothieno[3,2-b]pyridine 25a with 6-hydroxy-2-ethylbenzofuran-3-carboxylic acid methyl amide 14c and Cs$_2$CO$_3$ in a manner as previously described for example 1. $^1$H NMR (DMSO-d$_6$) δ 8.56 (1H, d, J=5.6 Hz), 7.99 (1H, m), 7.89 (1H, s), 7.82 (1H, d, J=8.6 Hz), 7.67 (1H, d, J=2.0 Hz), 7.25 (1H, dd, J=8.6, 2.3 Hz), 6.72 (1H, d, J=5.3 Hz), 4.62 (2H, t, J=7.8 Hz), 4.11 (2H, t, J=7.8 Hz), 3.04 (2H, q, J=7.6 Hz), 2.81 (3H, d, J=4.6 Hz), 2.35 (2H, p, J=7.7 Hz), 1.26 (3H, t, J=7.6 Hz).

Anal. Calcd for $C_{23}H_{21}N_3O_4S.0.3$ $H_2O$: C, 62.65; H, 4.94; N, 9.53; S, 7.27. Found: C, 62.66; H, 4.84; N, 9.47; S, 7.52.

Example 99

6-[Thieno(3,2-b)pyridin-7-yloxy]-2-methyl-benzofuran-3-carboxylic acid methyl amide

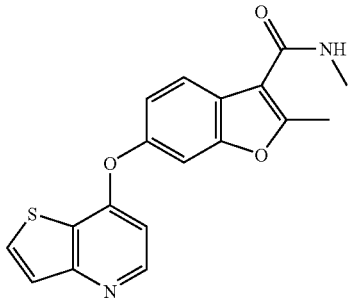

This material was prepared by the reaction of 7-chloro-thieno[3,2-b]pyridine with 6-hydroxy-2-methylbenzofuran-3-carboxylic acid methyl amide 12c and Cs$_2$CO$_3$ in a manner as previously described for example 1. $^1$H NMR (CD$_3$CN) δ 8.48 (1H,d, J=5.3 Hz), 7.91 (1H, d, J=5.6 Hz), 7.84 (1H, d, J=8.6 Hz), 7.53 (1H, d, J=5.6 Hz), 7.41 (1H, d, J=2.0 Hz), 7.20 (1H, dd, J=8.6, 2.0 Hz), 6.62 (1H, d, J=5.3 Hz), 6.60 (1H, bm), 2.91 (3H, d, J=4.6 Hz) 2.66 (3H, s).

Example 100(a)

Methyl 2-Methyl-6-[thieno[3,2-b]pyridin-7-yloxy]benzofuran-3-carboxylate

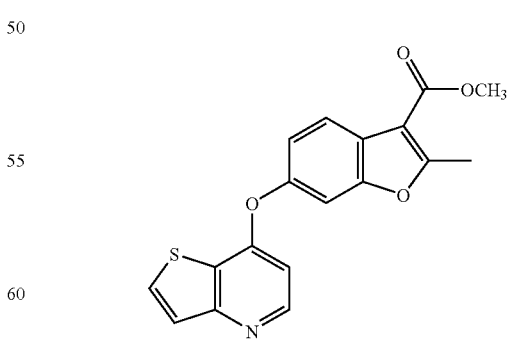

This material was prepared by the reaction of 7-chloro-thieno[3,2-b]pyridine with methyl 6-hydroxy-2-methylbenzofuran-3-carboxylate 89c and Cs$_2$CO$_3$ in a manner as previously described. $^1$H NMR (CDCl$_3$) δ 8.48 (1H,d, J=5.3

Hz), 7.99 (1H, d, J=8.3 Hz), 7.74 (1H, d, J=5.6 Hz), 7.56 (1H, d, J=5.3 Hz), 7.29 (1H, d, J=2.0 Hz), 7.16 (1H, dd, J=8.6, 2.3 Hz), 6.53 (1H, d, J=5.3 Hz), 3.96 (3H, s), 2.79 (3H, s).

Example 100

2-Methyl-6[thieno[3,2-b]pyridin-7-yloxy]benzofuran-3-carboxylic acid

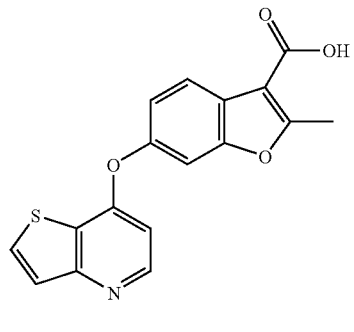

This material was prepared from methyl 2-methyl-6-[thieno[3,2-b]pyridin-7-yloxy]benzofuran-3-carboxylate 100a in a manner as previously described for example 89e. $^1$H NMR (DMSO-$d_6$) δ 12.95 (1H, bs), 8.50 (1H, d, J=5.3 Hz), 8.15 (1H, d, J=5.5 Hz), 7.97 (1H, d, J=8.3 Hz), 7.69 (1H, d, J=2.1 Hz), 7.59 (1H, d, J=5.5 Hz), 7.26 (1H, dd, J=8.5, 2.1 Hz), 6.64 (1H, d, J=5.5 Hz), 2.74 (3H, s).

Example 101

2-Methyl-6-[thieno[3,2-b]pyridin-7-yloxy]benzofuran-3-carbonyl chloride

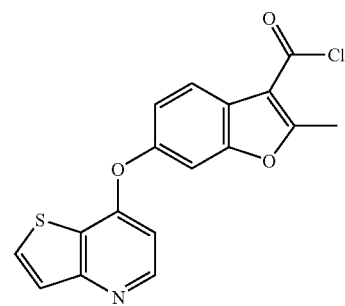

To a stirred suspension of 2-methyl-6-[thieno[3,2-b]pyridin-7-yloxy] benzofuran-3-carboxylic acid 100 (800 mg, 2.33 mmole) in CHCl$_3$ (20 ml) was added thionyl chloride (850 µl, 11.6 mmole) and a catalytic amount of DMF. The reaction was allowed to stir at 50° C. for 3 hr before the volatiles were removed under reduced pressure. The crude residue was triturated with MTBE to give the acid chloride as a pale yellow solid. $^1$H NMR (DMSO-$d_6$) δ 8.81 (1H, d, J=6.6 Hz), 8.57 (1H, d, J=5.6 Hz), 8.03 (1H, d, J=8.6 Hz), 7.86 (1H, d, J=2.0 Hz), 7.82 (1H, d, J=5.6 Hz), 7.39 (1H, dd, J=8.6, 2.0 Hz), 7.06 (1H, d, J=6.3 Hz), 2.76 (3H, s).

Example 102

2-Methyl-6-(thieno[3,2-b]pyridin-7-yloxy)benzofuran-3-carboxylic acid (6-morpholin-4-yl-pyridin-3-yl)amide

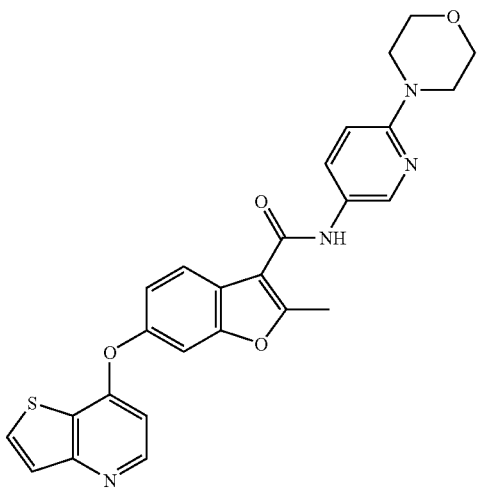

A solution of 2-methyl-6-[thieno[3,2-b]pyridin-7-yloxy] benzofuran-3-carboxylic acid 100 (70 mg, 0.215 mmole), 6-Morpholin-4-yl-pyridin-3-ylamine (77 mg, 0.43 mmole), HATU (163 mg, 0.43 mmole), and diisopropylethylamine (75 µl, 0.43 mmole) were stirred in DMF (2 ml) at ambient temperature for 17 hr. The mixture was then added dropwise to a solution of cold aqueous NaHCO$_3$ resulting in a precipitate which was collected by filtration. This material was purified on silica gel using a gradient of 0 to 5% methanol in a 1:1 mixture of ethyl acetate and dichloromethane as eluent to give 77 mg (74%) of a lavander solid. $^1$H NMR (CD$_3$CN) δ 8.50 (1H, d, J=5.3 Hz), 8.37 (1H, d, J=2.5 Hz), 8.29 (1H, s), 7.92–7.88 (3H, m), 7.54 (1H, d, J=5.3 Hz), 7.45 (1H, d, J=2.0 Hz), 7.23 (1H, dd, J=8.6, 2.0 Hz), 6.78 (1H, d, J=9.1 Hz), 6.64 (1H, d, J=5.3 Hz), 3.76 (4H, t, J=4.9 Hz), 3.44 (4H, t, J=4.9 Hz), 2.72 (3H, s).

Anal. Calcd for C$_{26}$H$_{22}$N$_4$O$_4$S: C, 64.18; H, 4.56; N, 11.52; S, 6.59. Found: C, 64.42; H, 4.77; N, 11.32; S, 6.50.

Example 103

2-Methyl-6-[thieno[3,2-b]pyridin-7-yloxy]benzofuran-3-carboxylic acid (2-morpholin-4-yl-ethyl)-amide

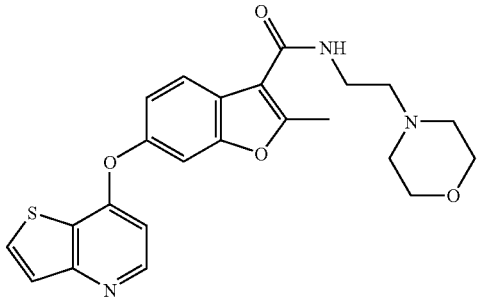

This material was prepared from 2-methyl-6-[thieno[3,2-b]pyridin-7-yloxy]benzofuran-3-carboxylic acid 100 and 2-(morpholin-4-yl)ethylamine in a similar manner as that described for example 102. $^1$H NMR (CD$_3$CN) δ 8.50 (1H, d, J=5.3 Hz), 7.92 (1H, d, J=5.6 Hz), 7.89 (1H, d, J=8.6 Hz), 7.54(1H, d, J=5.6 Hz), 7.42(1H, d, J=2.3 Hz), 7.23 (1H, dd, J=8.6, 2.3 Hz), 6.83 (1H, bm), 6.63 (1H, d, J=5.6 Hz), 3.65 (4H, t, J=4.6 Hz), 3.51 (2H, q, J=6.1 Hz), 2.69 (3H, s), 2.59 (2H, t, J=6.1 Hz), 2.50 (4H, bm).

Anal. Calcd for C$_{23}$H$_{23}$N$_3$O$_4$S.1.4H$_2$O.0.05 CH$_2$Cl$_2$: C, 59.28; H, 5.59; N, 9.00; S, 6.87. Found: C, 59.18; H, 5.23; N, 8.99; S, 6.74.

Example 104

2-Methyl-6-(thieno[3,2-b]pyridin-7-yloxy)-benzofuran-3-carboxylic acid [2-(6-fluoro-1H-indol-3-yl)ethyl]-amide

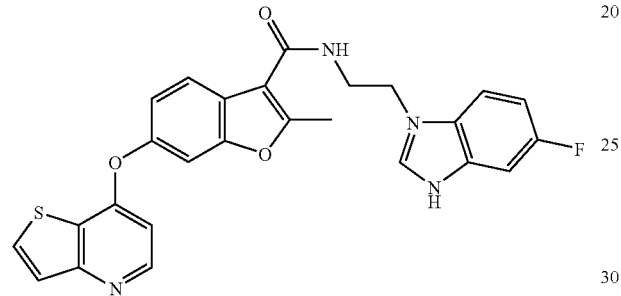

This material was prepared from 2-methyl-6-[thieno[3,2-b]pyridin-7-yloxy]benzofuran-3-carboxylic acid 100 and 2-(6-fluoro-1H-indol-3-yl)ethylamine in a similar manner as that described for example 102. $^1$H NMR (CD$_3$CN) δ 8.48 (1H, d, J=5.6 Hz), 7.91 (1H, d, J=5.6 Hz), 7.63–7.59 (2H, m), 7.54 (1H, d, J=5.6 Hz), 7.38 (1H, d, J=2.3 Hz), 7.17 (1H, d, J=2.3 Hz), 7.14 (1H, t, J=2.3 Hz), 7.11 (1H, d, J=2.3 Hz), 6.85 (1H, m), 6.65 (1H, bm), 6.61 (1H, d, J=5.6 Hz), 3.69 (2H, q, J=7.1 Hz), 3.06 (2H, t, J=7.1 Hz), 2.57 (3H, s).

Anal. Calcd for C$_{27}$H$_{20}$N$_3$O$_3$SF.0.7H$_2$O: C, 65.10; H, 4.33; N, 8.44; S, 6.44. Found: C, 65.04; H, 4.42; N, 8.34; S, 6.40.

Example 105

2-Methyl-6-[Thieno(3,2-b)pyridin-7-yloxy]benzofuran-3-carboxylic acid butyl amide

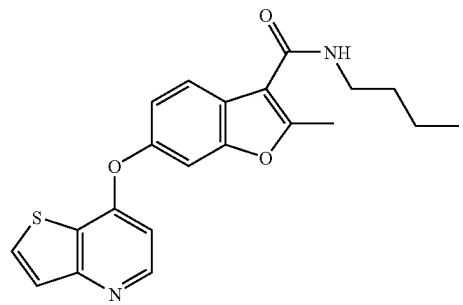

This material was prepared from 2-methyl-6-[thieno[3,2-b]pyridin-7-yloxy]benzofuran-3-carboxylic acid 100 and butylamine in a similar manner as that described for example 102. $^1$H NMR (CD$_3$CN) δ 8.48 (1H,d, J=5.3 Hz), 7.91 (1H, d, J=5.6 Hz), 7.81 (1H, d, J=8.6 Hz), 7.53 (1H, d, J=5.6 Hz), 7.41 (1H, d, J=2.3 Hz), 7.20 (1H, dd, J=8.6, 2.3 Hz), 6.62 (1H, d, J=5.3 Hz), 6.62 (1H, bm), 3.40 (2H, q, J=6.9 Hz), 2.65 (3H, s), 1.60 (2H, m), 1.42 (2H, m), 0.97 (3H, t, J=7.3 Hz).

Example 106

2-Methyl-6-(thieno[3,2-b]pyridin-7-yloxy)-benzofuran-3-carboxylic acid (5-phenyl-[1,3,4]thiadiazol-2-yl)-amide

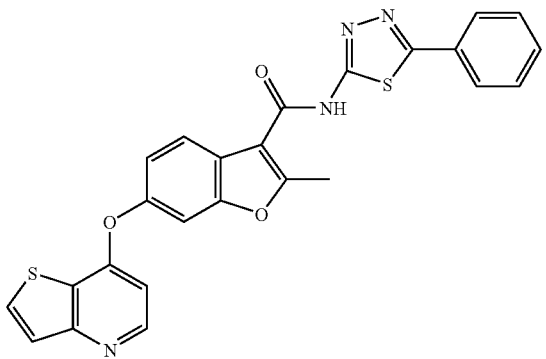

This material was prepared from 2-methyl-6-[thieno[3,2-b]pyridin-7-yloxy]benzofuran-3-carboxylic acid 100 and 5-phenyl-[1,3,4]thiadiazol-2-ylamine in a similar manner as that described for example 102. $^1$H NMR (CD$_3$CN/CD$_3$OD) δ 8.45 (1H, d, J=5.6 Hz), 8.00–7.95 (4H, m), 7.52–7.50 (4H, m), 7.48 (1H, d, J=2.3 Hz), 7.25 (1H, dd, J=8.6, 2.3 Hz), 6.66 (1H, d, J=5.3 Hz), 2.76 (3H, s).

Example 107

2-Methyl-6-[Thieno(3,2-b)pyridin-7-yloxy]benzofuran-3-carboxylic acid 2-[(4-pyridyl)-methyl] amide

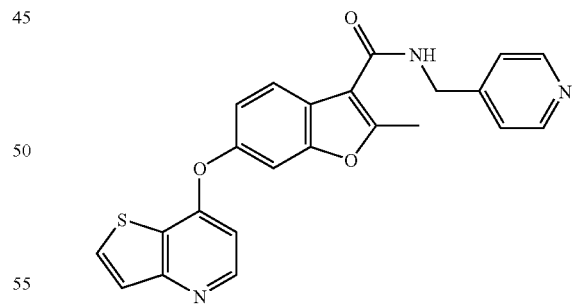

This material was prepared from 2-methyl-6-[thieno[3,2-b]pyridin-7-yloxy]benzofuran-3-carboxylic acid 100 and 4-(aminomethyl)pyridine in a similar manner as that described for example 102. $^1$H NMR (DMSO-d$_6$) δ 8.68 (1H, t, J=5.6 Hz), 8.53 (2H, d, J=5.3 Hz), 8.50 (1H, d, J=5.3 Hz), 8.15 (1H, d, J=5.3 Hz), 7.88 (1H, d, J=8.3 Hz), 7.68 (1H, d, J=2.0 Hz), 7.60 (1H, d, J=5.6 Hz), 7.36 (2H, d, J=5.6 Hz), 7.27 (1H, dd, J=8.6, 2.3 Hz), 6.62 (1H, d, J=5.3 Hz), 4.53 (2H, d, J=6.1 Hz), 2.67 (3H, s).

Anal. Calcd for C$_{23}$H$_{17}$N$_3$O$_3$S.0.4H$_2$O: C, 65.36; H, 4.25; N, 9.94; S, 7.59. Found: C, 65.33; H, 4.21; N, 9.92; S, 7.49.

Example 108

2-Methyl-6-(thieno[3,2-b]pyridin-7-yloxy)-benzofuran-3-carboxylic acid [2-(4-sulfamoyl-phenyl)-ethyl]-amide

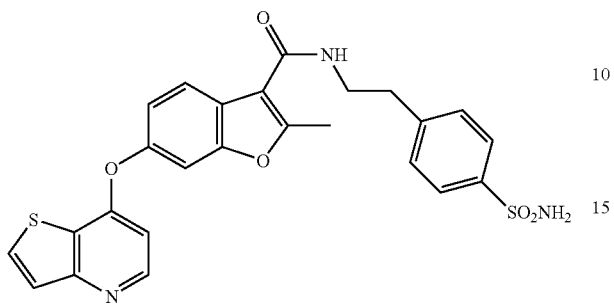

A suspension of 2-methyl-6-[thieno[3,2-b]pyridin-7-yloxy]benzofuran-3-carbonyl chloride 101 (100 mg, 0.29 mmol) in DMF (1 ml) was added dropwise to a solution of 2-(4-sulfamoyl-phenyl)-ethyl]-amine (116 mg, 0.58 mmol), triethylamine (80 μl, 0.58 mmol), and dimethylaminopyridine (5 mg) in DMF (2 ml) at 50 C. The resulting yellow solution was stirred at 50 C for 2 hr then added to an ice cold aqueous sodium bicarbonate solution. The resulting ppt was collected by filtration, washed with water and air dried. The filtrate was extracted with twice ethyl acetate. The extracts were washed with 1N NaOH, then combined with the earlier solid and dried over MgSO$_4$, and concentrated to dryness. The residue was triturated with MTBE then with EtOAc to obtain 49 mg (33%) of an off-white solid. $^1$H NMR (CD$_3$CN) δ 8.48 (1H, d, J=5.3 Hz), 7.91 (1H, d, J=5.6 Hz), 7.81 (1H, d, J=8.3 Hz), 7.64 (1H, d, J=8.6 Hz), 7.54 (1H, d, J=5.3 Hz), 7.48 (1H, d, J=8.3 Hz), 7.39 (1H, d, J=2.0 Hz), 7.16 (1H, dd, J=8.6, 2.0 Hz), 6.68 (1H, bm), 6.62 (1H, d, J=5.6 Hz), 5.62 (2H, bs), 3.69 (2H, q, J=6.8 Hz), 3.04 (2H, t, J=6.8 Hz), 2.57 (3H, s).

Anal. Calcd for C$_{25}$H$_{21}$N$_3$O$_5$S$_2$.0.9H$_2$O.0.4 EtOAc: C, 57.15; H, 4.69; N, 7.52; S, 11.47. Found: C, 57.15; H, 4.42; N, 7.60; S, 11.55.

Example 109

2-Methyl-6-(thieno[3,2-b]pyridin-7-yloxy)-benzofuran-3-carboxylic acid (2-isopropoxy-ethyl)-amide

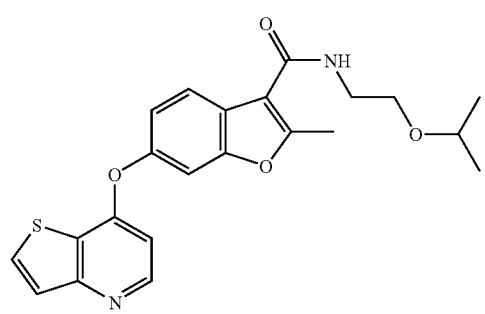

This material was prepared from 2-methyl-6-[thieno[3,2-b]pyridin-7-yloxy]benzofuran-3-carbonyl chloride 101 and 2-(isopropoxy)ethylamine in a similar manner as that described for example 108. $^1$H NMR (CD$_3$CN) δ 8.49 (1H, d, J=5.6 Hz), 7.91 (1H, d, J=5.6 Hz), 7.82 (1H, d, J=8.6 Hz), 7.54 (1H, d, J=5.6 Hz), 7.41 (1H, d, J=2.3 Hz), 7.20 (1H, dd, J=8:6, 2.3 Hz), 6.67 (1H, bm), 6.63 (1H, d, J=5.3 Hz), 3.8–3.51 (5H, m), 2.66 (3H, s), 1.15 (6H, d, J=6.1 Hz). Anal. Calcd for C$_{22}$H$_{22}$N$_2$O$_4$S: C, 64.37; H, 5.40; N, 6.82; S, 7.81. Found: C, 64.35; H, 5.51; N, 6.76; S, 7.74.

Example 110

2-Methyl-6-(thieno[3,2-b]pyridin-7-yloxy)-benzofuran-3-carboxylic acid [2-(1-methyl-pyrrolidin-2-yl)-ethyl]-amide

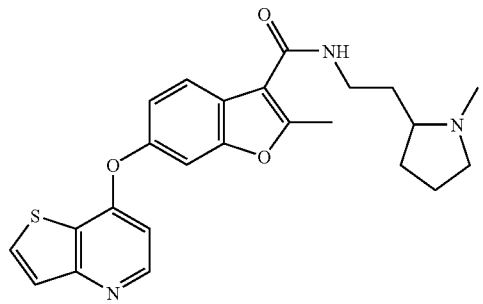

This material was prepared from 2-methyl-6-[thieno[3,2-b]pyridin-7-yloxy]benzofuran-3-carbonyl chloride 101 and 2-(1-methylpyrrolidin-2-yl)ethylamine in a similar manner as that described for example 108. $^1$H NMR (CD$_3$CN) δ 8.49 (1H, d, J=5.6 Hz), 7.91 (1H, d, J=5.3 Hz), 7.85 (1H, d, J=8.3 Hz), 7.61 (1H, bm), 7.53 (1H, d, J=5.6 Hz), 7.40 (1H, d, J=2.0 Hz, 7.20 (1H, dd, J=8.6, 2.3 Hz), 6.63 (1H, d, J=5.6 Hz), 3.61–3.53 (1H, m), 3.45–3.40 (1H, m), 3.05–3.00 (1H, m), 2.67 (3H, s), 2.42–2.36 (1H, m), 2.29 (3H, s), 2.18 (1H, q, J=8.8 Hz), 2.05–1.95 (1H, m, partially obscured by CD$_3$CN), 1.87–1.66 (5H, m).

Anal. Calcd for C$_{24}$H$_{25}$N$_3$O$_3$S.0.5 H$_2$O: C, 64.84; H, 5.90; N, 9.45; S, 7.21. Found: C, 64.73; H, 5.94; N, 9.41; S, 6.98.

Example 111

2-Methyl-6-(thieno[3,2-b]pyridin-7-yloxy)-benzofuran-3-carboxylic acid (5-methyl-1H-pyrazol-3-yl)-amide

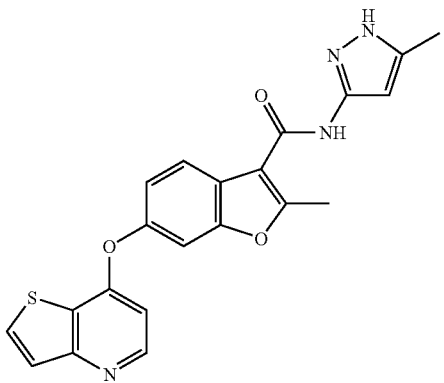

This material was prepared from 2-methyl-6-[thieno[3,2-b]pyridin-7-yloxy]benzofuran-3-carbonyl chloride 101 and (5-methyl-1H-pyrazol-3-yl)amine in a similar manner as that described for example 108. $^1$H NMR (DMSO-$d_6$) δ 12.09 (1H, bs), 10.45 (1H, s), 8.50 (1H, d, J=5.6 Hz), 8.14 (1H, d, J=5.6 Hz), 7.77 (1H, d, J=8.6 Hz), 7.65 (1H, d, J=2.3 Hz), 7.59 (1H, d, J=5.3 Hz), 7.24 (1H, dd, J=8.3, 2.0 Hz), 6.64 (1H, d, J=5.6 Hz), 6.39 (1H, bs), 2.64 (3H, s), 2.23 (3H, s).

Example 112

2-Methyl-6-(thieno[3,2-b]pyridin-7-yloxy)benzofuran-3-carboxylic acid (3-morpholin-4-ylpropyl)-amide

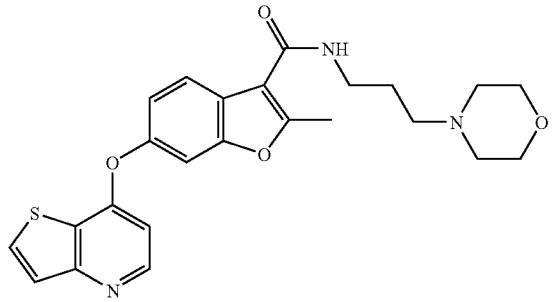

This material was prepared from 2-methyl-6-[thieno[3,2-b]pyridin-7-yloxy]benzofuran-3-carbonyl chloride 101 and 3-(morpholin-4-yl)propylamine in a similar manner as that described for example 108. $^1$H NMR (DMSO-$d_6$) δ 8.50 (1H, d, J=5.6 Hz), 8.14 (1H, d, J=5.6 Hz), 8.07 (1H, bm), 7.80 (1H, d, J=8.6 Hz), 7.64 (1H, d, J=2.0 Hz), 7.59 (1H, d, J=5.6 Hz), 7.24 (1H, dd, J=8.3, 2.0 Hz), 6.61 (1H, d, J=5.6 Hz), 3.56 (4H, bm), 3.35–3.27 (4H, m), 2.63 (3H, s), 2.36 (4H, bm), 1.73 (2H, bm).

Example 113

2-Methyl-6-(thieno[3,2-b]pyridin-7-yloxy)-benzofuran-3-carboxylic acid (1H-indol-5-yl)-amide

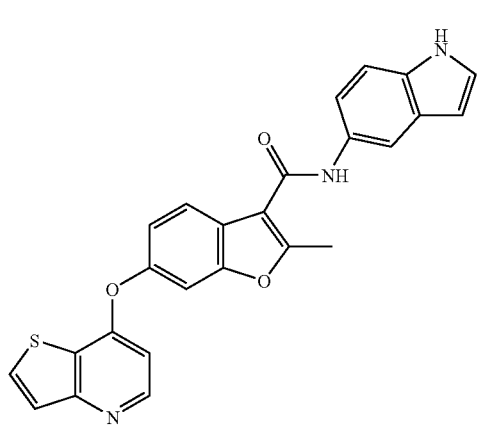

This material was prepared from 2-methyl-6-[thieno[3,2-b]pyridin-7-yloxy]benzofuran-3-carbonyl chloride 101 and 5-aminoindole in a similar manner as that described for example 108. $^1$H NMR (DMSO-$d_6$) δ 11.04(1H, s),9.96(1H, s),8.52(1H, d, J=5.6 Hz), 8.15(1H, d, J=5.3 Hz), 7.97 (1H, s), 7.83 (1H, d, J=8.3 Hz), 7.69 (1H, d, J=2.3 Hz), 7.60 (1H, d, J=5.6 Hz), 7.36 (2H, s), 7.33 (1H, t, J=2.8 Hz), 7.27 (1H, dd, J=8.6, 2.3 Hz), 6.64 (1H, d, J=5.3 Hz), 6.41 (1H, t, J=2.5 Hz), 2.69 (3H, s).

Example 114(a)

2-(Hydroxymethyl)-7-chlorothieno[3,2-b]pyridine

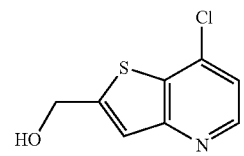

7-Chloro-thieno[3,2-b]pyridine-2-carboxylic acid lithium salt (2.0 g, 9.1 mmole) was dissolved in a solution of DMF (10 mL) and chloroform (50 mL). The carboxylate was treated with thionyl chloride (2.0 mL, 27.3 mmole) and refluxed for one hour. The resultant acid chloride was cooled to room temperature and added dropwise to a solution of sodium borohydride (0.7 g, 18.2 mmole) in DMF (10 mL) at 0° C. The temperature was allowed to reach room temperature over 2 hours and the reaction was quenched with concentrated HCl. The reaction mixture was neutralized with NaOH and the workup was performed with MTBE, brine and MgSO$_4$. The crude product was triturated with MTBE, which provided the title compound as a beige solid (0.7 g, 40%): $^1$H-NMR (DMSO-$d_6$, 400 MHz) δ 8.58 (1H, d, J=5.1 Hz), 7.51 (1H, d, J=5.1 Hz), 7.47 (1H, s), 5.94 (1H, t, J=5.8 Hz), 4.84–4.82 (2H, m); MS m/z 200 (M+H)$^+$.

Example 114(b)

7-Chloro-2-[2-(pyrrolidin-1-yl)ethoxymethyl)thieno[3,2-b]pyridine

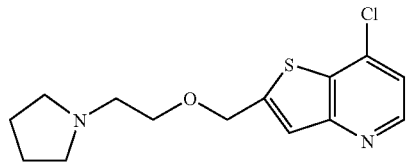

A mixture of 2-(hydroxymethyl)-7-chlorothieno[3,2-b]pyridine 114a (0.35 g, 1.8 mmole), 1-(2-chloro-ethyl)-pyrrolidine hydrochloride (31 g, 18 mmole), benzyltriethylammonium bromide (0.2 g, 0.7 mmole) and 19 M sodium hydroxide (10 mL) in toluene was refluxed for three hours. The reaction mixture was buffered with 50% saturated sodium bicarbonate and the workup was performed with ethyl acetate, brine and magnesium sulfate. The crude product was purified over silica gel (100 g) using 2–7% methanol-chloroform with 0.1% ammonium hydroxide, which provided the title compound as an amber oil (0.38 g, 62%): $^1$H-NMR (DMSO-$d_6$, 400 MHz) δ 8.62 (1H, d, J=5.0 Hz), 7.58 (1H, s), 7.54 (1H, d, J=5.1 Hz), 4.86 (2H, s), 3.62 (2H, t, J=6.0 Hz), 2.64 (2H, t, J=5.8 Hz), 2.49–2.47 (4H, m), 1.67–1.63 (4H, m); MS m/z 297 (M+H)$^+$.

Example 114

2-Methyl-6(2-[2-(pyrrolidin-1-yl)ethoxymethyl]thieno[3,2-b]pyridin-7-yloxy)benzo[b]thiophene-3-carboxylic acid methylamide

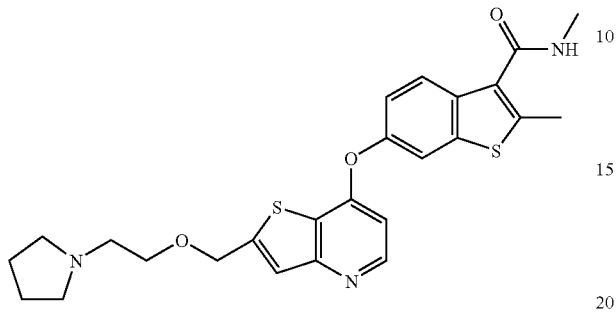

This material was prepared from 7-chloro-2-(2-pyrrolidin-1-yl-ethoxymethyl)-thieno[3,2-b]pyridine 114b (150 mg, 0.51 mmole), 6-hydroxy-2-methyl-benzo[b]thiophene-3-carboxylic acid methylamide 1d (123 mg, 0.56 mmole) and cesium carbonate (497 mg, 01.53 mmole) in a similar manner as described for example 1 to give a beige solid (0.1 g, 41%): $^1$H-NMR (DMSO-d$_6$, 400 MHz) δ 8.48 (1H, d, J=5.3 Hz), 8.28 (1H, q, J=4.5 Hz), 7.92 (1H, d, J=2.3 Hz), 7.84 (1H, d, J=8.9 Hz), 7.51 (1H, s), 7.30 (1H, dd, J=2.3, 8.9 Hz), 6.63 (1H, d, J=5.6 Hz), 4.82 (2H, s), 3.60 (2H, t, J=6.0 Hz), 2.82 (3H, d, J=4.5 Hz), 2.64–2.60 (5H, m), 2.47 (4H, bs), 1.66–1.63 (4H, m); MS m/z 482 (M+H)$^+$;

Anal. Calcd for C$_{25}$H$_{27}$N$_3$O$_3$S$_2$.0.3 H$_2$O: C, 61.65; H, 5.71; N, 8.63; S, 13.17: Found: C, 61.55; H, 5.71; N, 8.47; S, 12.97.

Example 115(a)

7-Chloro-2-(pyrrolidin-1-ylmethyl)thieno[3,2-b]pyridine

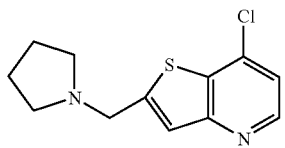

A solution of 2-(hydroxymethyl)-7-chlorothieno[3,2-b]pyridine 114a (100 mg, 0.5 mmole) in dichloroethane was treated with triethylamine (0.08 mL, 0.55 mmole) and mesyl chloride (0.04 mL, 0.55 mmole). The clear solution was stirred for 30 minutes and treated with pyrrolidine (0.12 mL, 1.5 mmole). After one hour, the reaction mixture was poured into 5% sodium bicarbonate and the workup was performed with dichloromethane, brine and magnesium sulfate. The crude product (167 mg greenish oil) was purified over silica gel (1 mm plate) using 2% methanol-chloroform with 0.1% ammonium hydroxide, which provided the title compound as a clear oil (71 mg, 56%): $^1$H-NMR (DMSO-d$_6$, 400 MHz) δ 8.58 (1H, d, J=5.1 Hz), 7.51–7.49 (2H, m), 3.96 (2H, s), 2.56 (4H, bs), 1.75–1.72 (4H, m); MS m/z 253 (M+H)$^+$.

Example 115

2-Methyl-6-(2-[pyrrolidin-1-ylmethyl]thieno[3,2-b]pyridin-7-yloxy)benzo[b]thiophene-3-carboxylic acid methylamide

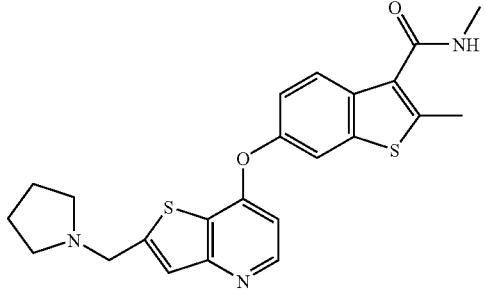

This material was prepared from 7-Chloro-2-(pyrrolidin-1-ylmethyl)thieno[3,2-b]pyridine 115a, 6-hydroxy-2-methyl-benzo[b]thiophene-3-carboxylic acid methylamide 1d and cesium carbonate in a similar manner as described in example 1. $^1$H-NMR (DMSO-d$_6$, 400 MHz) δ 8.44 (1H, d, J=5.3 Hz), 8.27 (1H, q, J=4.6 Hz), 7.91 (1H, d, J=2.3 Hz), 7.83 (1H, d, J=8.6 Hz), 7.43 (1H, s), 7.28 (1H, dd, J=2.3, 8.6 Hz), 6.60 (1H, d, J=5.6 Hz), 3.93 (2H, s), 2.82 (3H, d, J=4.8 Hz), 2.60 (3H, s), 2.54 (4H, bs), 1.72 (4H, s); MS m/z 438 (M+H)$^+$;

Anal. Calcd for C$_{23}$H$_{23}$N$_3$O$_2$S$_2$: C, 63.13; H, 5.30; N, 9.60; S, 14.66: Found: C, 62.75; H, 5.38; N, 9.35; S, 14.39.

Example 116

6-(2-[Dimethylaminomethyl]thieno[3,2-b]pyridin-7-yloxy)-2-methylbenzo[b]thiophene-3-carboxylic acid methylamide

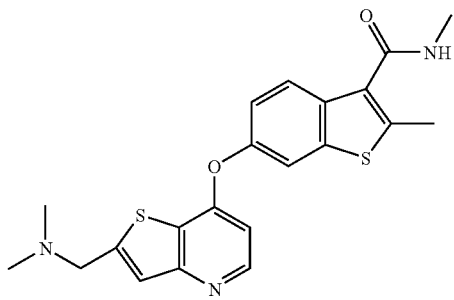

This material was prepared from 7-chloro-2-(dimethylaminomethyl)thieno[3,2-b]pyridine, 6-hydroxy-2-methyl-benzo[b]thiophene-3-carboxylic acid methylamide 1d and cesium carbonate in a similar manner as described for example 1. $^1$H-NMR (DMSO-d$_6$, 400 MHz) δ 8.45 (1H, d, J=5.3 Hz), 8.27 (1H, q, J=4.5 Hz), 7.92 (1H, d, J=2.3 Hz), 7.83 (1H, d, J=8.8 Hz), 7.44 (1H, s), 7.28 (1H, dd, J=2.3, 8.9 Hz), 6.62 (1H, d, J=5.3 Hz), 3.75 (2H, bs), 2.82 (3H, d, J=4.5 Hz), 2.60 (3H, s), 2.24 (6H, s); MS m/z 412 (M+H)$^+$;

Anal. Calcd for C$_{21}$H$_{21}$N$_3$O$_2$S$_2$.0.3 H$_2$O: C, 60.49; H, 5.22; N, 10.08; S, 15.38: Found: C, 60.47; H, 5.01; N, 9.76; S, 15.09.

Example 117(a)

Methyl 2-methyl-6-{[2-(1-methyl-1H-imidazol-2-yl)thieno[3,2-b]pyridin-7-yl]oxy}benzo[b]thiophene-3-carboxylate

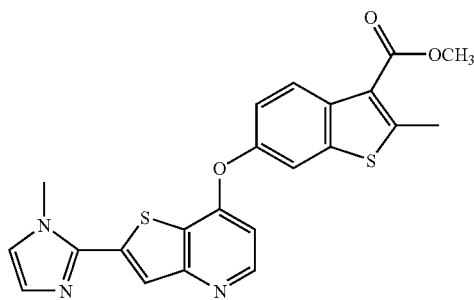

This material was prepared from the reaction of methyl 6-hydroxy-2-methylbenzo[b]thiophene-3-carboxylate 11a (200 mg, 0.90 mmole) with 7-chloro-2-(1-methyl-1H-imidazol-2-yl)thieno[3,2-b]pyridine 1e (188 mg, 0.75 mmole) and $Cs_2CO_3$ (1.22 g, 3.75 mmole) in a manner as previously described for example 1 to give a yellow solid (200 mg, 51%). $^1$H NMR (DMSO-$d_6$, 300 MHz) δ 8.52 (1H, d, J=5.46 Hz), 8.38 (1H, d, J=9.04 Hz), 8.02 (1H, d, J=2.26 Hz), 7.89 (1H, s), 7.40 (2H, s), 7.02 (1H, s), 6.73 (1H, d, J=5.46 Hz), 3.98 (3H, s), 3.91 (3H, s), 2.82 (3H, s).

Example 117(b)

2-Methyl-6-{[2-(1-methyl-1H-imidazol-2-yl)thieno[3,2-b]pyridin-7-yl]oxy}benzo[b]thiophene-3-carboxylic acid

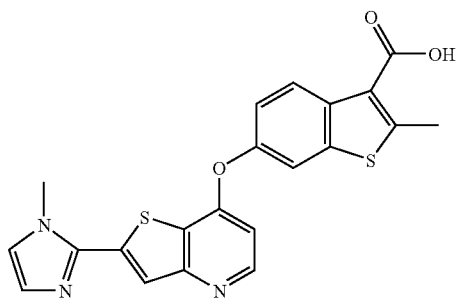

This material was prepared by the reaction of methyl 2-methyl-6-{[2-(1-methyl-1H-imidazol-2-yl)thieno[3,2-b]pyridin-7-yl]oxy}benzo[b]thiophene-3-carboxylate 117a (200 mg, 0.46 mmole) with $LiOH\cdot H_2O$ (192 mg, 4.6 mmole) in a manner as previously described for example 11c to give a yellow solid (165 mg, 85%). $^1$H NMR (DMSO-$d_6$, 300 MHz): δ 8.57 (1H, d, J=5.46 Hz), 8.45 (1H, d, J=8.85 Hz), 8.00 (2H, s), 7.53 (1H, s), 7.40 (1H, dd, J=2.35, 8.95 Hz), 7.22 (1H, s), 6.79 (1H, d, J=5.46 Hz), 4.00 (3H, s), 2.82 (3H, s).

Example 117

2-Methyl-6-{[2-(1-methyl-1H-imidazol-2-yl)thieno[3,2-b]pyridin-7-yl]oxy}benzo[b]thiophene-3-carboxylic acid cyclopropylamide

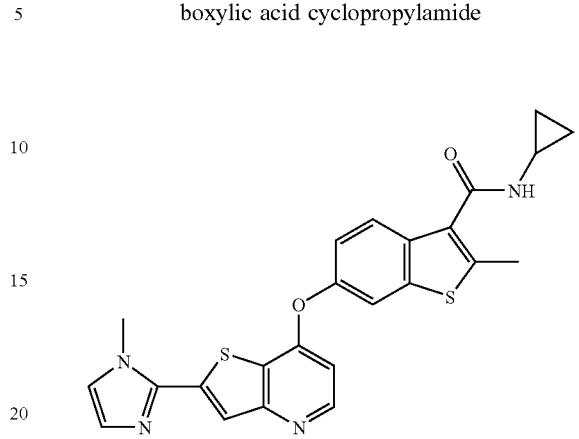

To a solution of 2-methyl-6-{[2-(1-methyl-1H-imidazol-2-yl)thieno[3,2-b]pyridin-7-yl]oxy}benzo[b]thiophene-3-carboxylic acid 117b (75 mg, 0.18 mmole) in DMF (1.5 mL) at 0° C. were added N,N-diisopropylethylamine (68 μL, 0.39 mmole) and HBTU (100 mg, 0.27 mmole). The reaction mixture was stirred 30 min at 0° C. then warmed to room temperature and stirred 18 hr. The mixture was poured onto $H_2O$ (25 mL) and the precipitate was collected by vacuum filtration. The filter paper was extracted with a mixture of $CH_2Cl_2$ (10 mL) and MeOH (10 mL). The solution was concentrated and the crude mixture was purified by silica gel chromatography (5% MeOH/EtOAc) to afford a pale yellow solid (58 mg, 71%). $^1$H NMR (DMSO-$d_6$, 300 MHz) δ 8.52 (1H, d, J=5.46 Hz), 8.46 (1H, d, J=4.33 Hz), 7.95 (1H, d, J=2.26 Hz), 7.88 (1H, s), 7.80 (1H, d, J=8.67 Hz), 7.40 (1H, s), 7.32 (1H, dd, J=2.26, 8.85 Hz), 7.02 (1H, s), 6.70 (1H, d, J=5.46 Hz), 3.98 (3H, s), 2.90 (1H, m), 2.57 (3H, s); 0.73 (2H, m), 0.57 (2H, m);

Anal. Calcd. for $C_{24}H_{20}N_4O_2S_2$: C, 62.59; H, 4.38; N, 12.17; S, 13.92. Found: C, 62.04; H, 4.22; N, 11.91; S, 13.49.

Example 118

2-Methyl-6-{[2-(1-methyl-1H-imidazol-2-yl)thieno[3,2-b]pyridin-7-yl]oxy}benzo[b]thiophene-3-carboxylic acid 3-hydroxypropylamide

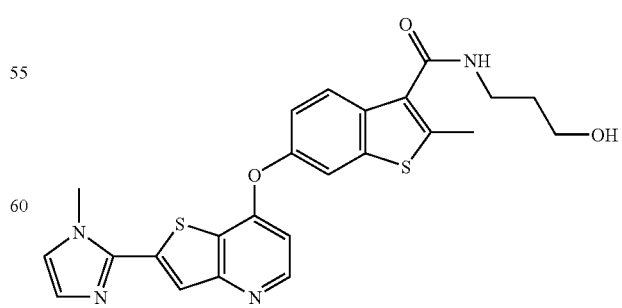

This material was prepared by the reaction of 2-methyl-6-{[2-(1-methyl-1H-imidazol-2-yl)thieno[3,2-b]pyridin-7- yl]oxy}benzo[b]thiophene-3-carboxylic acid 117b (85 mg, 0.20 mmole) with 3-amino-1-propanol (46 μL, 0.44 mmole), N,N-diisopropylethylamine (77 μL, 0.30 mmole), and HBTU (115 mg, 0.303 mmole) in a manner as previously described for example 117. The crude material was purified by silica gel chromatography (10:30:60% MeOH/CH$_2$Cl$_2$/EtOAc) to give a yellow solid (57 mg, 59%). $^1$H NMR (DMSO-d$_6$, 300 MHz) δ 8.52 (1H, d, J=5.27 Hz), 8.37 (1H, t, J=5.56 Hz), 7.95 (1H, d, J=2.26 Hz), 7.88 (1H, s), 7.82 (1H, d, J=8.85 Hz), 7.40 (1H, s), 7.33 (1H, dd, J=2.35, 8.76 Hz), 7.02 (1H, d, J=0.94 Hz), 6.70 (1H, d, J=5.46 Hz), 4.51 (1H, t, J=5.09 Hz), 3.98 (3H, s), 3.50 (2H, q, J=6.22 Hz), 3.35 (2H, m), 2.60 (3H, s), 1.71 (2H, m).

Anal. Calcd. for C$_{24}$H$_{22}$N$_4$O$_3$S$_2$: C, 60.23; H, 4.63; N, 11.71; S, 13.40. Found: C, 59.01; H, 4.70; N, 11.13; S, 12.89.

Example 119

2-Methyl-6-{[2-(1-methyl-1-imidazol-2-yl)thieno[3,2-b]pyridin-7-yl]oxy}benzo[b]thiophene-3-carboxylic acid (cyclopropylmethyl)amide

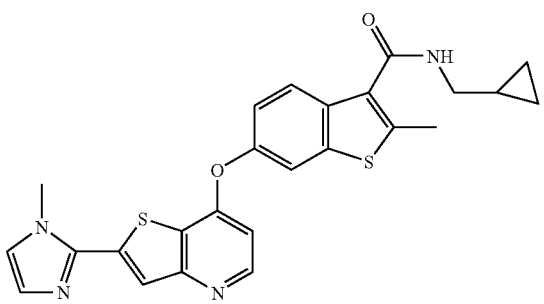

This material was prepared from the reaction of 2-methyl-6-{[2-(1-methyl-1H-imidazol-2-yl)thieno[3,2-b]pyridin-7-yl]oxy}benzo[b]thiophene-3-carboxylic acid 117b (70 mg, 0.166 mmole), (aminomethyl)cyclopropane (43 μL, 0.50 mmole) and diisopropylethylamine (58 μL, 0.33 mmole), and HBTU (94 mg, 0.25 mmole) in a manner similar to that previously described for example 117 to afford a pale yellow solid (64 mg, 53%). $^1$H NMR (DMSO-d$_6$, 300 MHz) δ 8.61 (1H, d, J=5.46 Hz), 8.49 (1H, t, J=5.65 Hz), 8.07 (1H, s), 7.99 (1H, d, J=2.26 Hz), 7.85 (1H, d, J=8.67 Hz), 7.63 (1H, s), 7.37 (1H, s), 7.36 (1H, dd, J=2.4, 8.67 Hz), 6.81 (1H, d, J=5.65 Hz), 4.01 (3H, s), 3.20 (2H, t, J=6.31 Hz), 2.62 (3H, s), 1.08 (1H, m), 0.47 (2H, m), 0.27 (2H, m).

Anal. Calcd. for C$_{25}$H$_{22}$N$_4$O$_2$S$_2$.2(CF$_2$CO$_2$H): C, 49.57; H, 3.44; N, 7.97; S, 9.13. Found: C, 48.25; H, 3.48; N, 7.64; S, 8.77.

Example 120

6-[(2-{[(2S)-2-(Methoxymethyl)pyrrolidin-1-yl]carbonyl}thieno[3,2-b]pyridin-7-yl)oxy]-2-methyl-benzo[b]thiophene-3-carboxylic acid cyclopropylamide

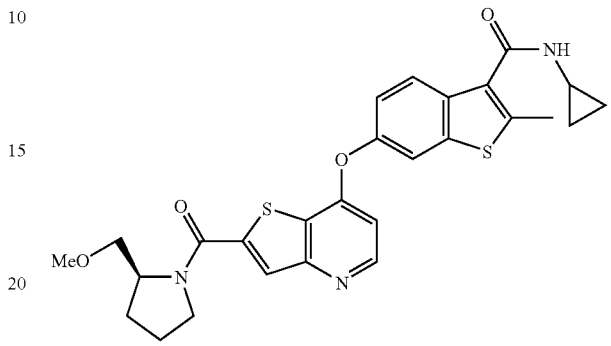

This material was prepared by the reaction of 7-chloro-2-{[(2S)-2-(methoxymethyl)pyrrolidin-1-yl]carbonyl}thieno[3,2-b]pyridine 2a (124 mg, 0.40 mmole) with 6-hydroxy-2-methylbenzo[b]thiophene-3-carboxylic acid cyclopropylamide 8c (119 mg, 0.48 mmole) and Cs$_2$CO$_3$ (391 mg, 1.2 mmole) in a manner as previously described for example 1 to give a yellow solid (146 mg, 70%). $^1$H NMR (DMSO-d$_6$, 300 MHz) δ 8.58 (1H, d, J=5.27 Hz), 8.46 (1H, d, J=4.33 Hz), 8.03 (1H, s), 7.96 (1H, d, J=2.26 Hz), 7.80 (1H, d, J=8.67 Hz), 7.32 (1H, dd, J=2.17, 8.76 Hz), 6.75 (1H, d, J=5.27 Hz), 4.30 (1H, m), 3.84 (2H, m), 3.53 (1H, m) 3.42 (1H, m), 3.27 (3H, s), 2.89 (1H, m), 2.57 (3H, s), 2.09–1.81 (4H, m) 0.72 (2H, m), 0.59 (2H, m).
Anal. Calcd. for C$_{27}$H$_{27}$N$_3$O$_4$S$_2$: C, 62.17; H, 5.22; N, 8.06; S, 12.19. Found: C, 60.94; H, 5.34; N, 7.71; S, 11.71.

Example 121

6[(2-{[(3R)-3-Hydroxypyrrolidin-1-yl]carbonyl}thieno[3,2-b]pyridin-7-yl)oxy]-2-methyl-benzo[b]thiophene-3-carboxylic acid cyclopropylamide

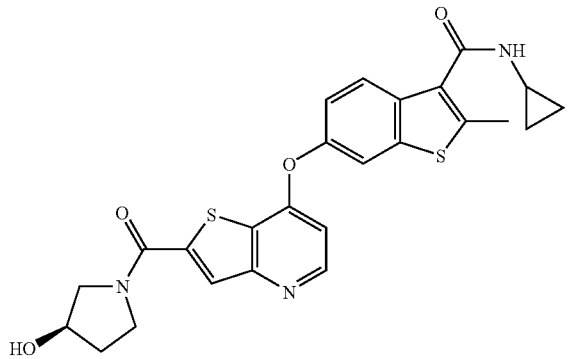

This material was prepared by the reaction of 7-chloro-2-[(R)-3-hydroxypyrrolidine-1-carbonyl]thieno[3,2-b]pyridine 4a (113 mg, 0.40 mmole) with 6-hydroxy-2-methylbenzo[b]thiophene-3-carboxylic acid cyclopropylamide 8c (119 mg, 0.48 mmole) and Cs$_2$CO$_3$ (391 mg, 1.2 mmole) in a manner as previously described for example 1 to give a yellow solid (130 mg, 66%). $^1$H NMR (DMSO-d$_6$, 300 MHz) δ 8.58 (1H, d, J=5.46 Hz), 8.46 (1H, d, J=4.33 Hz), 8.06, 8.00 (1H, s), 7.96 (1H, d, J=2.26 Hz), 7.80 (1H, d, J=8.85 Hz), 7.33 (1H, dd, J=2.35, 8.76 Hz), 6.75 (1H, d, J=5.27 Hz), 5.07 (1H, m), 4.38, 4.33 (1H, br s), 4.02–3.92 (2H, m), 3.67–3.44 (2H, m), 2.93–2.87 (1H, m), 2.57 (3H, s), 2.08–1.79 (2H, m), 0.76–0.70 (2H, m), 0.60–0.55 (2H, m).

Anal. Calcd. for C$_{25}$H$_{23}$N$_3$O$_4$S: C, 60.83; H, 4.70; N, 8.51; S, 12.99. Found: C, 57.46; H, 4.80; N, 7.81; S, 13.85.

Example 122(a)

Methyl 6-[(2-{[(2S)-2-(methoxymethyl)pyrrolidin-1-yl]carbonyl}thieno[3,2-b]pyridin-7-yl)oxy]-2-methylbenzo[b]thiophene-3-carboxylate

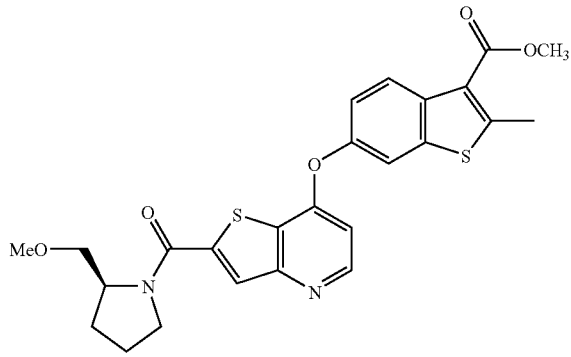

This material was prepared from the reaction of methyl 6-hydroxy-2-methylbenzo[b]thiophene-3-carboxylate 11a (85.8 mg, 0.386 mmole) with 7-chloro-2-{[(2S)-2-(methoxymethyl)pyrrolidin-1-yl]carbonyl}thieno[3,2-b]pyridine 2a (100 mg, 0.322 mmole) and Cs$_2$CO$_3$ (524 mg, 1.61 mmole) in a manner similar to that previously described for example 1 to give a brown solid (64 mg, 40%). $^1$H NMR (DMSO-d$_6$, 300 MHz) δ 8.70 (1H, d, J=4.90 Hz), 8.51 (1H, d, J=9.04 Hz), 8.15 (1H, s), 8.14 (1H, s), 7.54 (1H, dd, J=2.17, 8.95 Hz), 6.91 (1H, d, J=5.46 Hz), 4.47–4.38 (1H, m), 4.07–3.90 (2H, m), 4.03 (3H, s), 3.72–3.50 (2H, m), 3.42, 3.39 (3H, s), 2.94 (3H, s), 2.21–1.93 (4H, m).

Example 122(b)

6-[(2-{[(2S)-2-(Methoxymethyl)pyrrolidin-1-yl]carbonyl}thieno[3,2-b]pyridin-7-yl)oxy]-2-methylbenzo[b]thiophene-3-carboxylic acid

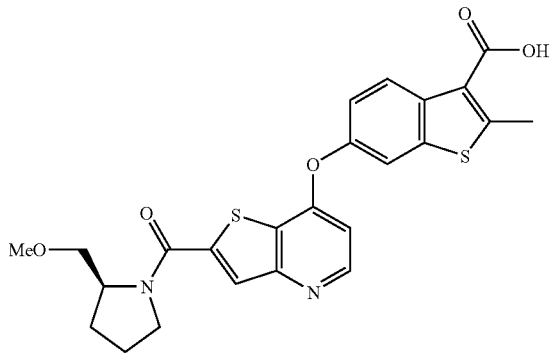

This material was prepared by the hydrolysis of methyl 6-[(2-{[(2S)-2-(methoxymethyl)pyrrolidin-1-yl]carbonyl}thieno[3,2-b]pyridin-7-yl)oxy]-2-methylbenzo[b]thiophene-3-carboxylate 122a (63 mg, 0.13 mmole) with LiOH.H$_2$O (54 mg, 13 mmole) in a manner as previously described for example 11c to give a white solid (46 mg, 75%). $^1$H NMR (DMSO-d$_6$, 300 MHz) δ 8.58 (1H, d, J=5.46 Hz), 8.44 (1H, d, J=8.85 Hz), 8.03 (1H, s), 8.00 (1H, d, J=2.26 Hz), 7.38 (1H, dd, J=2.45, 9.04 Hz), 6.78 (1H, d, J=5.84 Hz), 4.35–4.25 (1H, m), 3.93–3.76 (2 H, m), 3.59–3.50 (2H, m), 3.27, 3.15 (3H, s), 2.81 (3H, s), 2.11–1.83 (4H, m).

Example 122

6-[(2-{[(2S)-2-(Methoxymethyl)pyrrolidin-1-yl]carbonyl}thieno[3,2-b]pyridin-7-yl)oxy]-2-methyl-benzo[b]thiophene-3-carboxylic acid 3-hydroxypropylamide

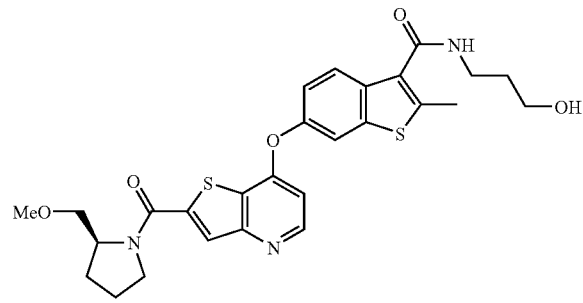

This material was prepared by the reaction of 6-[(2-{[(2S)-2-(methoxymethyl)-pyrrolidin-1-yl]carbonyl}thieno[3,2-b]pyridin-7-yl)oxy]-2-methylbenzo[b]thiophene-3-carboxylic acid 121b (45 mg, 0.093 mmole) with 3-amino-1-propanol (21 μL, 0.28 mmole), HBTU (53 mg, 0.14 mmole), and diisopropylethylamine (36 μL, 0.21 mmole) in a manner as previously described for example 117 to give a yellow solid (44 mg, 88%). $^1$NMR (DMSO-d$_6$, 300 MHz) δ 8.58 (1H, d, J=5.27 Hz), 8.36 (1H, t, J=5.46 Hz), 8.03 (1H, s), 7.96 (1H, d, J=2.26 Hz), 7.82 (1H, d, J=8.85 Hz), 7.33 (1H, dd, J=1.70, 8.67 Hz), 6.75 (1H, d, J=5.27 Hz), 4.51 (1H, t, J=5.18 Hz), 4.30 (1H, m), 3.85 (2H, m), 3.37 (2H, m), 3.27 (3H, s), 2.60 (3H, s), 2.09–1.83 (4H, m), 1.71 (2H, m).

Anal. Calcd. for C$_{27}$H$_{29}$N$_3$O$_5$S$_2$: C, 60.09; H, 5.42; N, 7.79; S, 11.88. Found: C, 57.22; H, 5.72; N, 7.22; S, 11.16.

Example 123(a)

Methyl 6-[(2-{[(3R)-3-methoxypyrrolidin-1-yl]carbonyl}thieno[3,2-b]pyridin-7-yl)oxy]-2-methyl-benzo[b]thiophene-3-carboxylate

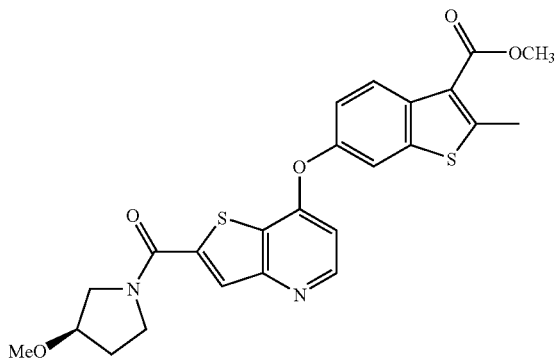

This material was prepared from the reaction of 6-hydroxy-2-methylbenzo[b]thiophene-3-carboxylate 11a (267 mg, 1.20 mmole) with 7-chloro-2-{[(3R)-3-methoxypyrrolidin-1-yl]carbonyl}thieno[3,2-b]pyridine 4b (297 mg, 1.00 mmole) and $Cs_2CO_3$ (977 mg, 3.00 mmole) in a manner similar to that previously described for example 1 to give a brown solid (480 mg, 100%). $^1$H NMR (DMSO-$d_6$, 300 MHz) δ 8.58 (1H, d, J=5.46 Hz), 8.39 (1H, d, J=8.85 Hz), 8.07 (1H, s), 8.02 (1H, d, J=2.26 Hz), 7.42 (1H, dd, J=2.35, 8.95 Hz), 6.79 (1H, d, J=5.46 Hz), 4.12–3.80 (3H, m), 3.91 (3H, s), 3.68–3.46 (2H, m), 3.27, 3.24 (3H, s), 2.82 (3H, s), 2.17–1.92 (2H, m).

Example 123(b)

6-[(2-{[(3R)-3-Methoxypyrrolidin-1-yl]carbonyl}thieno[3,2-b]pyridin-7-yl)oxy]-2-methyl-benzo[b]thiophene-3-carboxylic acid

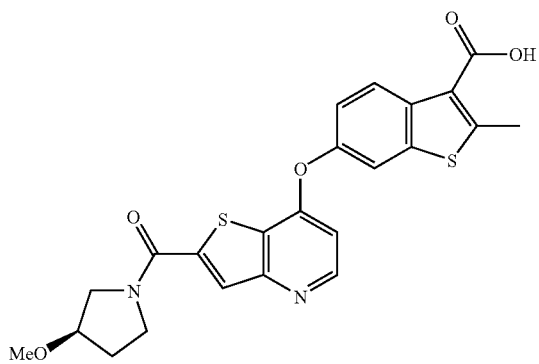

This material was prepared by the reaction of methyl 6-[(2-{[(3R)-3-methoxypyrrolidin-1-yl]carbonyl}thieno[3,2-b]pyridin-7-yl)oxy]-2-methylbenzo[b]thiophene-3-carboxylate 122a (483 mg, 1.00 mmole) with LiOH.H$_2$O (420 mg, 10.0 mmole) in a manner analogous to that described for example 11c. The crude material was flushed through a silica gel plug with 10% MeOH/CH$_2$Cl$_2$ and the resulting mixture of products was used in subsequent reaction without further purification.

Example 123

6-[(2-{[(3R)-3-Methoxypyrrolidin-1-yl]carbonyl}thieno[3,2-b]pyridin-7-yl)oxy]-2-methyl-benzo[b]thiophene-3-carboxylic acid 2-hydroxy-ethylamide

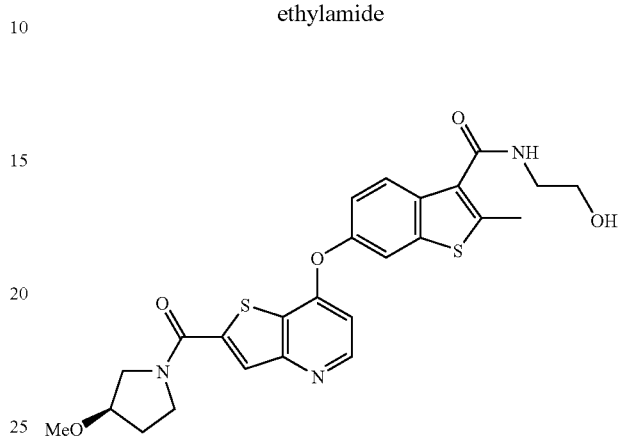

This material was prepared from the reaction of 6-[(2-{[(3R)-3-methoxypyrrolidin-1-yl]carbonyl}thieno[3,2-b]pyridin-7-yl)oxy]-2-methylbenzo[b]thiophene-3-carboxylic acid 123b (130 mg, 0.278 mmole) with ethanolamine (84 μL, 1.39 mmole), N,N-diisopropylethylamine (0.15 mL, 0.83 mmole), and HBTU (263 mg, 0.694 mmole) in a manner similar to that previously described for example 117 to give a yellow solid (40 mg, 28%). $^1$H NMR (DMSO-$d_6$, 300 MHz) δ 8.58 (1H, d, J=5.27 Hz), 8.33 (1H, t, J=5.56 Hz), 8.06 (1H, s), 7.96 (1H, d, J=2.26 Hz), 7.86 (1H, d, J=8.85 Hz), 7.32 (1H, dd, J=2.26, 8.85 Hz), 6.75 (1H, d, J=5.46 Hz), 4.76 (1H, br s), 4.13–3.81 (3H, m), 3.67–3.50 (4H, m), 3.43–3.32 (2H, m), 3.27, 3.24 (3H, s), 2.61 (3H, s), 2.18–1.94 (2H, m).

Anal. Calcd. for $C_{25}H_{25}N_3O_5S_2$: C, 58.69; H, 4.93; N, 8.21; S, 12.54. Found: C, 56.56; H, 5.01; N, 7.62; S, 11.67.

Example 124

6-[(2-{[(3R)-3-Methoxypyrrolidin-1-yl]carbonyl}thieno[3,2-b]pyridin-7-yl)oxy]-2-methyl-benzo[b]thiophene-3-carboxylic acid 3-hydroxypropylamide

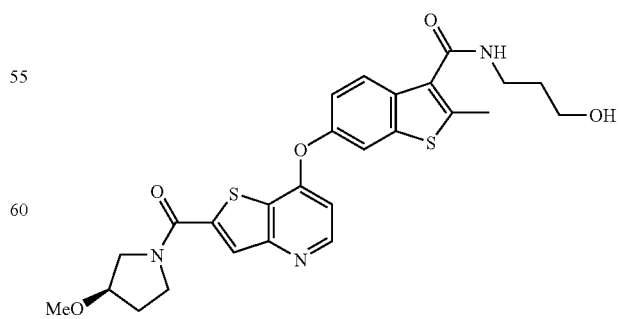

This material was prepared from the reaction of 6-[(2-{[(3R)-3-methoxypyrrolidin-1-yl]carbonyl}thieno[3,2-b]pyridin-7-yl)oxy]-2-methylbenzo[b]thiophene-3-carboxylic acid 123b (130 mg, 0.278 mmole) with 3-amino-1-propanol (106 μL, 1.39 mmole), N,N-diisopropylethylamine (0.15 mL, 0.83 mmole), and HBTU (263 mg, 0.694 mmole) in a manner similar to that previously described for example 117 to give a yellow solid (34 mg, 23%). $^1$H NMR (DMSO-$d_6$, 300 MHz) δ 8.58 (1H, d, J=5.27 Hz), 8.36 (1H, t, J=5.65 Hz), 8.06 (1H, s), 7.96 (1H, d, J=2.07 Hz), 7.83 (1H, d, J=8.85 Hz), 7.33 (1H, dd, J=2.07, 8.85 Hz), 6.75 (1H, d, J=5.27 Hz), 4.51 (1H, t, J=5.18 Hz), 4.13–3.82 (3H, m), 3.62 (2H, m), 3.50 (2H, m), 3.39–3.30 (2H, m), 3.27, 3.24 (3H, s), 2.60 (3H, s), 2.18–1.93 (2H, m), 1.71 (2H, quintet, J=6.6 Hz).

Anal. Calcd. for $C_{26}H_{27}N_3O_5S_2$·HCl: C, 55.56; H, 5.02; N, 7.48; S, 11.41. Found: C, 53.38; H, 4.96; N, 7.09; S, 10.83.

Example 125

6-[(2-{[(3R)-3-Methoxypyrrolidin-1-yl]carbonyl}thieno[3,2-b]pyridin-7-yl)oxy]-2-methyl-benzo[b]thiophene-3-carboxylic acid (cyclopropyl-methyl)amide

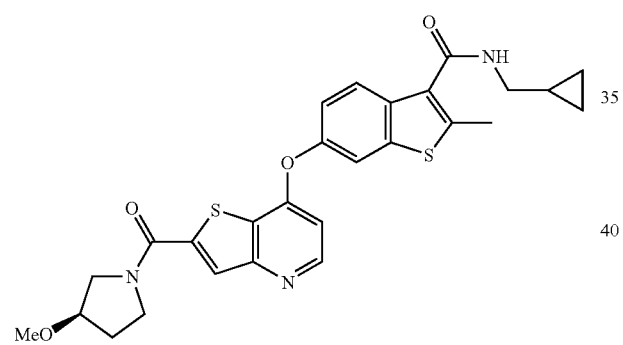

This material was prepared by the reaction of 6-[(2-{[(3R)-3-methoxypyrrolidin-1-yl]carbonyl}thieno[3,2-b]pyridin-7-yl)oxy]-2-methylbenzo[b]thiophene-3-carboxylic acid 123b (130 mg, 0.278 mmole) with (aminomethyl)cyclopropane (120 μL, 1.39 mmole), diisopropylethylamine (0.15 mL, 0.83 mmole), and HBTU (263 mg, 0.694 mmole) in a manner similar to that previously described for example 117 to afford a pale yellow solid (42 mg, 24%). $^1$H NMR (DMSO-$d_6$, 300 MHz) δ 8.61 (1H, d, J=5.56 Hz), 8.49 (1H, t, J=5.56 Hz), 8.06 (1H, s), 7.97 (1H, s), 7.84 (1H, d, J=8.59 Hz), 7.34 (1H, dd, J=2.27, 8.84 Hz), 6.79 (1H, d, J=5.56 Hz), 4.11–3.80 (3H, m), 3.70–3.46 (2H, m), 3.27, 3.24 (3H, s), 3.20 (2H, t, J=6.19 Hz), 2.62 (3H, s) 2.18–1.91 (2H, m), 1.08 (1H, m), 0.47 (2H, m), 0.26 (2H, m).

Anal. Calcd. for $C_{27}H_{27}N_3O_4S_2$·2($CF_2CO_2H$): C, 49.66; H, 3.90; N, 5.60; S, 8.55. Found: C, 49.29; H, 4.03; N, 5.64; S, 8.59.

Example 126(a)

6-[(2-{[(3R)-3-Hydroxypyrrolidin-1-yl]carbonyl}thieno[3,2-b]pyridin-7-yl)oxy]-2-methyl-benzo[b]thiophene-3-carboxylic acid

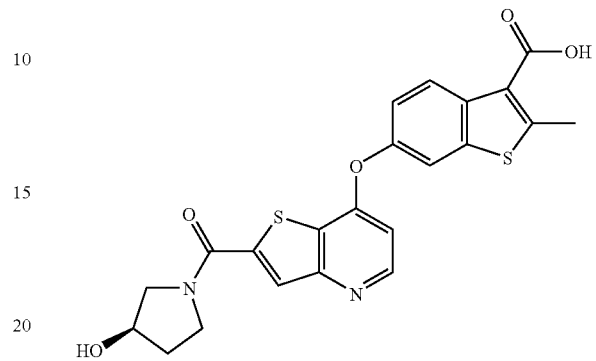

This material was prepared from the reaction of methyl 6-hydroxy-2-methylbenzo[b]thiophene-3-carboxylate 11a (283 mg, 1.00 mmole) with 7-chloro-2-[(R)-3-hydroxypyrrolidine-1-carbonyl]thieno[3,2-b]pyridine 4a and $Cs_2CO_3$ (977 mg, 3.00 mmole) in a manner as previously described for example 1. The crude product was then reacted with LiOH·$H_2O$ (227 mg, 5.4 mmole) in a manner similar to that described for example 11c to give a yellow solid (202 mg, 45%). $^1$H NMR (DMSO-$d_6$, 300 MHz) δ 8.58 (1H, d, J=5.31 Hz), 8.44 (1H, d, J=8.84Hz), 8.14, 8.07 (1H, s), 8.00 (1H, s), 7.39 (1H, dd, J=2.40, 8.97 Hz), 6.78 (1H, d, J=5.56 Hz), 4.38, 4.33 (1H, br s), 4.01–3.91 (1 H, m), 3.68–3.56 (2H, m), 3.49–3.22 (2H, m), 2.81 (3H, s), 2.07–1.79 (2H, m).

Example 126

6[(2-{[(3R)-3-Hydroxypyrrolidin-1-yl]carbonyl}thieno[3,2-b]pyridin-7-yl)oxy]-2-methyl-benzo[b]thiophene-3-carboxylic acid (cyclopropyl-methyl)amide

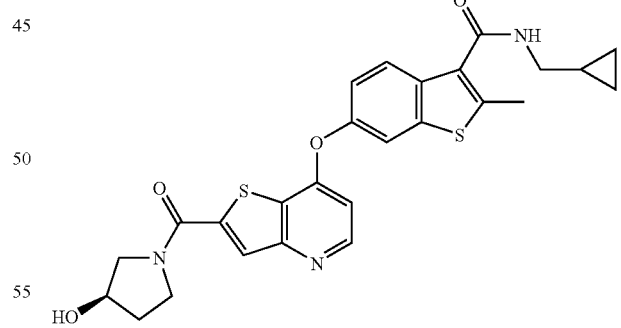

This material was prepared from the reaction of 6-[(2-{[(3R)-3-hydroxypyrrolidin-1-yl]carbonyl}thieno[3,2-b]pyridin-7-yl)oxy]-2-methylbenzo[b]thiophene-3-carboxylic acid 126a (65 mg, 0.14 mmole) with (aminomethyl)cyclopropane (37 μL, 0.43 mmole), diisopropylethylamine (50 μL, 0.29 mmole), and HBTU (81 mg, 0.22 mmole) in a similar manner previously described for example 117 to give a pale yellow solid (47 mg, 46%). $^1$H NMR (DMSO-$d_6$, 300 MHz) δ 8.60 (1H, d, J=5.56 Hz), 8.49 (1H, t, J=5.68 Hz), 8.07, 8.01 (1H, s), 7.97 (1H, d, J=2.27 Hz), 7.84 (1H, d, J=8.59 Hz), 7.34 (1H, dd, J=2.27, 8.84 Hz), 6.78 (1H, d, J=5.31 Hz), 4.38, 4.33 (0.5H, br s), 4.01–3.93 (3H, m), 3.67–3.47 (2H, m), 3.20 (2H, t, J=6.19 Hz), 2.62 (3H, s), 2.07–1.81 (2H, m), 1.08 (1H, m), 0.46 (2H, m), 0.26 (2H, m).

Anal. Calcd. for $C_{26}H_{25}N_3O_4S_2.2(CF_2CO_2H)$: C, 49.72; H, 3.77; N, 5.86; S, 8.95. Found: C, 49.52; H, 3.71; N, 5.83; S, 8.92.

Example 127

6-{[2-(Azetidin-1-ylcarbonyl)thieno[3,2-b]pyridin-7-yl]oxy}2-methylbenzo[b]thiophene-3-carboxylic acid cyclopropylamide

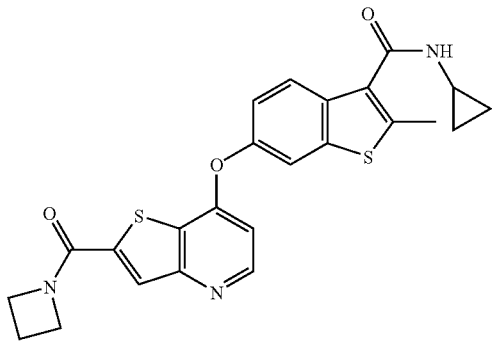

This material was prepared by reacting 2-(azetidin-1-ylcarbonyl)-7-chlorothieno[3,2-b]pyridine 25a (90 mg, 0.36 mmole) with 6-hydroxy-2-methylbenzo[b]thiophene-3-carboxylic acid cyclopropyl amide 8c (106 mg, 0.43 mmole) and $Cs_2CO_3$ (349 mg, 1.07 mmole) in a manner analogous to that described for example 1 to give a yellow solid (106 mg, 47%). $^1$H NMR (DMSO-$d_6$, 300 MHz), δ 8.58 (1H, d, J=5.27), 8.45 (1H, d, J=3.77 Hz), 7.95 (1H, d, J=2.07 Hz), 7.89 (1H, s), 7.80 (1H, d, J=8.67 Hz), 7.32 (1H, dd, J=2.17, 8.95 Hz), 6.75 (1H, d, J=5.46 Hz), 4.62 (2H, t, J=7.35 Hz), 4.10 (2H, t, J=7.72 Hz), 2.90 (1H, m), 2.57 (3H, s), 2.34 (2H, m), 0.73 (2H, m), 0.58 (2H, m).

Anal. Calcd. for $C_{24}H_{21}N_3O_3S_2.1.5$ $(CF_3CO_2H)$: C, 51.10; H, 3.57; N, 6.62; S, 10.11. Found: C, 51.40; H, 3.95; N, 6.85; S, 10.29.

Example 128

(6({2-[4-(hydroxymethyl)-1,3-thiazol-2-yl]thieno[3,2-b]pyridin-7-yl}oxy)-2-methylbenzo[b]thiophene-3-carboxylic acid methyylamide

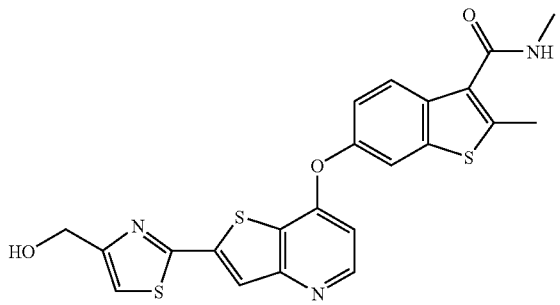

This material was prepared by reacting 7-chloro-2-[4-(hydroxymethyl)-1,3-thiazol-2-yl]thieno[3,2-b]pyridine (113 mg, 0.4 mmole) with 6-hydroxy-2-methylbenzo[b]thiophene-3-carboxylic acid methylamide 1d (111 mg, 0.5 mmole) and $Cs_2CO_3$ (6511 mg, 2 mmole) in a manner similar to that previously described for example 1 to give a yellow solid (99 mg, 53%). $^1$H NMR (DMSO-$d_6$, 300 MHz) δ 8.56 (1H, d, J=5.4 Hz), 8.29 (1H, q, J=4.5 Hz), 8.17 (1H, s), 7.96(1H, d, J=2.2 Hz), 7.85 (1H, d, J=8.7 Hz), 7.63 (1H, s), 7.33 (1H, dd, J=2.2, 8.7 Hz), 6.75 (1H, d, J=5.4 Hz), 5.45 (1H, bs), 4.60 (2H, s), 2.83 (3H, d, J=4.5 Hz), 2.60 (3H, s).

Anal. Calcd. for $C_{22}H_{17}N_3O_3S_3.0.3$ $CH_3OH.0.2$ EtOAc: C, 56.07; H, 4.03; N, 8.49; S, 19.44. Found: C, 56.05; H, 4.08; N, 8.43; S, 19.47.

Example 129

(6-({2-[4(Hydroxymethyl)-1,3-thiazol-2-yl]thieno[3,2-b]pyridin-7-yl}oxy)-2-methylbenzo[b]thiophene-3-carboxylic acid cyclopropylamide

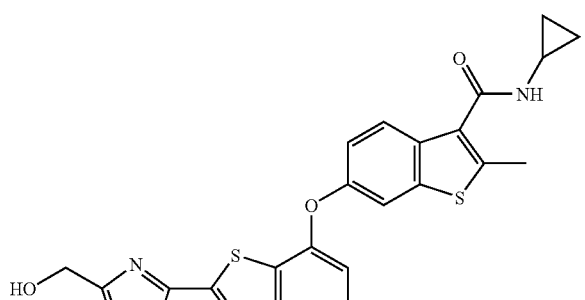

This material was prepared by reacting [2-(7-chlorothieno[3,2-b]pyridin-2-yl)-1,3-thiazol-4-yl]methanol (124 mg, 0.5 mmole) with 6-hydroxy-2-methylbenzo[b]thiophene-3-carboxylic acid cyclopropylamide 8c (113 mg, 0.4 mmole) and $Cs_2CO_3$ (391 mg, 1.2 mmole) in a manner similar to that previously described for example 1 to give a yellow solid (86 mg, 44%). $^1$H NMR (DMSO-$d_6$, 300 MHz) δ 8.56 (1H, d, J=5.4 Hz), 8.46 (1H, d, J=4.3 Hz), 8.17 (1H, s), 7.96 (1H, d, J=2.2 Hz), 7.81 (1H, d, J=8.8 Hz), 7.63 (1H, s), 7.34 (1H, dd, J=2.2, 8.8 Hz), 6.75 (1H, d, J=5.4 Hz), 4.60 (2H, d, J=4.9 Hz), 2.96–2.85 (1H, m), 2.57 (3H, s), 0.78–0.67 (2H, m), 0.62–0.53 (2H, m).

Anal. Calcd. for $C_{24}H_{19}N_3O_3S_3.1.2H_2O$: C, 55.94; H, 4.19; N, 8.16; S, 18.67. Found: C, 55.85; H, 4.19; N, 7.95; S, 19.01.

Example 130(a)

6-Hydroxy-2-methyl-1-benzo[b]thiophene-3-carboxylic acid (cyclopropylmethyl)amide

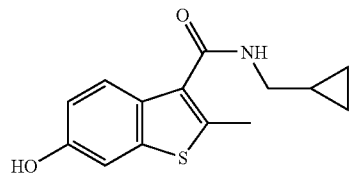

This material was prepared by the reaction of crude 3-(chlorocarbonyl)-2-methyl-1-benzothien-6-yl acetate (650 mg, 2.42 mmole (theoretical)) with (aminomethyl)cyclopropane (1.2 mL, 13.8 mmole) and N,N-diisopropylethylamine (0.5 mL, 2.9 mmole) in a manner similar to that previously described for example 8c. The crude product was purified by silica gel chromatography (25–50% EtOAc/hexanes) to afford a yellow glass (457 mg, 72%). $^1$H NMR δ 9.56 (1H, s), 8.31 (1H, t, J=5.56 Hz), 7.52 (1H, d, J=8.67 Hz), 7.18 (1H, d, J=2.07 Hz), 6.84 (1H, dd, J=2.26, 8.67 Hz), 3.16 (2H, m), 2.51 (3H, s), 1.05 (1H, m), 0.44 (2H, m), 0.24 (2H, m).

Example 130

(6-({2-[4-(Hydroxymethyl)-1,3-thiazol-2-yl]thieno[3,2-b]pyridin-7-yl}oxy)-2-methylbenzo[b]thiophene-3-carboxylic acid (cyclopropylmethyl)amide

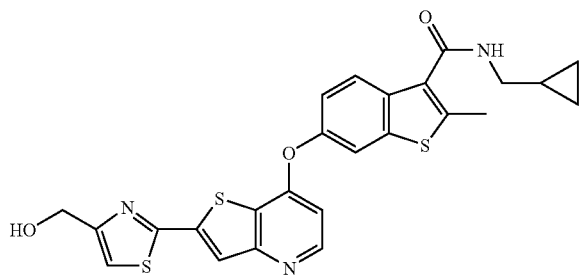

This material was prepared by reacting [2-(7-chlorothieno[3,2-b]pyridin-2-yl)-1,3-thiazol-4-yl]methanol (85 mg, 0.30 mmole) with 6-hydroxy-2-methylbenzo[b]thiophene-3-carboxylic acid (cyclopropylmethyl)amide 130a (94 mg, 0.36 mmole) and Cs$_2$CO$_3$ (195 mg, 0.60 mmole) in a manner similar to that previously described for example 1 to give a yellow solid (57 mg, 25%). $^1$H NMR (DMSO-d$_6$, 300 MHz) δ 8.56 (1H, d, J=5.46 Hz), 8.49 (1H, t, J=5.75 Hz), 8.17 (1H, s), 7.98 (1H, d, J=2.26 Hz), 7.84 (1H, d, J=8.67 Hz), 7.65 (1H, s), 7.36 (1H, dd, J=2.35, 8.76 Hz), 6.80 (1H, d, J=5.46 Hz), 4.60 (2H, s), 3.20 (2H, t, J=6.22 Hz), 2.62 (3H, s), 1.07 (1H, m), 0.47 (2H, m), 0.26 (2H, m).

Anal. Calcd. for C$_{25}$H$_{21}$N$_3$O$_3$S$_3$.2(CF$_3$CO$_2$H): C, 47.34; H, 3.15; N, 5.71; S, 13.08. Found: C, 46.72; H, 3.15; N, 5.71; S, 12.92.

Example 131

6-{[2-(Azetidin-1-ylcarbonyl)thieno[3,2-b]pyridin-7-yl]oxy}-2-methylbenzo[b]thiophene-3-carboxylic acid (cyclopropylmethyl)amide

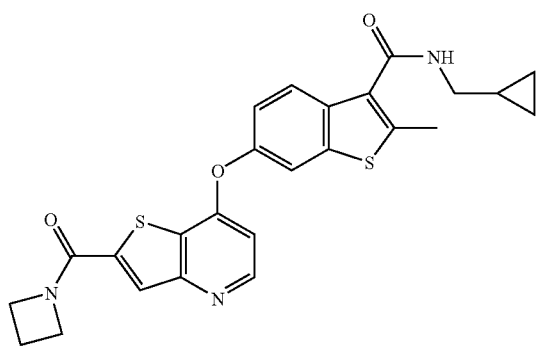

This material was prepared by reacting 2-(azetidin-1-ylcarbonyl)-7-chlorothieno[3,2-b]pyridine 25a (88 mg, 0.35 mmole) with 6-hydroxy-2-methyl-1-benzo[b]thiophene-3-carboxylic acid (cyclopropylmethyl)amide 130a (110 mg, 0.42 mmole) and Cs$_2$CO$_3$ (228 mg, 0.70 mmole) in a manner similar to that previously described for example 1 to give a yellow solid (90 mg, 54%). $^1$H NMR (DMSO-d$_6$, 300 MHz) δ 8.58 (1H, d, J=5.46 Hz), 8.49 (1H, t, J=5.46 Hz), 7.96 (1H, d, J=2.26 Hz), 7.89 (1H, s), 7.83 (1H, d, J=8.85 Hz), 7.33 (1H, dd, J=2.35, 8.76 Hz), 6.75 (1H, d, J=5.46 Hz), 4.62 (2H, t, J=7.72 Hz), 4.10 (2H, t, J=7.82 Hz), 3.20 (2H, t, J=6.31 Hz), 2.62 (3H, s), 2.35 (2H, m), 1.07 (1H, m), 0.46 (2H, m), 0.26 (2H, m).

Anal. Calcd. for C$_{25}$H$_{23}$N$_3$O$_3$S$_2$: C, 62.87; H, 4.85; N, 8.80; S, 13.43. Found: C, 62.58; H, 4.90; N, 8.66; S, 13.33.

Example 132

6[(2-{[(2S)-2-(Methoxymethyl)pyrrolidin-1-yl]carbonyl}thieno[3,2-b]pyridin-7-yl)oxy]-2-methylbenzo[b]thiophene-3-carboxylic acid (cyclopropylmethyl)amide

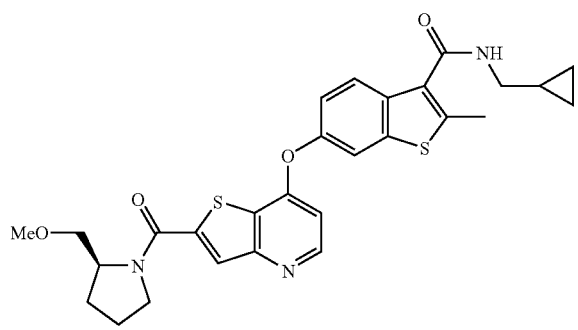

This material was prepared from 7-chloro-2-{[[(3R)-3-methoxypyrrolidin-1-yl]carbonyl}thieno[3,2-b]pyridine 2a (93 mg, 0.30 mmole), 6-hydroxy-2-methylbenzo[b]thiophene-3-carboxylic acid (cyclopropylmethyl)amide 130a (94 mg, 0.36 mmole) and Cs$_2$CO$_3$ (195 mg, 0.60 mmole) in a manner similar to that previously described for example 1 to give a yellow solid (33 mg, 18%). $^1$H NMR (DMSO-d$_6$, 300 MHz) δ 8.64 (1H, d, J=5.46 Hz), 8.51 (1H, t, J=5.65 Hz), 8.05 (1H, s), 7.99 (1H, d, J=2.26 Hz), 7.85 (1H, d, J=8.85 Hz), 7.36 (1H, dd, J=2.26, 8.85 Hz), 6.83 (1H, d, J=5.46 Hz), 4.30 (1H, m), 3.85 (2H, m), 3.53 (1H, m), 3.42 (1H, m), 3.27 (3H, s), 3.20 (2H, m), 2.63 (3H, s), 1.97 (2H, m), 1.90 (2H, m), 1.07 (1H, m), 0.46 (2H, m), 0.26 (2H, m).

Anal. Calcd. for $C_{28}H_{29}N_3O_4S_2 \cdot 1.5(HCl)$: C, 56.96; H, 5.21; N, 7.12; S, 10.86. Found: C, 56.05; H, 5.44; N, 709; S, 10.68.

Example 133(a)

2-Methyl-6-(thieno[3,2-b]pyridin-7-yloxy)benzo[b]thiophene-3-carboxylic acid

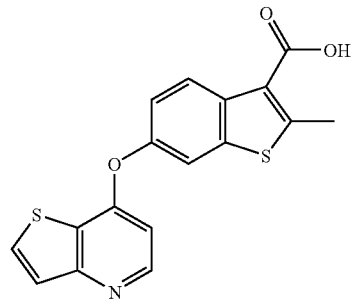

This material was prepared by reacting 7-chlorothieno[3,2-b]pyridine (170 mg, 1.0 mmole) with methyl 6-hydroxy-2-methylbenzo[b]thiophene-3-carboxylate 11a (267 mg, 1.2 mmole) and $Cs_2CO_3$ (488 mg, 1.5 mmole) in a manner similar to that previously described for example 1. Silica gel chromatography (10% MeOH/CHCl$_2$) provided the title compound as a brown viscous oil (93 mg, 27%) of. $^1$H NMR (DMSO-d$_6$, 300 MHz) δ 8.47 (1H, d, J=5.27 Hz), 8.41 (1H, d, J=8.85 Hz), 8.11 (1H, d, J=5.46 Hz), 7.93 (1H, d, J=2.07 Hz), 7.55 (1H, d, J=7.55 Hz), 7.32 (1H, dd, J=2.26, 8.85 Hz), 6.64 (1H, d, J=5.27 Hz), 2.77 (3H, s).

Example 133

2-Methyl 6-(thieno[3,2-b]pyridin-7-yloxy)benzo[b]thiophene-3-carboxylic acid (2-morpholin-4-yl)ethylamide

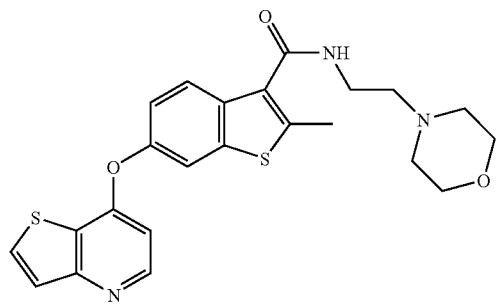

This material was prepared from the reaction of 2-methyl-6-(thieno[3,2-b]pyridin-7-yloxy)benzo[b]thiophene-3-carboxylic acid 133a (93 mg, 0.27 mmole) with 4-(2-aminoethyl)morpholine (0.12 mL, 0.82 mmole), diisopropylethylamine (0.10 mL, 0.55 mmole), and HBTU (155 mg, 0.41 mmole) in a manner similar to that previously described for example 117 to give a white crystalline solid (35 mg, 28%). $^1$H NMR (DMSO-d$_6$, 300 MHz) δ 8.51 (1H, d, J=5.27 Hz), 8.28 (1H, t, J=5.37 Hz), 8.15 (1H, d, J=5.46 Hz), 7.94 (1H, dd, J=2.26 Hz), 7.94 (1H, d, J=8.48 Hz), 7.59 (1H, d, J=5.46 Hz), 7.33 (1H, dd, J=2.26, 8.85 Hz), 6.64 (1H, d, J=5.27 Hz), 3.58 (4H, t, J=4.33 Hz), 3.43 (2H, q, J=6.09 Hz), 3.32 (2H, m), 2.63 (3H, s), 2.52–2.39 (4H, m).

Anal. Calcd. for $C_{23}H_{23}N_3O_3S_2$: C, 60.90; H, 5.11; N, 9.26; S, 14.4 Found: C, 61.12; H, 5.16; N, 9.16; S, 14.02.

Example 134(a)

2-Ethyl 6-hydroxybenzo[b]thiophene

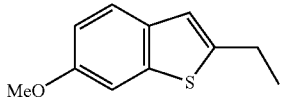

This material was prepared from 6-methoxybenzo[b]thiophene 1a (2.63 g, 16 mmole) by treatment with n-BuLi and ethyl iodide (7.80 g, 50 mmole) in a manner as previously described for example 1b to give a white solid (2.78 g, 90%). $^1$H NMR (DMSO-d$_6$) δ 7.58 (1H, d, J=8.7 Hz), 7.44 (1H, d, J=2.3 Hz), 7.02 (1H, s), 6.92 (1H, dd, J=2.3, 8.7 Hz), 2.84 (2H, q, J=7.5 Hz), 1.27 (3H, t, J=7.5 Hz).

Anal. Calcd. for $C_{11}H_{12}OS$: C, 68.71; H, 6.29; S, 16.68. Found: C, 68.50; H, 6.21; S, 16.93.

Example 134(b)

2-Ethyl-6-hydroxybenzo[b]thiophene

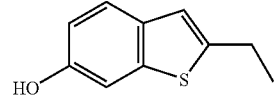

This material was prepared from 2-ethyl-6-methoxybenzo[b]thiophene 134a (2.30 g, 12 mmole) by treatment with BBr$_3$ in a manner as previously described for example 1d to give a white solid (1.75 g, 82%). $^1$H NMR (DMSO-d$_6$) δ 9.43 (1H, s), 7.48 (1H, d, J=8.5 Hz), 7.16 (1H, d, J=2.2 Hz), 6.95 (1H, s), 6.78 (1H, dd, J=2.2, 8.5 Hz), 2.81 (2H, q, J=7.5 Hz), 1.26 (3H, t, J=7.5 Hz).

Example 134(c)

6-Acetoxy-2-ethylbenzo[b]thiophene

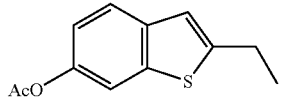

This material was prepared by treatment of 2-ethyl-6-hydroxybenzo[b]thiophene 134b (1.60 g, 9 mmole) with acetyl chloride (1 ml, 1.10 g, 14 mmole) and Et$_3$N (2 ml, 1.45 g, 14 mmole) in a manner as previously described for example 8b to give a white solid (2.93 g, 93%). $^1$H NMR (DMSO-d$_6$) δ 7.72 (1H, d, J=8.5 Hz), 7.68 (1H, d, J=2.2 Hz), 7.15 (1H, s), 7.08 (1H, dd, J=2.2, 8.5 Hz), 2.89 (2H, q, J=7.5 Hz), 2.28 (3H, s), 1.29 (3H, t, J=7.5 Hz).

Example 134(d)

2-Ethyl-6-hydroxybenzo[b]thiophene-3-carboxylic acid methylamide

This material was prepared from 6-acetoxy-2-ethylbenzo[b]thiophene 134c (1.77 g,

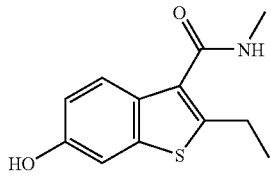

8 mmole) by acylation with oxalyl chloride in the presence of AlCl$_3$, followed by treatment with methylamine in a manner as previously described for example 1d to give a pale yellow solid (1.55 g, 82%). $^1$H NMR (DMSO-d$_6$) δ 9.57 (1H, s), 8.15 (1H, q, J=4.5 Hz), 7.48 (1H, d, J=8.6 Hz), 7.19 (1H, d, J=2.3 Hz), 6.84 (1H, dd, J=2.3, 8.6 Hz), 2.90 (2H, q, J=7.5 Hz), 2.78 (3H, d, J=4.5 Hz), 1.22 (3H, t, J=7.5 Hz).

Anal. Calcd for C$_{12}$H$_{13}$NO$_2$S: C, 61.25; H, 5.57; N, 5.95; S, 13.63. Found: C, 61.11; H, 5.68; N, 5.88; S, 13.41.

Example 134

2-Ethyl 6-{[2-(1-methyl-1H-imidazol-2-yl)thieno[3,2-b]pyridin-7-yl]oxy}benzo[b]thiophene-3-carboxylic acid methylamide

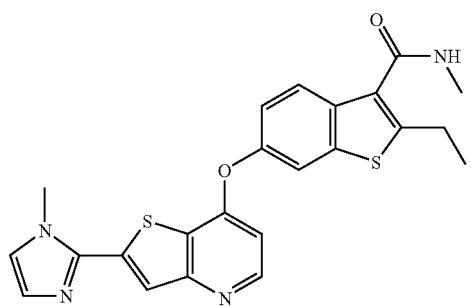

This material was prepared by reacting 7-chloro-2-(1-methyl-1H-imidazol-2-yl)thieno[3,2-b]pyridine 1e (87 mg, 0.35 mmole) with 2-ethyl-6-hydroxybenzo[b]thiophene-3-carboxylic acid methylamide 134d (99 mg, 0.42 mmole) and Cs$_2$CO$_3$ (342 mg, 1.05 mmole) in a manner analogous to that described for example 1 to give a yellow solid (89 mg, 37%). $^1$H NMR (DMSO-d$_6$, 300 MHz), δ 8.52 (1H, d, J=5.56 Hz), 8.33 (1H, m), 7.98 (1H, d, J=2.27 Hz), 7.89 (1H, s), 7.81 (1H, d, J=8.59 Hz), 7.40 (1H, s), 7.33 (1H, dd, J=2.27, 8.84 Hz), 7.02 (1H, s), 6.97 (1H, d, J=5.31 Hz), 3.98 (3H, s), 3.00 (2H, q, J=7.58 Hz), 2.83 (3H, d, J=4.80 Hz), 1.28 (3H, t, J=7.58 Hz).

Anal. Calcd. for C$_{23}$H$_{20}$N$_4$O$_2$S$_2$.2(CF$_2$CO$_2$H): C, 47.93; H, 3.28; N, 8.28; S, 9.48. Found: C, 47.63; H, 3.24; N, 8.14; S, 9.29.

Anal. Calcd. for C$_{12}$H$_{12}$O$_2$S: C, 65.43; H, 5.49; S, 14.56. Found: C, 65.64; H, 5.61; S, 14.49.

Example 135

2-Ethyl-6-[(2-{[(3R)-3-methoxypyrrolidin-1-yl]carbonyl}thieno[3,2-b]pyridin-7-yl)oxy]benzo[b]thiophene-3-carboxylic acid methylamide

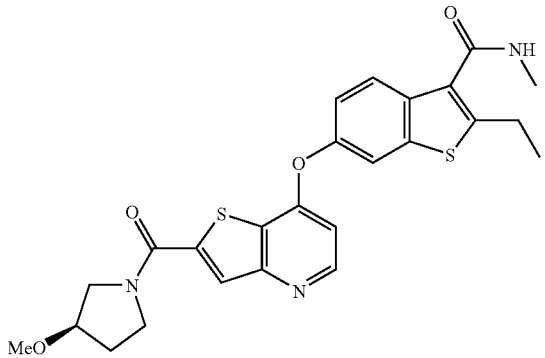

This material was prepared by reacting 7-chloro-2-{[(3R)-3-methoxypyrrolidin-1-yl]carbonyl}thieno[3,2-b]pyridine 4b (74 mg, 0.25 mmole) with 2-ethyl-6-hydroxybenzo[b]thiophene-3-carboxylic acid methylamide 134d (71 mg, 0.30 mmole) and Cs$_2$CO$_3$ (244 mg, 0.75 mmole) in a manner analogous to that described for example 1 to give a yellow solid (34 mg, 19%). $^1$H NMR (DMSO-d$_6$, 300 MHz), δ 8.59 (1H, d, J=5.31 Hz), 8.33 (1H, q, J=4.46 Hz), 8.06 (1H, s), 7.99 (1H, d, J=2.27 Hz), 7.81 (1H, d, J=8.84 Hz), 7.34 (1H, dd, J=2.27, 8.84 Hz), 6.76 (1H, d, J=5.56 Hz), 4.08–3.83 (3H, m), 3.67–3.48 (2H, m), 3.27, 3.24 (3H, s), 3.00 (2H, t, J=7.49 Hz), 2.83 (3H, d, J=4.55 Hz), 2.16–1.95 (2H, m), 1.28 (3H, t, J=7.58 Hz).

Anal. Calcd. for C$_{25}$H$_{25}$N$_3$O$_4$S$_2$.1.25(CH$_3$CO$_2$H): C, 51.76; H, 4.15; N, 6.58; S, 10.05. Found: C, 51.24; H, 4.23; N, 6.55; S, 10.05.

Example 136

2-Ethyl-6-[(2-{[(3R)-3-hydroxypyrrolidin-1-yl]carbonyl}thieno[3,2-b]pyridin-7-yl)oxy]benzo[b]thiophene-3-carboxylic acid methylamide

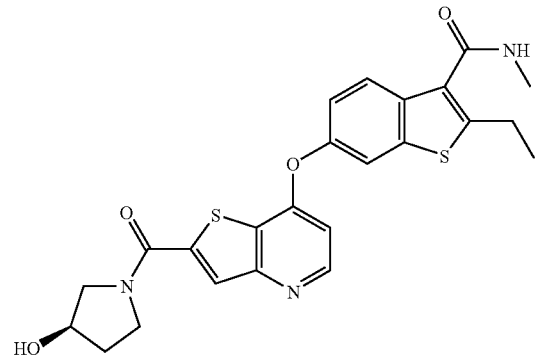

This material was prepared by reacting 7-chloro-2-{[(3R)-3-hydroxypyrrolidin-1-yl]carbonyl}thieno[3,2-b]pyridine 4a (71 mg, 0.25 mmole) with 2-ethyl-6-hydroxybenzo[b]thiophene-3-carboxylic acid methylamide 134d (71 mg, 0.30 mmole) and Cs$_2$CO$_3$ (244 mg, 0.75 mmole) in a manner analogous to that described for example 1 to give a light brown solid (76 mg, 63%). $^1$H NMR (DMSO-d$_6$, 300 MHz), δ 8.58 (1H, d, J=5.56 Hz), 8.32 (1H, q, J=4.38 Hz), 8.07, 8.00 (1H, s), 7.98 (1H, d, J=2.27 Hz), 7.80 (1H, d, J=8.84 Hz), 7.33 (1H, dd, J=2.27, 8.59 Hz), 6.75 (1H, d, J=5.31 Hz), 4.38, 4.33 (1H, br s), 4.01–3.93 (2H, m), 3.67–3.45 (3H, m), 3.00 (2H, t, J=7.49 Hz), 2.83 (3H, d, J=4.55 Hz), 2.06–1.80 (2H, m), 1.28 (3H, t, J=7.58 Hz).

Anal. Calcd. for $C_{24}H_{23}N_3O_4S_2$: C, 59.86; H, 4.81; N, 8.73; S, 13.32. Found: C, 58.63; H, 4.78; N, 8.46; S, 13.33.

Example 137

2-Ethyl-6-[(2-{[(2S)-2-(methoxymethyl)pyrrolidin-1-yl]carbonyl}thieno[3,2-b]pyridin-7-yl)oxy]benzo[b]thiophene-3-carboxylic acid methylamide

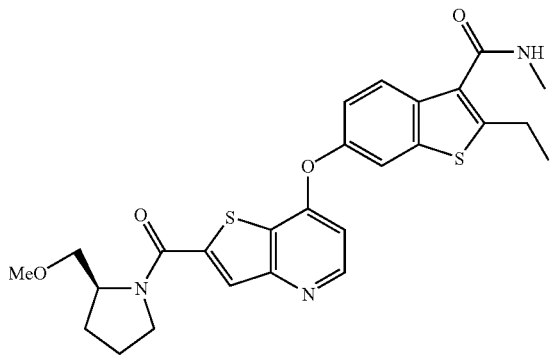

This material was prepared by reacting 7-chloro-2-{[(3R)-3-methoxypyrrolidin-1-yl]carbonyl}thieno[3,2-b]pyridine 2a (155 mg, 0.5 mmole) with 2-ethyl-6-hydroxybenzo[b]thiophene-3-carboxylic acid methylamide 134d (141 mg, 0.60 mmole) and $Cs_2CO_3$ (488 mg, 1.5 mmole) in a manner analogous to that described for example 1 to give a yellow solid (25 mg, 10%). $^1$H NMR (DMSO-$d_6$, 300 MHz), δ 8.59 (1H, d, J=5.56 Hz), 8.33 (1H, d, J=4.55 Hz), 8.03 (1H, s), 7.99 (1H, d, J=2.02 Hz), 7.81 (1H, d, J=8.59 Hz), 7.33 (1H, dd, J=2.27, 8.84 Hz), 6.77 (1H, d, J=5.56 Hz), 4.31 (1H, br s), 3.90–3.81 (2H, m), 3.37–3.15 (2H, m), 3.37 (3H, s), 3.00 (2H, q, J=7.41 Hz), 2.83 (3H, d, J=4.55 Hz), 2.09–1.84 (4H, m), 1.28 (3H, t, J=7.58 Hz).

Anal. Calcd. for $C_{26}H_{27}N_3O_4S_2$·1.75(HCl): C, 54.46; H, 5.05; N, 7.33; S, 11.18. Found: C, 54.50; H, 5.19; N, 7.30; S, 11.22.

Example 138

6-{[2-(Azetidin-1-ylcarbonyl)thieno[3,2-b]pyridin-7-yl]oxy}-2-ethylbenzo[b]thiophene-3-carboxylic acid methylamide

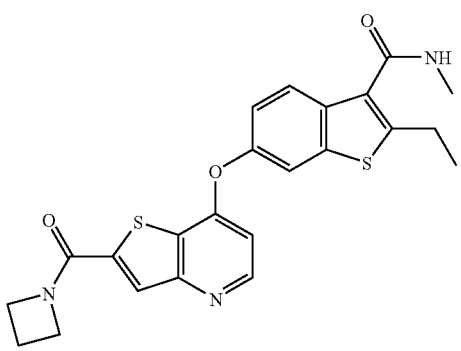

This material was prepared by reacting 2-(azetidin-1-ylcarbonyl)-7-chlorothieno[3,2-b]pyridine 25a (97 mg, 0.40 mmole) with 2-ethyl-6-hydroxybenzo[b]thiophene-3-carboxylic acid methylamide 134d (113 mg, 0.48 mmole) and $Cs_2CO_3$ (391 mg, 1.2 mmole) in a manner similar to that previously described for example 1 to give a yellow solid (120 mg, 52%). $^1$H NMR (DMSO-$d_6$, 300 MHz) δ 8.59 (1H, d, J=5.67 Hz), 8.31 (1H, m), 7.98 (1H, d, J=2.27 Hz), 7.89 (1H, s), 7.81 (1H, d, J=8.69 Hz), 7.33 (1H, dd, J=1.51, 8.69 Hz), 6.76 (1H, d, J=5.29 Hz), 4.62 (2H, t, J=7.37 Hz), 4.11 (2H, t, J=7.37 Hz), 3.00 (2H, q, J=7.55 Hz), 2.83 (3H, d, J=4.53 Hz), 2.35 (2H, m), 1.28 (3H, t, J=7.55 Hz).

Anal. Calcd. for $C_{24}H_{21}N_3O_3S_2 \cdot CF_3CO_2H$: C, 53.09; H, 3.92; N, 7.43; S, 11.34. Found: C, 52.58; H, 3.80; N, 7.26; S, 11.12.

Example 139(a)

7-Chloro-2-methylthieno[3,2-b]pyridine

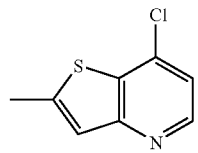

This material was prepared from 7-chlorothieno[3,2-b]pyridine (1.69 g, 10 mmole) by treatment with n-BuLi and iodomethane (2 ml, 4.56 g, 32 mmole) in a manner as previously described for example 1b to give a pale yellow, low-melting solid (1.48 g, 81%). $^1$H NMR (DMSO-$d_6$): δ 8.56 (1H, d, J=5.1 Hz), 7.48 (1H, d, J=5.1 Hz), 7.38 (1H, s), 2.65 (3H, s).

Anal. Calcd. for $C_8H_6NSCl$: C, 52.32; H, 3.29; N, 7.63; S, 17.46; Cl, 19.30. Found: C, 52.13; H, 3.36; N, 7.86; S, 17.44; Cl, 19.20.

Example 139(b)

Methyl 2-methyl-6-(2-methylthieno[3,2-b]pyridin-7-yloxy)-benzo[b]thiophene-3-carboxylate

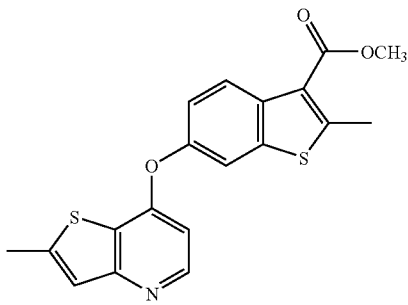

This material was prepared by the reaction of 7-chloro-2-methylthieno[3,2-b]pyridine 139a (1.29 g, 7 mmole) with methyl 6-hydroxy-2-methylbenzo[b]thiophene-3-carboxylate 11a (2.18 g, 9.8 mmole) and $Cs_2CO_3$ (6.51 g, 20 mmole) in a manner as previously described for example 1 to give a yellow solid (1.91 g, 74%). $^1$H NMR (CDCl$_3$) δ 8.43 (1H, d, J=5.4 Hz), 8.37 (1H, d, J=9.0 Hz), 7.97 (1H, d, J=2.2 Hz), 7.37 (1H, dd, J=2.2, 9.0 Hz), 7.30 (1H, s), 6.63 (1H, d, J=5.4 Hz), 3.91 (3H, s), 2.81 (3H, s), 2.61 (3H, s).

Anal. Calcd for $C_{19}H_{15}N_3O_2S \cdot 0.1 CH_2Cl_2$: C, 60.70; H, 4.05; N, 3.71; S, 16.97. Found: C, 60.71; H, 4.17; N, 3.60; S, 17.11.

Example 139(c)

2-Methyl-6-(2-methylthieno[3,2-b]pyridin-7-yloxy)benzo[b]thiophene-3-carboxylic acid

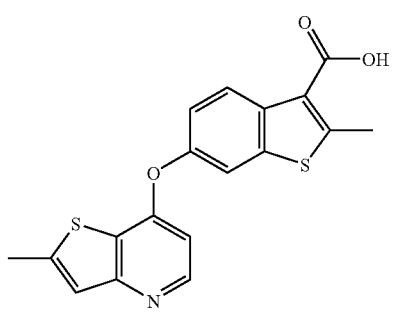

This material was prepared from methyl 2-methyl-6-(2-methylthieno[3,2-b]pyridin-7-yloxy)benzo[b]thiophene-3-carboxylate 139b (1.80 g, 4.8 mmole) in a manner as previously described for example 11c to give a yellow solid (1.41 g, 82%). $^1$H NMR (DMSO-$d_6$) δ 13.08 (1H, bs), 8.45 (1H, d, J=5.5 Hz), 8.43 (1H, d, J=8.8 Hz), 7.96 (1H, d, J=2.4 Hz), 7.35 (1H, dd, J=2.4, 8.8 Hz), 7.32 (1H, s), 6.66 (1H, d, J=5.5 Hz), 2.81 (3H, s), 2.62 (3H, s).

Anal. Calcd for $C_{18}H_{13}NO_3S_2 \cdot 0.5H_2O$: C, 59.32; H, 3.87; N, 3.84; S, 17.60. Found: C, 59.31; H, 3.74; N, 3.79; S, 17.49.

Example 139(d)

2-Methyl-6-(2-methylthieno[3,2-b]pyridin-7-yloxy)benzo[b]thiophene-3-carbonyl chloride

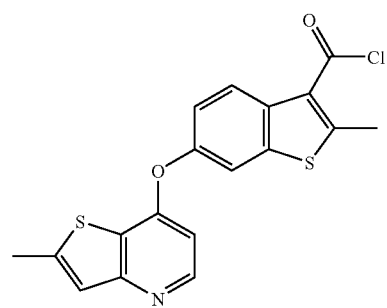

This material was prepared from 2-methyl-6(2-methylthieno[3,2-b]pyridin-7-yloxy)benzo[b]thiophene-3-carboxylic acid 139c (1.34 g, 3.8 mmole) by treatment with thionyl chloride (1 ml, 1.63 g, 13.7 mmole) in a manner as previously described for example 11 to give an orange solid (1.37 g, 97%). $^1$H NMR (DMSO-$d_6$): δ 8.74 (1H, d, J=6.6 Hz), 8.50 (1H, d, J=9.0 Hz), 8.12 (1H, d, J=2.4 Hz), 7.60 (1H, s), 7.48 (1H, dd, J=2.4, 9.0 Hz), 7.05 (1H, d, J=6.6 Hz), 2.83 (3H, s), 2.75 (3H, s).

Anal. Calcd for $C_{18}H_{12}NOS_2Cl \cdot 0.9$ HCl: C, 50.69; H, 3.57; N, 3.28; S, 15.04; Cl, 15.79. Found: C, 50.64; H, 3.56; N, 3.22; S, 14.98; Cl, 15.65.

Example 139

2-Methyl-6-(2-methylthieno[3,2-b]pyridin-7-yloxy)benzo[b]thiophene-3-carboxylic acid (2-morpholin-4-yl-ethyl)-amide

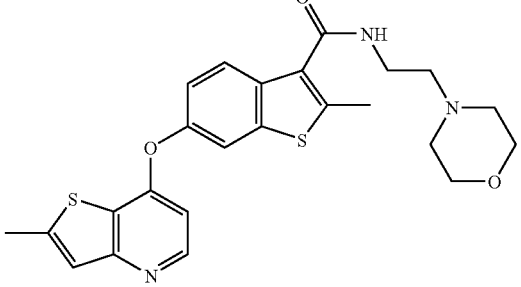

This material was prepared from 2-methyl-6-(2-methylthieno[3,2-b]pyridin-7-yloxy)benzo[b]thiophene-3-carbonyl chloride 139d (112 mg, 0.3 mmole) and 2-(morpholin-4-yl)ethylamine (157 mg, 1.2 mmole) in a similar manner as that described for example 108 to give a yellow solid (105 mg, 75%). $^1$H NMR (DMSO-$d_6$) δ 8.44 (1H, d, J=5.5 Hz), 8.29 (1H, t, J=4.8 Hz), 7.94 (1H, d, J=8.7 Hz), 7.92 (1H, d, J=2.3 Hz), 7.31 (1H, s), 7.30 (1H, dd, J=2.3, 8.7 Hz), 6.60 (1H, d, J=5.5 Hz), 3.60 (4H, t, J=4.2 Hz), 3.45 (2H, dt, J=4.8, 6.2 Hz), 2.64 (3H, s), 2.62 (3H, s), 2.55–2.41 (6H, m).

Anal. Calcd for $C_{24}H_{25}N_3O_3S_2$: C, 61.64; H, 5.39; N, 8.99; S, 13.71. Found: C, 61.34; H, 5.49; N, 8.90; S, 13.68.

Example 140

2-Methyl-6-(2-methylthieno[3,2-b]pyridin-7-yloxy)benzo[b]thiophene-3-carboxylic acid (3-morpholin-4ylpropyl)-amide

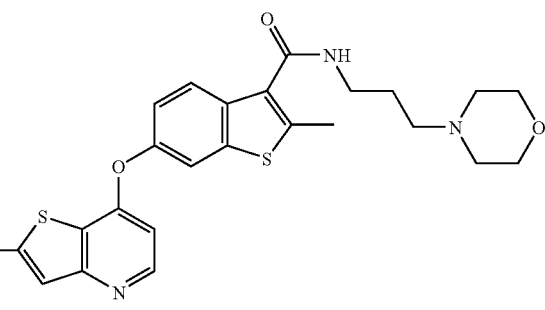

This material was prepared from 2-methyl-6-(2-methylthieno[3,2-b]pyridin-7-yloxy)benzo[b]thiophene-3-carbonyl chloride 139d (112 mg, 0.3 mmole) and 3-(morpholin-4-yl)propylamine (175 mg, 1.2 mmole) in a similar manner as that described for example 108 to give a yellow solid (64 mg, 44%). $^1$H NMR (DMSO-$d_6$) δ 8.43 (1H, d, J=5.5 Hz), 8.38 (1H, t, J=5.3 Hz), 7.91 (1H, d, J=2.3 Hz), 7.81 (1H, d, J=8.6 Hz), 7.30 (1H, s), 7.28 (1H, dd, J=2.3, 8.6 Hz), 6.59 (1H, d, J=5.5 Hz), 3.56 (4H, t, J=4.3 Hz), 3.33 (2H, dt, J=5.3, 6.8 Hz), 2.61 (3H, s), 2.60 (3H, s), 2.42–2.31 (6H, m), 1.72 (2H, tt, J=6.8, 7.0 Hz).

Anal. Calcd for $C_{25}H_{27}N_3O_3S_2 \cdot 0.1\ CH_2Cl_2$: C, 61.51; H, 5.59; N, 8.57; S, 13.08. Found: C, 61.53; H, 5.55; N, 8.25; S, 13.08.

The exemplary compounds described above may be tested for their activity using the tests described below.

Biological Testing; Enzyme Assays

The stimulation of cell proliferation by growth factors such as VEFG, FGF, and others is dependent upon their induction of autophosphorylation of each of their respective receptors tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

VEGF-R2 Construct for Assay:

This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ50 contains residues 806–939 and 990–1171, and also one point mutation (E990V) within the kinase insert domain relative to wild-type VEGF-R2. Autophosphorylation of the purified construct was performed by incubation of the enzyme at a concentration of 4 µM in the presence of 3 mM ATP and 40 mM $MgCl_2$ in 100 mM HEPES, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, 37, 16788–16801 (1998).

FGF-R1 Construct for Assay:

The intracellular kinase domain of human FGF-R1 was expressed using the baculovirus vector expression system starting from the endogenous methionine residue 456 to glutamate 766, according to the residue numbering system of Mohammadi et al., *Mol. Cell. Bio.*, 16, 977–989 (1996). In addition, the construct also has the following 3 amino acid substitutions: L457V, C488A, and C584S.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 $cm^{-1}\ mM^{-1}$) using a Beckman DU 650 spectrophotometer. Assay conditions for phosphorylated VEGF-R2Δ50 (indicated as FLVK-P in the tables below) were the following: 1 mM PEP; 250 µM NADH; 50 units of LDH/mL; 20 units of PK/mL; 5 mM DTT; 5.1 mM poly($E_4Y_1$); 1 mM ATP; and 25 mM $MgCl_2$ in 200 mM HEPES, pH 7.5. Assay conditions for unphosphorylated VEGF-R2Δ50 (indicated as FLVK in the tables) were the following: 1 mM PEP; 250 µM NADH; 50 units of LDH/mL; 20 units of PK/mL; 5 mM DTT; 20 mM poly($E_4Y_1$); 3 mM ATP; and 60 mM $MgCl_2$ and 2 mM $MnCl_2$ in 200 mM HEPES, pH 7.5. Assays were initiated with 5 to 40 nM of enzyme. $K_i$ values were determined by measuring enzyme activity in the presence of varying concentrations of test compounds. The percent inhibition at 50 nm (% inhibition @ 50 nm) was determined by linear least-squares regression analysis of absorpbance as a function of time. The binding inhibitions were fitted to equation as described by Morrison. The data were analyzed using Enzyme Kinetic and Kaleidagraph software.

FGF-R Assay

The spectrophotometric assay was carried out as described above for VEGF-R2, except for the following changes in concentration: FGF-R=50 nM, ATP=2 mM, and poly(E4Y1)=15 mM.

HUVEC+VEGF Proliferation Assay

This assay determines the ability of a test compound to inhibit the growth factor-stimulated proliferation of human umbilical vein endothelial cells ("HUVEC"). HUVEC cells (passage 3–4; Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 µg/mL endothelial cell growth supplement (ECGS), and 0.1 mg/mL heparin). Exponentially-growing HUVEC cells were used in experiments thereafter. Ten to twelve thousand HUVEC cells were plated in 96-well dishes in 100 µl of rich, culture medium (described above). The cells were allowed to attach for 24 hours in this medium. The medium was then removed by aspiration and 105 µl of starvation media (F12K+1% FBS) was added to each well. After 24 hours, 15 µl of test agent dissolved in 1% DMSO in starvation medium or this vehicle alone was added into each treatment well; the final DMSO concentration was 0.1%. One hour later, 30 µl of VEGF (30 ng/mL) in starvation media was added to all wells except those containing untreated controls; the final VEGF concentration was 6 ng/mL. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595 nm was determined on a 96-well spectrophotometer plate reader.

Mouse PK Assay

The pharmacokinetics (e.g., absorption and elimination) of drugs in mice were analyzed using the following experiment. Test compounds were formulated as a suspension in a 30:70 (PEG 400:acidified $H_2O$) vehicle. This solution was administered orally (p.o.) and intraperitoneally (i.p.) at 50 mg/kg to two distinct groups (n=4) of B6 female mice. Blood samples were collected via an orbital bleed at time points: 0 hour (pre-dose), 0.5 hr, 1.0 hr, 2.0 hr, and 4.0 hr post dose. Plasma was obtained from each sample by centrifugation at 2500 rpm for 5 min. Test compound was extracted from the plasma by an organic protein precipitation method. For each time bleed, 50 µL of plasma was combined with 1.0 mL of acetonitrile, vortexed for 2 min. and then spun at 4000 rpm for 15 min. to precipitate the protein and extract out the test compound. Next, the acetonitrile supernatant (the extract containing test compound) was poured into new test tubes and evaporated on a hot plate (25° C.) under a steam of $N_2$ gas. To each tube containing the dried test compound extract, 125 µL of mobile phase (60:40, 0.025 M $NH_4H_2PO_4$+2.5 mL/L TEA:acetonitrile) was added. The test compound was resuspended in the mobile phase by vortexing and more protein was removed by centrifugation at 4000 rpm for 5 min. Each sample was poured into an HPLC vial for test compound analysis on an Hewlett Packard 1100 series HPLC with UV detection.

From each sample, 95 μL was injected onto a Phenomenex-Prodigy reverse phase C-18, 150×3.2 mm column and eluted with a 45–50% acetonitrile gradient run over 10 min. Test-compound plasma concentrations (μg/mL) were determined by a comparison to standard curve (peak area vs. conc. μg/mL) using known concentrations of test compound extracted from plasma samples in the manner described above. Along with the standards and unknowns, three groups (n=4) of quality controls (0.25 μg/mL, 1.5 μg/mL, and 7.5 μg/mL) were run to insure the consistency of the analysis. The standard curve had an $R_2>0.99$ and the quality controls were all within 10% of their expected values. The quantitated test samples were plotted for visual display using Kalidagraph software and their pharmacokinetic parameters were determined using WIN NONLIN software.

Human Liver Microsome (HLM) Assay

Compound metabolism in human liver microsomes was measured by LC-MS analytical assay procedures as follows. First, human liver microsomes (HLM) were thawed and diluted to 5 mg/mL with cold 100 mM potassium phosphate ($KPO_4$) buffer. Appropriate amounts of $KPO_4$ buffer, NADPH-regenerating solution (containing B-NADP, glucose-6-phosphate, glucose-6-phosphate dehydrogenase, and $MgCl_2$), and HLM were preincubated in 13×100 mm glass tubes at 37° C. for 10 min. (3 tubes per test compound—triplicate). Test compound (5 μM final) was added to each tube to initiate reaction and was mixed by gentle vortexing, followed by incubation at 37° C. At t=0, and 2 h, a 250-uL sample was removed from each incubation tube to separate 12×75 mm glass tubes containing 1 mL ice-cold acetonitrile with 0.05 μM reserpine. Samples were centrifuged at 4000 rpm for 20 min. to precipitate proteins and salt (Beckman Allegra 6KR, S/N ALK98D06, #634). Supernatant was transferred to new 12×75 mm glass tubes and evaporated by Speed-Vac centrifugal vacuum evaporator. Samples were reconstituted in 200 μL 0.1% formic acid/acetonitrile (90/10) and vortexed vigorously to dissolve. The samples were then transferred to separate polypropylene microcentrifuge tubes and centrifuged at 14000×g for 10 min. (Fisher Micro 14, S/N M0017580). For each replicate (#1–3) at each timepoint (0 and 2 h), an aliquot sample of each test compound was combined into a single HPLC vial insert (6 total samples) for LC-MS analysis, which is described below.

The combined compound samples were injected into the LC-MS system, composed of a Hewlett-Packard HP1100 diode array HPLC and a Micromass Quattro II triple quadruple mass spectrometer operating in positive electrospray SIR mode (programmed to scan specifically for the molecular ion of each test compound). Each test compound peak was integrated at each timepoint. For each compound, peak area at each timepoint (n=3) was averaged, and this mean peak area at 2 h was divided by the average peak area at time 0 hour to obtain the percent test compound remaining at 2 h.

KDR (VEGFR2) Phosphorylation in PAE-KDR Cells Assay

This assay determines the ability of a test compound to inhibit the autophosphorylation of KDR in porcine aorta endothelial (PAE)-KDR cells. PAE cells that overexpress human KDR were used in this assay. The cells were cultured in Ham's F12 media supplemented with 10% fetal bovine serum (FBS) and 400 ug/mL G418. Thirty thousands cells were seeded into each well of a 96-well plate in 75 μL of growth media and allowed to attach for 6 hours at 37° C. Cells were then exposed to the starvation media (Ham's F12 media supplemented with 0.1% FBS) for 16 hours. After the starvation period was over, 10 μL of test agent in 5% DMSO in starvation media were added to the test wells and 10 μL of the vehicle (5% DMSO in starvation media) were added into the control wells. The final DMSO concentration in each well was 0.5%. Plates were incubated at 37° C. for 1 hour and the cells were then stimulated with 500 ng/ml VEGF (commercially available from R & D System) in the presence of 2 mM $Na_3VO_4$ for 8 minutes. The cells were washed once with 1 mm $Na_3VO_4$ in HBSS and lysed by adding 50 μL per well of lysis buffer. One hundred μL of dilution buffer were then added to each well and the diluted cell lysate was transferred to a 96-well goat ant-rabbit coated plate (commercially available from Pierce) which was pre-coated with Rabbit anti Human Anti-flk-1 C-20 antibody (commercially available from Santa Cruz). The plates were incubated at room temperature for 2 hours and washed seven times with 1% Tween 20 in PBS. HRP-PY20 (commercially available from Santa Cruz) was diluted and added to the plate for a 30-minute incubation. Plates were then washed again and TMB peroxidase substrate (commercially available from Kirkegaard & Perry) was added for a 10-minute incubation. One hundred μL of 0.09 N $H_2SO_4$ was added to each well of the 96-well plates to stop the reaction. Phosphorylation status was assessed by spectrophotometer reading at 450 nm. $IC_{50}$ values were calculated by curve fitting using a four-parameter analysis.

PAE-PDGFRβ Phosphorylation in PAE-PDGFRB Cells Assay

This assay determines the ability of a test compound to inhibit the autophosphorylation of PDGFRβ in porcine aorta endothelial (PAE)-PDGFRβ cells. PAE cells that overexpress human PDGFRβ were used in this assay. The cells were cultured in Ham's F12 media supplemented with 10% fetal bovine serum (FBS) and 400 ug/ml G418. Twenty thousands cells were seeded in each well of a 96-well plate in 50 μL of growth media and allowed to attach for 6 hours at 37° C. Cells were then exposed to the starvation media (Ham's F12 media supplemented with 0.1% FBS) for 16 hours. After the starvation period was over, 10 μL of test agent in 5% DMSO in starvation media were added to the test wells and 10 μL of the vehicle (5% DMSO in starvation media) were added into the control wells. The final DMSO concentration in each well was 0.5%. Plates were incubated at 37° C. for 1 hour and the cells were then stimulated with 1 μg/mL PDGF-BB (R & D System) in the presence of 2 mM $Na_3VO_4$ for 8 minutes. The cells were washed once with 1 mm $Na_3VO_4$ in HBSS and lysed by adding 50 μL per well of lysis buffer. One hundred μL of dilution buffer were then added to each well and the diluted cell lysate was transferred to a 96-well goat ant-rabbit coated plate (Pierce), which was pre-coated with Rabbit anti Human PDGFRβ antibody (Santa Cruz). The plates were incubated at room temperature for 2 hours and washed seven times with 1% Tween 20 in PBS. HRP-PY20 (Santa Cruz) was diluted and added to the plate for a 30-minute incubation. Plates were then washed again and TMB peroxidase substrate (Kirkegaard & Perry) was added for a 10-minute incubation. One hundred μL of 0.09 N $H_2SO_4$ was added into each well of the 96-well plate to stop the reaction. Phosphorylation status was assessed by spectrophotometer reading at 450 nm. $IC_{50}$ values were calculated by curve fitting using a four-parameter analysis.

The results of the testing of the compounds using various assays are summarized in Tables 1 and 2 below, where a notation of "% @" indicates the percent inhibition at the stated concentration.

All of the amines listed in Table 3 were reacted with Example 101, denoted as $R_{101}$ in Table 3 having the following structure:

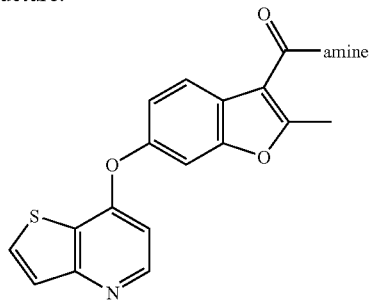

The library plates for Table 3 were prepared in the following general manner:

General Procedure for Amide Bond Formation:

0.13 M solution of each amine in Table 3 in a 1:1 mixture of anhydrous pyridine and DMF were prepared and placed into the appropriate wells of a 1 mL deepwell plate. 0.10 M solution of Example 101, denoted as $R_{101}$ in Table 3, in a DMF solution was prepared and added to each well. The reactions were agitated at 50° C. for 4 h. The volatiles were removed using the Speedvac™ apparatus, and the crude mixtures were reconstituted in DMSO to afford solutions with a final theoretical concentration of 0.01M.

TABLE 1

| Compound | FLVK (% inh @ 50 nM) | FLVK Ki (nM) | HUVEC + VEGF IC50 (nM) AVG | PAE KDR autophos IC50 (nM) AVG | PAE PDGFR autophos IC50 (nM) AVG | bFGF Huvec IC50 (nM) Avg. |
|---|---|---|---|---|---|---|
| 1 | 92% | 1.02 | 0.68 | 0.31 | 164 | 122 |
| 2 | 75% | 4.14 | 2.3 | 1.8 | 912 | 3333 |
| 3 | 59% | 0.811 | 0.442 | 0.9 | 756 | 942 |
| 4 | 88% | 2.58 | 0.404 | 0.47 | 284 | NT |
| 5 | 73% | 1.91 | 1.55 | NT | 1000 | 235 |
| 6 | 94% | 0.721 | 1.2 | NT | 255 | 145 |
| 7 | 95% | 1.04 | 1.21 | 1.95 | 1000 | 2474 |
| 8 | 94% | 0.403 | 1.37 | NT | 1000 | 504 |
| 9 | 83% | 1.57 | 13 | NT | 313 | 135 |
| 10 | 74% | 2.31 | 10 | NT | 451 | 99 |
| 11 | 93% | 0.492 | 0.56 | NT | 103.5 | 40 |
| 12 | 100% | 0.314 | 0.26 | 0.14 | 14.4 | 20 |
| 13 | 97% | 0.322 | 0.082 | 0.21 | 41 | 27 |
| 14 | 81% | 1.46 | 9.4 | NT | NT | 287 |
| 15 | 13% | 48.3 | NT | NT | NT | NT |
| 16 | 46% | 8.14 | 10 | NT | NT | 1000 |
| 17 | 77% | 2.77 | 1.2 | 0.47 | 20 | 847 |
| 18 | 78% | 2.373 | 0.64 | 0.62 | 32 | 1000 |
| 19 | 75% | 2.63 | 2.7 | 1.7 | 172 | 10000 |
| 20 | 99% | 0.082 | 0.19 | 0.217 | 43 | 1902 |
| 21 | 43% | 13.11 | NT | NT | NT | NT |
| 22 | 38% | 25.8 | NT | NT | NT | NT |
| 23 | 19% | 78 | NT | NT | NT | NT |
| 24 | 69% | 4.2 | 32 | NT | NT | 10000 |
| 25 | 70% | 4.08 | 0.45 | NT | 12 | 7460 |
| 26 | 83% | 3.66 | 0.74 | NT | 13 | 2233 |
| 27 | 13% | 96 | NT | NT | 205 | NT |
| 28 | 78% | 2.8 | 0.272 | NT | 15 | 462 |
| 29 | 6% | 88.77 | NT | NT | NT | NT |
| 30 | 63% | 6 | 33.6 | NT | 74 | 10000 |
| 31 | 25% | 30.2 | NT | NT | NT | NT |
| 32 | 22% | 39.4 | NT | NT | 29.2 | NT |
| 33 | 61% | 11.5 | 10 | NT | 63 | 10000 |
| 34 | 45% | 11.4 | NT | NT | 31.3 | NT |
| 35 | 23% | 35.166 | NT | NT | 70 | NT |
| 36 | 41% | 11.513 | NT | NT | NT | NT |
| 37 | 66% | 4.3 | 10 | NT | 1000 | NT |
| 38 | 60% | 6.12 | 27 | NT | 12.3 | 10000 |
| 39 | 12% | 47 | 8.7 | NT | 61 | NT |
| 40 | 77% | 2.95 | 1.12 | NT | 24.2 | 7798 |
| 41 | 71% | 3.3 | 3.7 | NT | 22.1 | 1224 |
| 42 | 76% | 2.8 | 4.34 | NT | 8.9 | NT |
| 43 | 67% | 3.21 | 10 | NT | 1000 | NT |
| 44 | 87% | 1.2 | 1.78 | NT | 21.26 | 6036 |
| 45 | 64% | 4.65 | 10 | NT | 26.9 | NT |
| 46 | 68% | 6.49 | 3.13 | NT | NT | NT |
| 47 | 41% | 19.7 | NT | NT | NT | NT |
| 48 | 91% | NT | 0.94 | NT | 21 | 239 |
| 49 | 67% | 16 | 7 | NT | NT | NT |
| 50 | 36% | 36.5 | NT | NT | NT | NT |
| 51 | 34% | 27.7 | 82 | NT | NT | NT |
| 52 | 41% | 24.9 | NT | NT | NT | NT |
| 53 | 93% | 1.07 | 1.8 | NT | 229 | 7233 |

TABLE 1-continued

| Compound | FLVK (% inh @ 50 nM) | FLVK Ki (nM) | HUVEC + VEGF IC50 (nM) AVG | PAE KDR autophos IC50 (nM) AVG | PAE PDGFR autophos IC50 (nM) AVG | bFGF Huvec IC50 (nM) Avg. |
|---|---|---|---|---|---|---|
| 54 | 89% | 1.71 | 1.8 | NT | 133 | 10000 |
| 55 | 62% | 4.86 | 5.8 | NT | 31 | NT |
| 56 | 60% | 3.8 | 22 | NT | 109 | 10000 |
| 57 | 63% | 9.8 | NT | 87 | NT | |
| 58 | 55% | 7.59 | 3.65 | NT | 124 | 7830 |
| 59 | 81% | 1.378 | 0.045 | NT | 115 | 1164 |
| 60 | 81% | 2.17 | 1.34 | NT | 38.3 | 1703 |
| 61 | 89% | NT | 0.605 | 0.4 | 17.8 | 3995 |
| 62 | 91% | 0.57 | 2.15 | 0.24 | 18.7 | 619 |
| 63 | 67% | 9.33 | 10 | NT | 84 | 10000 |
| 64 | 64% | 11.8 | 10 | NT | 1000 | 10000 |
| 65 | 65% | 7.97 | 10 | NT | 59 | 10000 |
| 66 | 75% | 5.2 | 5.8 | NT | 90.7 | NT |
| 67 | 58% | 12.51 | NT | NT | NT | NT |
| 68 | 37% | NT | NT | NT | NT | NT |
| 69 | 95% | 0.3 | 0.57 | NT | 6.52 | 4314 |
| 70 | 95% | 0.43 | 0.537 | NT | 47.1 | 3975 |
| 71 | 5% | NT | NT | NT | NT | NT |
| 72 | 2% | NT | NT | NT | NT | NT |
| 73 | 48% | 10.286 | NT | NT | NT | NT |
| 74 | 43% | 12.721 | NT | NT | 312.5 | NT |
| 75 | 84% | 2.62 | 1.4 | NT | 16.6 | 10000 |
| 76 | 36% | 6.26 | NT | NT | NT | NT |
| 77 | 99% | 0.2 | 0.2 | NT | 7.4 | 8 |
| 78 | 93% | 0.221 | 0.507 | NT | 14.8 | 30 |
| 79 | 90% | 0.276 | 0.223 | NT | 15.5 | 130 |
| 80 | 95% | 0.438 | 0.239 | NT | 31 | 60 |
| 81 | 100% | 0.2 | 0.09 | NT | 7 | 25.96 |
| 82 | 89% | 0.884 | 2.28 | NT | 53.1 | 2058 |
| 83 | 98% | 0.2 | 0.77 | NT | 28.8 | 142 |
| 84 | 94% | 0.58 | 0.322 | NT | 12.4 | 429 |
| 85 | 83% | 1.71 | 3.92 | NT | 27.3 | 6987 |
| 86 | 81% | 1.44 | 3.07 | NT | 17.9 | |
| 87 | 96% | 0.615 | 1.25 | NT | 17.8 | 6044 |
| 88 | 94% | 0.574 | 0.46 | NT | 15.1 | 363 |
| 89 | 95% | 0.419 | NT | NT | 250 | 5.2 |
| 90 | 93% | 0.739 | 2.14 | NT | 33 | 745 |
| 91 | 94% | 0.356 | 0.168 | NT | 16.5 | 250 |
| 92 | 100% | 0.2 | 0.18 | NT | 4.4 | 13 |
| 93 | 84% | 2.72 | NT | NT | 44 | NT |
| 94 | 81% | 1.453 | 0.7 | NT | 112 | 251 |
| 95 | 89% | 0.848 | 10 | NT | 235 | 96 |
| 96 | 51% | 9.61 | NT | NT | NT | NT |
| 97 | 70% | 4.84 | 10 | NT | 293 | 223 |
| 98 | 86% | 0.38 | 9.4 | NT | 126.6 | NT |
| 99 | 66% | 4.68 | NT | NT | 562.6 | NT |
| 100 | 0% | NT | NT | NT | NT | NT |
| 102 | 96% | 0.91 | 0.186 | NT | 49 | 1718 |
| 103 | 52% | 7 | NT | NT | 203.4 | NT |
| 104 | 100% | NT | 8.4 | NT | 163.9 | 227 |
| 105 | 61% | 8.37 | NT | NT | 127 | NT |
| 106 | 98% | NT | 10 | NT | 1000 | 638 |
| 107 | 17% | 36.69 | NT | NT | NT | NT |
| 108 | 61% | NT | NT | NT | NT | NT |
| 109 | 82% | NT | NT | NT | NT | NT |
| 110 | 21% | NT | NT | NT | NT | NT |
| 111 | 96% | NT | NT | NT | NT | NT |
| 112 | 91% | NT | NT | NT | NT | NT |
| 113 | 99% | NT | NT | NT | NT | NT |
| 114 | 16% | 118.85 | NT | NT | 1000 | NT |
| 115 | 4% | NT | NT | NT | 1000 | NT |
| 116 | 4% | NT | NT | NT | NT | NT |
| 117 | 87% | 0.2 | 0.07 | NT | 189 | 86 |
| 118 | 84% | 1.2 | 0.9 | NT | 1000 | 736 |
| 119 | 95% | 0.375 | 1.46 | NT | 90.6 | 1827 |
| 120 | 93% | 0.6 | 0.491 | NT | 405 | 489 |
| 121 | 94% | 0.2 | 0.24 | NT | 220 | 100 |
| 122 | 58% | 5.14 | NT | NT | 351 | NT |
| 123 | 74% | 2.63 | 10 | NT | 229 | NT |
| 124 | 82% | 2.19 | 1.6 | NT | 376 | 8243 |
| 125 | 95% | 0.219 | 2 | NT | 179 | 969 |
| 126 | 96% | 0.5896 | 10 | NT | 336 | 5656 |
| 127 | 100% | 0.2 | 1 | NT | 102 | 41 |

TABLE 1-continued

| Compound | FLVK (% inh @ 50 nM) | FLVK Ki (nM) | HUVEC + VEGF IC50 (nM) AVG | PAE KDR autophos IC50 (nM) AVG | PAE PDGFR autophos IC50 (nM) AVG | bFGF Huvec IC50 (nM) Avg. |
|---|---|---|---|---|---|---|
| 128 | 91% | 0.57 | 0.13 | NT | 148 | 100 |
| 129 | 88% | 0.2 | 0.219 | NT | 168 | 100 |
| 130 | 95% | 0.39 | 0.49 | NT | 335 | 100 |
| 131 | 96% | 0.2 | 1.89 | NT | 97 | 260 |
| 132 | 80% | 1.78 | 5.8 | NT | 467 | NT |
| 133 | 40% | 5.9 | NT | NT | 467.9 | NT |
| 134 | 94% | 1.44 | 0.656 | NT | 176.9 | 1070 |
| 135 | 87% | 1.5411 | 1.02 | NT | 212 | 559 |
| 136 | 88% | 1.1704 | 10 | NT | 609 | NT |
| 137 | 64% | 5.1 | 2.1 | NT | 213 | 294 |
| 138 | 85% | 0.78 | 9.9 | NT | 110 | NT |
| 139 | 40% | NT | NT | NT | NT | NT |
| 140 | 90% | NT | NT | NT | NT | NT |

TABLE 2

| Compound | mouse PK AUC, po ng-h/mL** | mouse Cmax, po (ng/mL) | mouse Cmin, po (ng/mL) | % remain (HLM-UDPGA, 0.5 h) | % remain (HLM-NADPH, 0.5 h) |
|---|---|---|---|---|---|
| 1 | 182608 | 124745 | 2793 | NT | NT |
| 2 | NT | NT | NT | NT | NT |
| 3 | 2450 | 956 | 66 | NT | NT |
| 4 | 7674 | 2340 | 200 | NT | NT |
| 5 | 12254 | 6743 | 256 | NT | NT |
| 6 | 586 | 355 | 20 | NT | NT |
| 7 | NT | NT | NT | NT | NT |
| 8 | 2348 | 666 | 105 | NT | NT |
| 9 | NT | NT | NT | NT | NT |
| 10 | NT | NT | NT | NT | NT |
| 11 | NT | NT | NT | NT | NT |
| 12 | 11970 | 5423 | 270 | NT | NT |
| 13 | 63000 | 24760 | 1700 | NT | NT |
| 14 | NT | NT | NT | NT | NT |
| 15 | NT | NT | NT | NT | NT |
| 16 | NT | NT | NT | NT | NT |
| 17 | 71580 | 28817 | 2334 | NT | NT |
| 18 | 8724 | 4120 | 342 | NT | NT |
| 19 | 120 | 51 | 4 | NT | NT |

TABLE 3

| Amine | % TIC | FLVK (% @ 100 nM) | FGF (% @ 100 nM) | PAE PDGFR autophos IC50 (nM) |
|---|---|---|---|---|
| 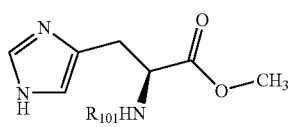 | 56.552 | 52 | NT | 49 |
| 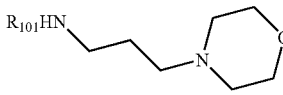 | 53.7991 | 103 | 2 | 53 |
| 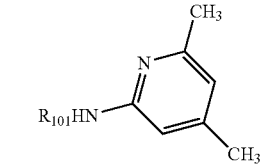 | 0 | 26 | NT | NT |

TABLE 3-continued
| Amine | % TIC | FLVK (% @ 100 nM) | FGF (% @ 100 nM) | PAE PDGFR autophos IC50 (nM) |
|---|---|---|---|---|
| 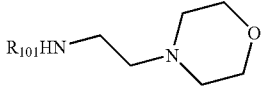 | 51.8111 | 79 | 20 | 50 |
| 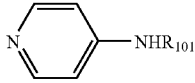 | 5.4277 | 20 | NT | NT |
| 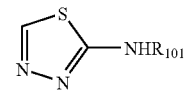 | 88.1771 | 75 | 35 | >100 |
| 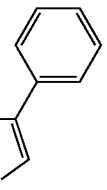 | 0 | 16 | NT | NT |
| 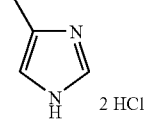 | 55.2161 | 17 | NT | NT |
| 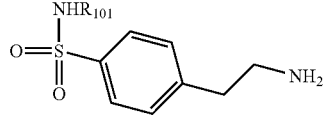 | 65.4679 | 68 | 0 | >100 |
| 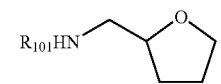 | 95.752 | 36 | NT | NT |
| 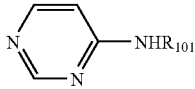 | 97.7442 | 24 | NT | NT |
| 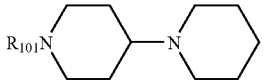 | 65.2303 | 20 | NT | NT |
| 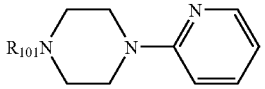 | 48.6673 | 22 | NT | NT |
| 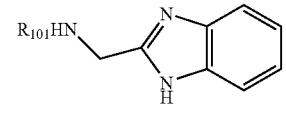 | 45.8972 | 24 | NT | NT |
| 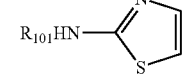 | 12.783 | 90 | 20 | >100 |

TABLE 3-continued
| Amine | % TIC | FLVK (% @ 100 nM) | FGF (% @ 100 nM) | PAE PDGFR autophos IC50 (nM) |
|---|---|---|---|---|
| 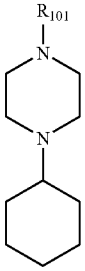 | 55.6 | 14 | NT | NT |
| 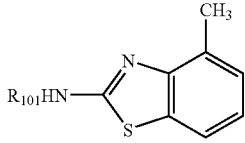 | 0 | 20 | NT | NT |
| 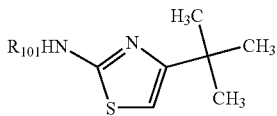 | 0 | 27 | NT | NT |
| 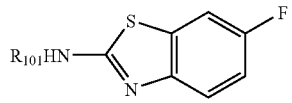 | 0 | 26 | NT | NT |
| 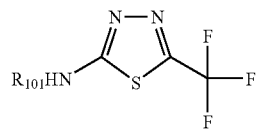 | 0 | 14 | NT | NT |
| 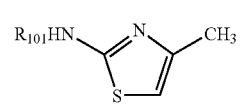 | 5.35845 | 62 | 7 | >100 |
| 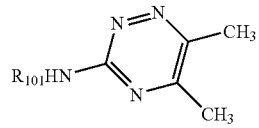 | 0 | 14 | NT | NT |
| 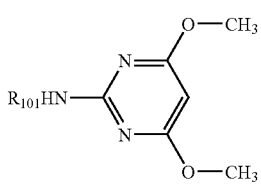 | 0 | 16 | NT | NT |
| 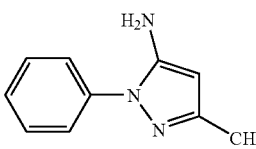 | 0 | 30 | NT | NT |

TABLE 3-continued
| Amine | % TIC | FLVK (% @ 100 nM) | FGF (% @ 100 nM) | PAE PDGFR autophos IC50 (nM) |
|---|---|---|---|---|
| 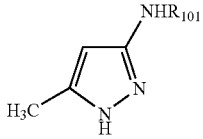 | 19.2675 | 100 | 4 | 46 |
| 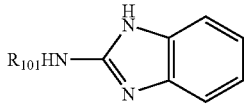 | 58.6779 | 16 | NT | NT |
| 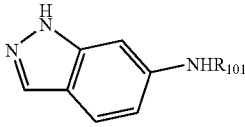 | 29.8321 | 87 | 0 | 57 |
| 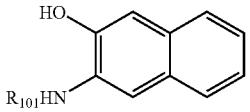 | 10.8303 | 29 | NT | NT |
| 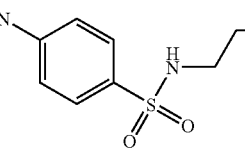 | 77.1177 | 16 | NT | NT |
| 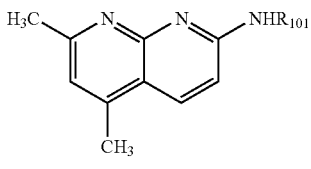 | 0 | 20 | NT | NT |
| 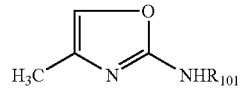 | 0 | 13 | NT | NT |
| 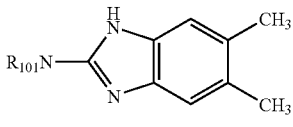 | 55.2355 | 14 | NT | NT |
| 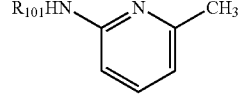 | 0 | 14 | NT | NT |
| 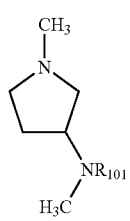 | 49.6134 | 25 | NT | NT |
| 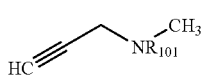 | 43.8419 | 25 | NT | NT |

TABLE 3-continued

| Amine | % TIC | FLVK (% @ 100 nM) | FGF (% @ 100 nM) | PAE PDGFR autophos IC50 (nM) |
|---|---|---|---|---|
| 4-phenoxyphenethylamine (NHR₁₀₁) | 11.5047 | 21 | NT | NT |
| 5-amino-1H-indazole (R₁₀₁HN-) | 75.9693 | 96 | 0 | ~100 |
| 2-amino-4-methylpyrimidine (R₁₀₁HN-) | 0 | 10 | NT | NT |
| methyl histidinate derivative (R₁₀₁HN-) | 28.1067 | 13 | NT | NT |
| 3-(trifluoromethyl)phenethylamine (R₁₀₁HN-) | 28.1967 | 97 | 0 | >100 |
| 2-amino-4-(tert-pentyl)phenol (R₁₀₁HN-) | 24.8781 | 28 | NT | NT |
| 2-aminopyrazine (R₁₀₁HN-) | 0 | 10 | NT | NT |
| 5-amino-1H-tetrazole (NHR₁₀₁) | 22.1224 | 8 | NT | NT |
| sulfamethoxazole derivative (NHR₁₀₁) | 1.78077 | 7 | NT | NT |

TABLE 3-continued
| Amine | % TIC | FLVK (% @ 100 nM) | FGF (% @ 100 nM) | PAE PDGFR autophos IC50 (nM) |
|---|---|---|---|---|
| 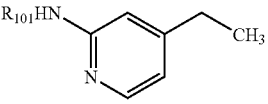 | 0 | 18 | NT | NT |
| 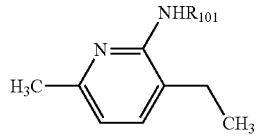 | 0 | 22 | NT | NT |
| 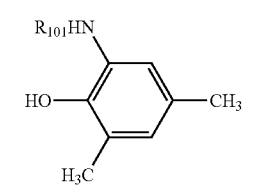 | 28.8916 | 87 | 13 | ~100 |
| 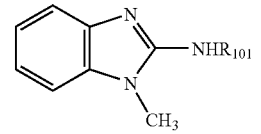 | 50.8697 | 12 | NT | NT |
| 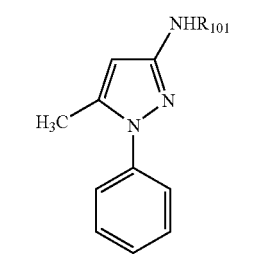 | 1.10495 | 13 | NT | NT |
| 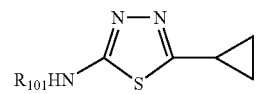 | 36.7228 | 100 | 4 | >100 |
| 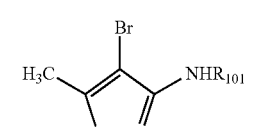 | 0 | 4 | NT | NT |
| 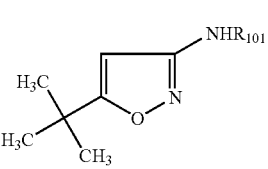 | 0 | 15 | NT | NT |
| 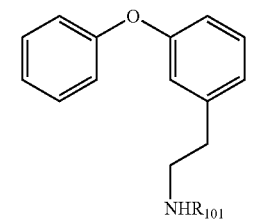 | 24.5486 | 36 | NT | NT |

TABLE 3-continued

| Amine | % TIC | FLVK (% @ 100 nM) | FGF (% @ 100 nM) | PAE PDGFR autophos IC50 (nM) |
|---|---|---|---|---|
| (CH₃)₂CH-N(CH₃)-R₁₀₁ | 22.7289 | 17 | NT | NT |
| isopropoxyethyl-NHR₁₀₁ | 55.7071 | 94 | 0 | 61 |
| methyl aziridine-2-carboxylate, N-R₁₀₁ | 25.3022 | 51 | NT | >100 |
| 3-amino-1H-pyrazole, NHR₁₀₁ | 74.3164 | 91 | NT | >100 |
| 4-hydroxyquinolin-2-yl-NHR₁₀₁ | 0 | 23 | 8 | NT |
| ethyl 3-amino-1H-pyrazole-4-carboxylate, NH-R₁₀₁ | 4.01991 | 13 | NT | NT |
| quinolin-3-yl-NHR₁₀₁ | 143.6451 | 85 | 7 | >100 |
| benzothiazol-6-yl-NHR₁₀₁ | 15.565 | 96 | 0 | >100 |
| 5-cyano-1H-imidazol-4-yl-NHR₁₀₁ | 0 | 5 | NT | NT |
| 2-morpholinopyridin-4-yl-NHR₁₀₁ | 58.6541 | 101 | 0 | 57 |

TABLE 3-continued

| Amine | % TIC | FLVK (% @ 100 nM) | FGF (% @ 100 nM) | PAE PDGFR autophos IC50 (nM) |
|---|---|---|---|---|
| 3-(2-methylpropan-2-yl)-1H-pyrazol-5-yl NHR₁₀₁ | 20.5224 | 100 | 56 | >100 |
| 2-(1H-benzimidazol-2-yl)ethyl NHR₁₀₁ | 29.3082 | 22 | NT | NT |
| 3-cyclopropyl-1-methyl-1H-pyrazol-5-yl NHR₁₀₁ | 3.03715 | 56 | 3 | >100 |
| 8-hydroxyquinolin-2-yl NHR₁₀₁ | 54.7208 | 24 | NT | NT |
| 5-(trifluoromethyl)pyridin-2-yl NHR₁₀₁ | 0 | 27 | NT | NT |
| methyl 5-amino-furan-2-carboxylate R₁₀₁HN | 0 | 24 | NT | NT |
| 3-(1H-pyrazol-3-yl)phenyl NHR₁₀₁ | 27.931 | 94 | 0 | >100 |
| 2,6-dimethoxypyridin-3-yl R₁₀₁HN | 16.4145 | 92 | 1 | >100 |
| 1,7-naphthyridin-8-yl NHR₁₀₁ | 0 | 10 | NT | NT |

TABLE 3-continued
| Amine | % TIC | FLVK (% @ 100 nM) | FGF (% @ 100 nM) | PAE PDGFR autophos IC50 (nM) |
|---|---|---|---|---|
| 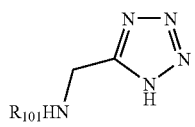 | 49.5375 | 10 | NT | NT |
| 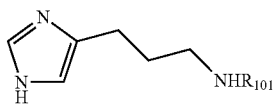 | 41.0058 | 25 | NT | NT |
| 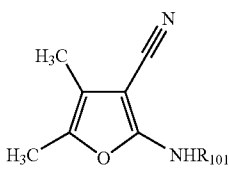 | 0 | 13 | NT | NT |
| 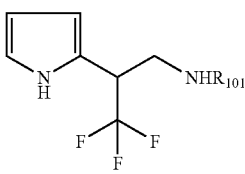 | 45.0518 | 85 | 3 | >100 |
| 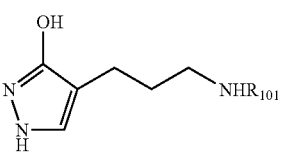 | 38.7067 | 12 | NT | NT |
| 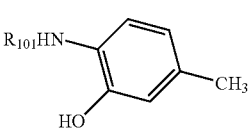 | 33.1065 | 85 | 0 | ~100 |
| 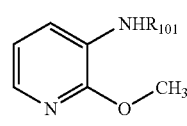 | 1.9193 | 35 | NT | NT |
| 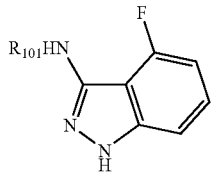 | 0 | 61 | 0 | >100 |
| 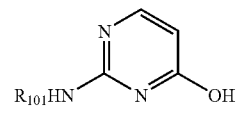 | 0 | 19 | NT | NT |
| 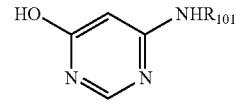 | 0 | 17 | NT | NT |

TABLE 3-continued

| Amine | % TIC | FLVK (% @ 100 nM) | FGF (% @ 100 nM) | PAE PDGFR autophos IC50 (nM) |
|---|---|---|---|---|
| 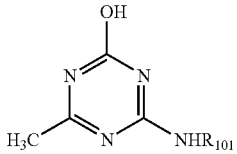 | 0 | 15 | NT | NT |
| 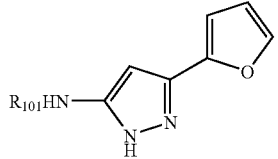 | 15.0813 | 101 | 1 | >100 |
| 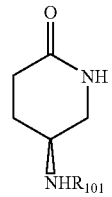 | 19.6253 | 19 | NT | NT |
| 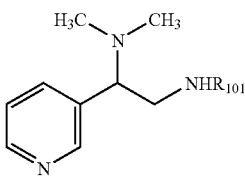 | 64.8885 | 16 | NT | NT |
| 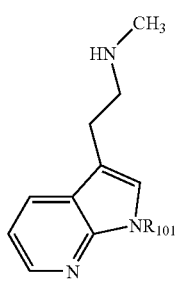 | 20.3244 | 9 | NT | NT |
| 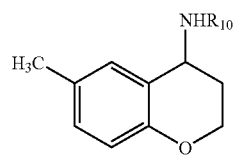 | 24.2001 | 46 | NT | NT |

The exemplary compounds described above may be formulated into pharmaceutical compositions according to the following general examples.

EXAMPLE 1

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

EXAMPLE 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

We claim:

1. A compound represented by the formula I:

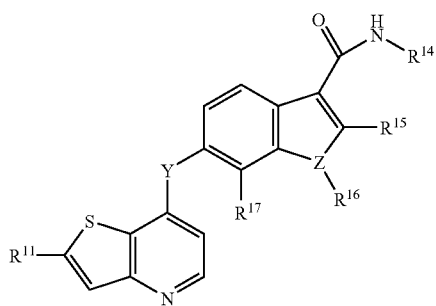

wherein:

Y is —NH—, —O—, —S—, or —CH$_2$—;

Z is —O—, or —N—;

$R^{14}$ is a $C_1$–$C_6$ alkyl, $C_1$–$C_6$ alkylamino, $C_1$–$C_6$ alkylhydroxy, $C_3$–$C_{10}$ cycloalkyl, $C_1$–$C_6$ alkyl $C_3$–$C_{10}$ cycloalkyl, or methylureido group;

$R^{15}$ and $R^{17}$ are independently H, halo, or a $C_1$–$C_6$ alkyl group unsubstituted or substituted by one or more $R^5$ groups;

$R^{16}$ is H or a $C_1$–$C_6$ alkyl group when Z is N, and $R^{16}$ is absent when Z is —O—;

$R^{11}$ is H, $C_1$–$C_6$ alkyl, $C_3$–$C_{10}$ cycloalkyl, —C(O)NR$^{12}$R$^{13}$, —C(O)(C$_6$–C$_{10}$ aryl), —(CH$_2$)$_t$(C$_6$–C$_{10}$ aryl), —(CH$_2$)$_t$(5 to 10 membered heterocyclic), —(CH$_2$)$_t$NR$^{12}$R$^{13}$, —SO$_2$NR$^{12}$R$^{13}$ or —CO$_2$R$^{12}$, wherein said C$_1$–C$_6$ alkyl, —C(O)(C$_6$–C$_{10}$ aryl), —(CH$_2$)$_t$(C$_6$–C$_{10}$ aryl), and —(CH$_2$)$_t$(5 to 10 membered heterocyclic) moieties of the said $R^{11}$ groups are unsubstituted or substituted by one or more $R^5$ groups;

each $R^5$ is independently selected from halo, cyano, nitro, trifluoromethoxy, trifluoromethyl, azido, —C(O)R$^8$, —C(O)OR$^8$, —OC(O)R$^8$, —OC(O)OR$^8$, —NR$^6$C(O)R$^7$, —C(O)NR$^6$R$^7$, —NR$^6$R$^7$, —OR$^9$, —SO$_2$NR$^6$R$^7$, C$_1$–C$_6$ alkyl, C$_3$–C$_{10}$ cycloalkyl, C$_1$–C$_6$ alkylamino, —(CH$_2$)O(CH$_2$)$_q$NR$^6$R$^7$, —(CH$_2$)$_t$O(CH$_2$)$_q$OR$^9$, —(CH$_2$)$_t$OR$^9$, —S(O)$_j$(C$_1$–C$_6$ alkyl), —(CH$_2$)$_t$(C$_6$–C$_{10}$ aryl), —(CH$_2$)$_t$(5 to 10 membered heterocyclic), —C(O)(CH$_2$)$_t$(C$_6$–C$_{10}$ aryl), CH$_2$)$_t$O(CH$_2$)$_t$(C$_6$–C$_{10}$ aryl), —(CH$_2$)$_t$O(CH$_2$)$_q$(5 to 10 membered heterocyclic), —C(O)(CH$_2$)$_t$(5 to 10 membered heterocyclic), —(CH$_2$)$_t$NR$^7$(CH$_2$)$_q$NR$^6$R$^7$, —(CH$_2$)$_t$NR$^7$CH$_2$C(O) NR$^6$R$^7$, —(CH$_2$)$_t$NR$^7$(CH$_2$)$_q$NR$^9$C(O)R$^8$, (CH$_2$)$_t$NR$^7$ (CH$_2$)$_t$O(CH$_2$)$_q$OR$^9$, —(CH$_2$)$_t$NR$^7$(CH$_2$)$_q$S(O)$_j$(C$_1$–C$_6$ alkyl), —(CH$_2$)$_j$NR$^7$(CH$_2$)$_t$R$^6$, —SO$_2$(CH$_2$)$_t$(C$_6$–C$_{10}$ aryl), and —SO$_2$(CH$_2$)$_t$(5 to 10 membered heterocyclic), the —(CH$_2$)$_q$— and —(CH$_2$)$_t$— moieties of the said $R^5$ groups optionally include a carbon-carbon double or triple bond, and the alkyl, aryl and hetero cyclic moieties of the said $R^5$ groups are unsubstituted or substituted with one or more substituents independently selected from halo, cyano, nitro, trifluoromethyl, azido, —OH, —C(O)R$^8$, —C(O)OR$^8$, —OC(O)R$^8$, —OC(O)OR$^8$, —NR$^6$C(O)R$^7$, —C(O)NR$^6$R$^7$, —(CH$_2$)$_t$NR$^6$R$^7$, C$_1$–C$_6$ alkyl, C$_3$–C$_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$ OR$^9$;

each $R^6$ and $R^7$ is independently selected from H, OH, C$_1$–C$_6$ alkyl, C$_3$–C$_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, —(CH$_2$)$_t$CN(CH$_2$)$_t$OR$^9$, —(CH$^2$)$_t$CN(CH$_2$)$_t$R$^9$ and —(CH$_2$)$_t$OR$^9$, and the alkyl, aryl and heterocyclic moieties of the said $R^6$ and $R^7$ groups are unsubstituted or substituted with one or more substituents independently selected from hydroxy, halo, cyano, nitro, trifluoromethyl, azido, —C(O)R$^8$, —C(O)OR$^8$, —CO(O)R$^8$, —OC(O)OR$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, where when $R^6$ and $R^7$ are both attached to the same nitrogen, then $R^6$ and $R^7$ are not both bonded to the nitrogen directly through an oxygen;

each $R^8$ is independently selected from H, C$_1$–C$_{10}$ alkyl, C$_3$–C$_{10}$ cycloalkyl, —(CH$_2$)$_t$(C$_6$–C$_{10}$ aryl), and —(CH$_2$)$_t$(5 to 10 membered heterocyclic);

t is an integer from 0 to 6; j is an integer from 0 to 2; q is an integer from 2 to 6;

each $R^9$ and $R^{10}$ is independently selected from H, —OR$^6$, C$_1$–C$_6$ alkyl, and C$_3$–C$_{10}$ cycloalkyl; and each $R^{12}$ and $R^{13}$ is independently selected from H, C$_1$–C$_6$ alkyl, C$_3$–C$_{10}$ cycloalkyl, —(CH$_2$)$_t$(C$_3$–C$_{10}$ cycloalkyl), —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, and the alkyl, aryl and heterocyclic moieties of the said $R^{12}$ and $R^{13}$ groups are unsubstituted or substituted with one or more substituents independently selected from $R^5$, or $R^{12}$ and $R^{13}$ are taken together with the nitrogen to which they are attached to form a C$_5$–C$_9$ azabicyclic, aziridinyl, azetidinyl, pyrrolidinyl, piperidyl, piperazinyl, morpholinyl, thiomorpholinyl, isoquinolinyl, or dihydroisoquinolinyl ring, wherein said C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl rings are unsubstituted or substituted with one or more $R^5$ substituents, where $R^{12}$ and $R^{13}$ are not both bonded to the nitrogen directly through an oxygen;

or pharmaceutically acceptable salts or solvates thereof.

2. The compound, salt, or solvate of claim 1, wherein $R^{11}$ is —(CH$_2$)$_t$(5 to 10 membered heterocyclic), —C(O)NR$^{12}$R$^{13}$, —(CH$_2$)$_t$NR$^{12}$R$^{13}$, —SO$_2$NR$^{12}$R$^{13}$ or —CO$_2$R$^{12}$.

3. The compound of claim 2, wherein $R^{11}$ is —(CH$_2$)$_t$(5 to 10 membered heterocyclic), —C(O)NR$^{12}$R$^{13}$, —SO$_2$NR$^{12}$R$^{13}$ or —CO$_2$R$^{12}$.

4. The compound of claim 3, wherein $R^{11}$ is —(CH$_2$)$_t$(5 to 10 membered heterocyclic) or —C(O)NR$^{12}$R$^{13}$.

5. The compound of claim 4, wherein $R^{11}$ is —C(O)NR$^{12}$R$^{13}$, wherein $R^{12}$ and $R^{13}$ are independently selected from H, C$_1$–C$_6$ alkyl, C$_3$–C$_{10}$ cycloalkyl, —(CH$_2$)$_t$(C$_3$–C$_{10}$ cycloalkyl), —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$ OR$^9$.

6. The compound of claim 5, wherein $R^{11}$ is —C(O)NR$^{12}$R$^{13}$, and wherein $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring is unsubstituted or substituted by 1 to 5 $R^5$ substituents.

7. The compound of claim 6, wherein $R^{12}$ and $R^{13}$ are taken together with the nitrogen to which they are attached to form a pyrrolidinyl, piperidinyl, piperazinyl, morpholinyl, thiomorpholinyl, isoquinolinyl, or dihydroisoquinolinyl ring, wherein said pyrrolidinyl, piperidinyl, piperazinyl, morpholinyl, thiomorpholinyl, isoquinolinyl, or dihydroisoquinolinyl ring is unsubstituted or substituted with 1 to 5 $R^5$ substituents.

8. The compound of claim 7, wherein $R^{12}$ and $R^{13}$ are taken together with the nitrogen to which they are attached to form a pyrrolidinyl, piperidinyl, piperazinyl, morpholinyl, or thiomorpholinyl ring, wherein said pyrrolidinyl, piperidinyl, piperazinyl, morpholinyl, or thiomorpholinyl ring is unsubstituted or substituted with 1 to 5 $R^5$ substituents.

9. The compound of claim 8, wherein $R^{12}$ and $R^{13}$ are taken together with the nitrogen to which they are attached to form a pyrrolidinyl or piperidinyl ring, wherein said pyrrolidinyl or piperidinyl ring is unsubstituted or substituted with 1 to 5 $R^5$ substituents.

10. The compound of claim 9, wherein $R^{12}$ and $R^{13}$ are taken together with the nitrogen to which they are attached to form a pyrrolidinyl ring, wherein said pyrrolidinyl is unsubstituted or substituted with 1 to 5 $R^5$ substituents.

11. The compound of claim 10, wherein $R^{12}$ and $R^{13}$ are taken together with the nitrogen to which they are attached to form a pyrrolidin-1-yl ring, wherein said pyrrolidin-1-yl ring is unsubstituted or substituted with 1 to 5 $R^5$ substituents.

12. The compound of claim 4, wherein $R^{11}$ is a —(CH$_2$)$_t$(5 to 10 membered heterocyclic) group unsubstituted or substituted with 1 to 5 $R^5$ groups.

13. The compound of claim 12, wherein $R^{11}$ is a —(CH$_2$)$_t$(5–8 membered heterocyclic) group unsubstituted or substituted with 1 to 5 $R^5$ groups.

14. The compound of claim 13, wherein $R^{11}$ is a —(CH$_2$)$_t$(5 or 6 membered heterocyclic) group is unsubstituted or substituted with 1 to 5 $R^5$ groups.

15. The compound of claim 14, wherein $R^{11}$ is a —(CH$_2$)$_t$(5 membered heterocyclic) group unsubstituted or substituted with 1 to 5 $R^5$ groups.

16. The compound of claim 15, wherein $R^{11}$ is a thiazolyl, unsubstituted or substituted by 1 to 5 $R^5$ groups.

17. The compound of claim 15, wherein $R^{11}$ is an imidazolyl, unsubstituted or substituted by 1 to 5 $R^5$ groups.

18. The compound of claim 1, wherein $R^{16}$ is a $C_1$–$C_6$ alkyl group.

19. The compound of claim 18, wherein $R^{16}$ is methyl.

20. The compound of claim 1, wherein $R^{14}$ is methyl.

21. The compound represented by the formula II:

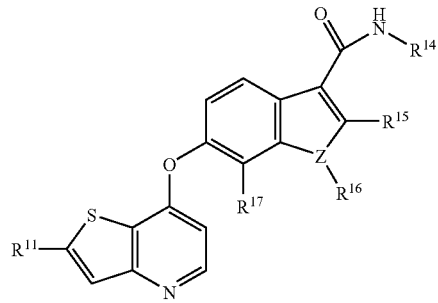

wherein:

Z is —O—, or —N—;

$R^{14}$ is a $C_1$–$C_6$ alkyl, $C_1$–$C_6$ alkylamino, $C_1$–$C_6$ alkylhydroxy, $C_3$–$C_{10}$ cycloalkyl, $C_1$–$C_6$ alkyl $C_3$–$C_{10}$ cycloalkyl, or methylureido group;

$R^{15}$ and $R^{17}$ are independently H, halo, or a $C_1$–$C_6$ alkyl group;

$R^{16}$ is H or a $C_1$–$C_6$ alkyl group when Z is —N— and $R^{16}$ is absent when Z is —O—;

$R^{11}$ is a heteroaryl group unsubstituted or substituted by one or more halo, cyano, nitro, trifluoromethoxy, trifluoromethyl, azido, —C(O)R, —C(O)OR$^8$, —OC(O)R$^8$, —OC(O)OR$^8$, —NR$^6$C(O)R$^7$, —C(O)NR$^6$R$^7$, —NR$^6$R$^7$, —OR$^9$, —SO$_2$NR$^6$R$^7$, $C_1$–$C_6$ alkyl, $C_3$–$C_{10}$ cycloalkyl, —(CH$_2$)$_j$O(CH$_2$)$_q$NR$^6$R$^7$, —(CH$_2$)$_t$O(CH$_2$)$_q$OR$^9$, —(CH$_2$)$_t$OR$^9$, —S(O)$_j$(C$_1$–C$_6$ alkyl), —(CH$_2$)$_t$(C$_8$–C$_{10}$ aryl), —(CH$_2$)$_t$(5 to 10 membered heterocyclic), —C(O)(CH$_2$)$_t$(C$_6$–C$_{10}$ aryl), —(CH$_2$)$_t$O(CH$_2$)$_j$(C$_6$–C$_{10}$ aryl), —(CH$_2$)$_t$O(CH$_2$)$_q$(5 to 10 membered heterocyclic), —C(O)(CH$_2$)$_t$(5 to 10 membered heterocyclic), —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_q$O(CH$_2$)$_q$OR$^9$, —(CH$_2$)$_j$NR$^7$(CH$_2$)$_q$S(O)$_j$(C$_1$C$_6$ alkyl), —(CH$_2$)$_j$NR$^7$ —(CH$_2$)$_t$R$^6$, —SO$_2$(CH$_2$)$_t$(C6–C$_{10}$ aryl), and —SO$_2$(CH$_2$)$_t$(5 to 10 membered heterocyclic), the —(CH$_2$)$_q$— and —(CH$_2$)$_t$— moieties of the said $R^5$ groups optionally include a carbon-carbon double or triple bond, and the alkyl, aryl and heterocyclic moieties of the said $R^5$ groups are unsubstituted or substituted with one or more substituents independently selected from halo, cyano, nitro, trifluoromethyl, azido, —OH, —C(O)R$^8$, —C(O)OR$^8$, —OC(O)R$^8$, —OC(O)OR$^8$, —NR$^6$C(O)R$^7$, —C(O)NR$^6$R$^7$, —(CH$_2$)$_t$NR$^6$R$^7$, $C_1$–$C_6$ alkyl, $C_3$–$C_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$ and —(CH$_2$)$_t$OR$^9$;

each $R^6$ and $R^7$ is independently selected from H, OH, $C_1$–$C_6$ alkyl, $C_3$–$C_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, —(CH$_2$)$_t$CN(CH$_2$)$_q$OR$^9$, —(CH$_2$)$_t$CN(CH$_2$)$_t$R$^9$ and —(CH$_2$)$_t$OR$^9$, and the alkyl, aryl and heterocyclic moieties of the said $R^6$ and $R^7$ groups are unsubstituted or substituted with one or more substituents independently selected from hydroxy, halo, cyano, nitro, trifluoromethyl, azido, —C(O)R$^8$, —C(O)OR$^8$, —CO(O)R$^8$, —OC(O)OR$^8$, —NR$^9$C(O)R$^{10}$, —C(O)NR$^9$R$^{10}$, —NR$^9$R$^{10}$, $C_1$–$C_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, where when $R^6$ and $R^7$ are both attached to the same nitrogen, then $R^6$ and $R^7$ are not both bonded to the nitrogen directly through an oxygen;

each R⁸ is independently selected from H, $C_1$–$C_{10}$ alkyl, $C_3$–$C_{10}$ cycloalkyl, —(CH₂)$_t$($C_6$–$C_{10}$ aryl), and —(CH₂)$_t$(5 to 10 membered heterocyclic);

each R⁹ and R¹⁰ is independently selected from H, $C_1$–$C_6$ alkyl, and $C_3$–$C_{10}$ cycloalkyl;

t is an integer from 0 to 6; j is an integer from 0 to 2; q is an integer from 2 to 6;

or pharmaceutically acceptable salts or solvates thereof.

22. The compound of claim 21, wherein R¹⁶ is a $C_1$–$C_6$ alkyl group.

23. The compound of claim 22, wherein R¹⁶ is methyl.

24. The compound of claim 21, wherein R¹⁴ is methyl.

25. The compound represented by the formula IV:

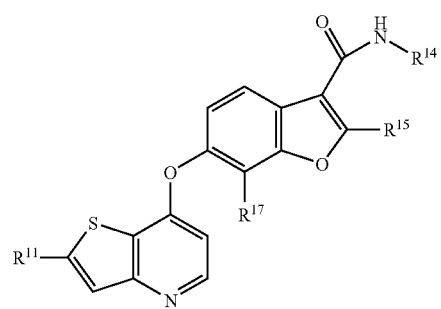

IV wherein:
R¹⁴ is a $C_1$–$C_6$ alkyl, $C_1$–$C_6$ alkylamino, $C_1$–$C_6$ alkylhydroxy, $C_3$–$C_{10}$ cycloalkyl, $C_1$–$C_6$ alkyl $C_3$–$C_{10}$ cycloalkyl, or methylureido group;

R¹⁵ and R¹⁷ are independently H, halo, or a $C_1$–$C_6$ alkyl group;

R¹¹ is a heterocyclic or a heteroaryl group unsubstituted or substituted by one or more groups selected from —C(O)OR⁸, $C_1$–$C_6$ alkyl, and —(CH₂)$_t$OR⁹;

each R⁸ is independently selected from H, $C_1$–$C_{10}$ alkyl, $C_3$–$C_{10}$ cycloalkyl, —(CH₂)$_t$($C_6$–$C_{10}$ aryl), and —(CH₂)$_t$(5 to 10 membered heterocyclic);

each R⁹ is independently selected from H, $C_1$–$C_6$ alkyl, and $C_3$–$C_{10}$ cycloalkyl; and t is an integer from 0 to 6; j is an integer from 0 to 2; q is an integer from 2 to 6;

or pharmaceutically acceptable salts or solvates thereof.

26. The compound of claim 25, wherein R¹⁴ is methyl.

27. A compound selected from the group consisting of:

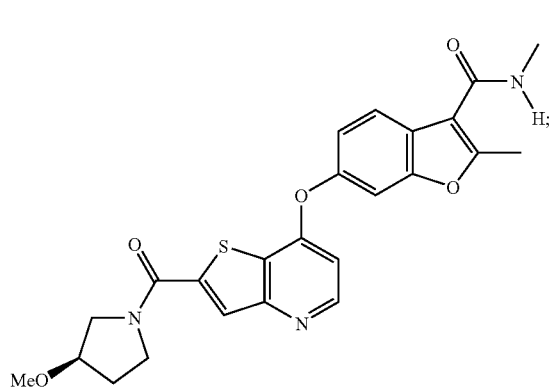

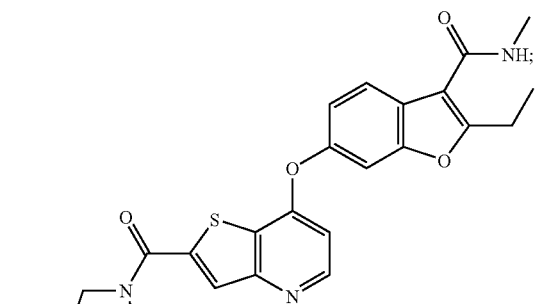

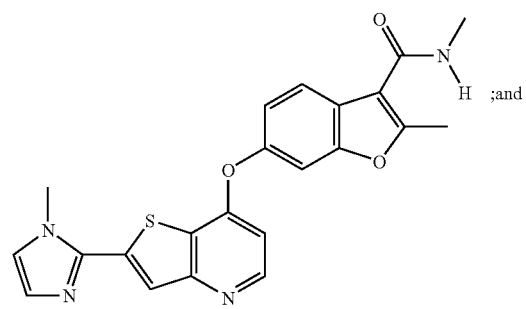

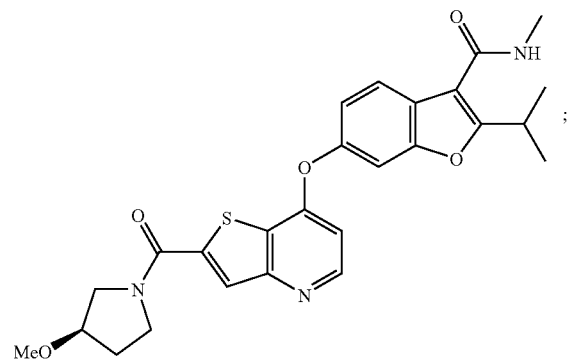

or a pharmaceutically acceptable salt or solvate thereof.

28. A compound selected from the group consisting of:

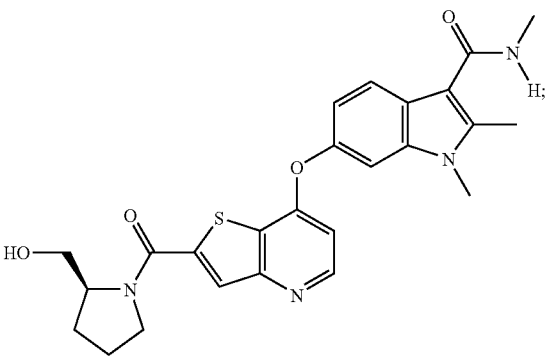

-continued
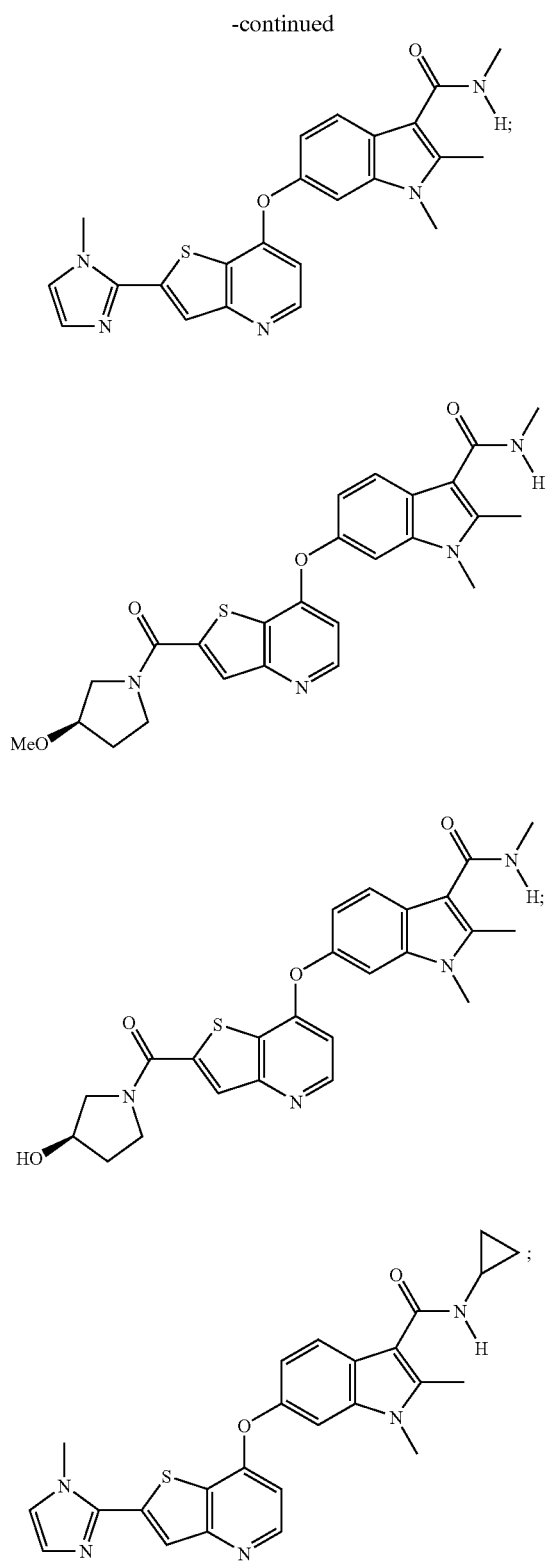
-continued
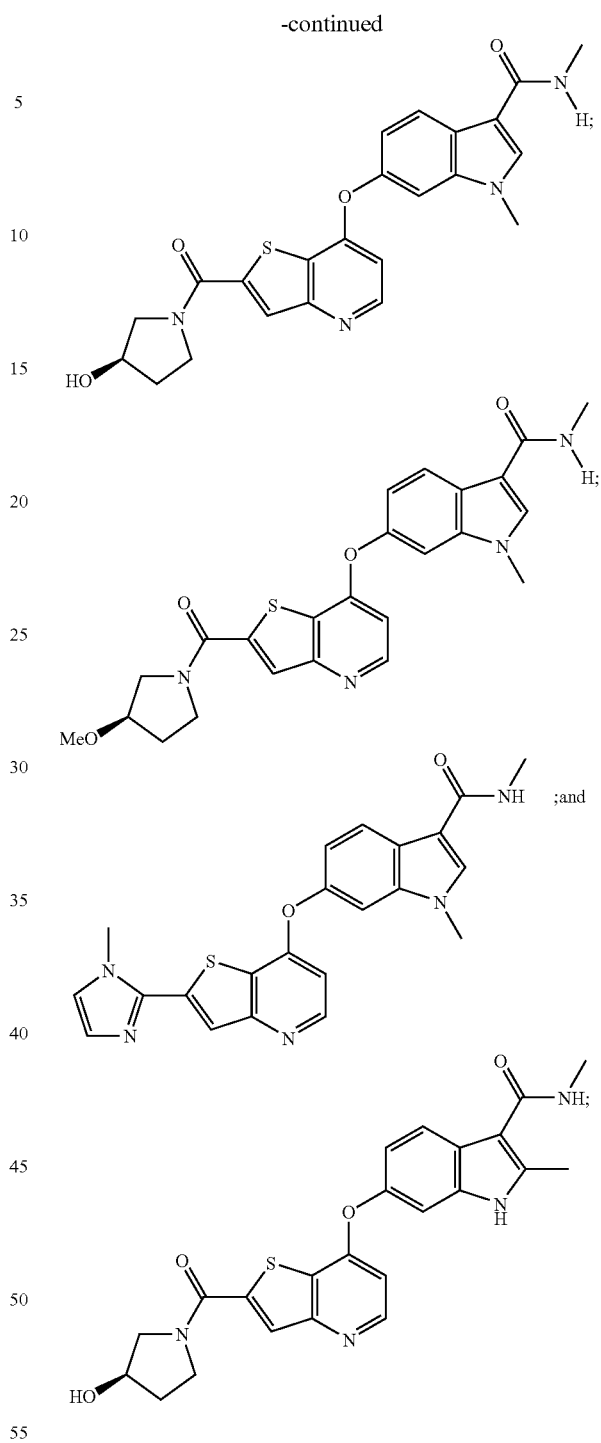
or a pharmaceutically acceptable salt or solvate thereof.
29. The compound of claim 1, wherein $R^{14}$ is cyclopropyl.
30. The compound of claim 21, wherein $R^{14}$ is cyclopropyl.
* * * * *